United States Patent
Liu et al.

(10) Patent No.: US 9,045,491 B2
(45) Date of Patent: Jun. 2, 2015

(54) THIENYL [3,2-D] PYRIMIDIN-4-ONE COMPOUNDS, PREPARATION METHOD, PHARMACEUTICAL COMPOSITIONS AND USE THEREOF

(71) Applicants: SHANGHAI INSTITUTE OF MATERIA MEDICA, CHINESE ACADEMY OF SCIENCES, Shanghai (CN); CISEN PHARMACEUTICAL CO., LTD., Jining (CN)

(72) Inventors: Hong Liu, Shanghai (CN); Jia Li, Shanghai (CN); Jian Li, Shanghai (CN); Jingya Li, Shanghai (CN); Jiang Wang, Shanghai (CN); Mingbo Su, Shanghai (CN); Jie Lian, Shanghai (CN); Hualiang Jiang, Shanghai (CN); Kaixian Chen, Shanghai (CN)

(73) Assignees: Shanghai Institute of Materia Medica, Chinese Academy of Sciences, Shanghai (CN); Cisen Pharmaceutical Co., Ltd., Jining (CN)

( * ) Notice: Subject to any disclaimer, the term of this patent is extended or adjusted under 35 U.S.C. 154(b) by 0 days.

(21) Appl. No.: 14/361,920

(22) PCT Filed: Oct. 23, 2012

(86) PCT No.: PCT/CN2012/001422
§ 371 (c)(1),
(2) Date: May 30, 2014

(87) PCT Pub. No.: WO2013/078765
PCT Pub. Date: Jun. 6, 2013

(65) Prior Publication Data
US 2014/0323466 A1    Oct. 30, 2014

(30) Foreign Application Priority Data

Dec. 1, 2011   (CN) .......................... 2011 1 0393905
Jul. 26, 2012  (CN) .......................... 2012 1 0262331

(51) Int. Cl.
C07D 495/04    (2006.01)
A61K 31/55     (2006.01)
(52) U.S. Cl.
CPC .................................. *C07D 495/04* (2013.01)
(58) Field of Classification Search
CPC ................................................... C07D 495/04
USPC ......................................... 544/278; 514/260.1
See application file for complete search history.

(56) References Cited

FOREIGN PATENT DOCUMENTS

| CN | 1894234 A | 1/2007 |
|----|-----------|--------|
| CN | 101817833 A | 9/2010 |
| CN | 102311448 A * | 1/2011 |
| CN | 102311448 A | 1/2012 |
| WO | 2004/087053 A2 | 10/2004 |

OTHER PUBLICATIONS

Deng, Jifeng et al., "The highly potent and selective dipeptidyl peptidase IV inhibitors bearing a thienopyrimidine scaffold effectively treat type 2 diabetes," *European Journal of Medicinal Chemistry* (2011) 46:71-76.
Feng, Jun et al., "Discovery of Alogliptin: A Potent, Selective, Bioavailable, and Efficacious Inhibitor of Dipeptidyl Peptidase IV," *J. Med. Chem.* (2007) 50:2297-2300.
Kim, Dooseop et al., "(2R)-4-Oxo-4-[Trifluoromethyl)-5,6-dihydro[1,2,4]triazola[4,3-a]pyrazin-7(8H)-yl]-1-2(2,4,5-trifluorophenyl)butan-2-amine: A Potent, Orally Active Dipeptidyl Peptidase IV Inhibitor for the Treatment of Type 2 Diabetes," *J. Med. Chem.* (2005) 48:141-151.
Villhauer, Edwin B. et al., "1-[[3-Hydroxy-1-adamantyl)amino]acetl]2-cyano-(S)-pyrrolidine: A Potent, Selective, and Orally Bioavailable Dipeptidyl Peptidase IV Inhibitor with Antihyperglycemic Properties," *J. Med. Chem.* (2003) 46:2774-2789.
English translation of International Search Report corresponding to PCT/CN2012/001422 mailed Feb. 14, 2013 (4 pages).
Boudet, Nadege et al., "Chemo- and Regioselective Functionalization of Uracil Derivatives. Applications to the Synthesis of Oxypurinol and Emivirine." *Org. Lett.* (2006) 8(17)3737-3740.

* cited by examiner

*Primary Examiner* — Kahsay Habte
(74) *Attorney, Agent, or Firm* — Kilpatrick Townsend & Stockton LLP

(57) ABSTRACT

Disclosed are new thienyl [3,2-d] pyrimidin-4-one compounds shown as the general formula (I), preparation method, pharmaceutical compositions and pharmacological use thereof. The compounds are strong DPPIV (dipeptide peptidase IV) inhibitors and can treat type II diabetes through well inhibiting DPPIV indirectly increasing the content of GLP-1 in vivo and inducing a series of physiological actions in vivo. Therefore, the compounds could be developed as new promising drugs for treating diabetes.

(I)

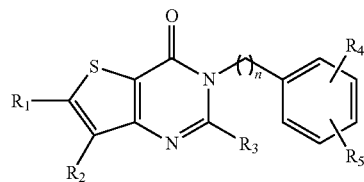

19 Claims, 10 Drawing Sheets

THIENYL [3,2-D] PYRIMIDIN-4-ONE COMPOUNDS, PREPARATION METHOD, PHARMACEUTICAL COMPOSITIONS AND USE THEREOF

TECHNICAL FIELD

The invention relates to the field of pharmaceutical chemistry and pharmacotherapy, specially to thieno[3,2-d]pyrimidin-4-one compounds, preparation method thereof, a pharmaceutical composition containing such compound and use thereof.

BACKGROUND ART

Diabetes is a common metabolic disease. It is characterized by abnormally high plasma glucose concentration showed in the fasting state or during the oral glucose tolerance test and hyperglycemia. The World Health Organization divides diabetes into type 1 and type 2 according to the clinical forms, and most diabetes patients suffer from type 2 diabetes mellitus (T2DM). Type 2 diabetes mellitus, also known as non-insulin dependent diabetes mellitus, is accompanied by high vascular complications, such as coronary artery disease, stroke, high blood pressure, kidney disease, peripheral vascular disease, neurological disease and retinopathy. This metabolic disorder has become a public health problem. There are nearly 194 million diabetics in the world according to a survey from World Health Organization and will be increased to 366 million by 2030. Promoting insulin secretion from pancreatic β-cells is the primary means for treating T2DM, however, in addition to therapeutic effects, there would be some side effects, such as: low blood sugar, weight gain, cardiovascular morbid reaction and β-cell death and the like.

Studies have shown that the complications in T2DM patients will decrease by 35%, when glycosylated hemoglobin Alc (HbAlc) decreases by 1%. Therefore, how to reduce complications and adverse side effects has been a major theme for treating type 2 diabetes. The targets for treating diabetes validated clinically include peroxisome proliferators-activated receptors (PPAR)α/γ, glucagon like peptidase-1 (GLP-1), dipeptidyl peptidase IV (DPPIV, DPP4) and the like. The DPPIV inhibitors have been a new choice for treating type 2 diabetes, and are relatively safe and effective medicaments so far whether administered alone or in combination.

Dipeptidyl peptidase IV (DPPIV; also known as T-cell antigen CD26), is a serine protease with high specificity in the form of dimer. It contains two states, one of which is trans-membrane protease, comprising 766 amino acids, widely distributed in the kidney, intestine villus-like wall, cell membrane, hepatocytes, vascular endothelium, T cells, B cells, and NK cells. The other exists in the plasma in the form of dissolved state. The most important enzyme action for DPPIV is hydrolyzing polypeptides which contain alanine or prolinechain in N-terminal of the peptide chain, such as hydrolyzing GLP-1. If the activities of DPPIV can be inhibited, the content of GLP-1 in vivo can be improved indirectly which can induce a series of physiological actions in vivo and achieve the purpose of the treatment of type 2 diabetes.

Currently, the most widely used medicaments in clinic are anti-type 2 diabetes medicaments associated with GLP-1, such as (a) GLP-1 analogues resistant to DPPIV; (2) small molecule GLP-1 receptor agonists; and (c) DPPIV inhibitors. As a new oral antidiabetic agent, DPPIV inhibitor can prevent the rapid degradation of incretin hormone and improve the postprandial GLP-1 level with little side effects and good effects. The recent studies have shown that DPPIV inhibitors can reduce the level of glycosylated hemoglobin Alc whether administered alone or in combination with other antidiabetic agents. Also, the risk of hypoglycemia is small so that DPPIV inhibitors have already attracted more and more attention from pharmaceutical firms.

The studies on DPPIV inhibitors have already made a great breakthrough. Now the medicaments in the market include sitagliptin from Merck, vildagliptin from Novartis, saxagliptin from Bristol-Myers Squibb, alogliptin from Takeda, linagliptin from Boehringer Ingelheim and the like. Since the serine proteinase also has other families, their selectivity problems should be firstly considered and other side effects should be avoided. Therefore, the study on the DPPIV inhibitors still has a great challenge.

SUMMARY OF THE INVENTION

One object of the present invention is to provide novel thieno[3,2-d]pyrimidin-4-one compounds with DPPIV inhibitory activity, the structure general formula of which is shown as the following formula (I).

Another object of the present invention is to provide a method for synthesizing the novel thieno[3,2-d]pyrimidin-4-one compounds by using 6,7-substituted 2,4-dimethoxy thienyl[3,2-d]pyrimidine as raw materials.

A further object of the present invention is to provide a pharmaceutical composition containing the thieno[3,2-d]pyrimidin-4-one compound.

A still further object of the present invention is to provide a use of thieno[3,2-d]pyrimidin-4-one compound in the preparation of a medicament for the treatment of diabetes.

The compounds according to the present invention can be used as the non-peptide small molecule inhibitor for DPPIV and can achieve the purpose of the treatment of type 2 diabetes by inhibiting the activity of DPPIV, indirectly increasing the content of GLP-1 in vivo and inducing a series of physiological actions in vivo. Therefore, the compounds could be developed as novel promising drugs for treating type 2 diabetes.

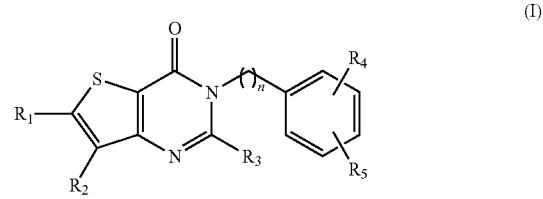

(I)

wherein, n is an integer from 1 to 3;

$R_1$ and $R_2$ are identical or different, and not hydrogen simultaneously, and each of $R_1$ and $R_2$ is independently H, a halogen, $CBr_2H$, $CCl_2H$, $CF_2H$, a cyano, $CF_3$, an aldehyde group, $(CH_2)_mOR_6$, $(CH_2)_mNR_6R_7$,

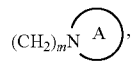, $(CH_2)_mCOOR_8$, $CONR_9R_{10}$, or

, wherein,

R₁ and R₂ can be linked together to form C3-C6 alkylidene, but not necessarily;

m is an integer from 0 to 3;

R₆ and R₇ are identical or different, and each of R₆ and R₇ is independently selected from H, a linear or branched saturated or unsaturated C1-C6 hydrocarbyl, a C3-C7 cyclic hydrocarbyl, a C1-C3 alkoxy, a 4-7 member heterocyclic group, a C1-C4 alkyloyl RCO, a C5-C7 aroyl ArCO, a C1-C4 alkylsulfonyl RSO₂, a C5-C7 arylsulfonyl ArSO₂, a C5-C7 aroylmethylene, a 5-7 member heteroaroylmethylene, a benzyl, a pyridinedimethylene, a C5-C7 aryl Ar or a 5-7 member heteroaryl; wherein, the linear or branched saturated or unsaturated C1-C6 hydrocarbyl is substituted by one or more substituents selected from a methylsulfonyl, a cyclopropyl, a hydroxy, a C1-C3 alkoxy, a C1-C3 alkoxycarbonyl, and an epoxypropyl, but not necessarily; the heterocyclic group contains 1-3 heteroatoms selected from O, S and N, the methylene of the heterocyclic group is substituted by carbonyl or sulfonyl, but not necessarily, or the heterocyclic group is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a C1-C4 alkoxy carbonyl, a mercapto, a C1-C4 acyl and a C5-C7 aryl Ar, but not necessarily; the aryl or the benzyl is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar, but not necessarily; the heteroaryl contains 1-3 heteroatoms selected from O, S and N, is combined with a phenyl or a C5-C7 heteroaryl, but not necessarily, or is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

R₈ is selected from H, a linear or branched saturated or unsaturated C1-C6 hydrocarbyl, a C3-C7 cyclic hydrocarbyl;

R₉ and R₁₀ are identical or different, and each is independently selected form H,

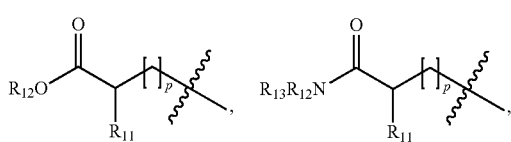

a linear or branched saturated or unsaturated C1-C6 hydrocarbyl, a C3-C7 cyclic hydrocarbyl, a C4-C7 heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched saturated or unsaturated C1-C6 hydrocarbyl is substituted by one or more substituents selected from a methylsulfonyl, a cyclopropyl, a hydroxy, a C1-C3 alkoxy, a C1-C3 alkoxycarbonyl, and an epoxypropyl, but not necessarily; the heterocyclic group contains 1-3 heteroatoms selected from O, S and N, the methylene of the heterocyclic group is substituted by carbonyl or sulfonyl, but not necessarily, or the heterocyclic group is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar, but not necessarily; the aryl or the benzyl is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the heteroaryl contains 1-3 heteroatoms selected from O, S and N, is combined with a phenyl or a C5-C7 heteroaryl, but not necessarily, or is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

P is an integer from 0 to 2;

R₁₁, R₁₂ and R₁₃ are identical or different, each of which is independently selected form H, a linear or branched saturated or unsaturated C1-C6 hydrocarbyl, a C3-C7 cyclic hydrocarbyl, a phenyl or a benzyl; wherein the phenyl or the benzyl is substituted by one or more substituents selected from a halogen, a linear or branched C1-C3 hydrocarbyl, a cyano, a nitro, an amino, a hydroxy, a hydroxymethyl, a trifluoromethyl, a trifluoromethoxy, a carboxyl, and a C1-C4 alkoxy, but not necessarily;

is a 3-7 member nitrogen-containing heterocyclic group, the heterocyclic group further contains 1-3 heteroatoms selected from O, S and N, and the methylene of the heterocyclic group is substituted by carbonyl or sulfonyl, but not necessarily, and the heterocyclic group is substituted by 1-5 substituents selected from H, a linear or branched C1-C6 hydrocarbyl, a halogen, a cyano, a nitro, an amino, a hydroxy, a hydroxymethyl, a trifluoromethyl, a trifluoromethoxy, a carboxyl, an acylamino, a carboxylate group, C1-C4 alkoxy carbonyl, a mercapto, a C1-C4 alkoxy and hydroxamino, but not necessarily;

R₃ is selected from NR₁₄R₁₅ or

, wherein R₁₄ and R₁₅ are identical or different, and each of R₁₄ and R₁₅ is independently H, a linear or branched saturated or unsaturated C1-C6 hydrocarbyl and hydrocarboxyl, a C3-C7 cyclic hydrocarbyl, a C1-C6 hydrocarbyl amino, a C1-C6 hydrocarbyl amino hydroxy, a C1-C6 hydrocarbyl amidino, a C1-C6 hydrocarbyl guanidyl, a benzyl, a C5-C7 aryl Ar or a 5-7 member heteroaryl, and the heteroaryl contains 1-3 heteroatoms selected from O, S and N, is combined with a phenyl or a C5-C7 heteroaryl, but not necessarily, or is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

is a 3-7 member nitrogen-containing heterocyclic group, and the heterocyclic group further contains 1-4 heteroatoms selected from O, S and N, and is substituted by 1-5 substituents selected from H, a linear or branched C1-C6 hydrocarbyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, an amidino, a guanidyl and hydroxamino;

$R_4$, and $R_5$ are identical or different, and each of $R_4$ and $R_5$ is independently H, a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl, a C1-C4 sulfonyl, a C1-C4 sulfonyl amino, an aminoacyl or a C1-C4 linear or branched alkyl substituted sulfonyl;

the halogen is a fluoro, a chloro, a bromo or an iodo.

One preferable embodiment of formula (I) compound according to the present invention is the following thieno[3,2-d]pyrimidin-4-one compound, enantiomer, diastereoisomer, racemate and mixtures thereof, or pharmaceutically acceptable salt thereof, wherein:

n is 1;

$R_1$ and $R_2$ are identical or different, and not hydrogen simultaneously, each of which is independently H, a halogen, $CBr_2H$, $CCl_2H$, $CF_2H$, a cyano, $CF_3$, an aldehyde group, $(CH_2)_mOR_6$, $(CH_2)_mNR_6R_7$,

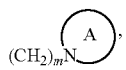

$(CH_2)_mCOOR_8$, $CONR_9R_{10}$, or

wherein, $R_1$ and $R_2$ can be linked together to form C3-C6 alkylidene, but not necessarily;

m is an integer from 0 to 3;

$R_6$ and $R_7$ are identical or different, and each of $R_6$ and $R_7$ is independently selected from H, a linear or branched C1-C6 alkyl, a C3-C7 cycloalkyl, a C1-C3 alkoxy, a 4-7 member heterocyclic group, a C1-C4 alkyloyl RCO, a C5-C7 aroyl ArCO, a C1-C4 alkylsulfonyl $RSO_2$, a C5-C7 arylsulfonyl $ArSO_2$, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C6 alkyl is substituted by one or more substituents selected from a methylsulfonyl, a cyclopropyl, a hydroxy, a C1-C3 alkoxy, a C1-C3 alkoxycarbonyl, and an epoxypropyl, but not necessarily; the heterocyclic group contains 1-3 heteroatoms selected from O, S and N; the aryl or the benzyl is substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar, but not necessarily; the heteroaryl contains 1-3 heteroatoms selected from O, S and N, is combined with a phenyl or a C5-C7 heteroaryl, but not necessarily, or is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

$R_8$ is selected from H, a linear or branched C1-C6 alkyl;

$R_9$ and $R_{10}$ are identical or different, each of which is independently selected form H,

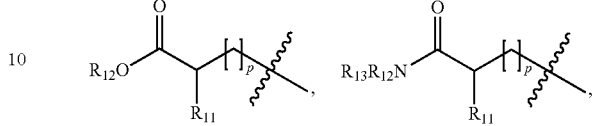

a linear or branched C1-C6 alkyl, a C3-C7 cycloalkyl, a 4-7 member heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C6 alkyl is substituted by one or more substituents selected from a methylsulfonyl, a cyclopropyl, a hydroxy, a C1-C3 alkoxy, a C1-C3 alkoxycarbonyl, and an epoxypropyl, but not necessarily; the heterocyclic group contains 1-3 heteroatoms selected from O, S and N, and the methylene of the heterocyclic group is substituted by carbonyl or sulfonyl, but not necessarily, or the heterocyclic group is substituted by one or more substituents selected from a halogen, a linear or branched C1-C6 alky, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar, but not necessarily; the aryl or the benzyl can be substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the heteroaryl contains 1-3 heteroatoms selected from O, S and N, is combined with a phenyl or a C5-C7 heteroaryl, but not necessarily, or is substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

p is an integer from 0 to 2;

$R_{11}$, $R_{12}$ and $R_{13}$ are identical or different, and each of $R_{11}$, $R_{12}$ and $R_{13}$ is independently selected form H, a linear or branched C1-C6 alkyl, a C3-C7 cycloalkyl, a phenyl or a benzyl; the phenyl or the benzyl is substituted by one or more substituents selected from a halogen, a linear or branched C1-C3 alky, a cyano, a nitro, an amino, a hydroxy, a hydroxymethyl, a trifluoromethyl, a trifluoromethoxy, a carboxyl, and a C1-C4 alkoxy, but not necessarily;

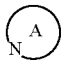

is a 3-7 member nitrogen-containing heterocyclic group, the heterocyclic group further contains 1-3 heteroatoms selected from O, S and N, and the methylene of the heterocyclic group is substituted by carbonyl or sulfonyl, but not necessarily, and is substituted by 1-5 substituents selected from H, a linear or branched C1-C6 hydrocarbyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, a C1-C4 alkoxy and hydroxamino, but not necessarily;

$R_3$ is selected from $NR_{14}R_{15}$ or

wherein $R_{14}$ and $R_{15}$ are identical or different, and each of $R_{14}$ and $R_{15}$ is independently H, a linear or branched C1-C6 alkyl and alkoxy, a C3-C7 cycloalkyl, a C1-C6 alkylamino, a C1-C6 alkylamino hydroxy, a C1-C6 alkyl amidino, a C1-C6 alkyl guanidyl, a benzyl, a C5-C7 aryl Ar or a 5-7 member heteroaryl, and the heteroaryl contains 1-3 heteroatoms selected from O, S and N, is combined with a phenyl or a C5-C7 heteroaryl, but not necessarily, or is substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

is a 3-7 member nitrogen-containing heterocyclic group, and the heterocyclic group further contains 1-4 heteroatoms selected from O, S and N, and is substituted by 1-5 substituents selected from H, a linear or branched C1-C6 alkyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, an amidino, a guanidyl and hydroxamino;

$R_4$, and $R_5$ are identical or different, and each of $R_4$ and $R_5$ is independently H, a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl, a C1-C4 sulfonyl, a C1-C4 sulfonyl amino, an aminoacyl or a C1-C4 linear or branched alkyl substituted sulfonyl;

the halogen is a fluoro, a chloro, a bromo or an iodo.

One preferable embodiment of formula (1) compound according to the present invention is the following thieno[3,2-d]pyrimidin-4-one compound, an enantiomer, diastereoisomer, racemate and mixtures thereof, or pharmaceutically acceptable salt thereof, wherein:

n=1;

$R_1$ and $R_2$ are identical or different, and not hydrogen simultaneously, each of which is independently H, a halogen, $CBr_2H$, $CCl_2H$, $CF_2H$, a cyano, $CF_3$, an aldehyde group, $(CH_2)_mOR_6$, $(CH_2)_mNR_6R_7$,

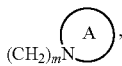

$(CH_2)_mCOOR_8$, $CONR_9R_{10}$, or

wherein, $R_1$ and $R_2$ can be linked together to form C3-C6 alkylidene, but not necessarily;

m is an integer from 0 to 3;

$R_6$ and $R_7$ are identical or different, and each of $R_6$ and $R_7$ is independently selected from H, a linear or branched C1-C3 alkyl, a C3-C5 cycloalkyl, a C1-C3 alkoxy, a 4-7 member heterocyclic group, a C1-C3 alkyloyl RCO, a C5-C7 aroyl ArCO, a C1-C3 alkylsulfonyl $RSO_2$, a C5-C7 arylsulfonyl $ArSO_2$, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C3 alkyl is substituted by one or more substituents selected from a methylsulfonyl, a cyclopropyl, a hydroxy, a C1-C3 alkoxy, a C1-C3 alkoxycarbonyl, and an epoxypropyl, but not necessarily; the heterocyclic group contains 1-3 heteroatoms selected from O, S and N; the aryl or the benzyl is substituted by a substituent selected from a halogen, a linear or branched C1-C3 alkyl, an amino, a hydroxy, a hydroxymethyl, a trifluoromethyl, and a trifluoromethoxy, but not necessarily; the heteroaryl contains 1-3 heteroatoms selected from O, S and N;

$R_8$ is selected from H, a linear or branched C1-C3 alkyl and C3-C5 cycloalkyl;

$R_9$ and $R_{10}$ are identical or different, each of which is independently selected form H,

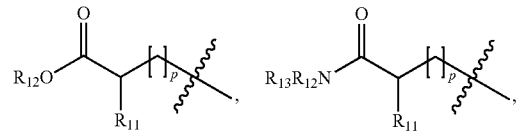

a linear or branched C1-C5 alkyl, a C3-C7 cycloalkyl, a 4-7 member heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C3 alkyl is substituted by one or more substituents selected from a methylsulfonyl, a cyclopropyl, a hydroxy, a C1-C3 alkoxy, a C1-C3 alkoxycarbonyl, and an epoxypropyl, but not necessarily; the heterocyclic group contains 1-3 heteroatoms selected from O, S and N, the methylene of the heterocyclic group is substituted by carbonyl or sulfonyl, but not necessarily, or the heterocyclic group is substituted by one or more substituents selected from a halogen, a linear or branched C1-C3 alky, an amino, a hydroxy, a hydroxymethyl, a trifluoromethyl, and a trifluoromethoxy, but not necessarily; the aryl or the benzyl can be substituted by one or more substituents selected from a halogen, a linear or branched C1-C3 alky, an amino, a hydroxy, a hydroxymethyl, a trifluoromethyl, and a trifluoromethoxy; the heteroaryl contains 1-3 heteroatoms selected from O, S and N;

P is an integer from 0 to 2;

$R_{11}$, $R_{12}$ and $R_{13}$ are identical or different, and each of $R_{11}$, $R_{12}$ and $R_{13}$ is independently selected form H, a linear or branched C1-C3 alkyl, a C3-C7 cyclic hydrocarbyl, a phenyl or a benzyl; the phenyl or the benzyl is substituted by one or more substituents selected from a halogen, a linear or branched C1-C3 alky, an amino, a hydroxy, a hydroxymethyl, a trifluoromethyl, and a trifluoromethoxy, but not necessarily;

is a 3-7 member nitrogen-containing heterocyclic group, the heterocyclic group further contains 1-3 heteroatoms selected from O, S and N, and the methylene of the heterocyclic group is substituted by carbonyl or sulfonyl, but not necessarily, and is substituted by 1-2 substituents selected from H, a linear or branched C1-C3 alkyl, a halogen, an amino, a hydroxy, a hydroxymethyl, a trifluoromethyl, a trifluoromethoxy, a C1-C4 alkoxy carbonyl, and a C1-C4 alkoxy, but not necessarily;

$R_3$ is selected from $NR_{14}R_{15}$ or

wherein $R_{14}$ and $R_{15}$ are identical or different, and each of $R_{14}$ and $R_{15}$ is independently H, a linear or branched C1-C3 alkyl and alkoxy, a C3-C5 cycloalkyl, a C1-C3 alkylamino, a C1-C3 alkylamino hydroxy, a C1-C3 alkyl amidino, a C1-C3 alkyl guanidyl, a benzyl, a C5-C7 aryl Ar or a 5-7 member heteroaryl, and the heteroaryl contains 1-3 heteroatoms selected from O, S and N;

is a 3-7 member nitrogen-containing heterocyclic group, and said heterocyclic group further contains 1-4 heteroatoms selected from O, S and N, and is substituted by 1-3 substituents selected from H, a linear or branched C1-C6 alkyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, an amidino, a guanidyl and hydroxamino;

$R_4$, and $R_5$ are identical or different, and each of $R_4$ and $R_5$ is independently H, a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl, a C1-C4 sulfonyl, a C1-C4 sulfonyl amino, an aminoacyl or a C1-C4 linear or branched alkyl substituted sulfonyl;

the halogen is a fluoro, a chloro, a bromo or an iodo.

Still another preferable embodiment of formula (I) compound according to the present invention is the following thieno[3,2-d]pyrimidin-4-one compound, an enantiomer, a diastereoisomer, a racemate and mixtures thereof, or a pharmaceutically acceptable salt thereof, wherein:

$R_3$ is $NR_{10}(CH_2)_kNH_2$, $NR_{10}(CH_2)_kOH$, $NR_{10}(CH_2)_kNHCNHNH_2$, $NR_{10}(CH_2)_kCNHNH_2$ or $NR_{10}(CH_2)_kNHOH$;

Wherein, k is an integer from 0 to 4;

n, $R_1$, $R_2$, and $R_4$-$R_{15}$ are defined as above.

A further preferable embodiment of formula (I) compound according to the present invention is the following thieno[3,2-d]pyrimidin-4-one compound, an enantiomer, a diastereoisomer, a racemate and mixtures thereof, or a pharmaceutically acceptable salt thereof, wherein:

$R_3$ is

Wherein

is an aziridinyl, an azacyclobutyl, a pyrrolidinyl, a piperidyl, an azacycloheptyl, a morpholinyl, a piperazinyl, a homopiperazinyl, a thiomorpholinyl, a thiomorpholinyl with S on the cycle being substituted by sulfoxide or sulphone, an imidazolidinyl, a pyrazinyl or a hexahydropyrimidinyl, and is substituted by 1-3 substituents selected from H, a linear or branched C1-C3 alky, a halogen, a cyano, a nitro, an amino, a hydroxy, a hydroxymethyl, a trifluoromethyl, a trifluoromethoxy, a carboxyl, an acylamino, a carboxylate group, a mercapto, an amidino, a guanidyl and hydroxamino;

n, $R_1$, $R_2$, and $R_4$-$R_{15}$ are defined as above.

The fourth preferable embodiment of formula (I) compound according to the present invention is the following thieno[3,2-d]pyrimidin-4-one compound, an enantiomer, a diastereoisomer, a racemate and mixtures thereof, or a pharmaceutically acceptable salt thereof, wherein:

$R_3$ is

and is substituted by 1-3 substituents selected from H, a cyano, an amino, a hydroxy, a trifluoromethyl, an amidino, a guanidyl, a carboxylate group and hydroxamino;

n, $R_1$, $R_2$,

and $R_4$-$R_{15}$ are defined as above.

The fourth preferable embodiment of formula (I) compound according to the present invention is the following thieno[3,2-d]pyrimidin-4-one compound, an enantiomer, a diastereoisomer, a racemate and mixtures thereof, or a pharmaceutically acceptable salt thereof, wherein:

n=1

$R_1$ and $R_2$ are identical or different, and not hydrogen simultaneously, each of $R_1$ and $R_2$ is independently H, a halogen, $CBr_2H$, $CCl_2H$, $CF_2H$, a cyano, $CF_3$, an aldehyde group, $(CH_2)_mOR_6$, $(CH_2)_mNR_6R_7$,

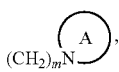

$(CH_2)_mCOOR_8$, $CONR_9R_{10}$, or

wherein, m is an integer from 0 to 3;

$R_6$ and $R_7$ are identical or different, and each of $R_6$ and $R_7$ is independently selected from H, a linear or branched C1-C3 alkyl, a C3-C5 cycloalkyl, a C1-C3 alkoxy, a 4-6 member heterocyclic group, a C1-C3 alkyloyl RCO, a C5-C7 aroyl ArCO, a benzyl and a C5-C7 aryl Ar; the linear or branched C1-C3 alkyl is substituted by one or more substituents selected from a methylsulfonyl, a C1-C3 alkoxy, and a C1-C3 alkoxycarbonyl, but not necessarily; the heterocyclic group contains one heteroatom selected from O, S and N;

$R_8$ is selected from H, and a linear or branched C1-C3 alkyl;

$R_9$ and $R_{10}$ are identical or different, each of which is independently selected form H,

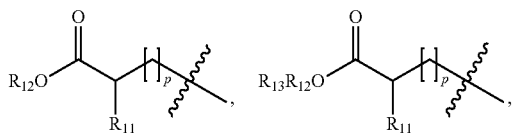

a linear or branched C1-C5 alkyl, a C3-C6 cycloalkyl, a 4-6 member heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C3 alkyl is substituted by one or more substituents selected from a methylsulfonyl, a cyclopropyl, a hydroxy, a C1-C3 alkoxy, a C1-C3 alkoxycarbonyl, and an epoxypropyl, but not necessarily; the heterocyclic group contains 1-2 heteroatoms selected from O, S and N; the aryl or the benzyl can be substituted by one or more substituents selected from a halogen, a linear or branched C1-C3 alky, a hydroxy, a hydroxymethyl, a trifluoromethyl and a trifluoromethoxy; the heteroaryl contains 1-2 heteroatoms selected from O, S and N;

P is an integer from 0 to 2;

$R_{11}$, $R_{12}$ and $R_{13}$ are identical or different, and each of $R_{11}$, $R_{12}$ and $R_{13}$ is independently selected form H, a linear or branched C1-C3 alkyl, a phenyl or a benzyl; the phenyl or the benzyl is substituted by one or more substituents selected from a halogen, a linear or branched C1-C3 alky, and a hydroxyl, but not necessarily;

is an aziridinyl, an azacyclobutyl, a pyrrolidinyl, a piperidyl, an azacycloheptyl, a morpholinyl, a piperazinyl, a homopiperazinyl, a thiomorpholinyl, a thiomorpholinyl with S on the cycle being substituted by sulfoxide or sulphone, an imidazolidinyl, a pyrazinyl, a hexahydropyrimidinyl or

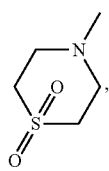

and is substituted by 1-2 substituents selected from H, a linear or branched C1-C3 alkyl, a halogen, a hydroxy, and a C1-C4 alkoxycarbonyl, but not necessarily;

$R_4$ and $R_5$ are identical or different, and each of $R_4$ and $R_5$ is independently H, a halogen, a methyl, an ethyl, a cyano, a hydroxy, a carboxyl, a methoxyl, an ethoxyl or an aminoacyl;

the halogen is a fluoro, a chloro, a bromo or an iodo;

$R_3$ is defined as above.

The fourth preferable embodiment of formula (I) compound according to the present invention is the following thieno[3,2-d]pyrimidin-4-one compound, an enantiomer, a diastereoisomer, a racemate and mixtures thereof, or a pharmaceutically acceptable salt thereof, wherein:

n=1, $R_1$ and $R_2$ are identical or different, and not hydrogen simultaneously, each of which is independently H, a halogen, $(CH_2)_m COOR_8$, $CONR_9R_{10}$, or

wherein, m is an integer from 0 to 3;

$R_8$ is selected from H, or a linear or branched C1-C3 alkyl;

$R_9$ and $R_{10}$ are identical or different, each of which is independently selected form H, a linear or branched C1-C3 alkyl, a C3-C6 cycloalkyl, a C4-C6 heterocyclic group, a phenyl or a 5-7 member heteroaryl; wherein the linear or branched C1-C3 alkyl is substituted by a C1-C3 alkoxycarbonyl, but not necessarily; the heterocyclic group contains one heteroatom selected from O, S and N; the heteroaryl contains one heteroatom selected from O, S and N;

is a pyrrolidinyl, a piperidyl, a morpholinyl, a piperazinyl, a homopiperazinyl, or a thiomorpholinyl, and is substituted by 1-2 substituents selected from H, a linear or branched C1-C3 alkyl, a halogen, a hydroxy, and a C1-C4 alkoxycarbonyl, but not necessarily;

$R_3$ is a pyrrolidinyl, a piperidyl, a morpholinyl, a piperazinyl, a homopiperazinyl, or a thiomorpholinyl, and is substituted by a cyano, an amino or a hydroxyl;

$R_4$ and $R_5$ are identical or different, and each of $R_4$ and $R_5$ is independently H, a fluoro, a chloro, a bromo, a methyl, an ethyl, a cyano, or a hydroxyl.

Preferably, the fourth preferable embodiment of formula (I) compound according to the present invention is the following thieno[3,2-d]pyrimidin-4-one compound, an enantiomer, a diastereoisomer, a racemate and mixtures thereof, or a pharmaceutically acceptable salt thereof, wherein:

$R_1$ and $R_2$ are identical or different, and not hydrogen simultaneously, each of which is independently H, a halogen, $(CH_2)_m COOR_8$, $CONR_9R_{10}$, or

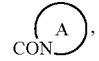

wherein, m is 0;

$R_8$ is selected from H, or a linear or branched C1-C3 alkyl;

$R_9$ and $R_{10}$ are identical or different, each of which is independently selected form H, a linear or branched C1-C3 alkyl, a cyclopropyl, a tetrahydropyran-4-yl or pyridinyl; wherein the linear or branched C1-C3 alkyl is substituted by a C1-C3 alkoxycarbonyl, but not necessarily;

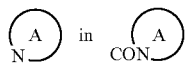

is a piperidyl, and is substituted by 1-2 substituents selected from H, a linear or branched C1-C3 alkyl, a halogen, a hydroxy, and a C1-C4 alkoxycarbonyl, but not necessarily;

$R_3$ is a pyrrolidinyl, a piperidyl, a morpholinyl, or a piperazinyl, and is substituted by a cyano, an amino or a hydroxyl;

$R_4$ and $R_5$ are identical or different, and each of $R_4$ and $R_5$ is independently H, a fluoro, a chloro, a bromo, a methyl, an ethyl, a cyano, or a hydroxyl.

Specifically, the thieno[3,2-d]pyrimidin-4-one compound, enantiomer, diastereoisomer, racemate and mixtures thereof, and the pharmaceutically acceptable salt thereof according to the present invention is selected from one of the following compounds:

| Designation | Structure |
|---|---|
| 1 (R)-2-((2-(3-aminopiperidin-1-yl)-6-fluoro-4-oxothieno[3,2-d]pyrimidin-3(4H)-yl)methyl)benzonitrile | |
| 2 (R)-2-((2-(3-aminopiperidin-1-yl)-7-fluoro-4-oxothieno[3,2-d]pyrimidin-3(4H)-yl)methyl)benzonitrile | |
| 3 (R)-2-((2-(3-aminopiperidin-1-yl)-6-bromo-4-oxothieno[3,2-d]pyrimidin-3(4H)-yl)methyl)benzonitrile | |
| 4 (R)-2-((2-(3-aminopiperidin-1-yl)-7-bromo-4-oxothieno[3,2-d]pyrimidin-3(4H)-yl)methyl)benzonitrile | |

-continued
| Designation | Structure |
|---|---|
| 5 (R)-2-((2-(3-aminopiperidin-1-yl)-6-iodo-4-oxothieno[3,2-d]pyrimidin-3(4H)-yl)methyl)benzonitrile | 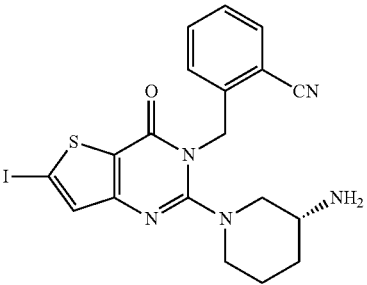<br>5 |
| 6 (R)-2-((2-(3-aminopiperidin-1-yl)-7-iodo-4-oxothieno[3,2-d]pyrimidin-3(4H)-yl)methyl)benzonitrile | 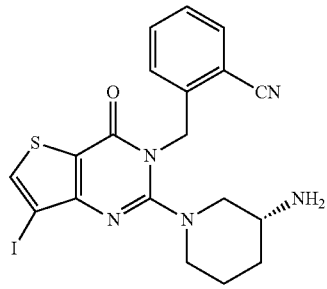 [SMILES: N#Cc1ccccc1Cn1c(N2CCC[C@@H](N)C2)nc2c(F)csc2c1=O]<br>6 |
| 7 (R)-2-((2-(3-aminopiperidin-1-yl)-4-oxo-7-(trifluoromethyl)thieno[3,2-d]-pyrimidin-3(4H)-yl)methyl)benzonitrile | 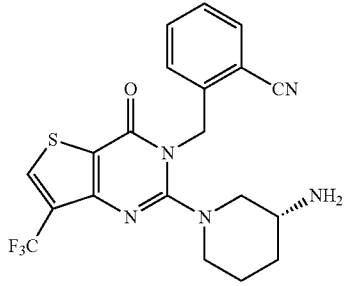 [SMILES: N#Cc1ccccc1Cn1c(N2CCC[C@@H](N)C2)nc2c(C(F)(F)F)csc2c1=O]<br>7 |
| 8 (R)-2-((2-(3-aminopiperidin-1-yl)-6-chloro-4-oxothieno[3,2-d]pyrimidin-3(4H)-yl)methyl)benzonitrile | 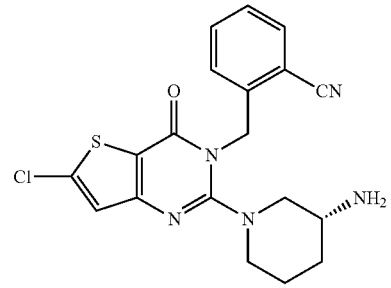 [SMILES: N#Cc1ccccc1Cn1c(N2CCC[C@@H](N)C2)nc2cc(Cl)sc2c1=O]<br>8 |

-continued

| Designation | Structure |
|---|---|
| 9 (R)-2-((2-(3-aminopiperidin-1-yl)-7-chloro-4-oxothieno[3,2-d]pyrimidin-3-(4H)-yl)methyl)benzonitrile | 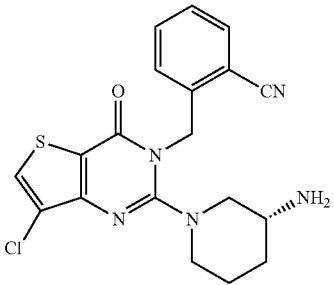 [SMILES: N#Cc1ccccc1Cn1c(N2CCC[C@@H](N)C2)nc2c(Cl)csc2c1=O]<br>9 |
| 10 (R)-2-((2-(3-aminopiperidin-1-yl)-6,7-dichloro-4-oxothieno[3,2-d]pyrimidin-3(4H)-yl)methyl)benzonitrile | 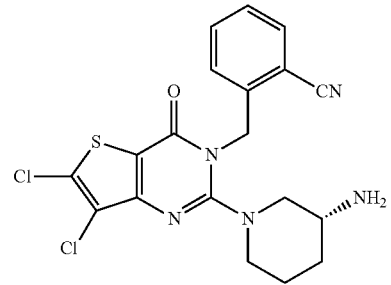 [SMILES: N#Cc1ccccc1Cn1c(N2CCC[C@@H](N)C2)nc2c(Cl)c(Cl)sc2c1=O]<br>10 |
| 11 (R)-2-((2-(3-aminopiperidin-1-yl)-6-(methylamino)-4-oxothieno[3,2-d]-pyrimidin-3(4H)-yl)methyl)benzonitrile | 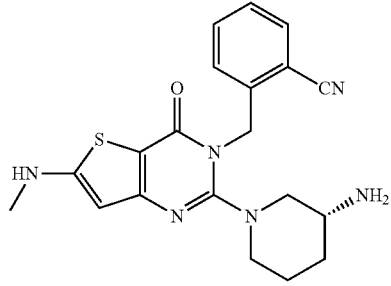 [SMILES: CNc1cc2nc(N3CCC[C@@H](N)C3)n(Cc3ccccc3C#N)c(=O)c2s1]<br>11 |
| 12 (R)-2-((2-(3-aminopiperidin-1-yl)-6-(ethylamino)-4-oxothieno[3,2-d]-pyrimidin-3(4H)-yl)methyl)benzonitrile | 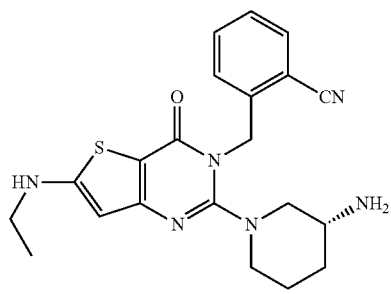 [SMILES: CCNc1cc2nc(N3CCC[C@@H](N)C3)n(Cc3ccccc3C#N)c(=O)c2s1]<br>12 |

| Designation | Structure |
|---|---|
| 13  (R)-2-((2-(3-aminopiperidin-1-yl)-4-oxo-6-(phenylamino)thieno[3,2-d]pyrimidin-3(4H)-yl)methyl)benzonitrile | 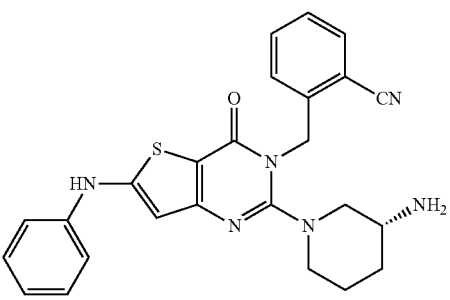 [SMILES: N#Cc1ccccc1Cn1c(N2CCC[C@@H](N)C2)nc2cc(Nc3ccccc3)sc2c1=O]<br>13 |
| 14  (R)-2-((2-(3-aminopiperidin-1-yl)-6-(benzylamino)-4-oxothieno[3,2-d]-pyrimidin-3(4H)-yl)methyl)benzonitrile | 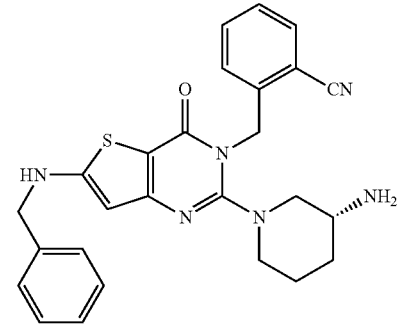 [SMILES: N#Cc1ccccc1Cn1c(N2CCC[C@@H](N)C2)nc2cc(NCc3ccccc3)sc2c1=O]<br>14 |
| 15  (R)-2-((2-(3-aminopiperidin-1-yl)-6-((methylamino)methyl)-4-oxothieno-[3,2-d]pyrimidin-3(4H)-yl)methyl)-benzonitrile | 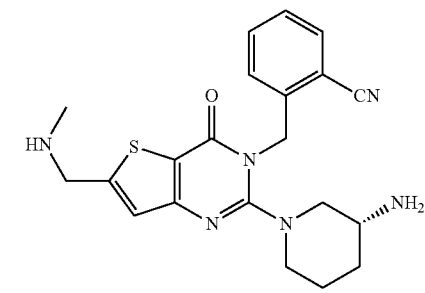 [SMILES: CNCc1cc2nc(N3CCC[C@@H](N)C3)n(Cc3ccccc3C#N)c(=O)c2s1]<br>15 |
| 16  (R)-2-((2-(3-aminopiperidin-1-yl)-6-((dimethylamino)methyl)-4-oxothieno-[3,2-d]pyrimidin-3(4H)-yl)methyl)-benzonitrile | 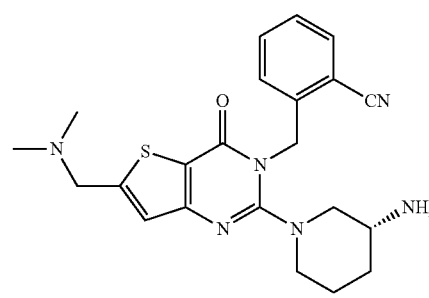<br>16 |

-continued

| Designation | Structure |
| --- | --- |
| 17 (R)-2-((2-(3-aminopiperidin-1-yl)-6--((benzylamino)methyl)-4-oxothieno-[3,2-d]pyrimidin-3(4H)-yl)methyl)-benzonitrile | 17 |
| 18 (R)-2-((2-(3-aminopiperidin-1-yl)-7-(methylamino)-4-oxothieno[3,2-d]-pyrimidin-3(4H)-yl)methyl)benzonitrile | 18 |
| 19 (R)-2-((2-(3-aminopiperidin-1-yl)-7-(ethylamino)-4-oxothieno[3,2-d]-pyrimidin-3(4H)-yl)methyl)benzonitrile | 19 |
| 20 (R)-2-((2-(3-aminopiperidin-1-yl)-7-(benzylamino)-4-oxothieno[3,2-d]-pyrimidin-3(4H)-yl)methyl)benzonitrile | 20 |

-continued

| Designation | Structure |
|---|---|
| 21 (R)-2-(3-aminopiperidin-1-yl)-7-bromo-3-(2-chlorobenzyl)thieno[3,2-d]-pyrimidin-4(3H)-one | 21 |
| 22 (R)-2-(3-aminopiperidin-1-yl)-7-bromo-3-(4-chlorobenzyl)thieno[3,2-d]-pyrimidin-4(3H)-one | 22 |
| 23 (R)-2-(3-aminopiperidin-1-yl)-7-bromo-3-(4-methoxybenzyl)thieno-[3,2-d]pyrimidin-4(3H)-one | 23 |
| 24 (R)-2-(3-aminopiperidin-1-yl)-7-bromo-3-(4-methylbenzyl)thieno-[3,2-d]pyrimidin-4(3H)-one | 24 |

-continued

| Designation | Structure |
|---|---|
| 25  2-((2-((2-aminoethyl)amino)-7-bromo-4-oxothieno[3,2-d]pyrimidin-3(4H)-yl)methyl)benzonitrile | 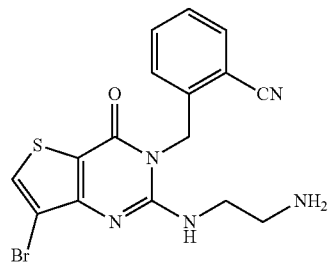 [SMILES: N#Cc1ccccc1Cn1c(NCCN)nc2c(Br)csc2c1=O]<br>25 |
| 26  (R)-2-((2-(3-aminopyrrolidin-1-yl)-7-bromo-4-oxothieno[3,2-d]pyrimidin-3-(4H)-yl)methyl)benzonitrile | 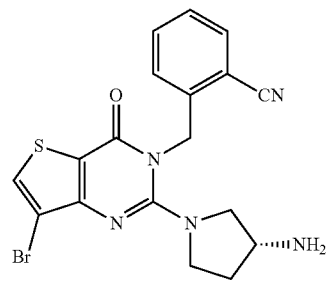 [SMILES: N#Cc1ccccc1Cn1c(N2CC[C@@H](N)C2)nc2c(Br)csc2c1=O]<br>26 |
| 27  (R)-2-((2-(3-aminopiperidin-1-yl)-4-oxo-6,7,8,9-tetrahydrobenzo[4,5]thieno-[3,2-d]pyrimidin-3(4H)-yl)methyl)-benzonitrile | 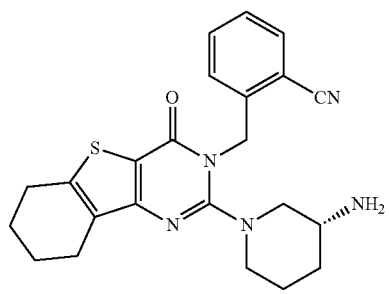 [SMILES: N#Cc1ccccc1Cn1c(N2CCC[C@@H](N)C2)nc2c3c(sc2c1=O)CCCC3]<br>27 |
| 28  (R)-2-((2-(3-aminopiperidin-1-yl)-6-(hydroxymethyl)-4-oxothieno[3,2-d]-pyrimidin-3(4H)-yl)methyl)benzonitrile | 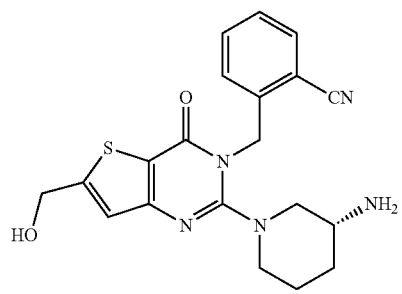 [SMILES: N#Cc1ccccc1Cn1c(N2CCC[C@@H](N)C2)nc2cc(CO)sc2c1=O]<br>28 |

-continued

| Designation | Structure |
|---|---|
| 29 2-((7-bromo-2-((2-hydroxyethyl)-amino)-4-oxothieno[3,2-d]pyrimidin-3(4H)-yl)methyl)benzonitrile | 29 |
| 30 2-((2-((2-aminoethyl)(methyl)amino)-7-bromo-4-oxothieno[3,2-d]pyrimidin-3(4H)-yl)methyl)benzonitrile | 30 |
| 31 2-((2-((2-aminoethyl)(phenyl)amino)-7-bromo-4-oxothieno[3,2-d]pyrimidin-3(4H)-yl)methyl)benzonitrile | 31 |
| 32 (R)-2-((2-(3-aminoazepan-1-yl)-7-bromo-4-oxothieno[3,2-d]pyrimidin-3(4H)-yl)methyl)benzonitrile | 32 |

-continued

| Designation | Structure |
|---|---|
| 33 (R)-ethyl 1-(7-bromo-3-(2-cyanobenzyl)-4-oxo-3,4-dihydrothieno[3,2-d]pyrimidin-2-yl)piperidine-3-carboxylate | 33 |
| 34 (R)-2-((2-(3-aminopiperidin-1-yl)-7-bromo-6-fluoro-4-oxothieno[3,2-d]-pyrimidin-3(4H)-yl)methyl)benzonitrile | 34 |
| 35 (R)-2-((2-(3-aminopiperidin-1-yl)-6,7-dibromo-4-oxothieno[3,2-d]pyrimidin-3(4H)-yl)methyl)benzonitrile | 35 |
| 36 (R)-2-((2-(3-aminopiperidin-1-yl)-7-chloro-6-fluoro-4-oxothieno[3,2-d]-pyrimidin-3(4H)-yl)methyl)benzonitrile | 36 |

| Designation | Structure |
|---|---|
| 37 (R)-2-((2-(3-aminopiperidin-1-yl)-6,7-difluoro-4-oxothieno[3,2-d]pyrimidin-3(4H)-yl)methyl)benzonitrile | 37 |
| 38 (R)-methyl 2-(3-aminopiperidin-1-yl)-3-(2-cyanobenzyl)-4-oxo-3,4-dihydrothieno[3,2-d]pyrimidine-6-carboxylate | 38 |
| 39 (R)-2-(3-aminopiperidin-1-yl)-3-(2-cyanobenzyl)-4-oxo-3,4-dihydrothieno-[3,2-d]pyrimidine-6-carboxylic acid hydrochloride | 39 |
| 40 (R)-2-(3-aminopiperidin-1-yl)-3-(2-cyanobenzyl)-N-cyclopropyl-4-oxo-3,4-dihydrothieno[3,2-d]pyrimidine-6-carboxamide | 40 |

-continued

| Designation | Structure |
|---|---|
| 41 (R)-2-(3-aminopiperidin-1-yl)-N-benzyl-3-(2-cyanobenzyl)-4-oxo-3,4-dihydrothieno[3,2-d]pyrimidine-6-carboxamide | 41 |
| 42 (R)-2-(3-aminopiperidin-1-yl)-3-(2-cyanobenzyl)-4-oxo-N-phenyl-3,4-dihydrothieno[3,2-d]pyrimidine-6-carboxamide | 42 |
| 43 (R)-2-((2-(3-aminopiperidin-1-yl)-7-(hydroxymethyl)-4-oxothieno[3,2-d]-pyrimidin-3(4H)-yl)methyl)benzonitrile | 43 |
| 44 (R)-2-(3-aminopiperidin-1-yl)-3-(2-cyanobenzyl)-4-oxo-3,4-dihydrothieno-[3,2-d]pyrimidine-7-carboxylic acid hydrochloride | 44 |

| Designation | Structure |
|---|---|
| 45 (R)-2-(3-aminopiperidin-1-yl)-3-(2-cyanobenzyl)-4-oxo-3,4-dihydrothieno-[3,2-d]pyrimidine-7-carboxamide | 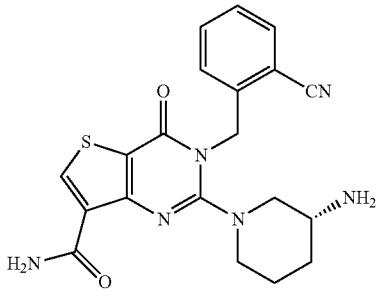 [SMILES: N#Cc1ccccc1Cn1c(N2CCC[C@@H](N)C2)nc2c(C(N)=O)csc2c1=O]<br>45 |
| 46 (R)-2-(3-aminopiperidin-1-yl)-3-(2-cyanobenzyl)-4-oxo-N-(pyridin-2-ylmethyl)-3,4-dihydrothieno[3,2-d]-pyrimidine-7-carboxamide | 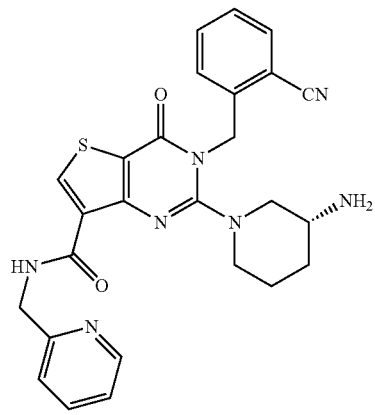 [SMILES: N#Cc1ccccc1Cn1c(N2CCC[C@@H](N)C2)nc2c(C(=O)NCc3ccccn3)csc2c1=O]<br>46 |
| 47 (R)-2-(3-aminopiperidin-1-yl)-3-(2-cyanobenzyl)-4-oxo-N-phenyl-3,4-dihydrothieno[3,2-d]pyrimidine-7-carboxamide | 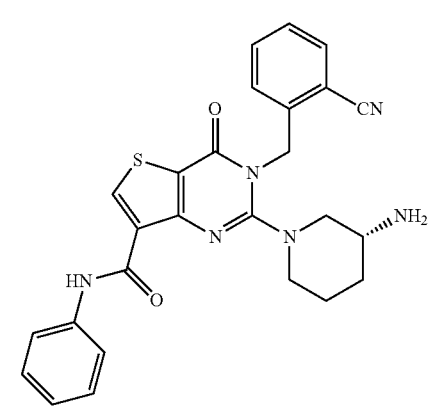 [SMILES: N#Cc1ccccc1Cn1c(N2CCC[C@@H](N)C2)nc2c(C(=O)Nc3ccccc3)csc2c1=O]<br>47 |

-continued

| Designation | Structure |
|---|---|
| 48 (R)-2-(3-aminopiperidin-1-yl)-N-benzyl-3-(2-cyanobenzyl)-4-oxo-3,4-dihydrothieno[3,2-d]pyrimidine-7-carboxamide | 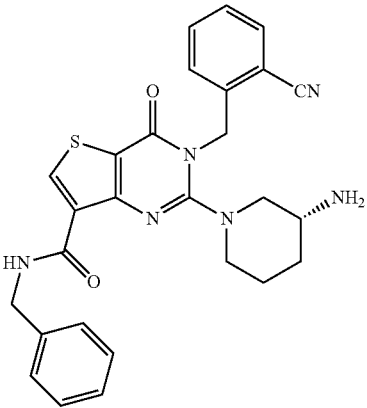 [SMILES: N#Cc1ccccc1Cn1c(N2CCC[C@@H](N)C2)nc2c(C(=O)NCc3ccccc3)csc2c1=O]<br>48 |
| 49 (R)-3-((2-(3-aminopiperidin-1-yl)-4-oxo-7-(trifluoromethyl)thieno[3,2-d]-pyrimidin-3(4H)-yl)methyl)-2-cyanobenzoic acid | 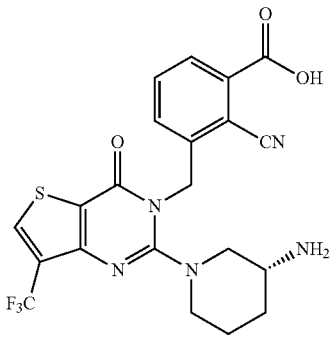 [SMILES: N#Cc1c(Cn2c(N3CCC[C@@H](N)C3)nc3c(C(F)(F)F)csc3c2=O)cccc1C(=O)O]<br>49 |
| 50 (R)-3-((2-(3-aminopiperidin-1-yl)-4-oxo-7-(trifluoromethyl)thieno[3,2-d]-pyrimidin-3(4H)-yl)methyl)-2-cyanobenzamide | 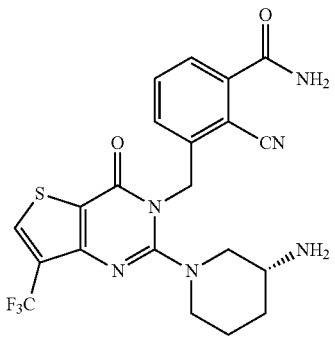 [SMILES: N#Cc1c(Cn2c(N3CCC[C@@H](N)C3)nc3c(C(F)(F)F)csc3c2=O)cccc1C(N)=O]<br>50 |
| 51 (R)-2-((2-(3-aminopiperidin-1-yl)-4-oxo-7-(trifluoromethyl)thieno[3,2-d]-pyrimidin-3(4H)-yl)methyl)-5-hydroxybenzonitrile | 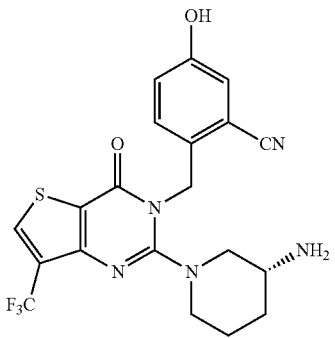 [SMILES: N#Cc1cc(O)ccc1Cn1c(N2CCC[C@@H](N)C2)nc2c(C(F)(F)F)csc2c1=O]<br>51 |

-continued

| Designation | Structure |
|---|---|
| 52 2-((4-oxo-2-(piperazin-1-yl)-7-(trifluoromethyl)thieno[3,2-d]pyrimidin-3(4H)-yl)methyl)benzonitrile | 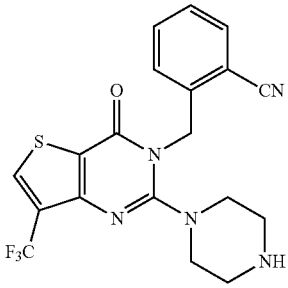 [SMILES: N#Cc1ccccc1Cn1c(N2CCNCC2)nc2c(C(F)(F)F)csc2c1=O] 52 |
| 53 (R)-2-((2-(3-aminopiperidin-1-yl)-4-oxo-4,6,7,8-tetrahydro-3H-cyclopenta[4,5]thieno[3,2-d]pyrimidin-3-yl)methyl)benzonitrile | 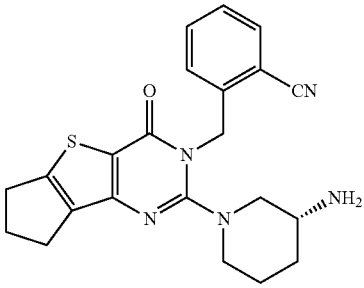 [SMILES: N#Cc1ccccc1Cn1c(N2CCC[C@@H](N)C2)nc2c3c(sc2c1=O)CCC3] 53 |
| 54 (R)-methyl 1-((2-(3-aminopiperidin-1-yl)-3-(2-cyanobenzyl)-4-oxo-3,4-dihydrothieno[3,2-d]pyrimidin-7-yl)methyl)piperidine-4-carboxylate | 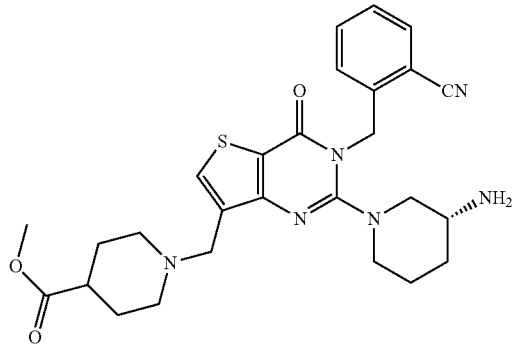 [SMILES: COC(=O)C1CCN(Cc2csc3c(=O)n(Cc4ccccc4C#N)c(N4CCC[C@@H](N)C4)nc23)CC1] 54 |
| 55 (R)-2-((2-(3-aminopiperidin-1-yl)-7-(morpholinomethyl)-4-oxothieno[3,2-d]pyrimidin-3(4H)-yl)methyl)benzonitrile | 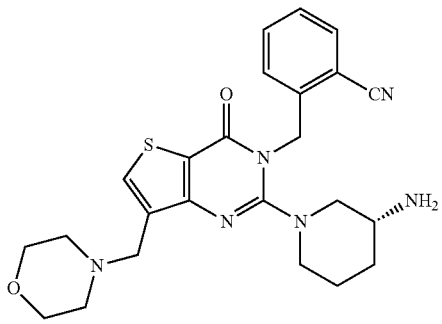 [SMILES: N#Cc1ccccc1Cn1c(N2CCC[C@@H](N)C2)nc2c(CN3CCOCC3)csc2c1=O] 55 |

-continued

| Designation | Structure |
|---|---|
| 56 (R)-(2-(3-aminopiperidin-1-yl)-3-(2-cyanobenzyl)-4-oxo-3,4-dihydrothieno-[3,2-d]pyrimidin-7-yl)methyl acetate | 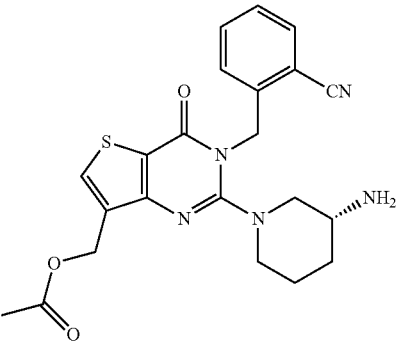 [SMILES: CC(=O)OCc1csc2c(=O)n(Cc3ccccc3C#N)c(N3CCC[C@@H](N)C3)nc12] 56 |
| 57 (R)-methyl 2-(3-aminopiperidin-1-yl)-3-(2-cyanobenzyl)-4-oxo-3,4-dihydrothieno[3,2-d]pyrimidine-7-carboxylate | 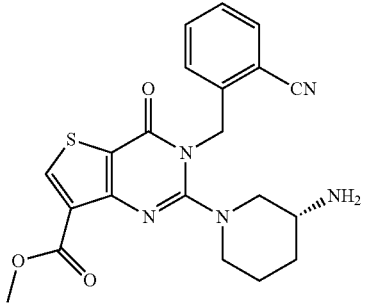 [SMILES: COC(=O)c1csc2c(=O)n(Cc3ccccc3C#N)c(N3CCC[C@@H](N)C3)nc12] 57 |
| 58 (R)-ethyl 2-(2-(3-aminopiperidin-1-yl)-3-(2-cyanobenzyl)-4-oxo-3,4-dihydrothieno[3,2-d]pyrimidine-7-carboxamido)acetate | 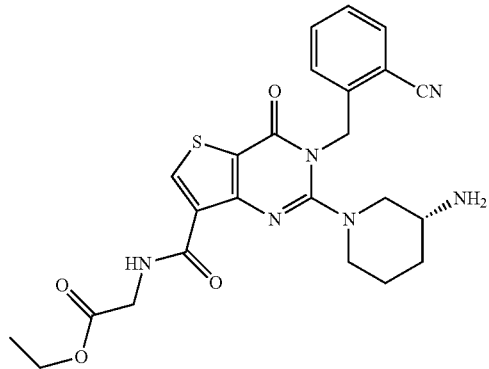 [SMILES: CCOC(=O)CNC(=O)c1csc2c(=O)n(Cc3ccccc3C#N)c(N3CCC[C@@H](N)C3)nc12] 58 |
| 59 (S)-methyl 2-(2-((R)-3-aminopiperidin-1-yl)-3-(2-cyanobenzyl)-4-oxo-3,4-dihydrothieno[3,2-d]pyrimidine-7-carboxamido)-3-methylbutanoate | 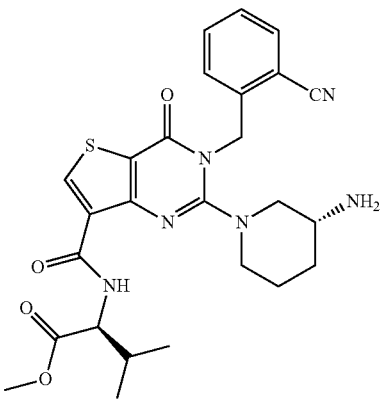 [SMILES: COC(=O)[C@@H](NC(=O)c1csc2c(=O)n(Cc3ccccc3C#N)c(N3CCC[C@@H](N)C3)nc12)C(C)C] 59 |

| Designation | Structure |
|---|---|
| 60 (R)-2-(3-aminopiperidin-1-yl)-3-(2-cyanobenzyl)-N-(2-hydroxyethyl)-4-oxo-3,4-dihydrothieno[3,2-d]-pyrimidine-7-carboxamide | 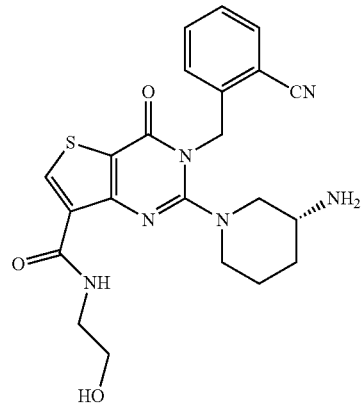 [SMILES: N#Cc1ccccc1Cn1c(N2CCC[C@@H](N)C2)nc2c(C(=O)NCCO)csc2c1=O]<br>60 |
| 61 (R)-2-(3-aminopiperidin-1-yl)-3-(2-cyanobenzyl)-N-methyl-4-oxo-3,4-dihydrothieno[3,2-d]pyrimidine-7-carboxamide | 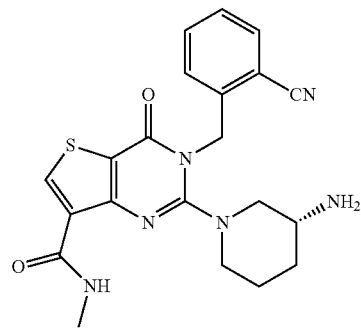 [SMILES: CNC(=O)c1csc2c(=O)n(Cc3ccccc3C#N)c(N3CCC[C@@H](N)C3)nc12]<br>61 |
| 62 (S)-methyl 2-(2-((R)-3-aminopiperidin-1-yl)-3-(2-cyanobenzyl)-4-oxo-3,4-dihydrothieno[3,2-d]pyrimidine-7-carboxamido)-3-(4-hydroxyphenyl)-propanoate | 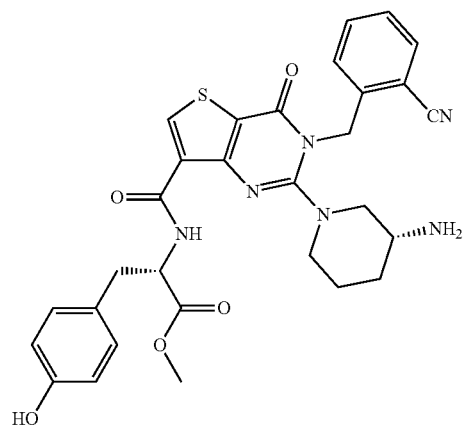 [SMILES: COC(=O)[C@H](Cc1ccc(O)cc1)NC(=O)c1csc2c(=O)n(Cc3ccccc3C#N)c(N3CCC[C@@H](N)C3)nc12]<br>62 |

| Designation | Structure |
|---|---|
| 63 (R)-2-(3-aminopiperidin-1-yl)-3-(2-cyanobenzyl)-N,N-dimethyl-4-oxo-3,4-dihydrothieno[3,2-d]pyrimidine-7-carboxamide | 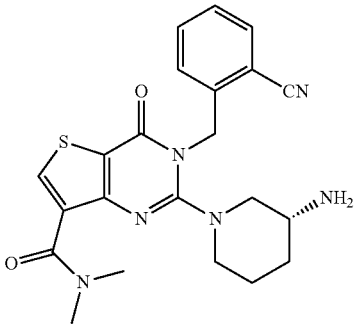 [SMILES: CN(C)C(=O)c1csc2c(=O)n(Cc3ccccc3C#N)c(N3CCC[C@@H](N)C3)nc12] 63 |
| 64 (R)-2-(3-aminopiperidin-1-yl)-3-(2-cyanobenzyl)-N-(4-methylbenzyl)-4-oxo-3,4-dihydrothieno[3,2-d]-pyrimidine-7-carboxamide | 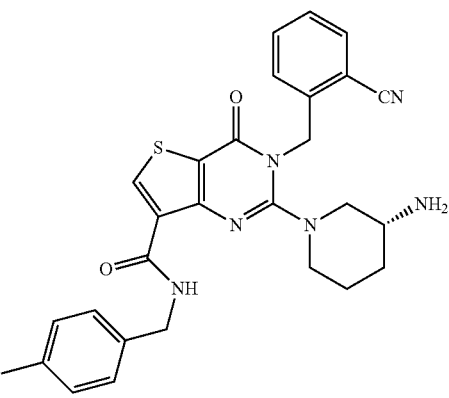 [SMILES: Cc1ccc(CNC(=O)c2csc3c(=O)n(Cc4ccccc4C#N)c(N4CCC[C@@H](N)C4)nc23)cc1] 64 |
| 65 (R)-2-(3-aminopiperidin-1-yl)-3-(2-cyanobenzyl)-N-cyclopropyl-4-oxo-3,4-dihydrothieno[3,2-d]pyrimidine-7-carboxamide | 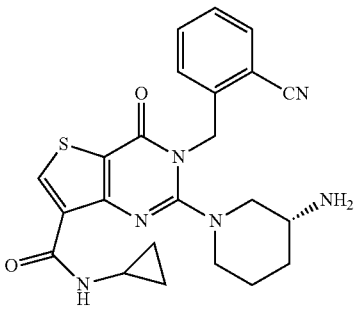 [SMILES: N#Cc1ccccc1Cn1c(N2CCC[C@@H](N)C2)nc2c(C(=O)NC3CC3)csc2c1=O] 65 |

-continued

| Designation | Structure |
|---|---|
| 66 (S)-methyl 2-(2-((R)-3-aminopiperidin-1-yl)-3-(2-cyanobenzyl)-4-oxo-3,4-dihydrothieno[3,2-d]pyrimidine-7-carboxamido)-2-phenylacetate | 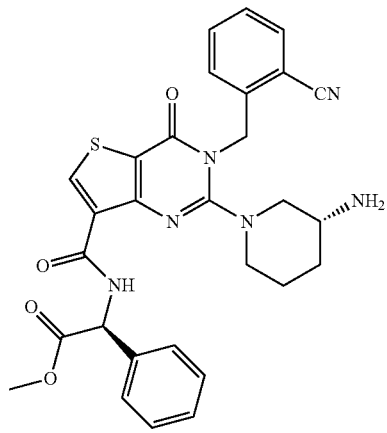 [SMILES: COC(=O)[C@@H](NC(=O)c1csc2c(=O)n(Cc3ccccc3C#N)c(N3CCC[C@@H](N)C3)nc12)c1ccccc1]<br>66 |
| 67 (S)-methyl 2-(2-((R)-3-aminopiperidin-1-yl)-3-(2-cyanobenzyl)-4-oxo-3,4-dihydrothieno[3,2-d]pyrimidine-7-carboxamido)-3-phenylpropanoate | 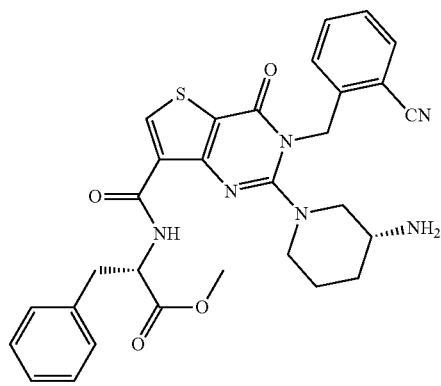 [SMILES: COC(=O)[C@H](Cc1ccccc1)NC(=O)c1csc2c(=O)n(Cc3ccccc3C#N)c(N3CCC[C@@H](N)C3)nc12]<br>67 |
| 68 (R)-2-(3-aminopiperidin-1-yl)-3-(2-cyanobenzyl)-4-oxo-N-(4-(trifluoromethyl)benzyl)-3,4-dihydrothieno[3,2-d]pyrimidine-7-carboxamide | 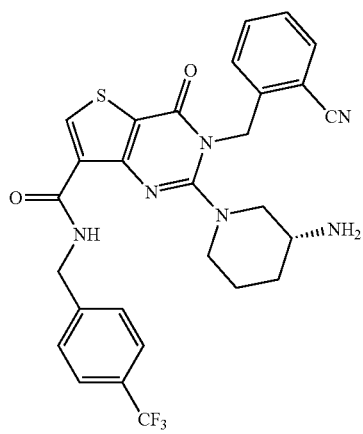 [SMILES: N#Cc1ccccc1Cn1c(N2CCC[C@@H](N)C2)nc2c(C(=O)NCc3ccc(C(F)(F)F)cc3)csc2c1=O]<br>68 |

-continued

| Designation | Structure |
|---|---|
| 69 (R)-2-((2-(3-aminopiperidin-1-yl)-7-(morpholine-4-carbonyl)-4-oxothieno-[3,2-d]pyrimidin-3(4H)-yl)methyl)-benzonitrile | 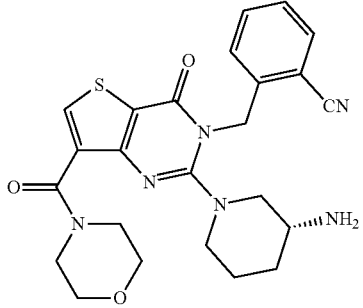 [SMILES: N#Cc1ccccc1Cn1c(N2CCC[C@@H](N)C2)nc2c(C(=O)N3CCOCC3)csc2c1=O] |
| 70 (R)-2-((2-(3-aminopiperidin-1-yl)-7-(4-methylpiperazine-1-carbonyl)-4-oxothieno[3,2-d]pyrimidin-3(4H)-yl)-methyl)benzonitrile | 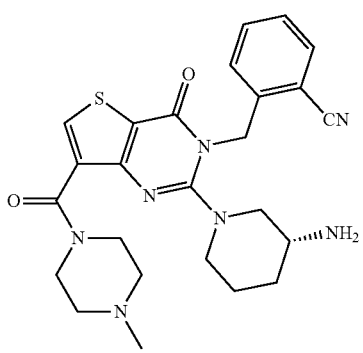 [SMILES: CN1CCN(C(=O)c2csc3c(=O)n(Cc4ccccc4C#N)c(N4CCC[C@@H](N)C4)nc23)CC1] |
| 71 (R)-2-(3-aminopiperidin-1-yl)-3-(2-cyanobenzyl)-N-ethyl-4-oxo-3,4-dihydrothieno[3,2-d]pyrimidine-7-carboxamide | 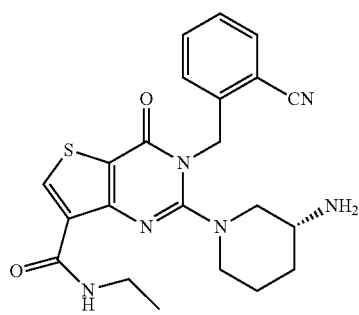 [SMILES: CCNC(=O)c1csc2c(=O)n(Cc3ccccc3C#N)c(N3CCC[C@@H](N)C3)nc12] |
| 72 (R)-2-(3-aminopiperidin-1-yl)-3-(2-cyanobenzyl)-N-isopropyl-4-oxo-3,4-dihydrothieno[3,2-d]pyrimidine-7-carboxamide | 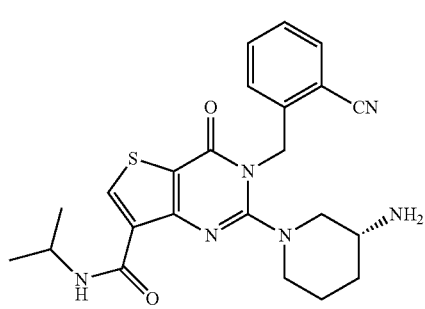 [SMILES: CC(C)NC(=O)c1csc2c(=O)n(Cc3ccccc3C#N)c(N3CCC[C@@H](N)C3)nc12] |

| Designation | Structure |
|---|---|
| 73 (R)-2-(3-aminopiperidin-1-yl)-3-(2-cyanobenzyl)-N-(cyclopropylmethyl)-4-oxo-3,4-dihydrothieno[3,2-d]-pyrimidine-7-carboxamide | 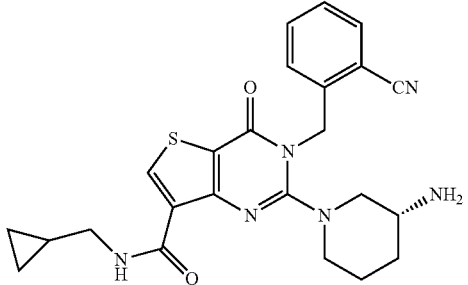 [SMILES: N#Cc1ccccc1Cn1c(N2CCC[C@@H](N)C2)nc2c(C(=O)NCC3CC3)csc2c1=O]<br>73 |
| 74 (R)-2-(3-aminopiperidin-1-yl)-3-(2-cyanobenzyl)-N-(2-methoxyethyl)-4-oxo-3,4-dihydrothieno[3,2-d]pyrimidine-7-carboxamide | 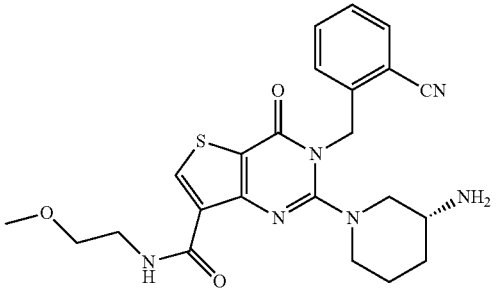 [SMILES: COCCNC(=O)c1csc2c(=O)n(Cc3ccccc3C#N)c(N3CCC[C@@H](N)C3)nc12]<br>74 |
| 75 (R)-2-(3-aminopiperidin-1-yl)-3-(2-cyanobenzyl)-N-(3-methoxypropyl)-4-oxo-3,4-dihydrothieno[3,2-d]pyrimidine-7-carboxamide | 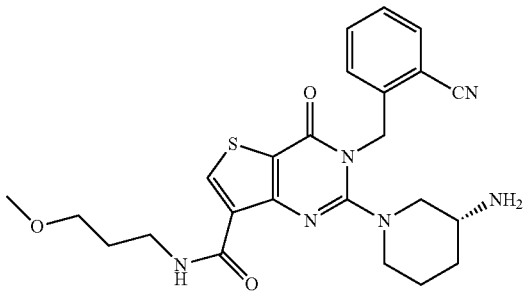 [SMILES: COCCCNC(=O)c1csc2c(=O)n(Cc3ccccc3C#N)c(N3CCC[C@@H](N)C3)nc12]<br>75 |
| 76 (R)-2-((2-(3-aminopiperidin-1-yl)-4-oxo-7-(pyrrolidine-1-carbonyl)thieno-[3,2-d]pyrimidin-3(4H)-yl)methyl)-benzonitrile | 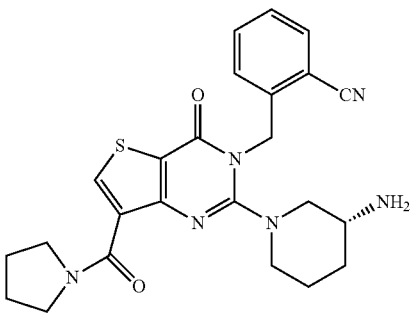 [SMILES: N#Cc1ccccc1Cn1c(N2CCC[C@@H](N)C2)nc2c(C(=O)N3CCCC3)csc2c1=O]<br>76 |

-continued

| Designation | Structure |
|---|---|
| 77 (R)-2-(3-aminopiperidin-1-yl)-N-butyl-3-(2-cyanobenzyl)-4-oxo-3,4-dihydrothieno[3,2-d]pyrimidine-7-carboxamide | 77 |
| 78 (R)-2-(3-aminopiperidin-1-yl)-3-(2-cyanobenzyl)-N-isopentyl-4-oxo-3,4-dihydrothieno[3,2-d]pyrimidine-7-carboxamide | 78 |
| 79 (R)-2-(3-aminopiperidin-1-yl)-3-(2-cyanobenzyl)-N-isobutyl-4-oxo-3,4-dihydrothieno[3,2-d]pyrimidine-7-carboxamide | 79 |
| 80 (R)-2-(3-aminopiperidin-1-yl)-3-(2-cyanobenzyl)-N-cyclohexyl-4-oxo-3,4-dihydrothieno[3,2-d]pyrimidine-7-carboxamide | 80 |

-continued

| Designation | Structure |
|---|---|
| 81 (R)-2-(3-aminopiperidin-1-yl)-3-(2-cyanobenzyl)-4-oxo-N-(tetrahydro-2H-pyran-4-yl)-3,4-dihydrothieno[3,2-d]-pyrimidine-7-carboxamide | 81 |
| 82 (R)-2-(3-aminopiperidin-1-yl)-3-(2-cyanobenzyl)-N-(oxetan-3-ylmethyl)-4-oxo-3,4-dihydrothieno[3,2-d]pyrimidine-7-carboxamide | 82 |
| 83 (R)-2-(3-aminopiperidin-1-yl)-3-(2-cyanobenzyl)-4-oxo-3,4-dihydrothieno-[3,2-d]pyrimidine-7-carbonitrile | 83 |
| 84 (R)-2-((7-amino-2-(3-aminopiperidin-1-yl)-4-oxothieno[3,2-d]pyrimidin-3(4H)-yl)methyl)benzonitrile | 84 |

-continued

| Designation | Structure |
|---|---|
| 85 (R)-N-(2-(3-aminopiperidin-1-yl)-3-(2-cyanobenzyl)-4-oxo-3,4-dihydrothieno-[3,2-d]pyrimidin-7-yl)methanesulfonamide | 85 |
| 86 (R)-N-(2-(3-aminopiperidin-1-yl)-3-(2-cyanobenzyl)-4-oxo-3,4-dihydrothieno-[3,2-d]pyrimidin-7-yl)acetamide | 86 |
| 87 2-((2-((R)-3-aminopiperidin-1-yl)-4-oxo-7-((((S)-tetrahydrofuran-3-yl)oxy)methyl)thieno[3,2-d]pyrimidin-3(4H)-yl)methyl)benzonitrile | 87 |
| 88 (R)-ethyl 3-(2-(3-aminopiperidin-1-yl)-3-(2-cyanobenzyl)-4-oxo-3,4-dihydrothieno[3,2-d]pyrimidine-7-carboxamido)propanoate | 88 |

| Designation | Structure |
|---|---|
| 89 (R)-ethyl 4-(2-(3-aminopiperidin-1-yl)-3-(2-cyanobenzyl)-4-oxo-3,4-dihydrothieno[3,2-d]pyrimidine-7-carboxamido)butanoate | 89 |
| 90 (R)-2-(3-aminopiperidin-1-yl)-3-(2-cyanobenzyl)-N-(2-(methylsulfonyl)-ethyl)-4-oxo-3,4-dihydrothieno[3,2-d]-pyrimidine-7-carboxamide | 90 |
| 91 (S)-methyl 1-(2-((R)-3-aminopiperidin-1-yl)-3-(2-cyanobenzyl)-4-oxo-3,4-dihydrothieno[3,2-d]pyrimidine-7-carbonyl)pyrrolidine-2-carboxylate | 91 |
| 92 2-((R)-3-aminopiperidin-1-yl)-3-(2-cyanobenzyl)-4-oxo-N-((S)-2-oxotetrahydrofuran-3-yl)-3,4-dihydrothieno[3,2-d]pyrimidine-7-carboxamide | 92 |

| Designation | Structure |
|---|---|
| 93 (R)-2-(3-aminopiperidin-1-yl)-3-(2-cyanobenzyl)-N-(3-hydroxypropyl)-4-oxo-3,4-dihydrothieno[3,2-d]pyrimidine-7-carboxamide | 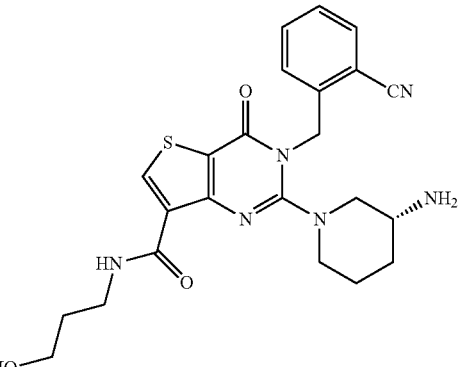<br>93 |
| 94 (R)-2-((2-(3-aminopiperidin-1-yl)-6-((benzyloxy)methyl)-4-oxothieno-[3,2-d]pyrimidin-3(4H)-yl)methyl)-benzonitrile | 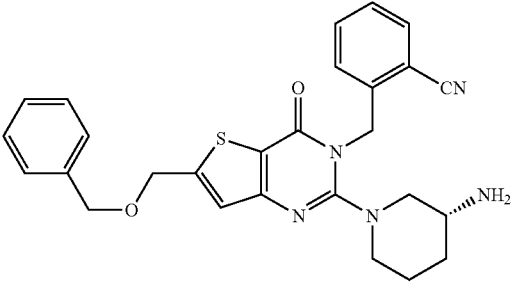<br>94 |
| 95 (R)-2-((2-(3-aminopiperidin-1-yl)-6-(morpholinomethyl)-4-oxothieno-[3,2-d]pyrimidin-3(4H)-yl)methyl)benzonitrile | 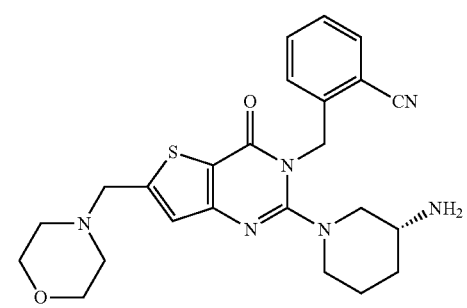<br>95 |
| 96 (R)-(2-(3-aminopiperidin-1-yl)-3-(2-cyanobenzyl)-4-oxo-3,4-dihydrothieno-[3,2-d]pyrimidin-6-yl)methyl acetate | 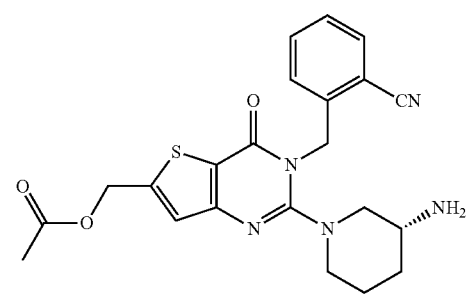<br>96 |

| Designation | Structure |
|---|---|
| 97 (R)-2-(3-aminopiperidin-1-yl)-3-(2-cyanobenzyl)-4-oxo-3,4-dihydrothieno-[3,2-d]pyrimidine-6-carboxamide | 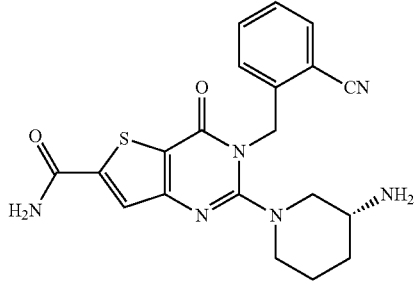<br>97 |
| 98 (R)-2-((2-(3-aminopiperidin-1-yl)-6-(dibromomethyl)-4-oxothieno[3,2-d]-pyrimidin-3(4H)-yl)methyl)benzonitrile | 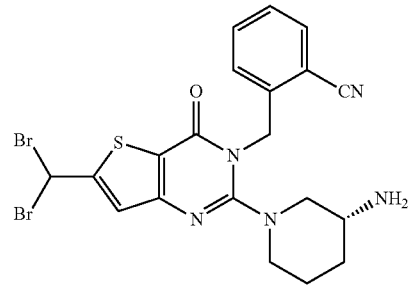<br>98 |
| 99 (R)-methyl 2-(2-(3-aminopiperidin-1-yl)-3-(2-cyanobenzyl)-4-oxo-3,4-dihydrothieno[3,2-d]pyrimidine-6-carboxamido)acetate | 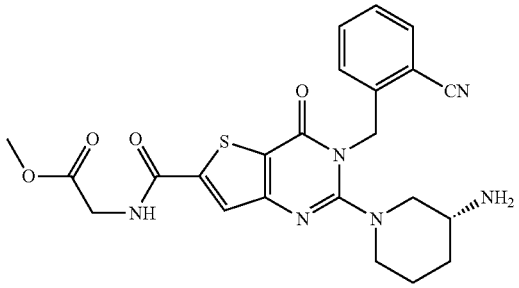<br>99 |
| 100 (S)-methyl 2-(2-((R)-3-aminopiperidin-1-yl)-3-(2-cyanobenzyl)-4-oxo-3,4-dihydrothieno[3,2-d]pyrimidine-6-carboxamido)-3-methylbutanoate | 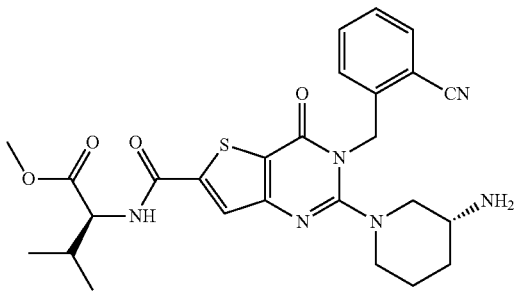<br>100 |

| Designation | Structure |
|---|---|
| 101 (S)-methyl 2-(2-((R)-3-aminopiperidin-1-yl)-3-(2-cyanobenzyl)-4-oxo-3,4-dihydrothieno[3,2-d]pyrimidine-6-carboxamido)-3-(4-hydroxyphenyl)-propanoate | 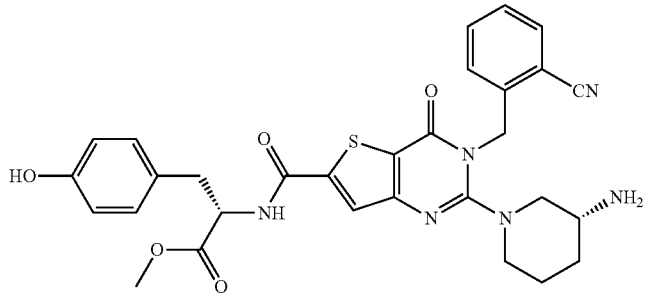 101 |
| 102 (S)-methyl 2-(2-((R)-3-aminopiperidin-1-yl)-3-(2-cyanobenzyl)-4-oxo-3,4-dihydrothieno[3,2-d]pyrimidine-6-carboxamido)-3-phenylpropanoate | 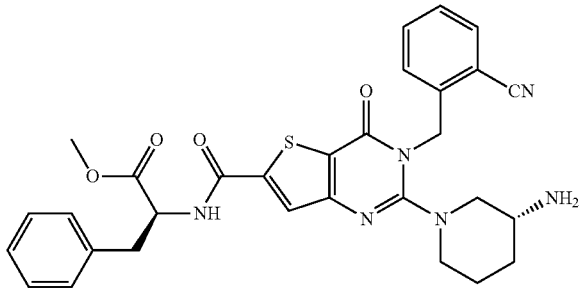 102 |
| 103 (R)-2-(3-aminopiperidin-1-yl)-3-(2-cyanobenzyl)-4-oxo-N-(4-(trifluoromethyl)benzyl)-3,4-dihydrothieno[3,2-d]pyrimidine-6-carboxamide | 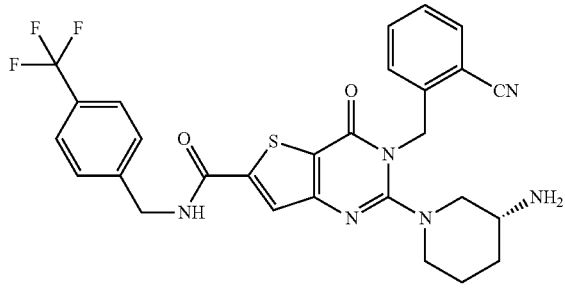 103 |
| 104 (R)-2-(3-aminopiperidin-1-yl)-3-(2-cyanobenzyl)-N-methyl-4-oxo-3,4-dihydrothieno[3,2-d]pyrimidine-6-carboxamide | 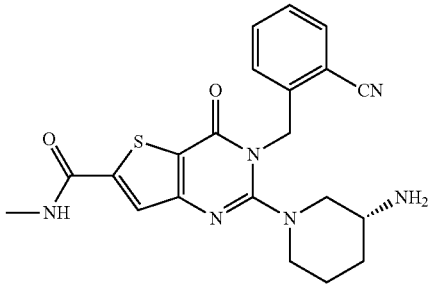 104 |

-continued

| Designation | Structure |
|---|---|
| 105 (R)-2-(3-aminopiperidin-1-yl)-3-(2-cyanobenzyl)-N,N-dimethyl-4-oxo-3,4-dihydrothieno[3,2-d]pyrimidine-6-carboxamide | 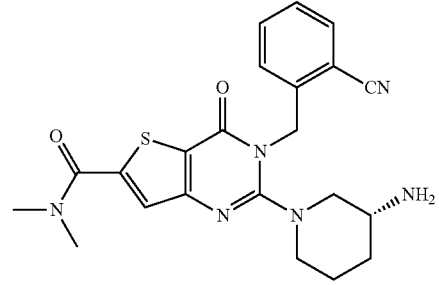<br>105 |
| 106 (R)-2-(3-aminopiperidin-1-yl)-3-(2-cyanobenzyl)-N-(cyclopropylmethyl)-4-oxo-3,4-dihydrothieno[3,2-d]pyrimidine-6-carboxamide | 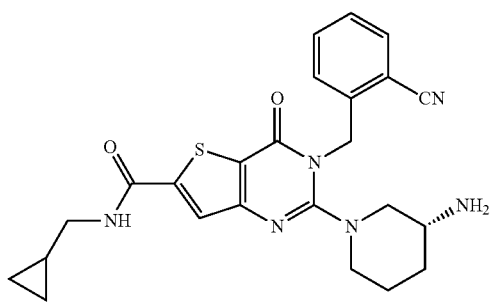<br>106 |
| 107 (R)-2-((2-(3-aminopiperidin-1-yl)-4-oxo-6-(pyrrolidine-1-carbonyl)thieno-[3,2-d]pyrimidin-3(4H)-yl)methyl)-benzonitrile | 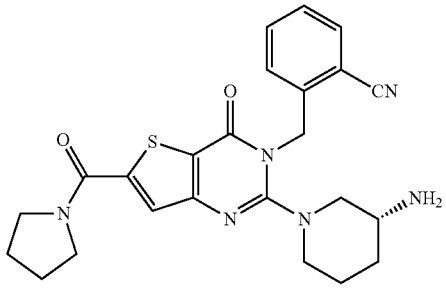<br>107 |
| 108 (R)-2-((2-(3-aminopiperidin-1-yl)-4-oxo-6-(piperidine-1-carbonyl)thieno-[3,2-d]pyrimidin-3(4H)-yl)methyl)-benzonitrile | 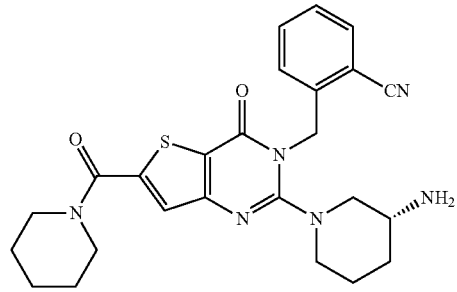<br>108 |

| Designation | Structure |
|---|---|
| 109 (R)-2-(3-aminopiperidin-1-yl)-3-(2-cyanobenzyl)-N-(2-fluorobenzyl)-4-oxo-3,4-dihydrothieno[3,2-d]pyrimidine-6-carboxamide | 109 |
| 110 (R)-2-(3-aminopiperidin-1-yl)-N-(2-chlorobenzyl)-3-(2-cyanobenzyl)-4-oxo-3,4-dihydrothieno[3,2-d]pyrimidine-6-carboxamide | 110 |
| 111 (R)-2-(3-aminopiperidin-1-yl)-3-(2-cyanobenzyl)-N-(2-methoxyethyl)-4-oxo-3,4-dihydrothieno[3,2-d]-pyrimidine-6-carboxamide | 111 |
| 112 (R)-2-(3-aminopiperidin-1-yl)-3-(2-cyanobenzyl)-N-(3-methoxypropyl)-4-oxo-3,4-dihydrothieno[3,2-d]-pyrimidine-6-carboxamide | 112 |

-continued

| Designation | Structure |
|---|---|
| 113 (R)-2-(3-aminopiperidin-1-yl)-3-(2-cyanobenzyl)-N-ethyl-4-oxo-3,4-dihydrothieno[3,2-d]pyrimidine-6-carboxamide | 113 |
| 114 (R)-2-((2-(3-aminopiperidin-1-yl)-6-(1,1-dioxidothiomorpholine-4-carbonyl)-4-oxothieno[3,2-d]pyrimidin-3(4H)-yl)-methyl)benzonitrile | 114 |
| 115 (R)-2-(3-aminopiperidin-1-yl)-3-(2-cyanobenzyl)-N-isopropyl-4-oxo-3,4-dihydrothieno[3,2-d]pyrimidine-6-carboxamide | 115 |
| 116 (R)-2-(3-aminopiperidin-1-yl)-3-(2-cyanobenzyl)-N-isobutyl-4-oxo-3,4-dihydrothieno[3,2-d]pyrimidine-6-carboxamide | 116 |

-continued

| Designation | Structure |
| --- | --- |
| 117 (R)-2-(3-aminopiperidin-1-yl)-N-butyl-3-(2-cyanobenzyl)-4-oxo-3,4-dihydrothieno[3,2-d]pyrimidine-6-carboxamide | 117 |
| 118 (R)-2-((2-(3-aminopiperidin-1-yl)-6-(morpholine-4-carbonyl)-4-oxothieno-[3,2-d]pyrimidin-3(4H)-yl)methyl)-benzonitrile | 118 |
| 119 (R)-2-(3-aminopiperidin-1-yl)-3-(2-cyanobenzyl)-N-cyclohexyl-4-oxo-3,4-dihydrothieno[3,2-d]pyrimidine-6-carboxamide | 119 |
| 120 (R)-2-(3-aminopiperidin-1-yl)-3-(2-cyanobenzyl)-4-oxo-N-(3-(trifluoromethyl)benzyl)-3,4-dihydrothieno[3,2-d]pyrimidine-6-carboxamide | 120 |

| Designation | Structure |
|---|---|
| 121 (R)-2-(3-aminopiperidin-1-yl)-3-(2-cyanobenzyl)-N-isopentyl-4-oxo-3,4-dihydrothieno[3,2-d]pyrimidine-6-carboxamide | 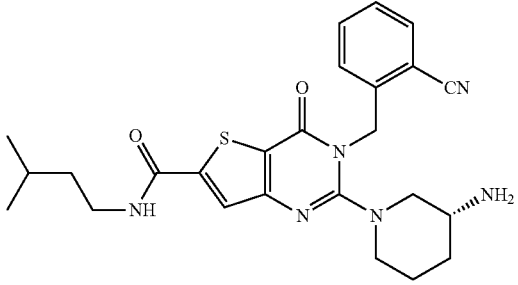<br>121 |
| 122 (R)-2-(3-aminopiperidin-1-yl)-3-(2-cyanobenzyl)-N-(4-methylbenzyl)-4-oxo-3,4-dihydrothieno[3,2-d]-pyrimidine-6-carboxamide | 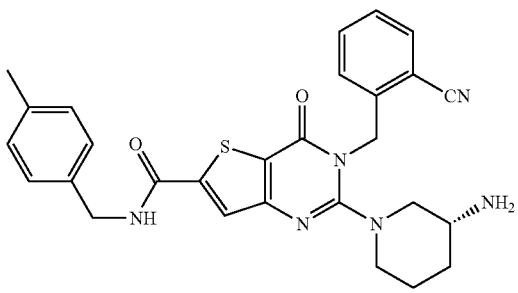<br>122 |
| 123 (R)-2-(3-aminopiperidin-1-yl)-3-(2-cyanobenzyl)-N-(2-hydroxyethyl)-4-oxo-3,4-dihydrothieno[3,2-d]-pyrimidine-6-carboxamide | 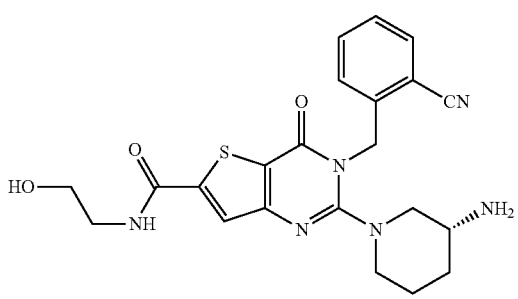<br>123 |
| 124 (R)-2-((2-(3-aminopiperidin-1-yl)-6-(4-(hydroxymethyl)piperidine-1-carbonyl)-4-oxothieno[3,2-d]pyrimidin-3(4H)-yl)methyl)benzonitrile | 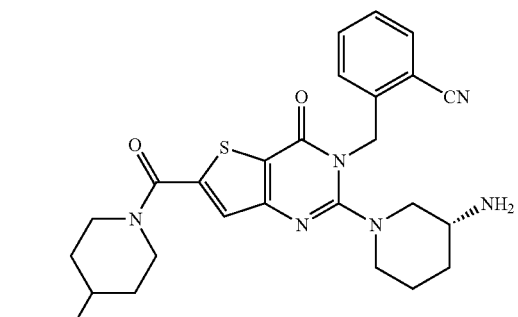<br>124 |

-continued

| Designation | Structure |
|---|---|
| 125 (S)-methyl 1-(2-((R)-3-aminopiperidin-1-yl)-3-(2-cyanobenzyl)-4-oxo-3,4-dihydrothieno[3,2-d]pyrimidine-6-carbonyl)pyrrolidine-2-carboxylate | 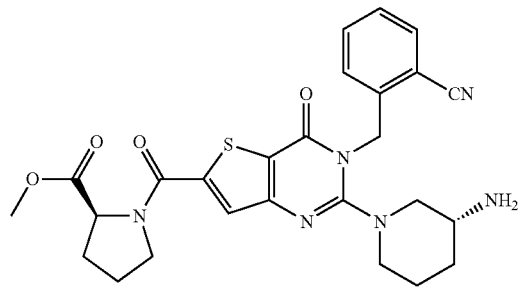<br>125 |
| 126 (R)-2-(3-aminopiperidin-1-yl)-3-(2-cyanobenzyl)-N-(2-(methylsulfonyl)-ethyl)-4-oxo-3,4-dihydrothieno[3,2-d]-pyrimidine-6-carboxamide | 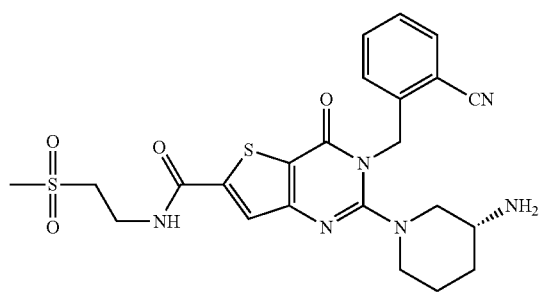<br>126 |
| 126 2-((R)-3-aminopiperidin-1-yl)-3-(2-cyanobenzyl)-4-oxo-N-((S)-2-oxotetrahydrofuran-3-yl)-3,4-dihydrothieno[3,2-d]pyrimidine-6-carboxamide | 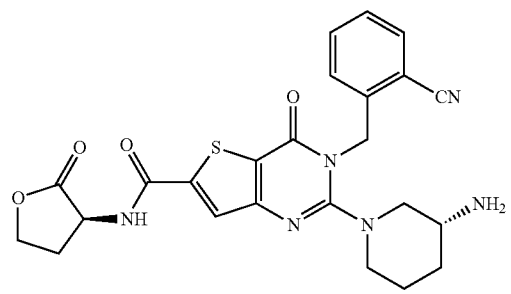<br>127 |
| 128 2-((2-((R)-3-aminopiperidin-1-yl)-6-((S)-2-(hydroxymethyl)pyrrolidine-1-carbonyl)-4-oxothieno[3,2-d]pyrimidin-3(4H)-yl)methyl)benzonitrile | 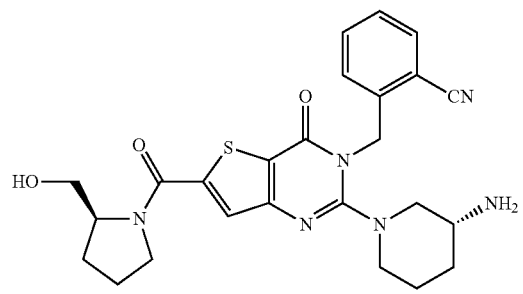<br>128 |

| Designation | Structure |
|---|---|
| 129 (R)-ethyl 1-(2-(3-aminopiperidin-1-yl)-3-(2-cyanobenzyl)-4-oxo-3,4-dihydrothieno[3,2-d]pyrimidine-6-carbonyl)piperidine-4-carboxylate | 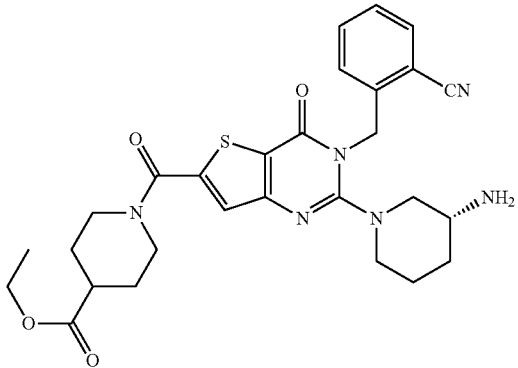<br>129 |
| 130 (R)-2-((2-(3-aminopiperidin-1-yl)-6-(((2-(methylsulfonyl)ethyl)amino)-methyl)-4-oxothieno[3,2-d]pyrimidin-3(4H)-yl)methyl)benzonitrile | 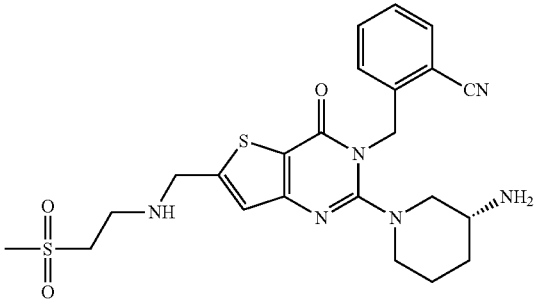<br>130 |
| 131 (R)-2-((2-(3-aminopiperidin-1-yl)-6-((2-methoxyethoxy)methyl)-4-oxothieno[3,2-d]pyrimidin-3(4H)-yl)-methyl)benzonitrile | 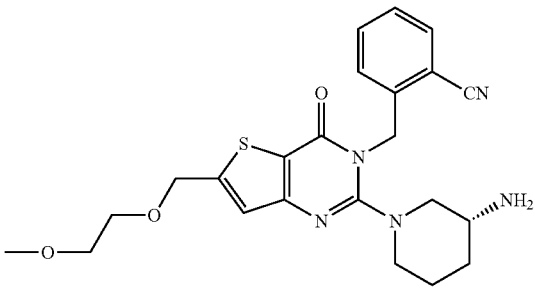<br>131 |
| 132 (R)-2-((2-(3-aminopiperidin-1-yl)-6-((cyclopropylamino)methyl)-4-oxothieno[3,2-d]pyrimidin-3(4H)-yl)-methyl)benzonitrile | 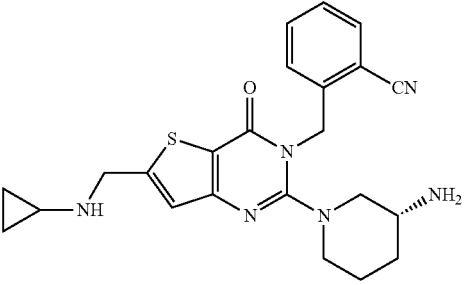<br>132 |

-continued

| Designation | Structure |
|---|---|
| 133 (R)-N-(2-(3-aminopiperidin-1-yl)-3-(2-cyanobenzyl)-4-oxo-3,4-dihydrothieno-[3,2-d]pyrimidin-7-yl)-4-methylbenzenesulfonamide | 133 |
| 134 (R)-2-((2-(3-aminopiperidin-1-yl)-4-oxo-6-((2-oxo-2-phenylethyl)amino)-thieno[3,2-d]pyrimidin-3(4H)-yl)-methyl)benzonitrile | 134 |
| 135 (R)-2-((2-(3-aminopiperidin-1-yl)-6-(difluoromethyl)-4-oxothieno[3,2-d]-pyrimidin-3(4H)-yl)methyl)benzonitrile | 135 |
| 136 (R)-2-((2-(3-aminopiperidin-1-yl)-7-(difluoromethyl)-4-oxothieno[3,2-d]-pyrimidin-3(4H)-yl)methyl)benzonitrile | 136 |

| Designation | Structure |
|---|---|
| 137 (R)-2-((2-(3-aminopiperidin-1-yl)-6-(3,3-difluoroazetidine-1-carbonyl)-4-oxothieno[3,2-d]pyrimidin-3(4H)-yl)-methyl)benzonitrile | 137 |
| 138 (R)-2-((2-(3-aminopiperidin-1-yl)-6-(3,3-difluoropyrrolidine-1-carbonyl)-4-oxothieno[3,2-d]pyrimidin-3(4H)-yl)-methyl)benzonitrile | 138 |
| 139 (R)-2-((2-(3-aminopiperidin-1-yl)-6-(4,4-difluoropiperidine-1-carbonyl)-4-oxothieno[3,2-d]pyrimidin-3(4H)-yl)-methyl)benzonitrile | 139 |
| 140 (R)-2-((2-(3-aminopiperidin-1-yl)-6-(3,3-difluoropiperidine-1-carbonyl)-4-oxothieno[3,2-d]pyrimidin-3(4H)-yl)-methyl)benzonitrile | 140 |

-continued

| Designation | Structure |
|---|---|
| 141 (R)-2-((2-(3-aminopiperidin-1-yl)-6-(4-fluoropiperidine-1-carbonyl)-4-oxothieno[3,2-d]pyrimidin-3(4H)-yl)methyl)benzonitrile | 141 |
| 142 (R)-2-((2-(3-aminopiperidin-1-yl)-6-(3-fluoroazetidine-1-carbonyl)-4-oxothieno[3,2-d]pyrimidin-3(4H)-yl)methyl)benzonitrile | 142 |
| 143 (R)-ethyl 3-(2-(3-aminopiperidin-1-yl)-3-(2-cyanobenzyl)-4-oxo-3,4-dihydrothieno[3,2-d]pyrimidine-6-carboxamido)propanoate | 143 |
| 144 (R)-ethyl 4-(2-(3-aminopiperidin-1-yl)-3-(2-cyanobenzyl)-4-oxo-3,4-dihydrothieno[3,2-d]pyrimidine-6-carboxamido)butanoate | 144 |

According to another object of the present invention, the present invention provides a method for preparing the thieno [3,2-d]pyrimidin-4-one compound, an enantiomer, a diastereoisomer, a racemate and mixtures thereof, or a pharmaceutically acceptable salt thereof, wherein $R_1$, $R_2$, $R_4$ and $R_5$ are defined as above, specifically,

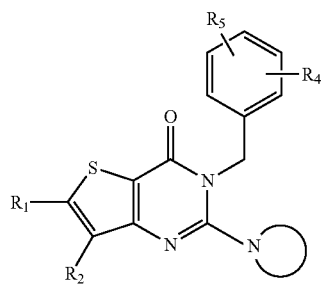

F wherein, a thieno[3,2-d]pyrimidin-4-one compound having the structure formula F, an enantiomer, a diastereoisomer, a racemate and mixtures thereof, or a pharmaceutically acceptable salt thereof is synthesized by using 2,4-dimethoxythienyl[3,2-d]pyrimidine, 7-bromo-2,4-dimethoxythienyl[3,2-d]pyrimidine and 7-methyl-2,4-dimethoxythienyl[3,2-d]pyrimidine as raw material, and performing substitution, chlorination, hydrolysis, benzyl substitution and amino substitution on 6,7-position.

Synthesis strategy is shown in the following reaction route:

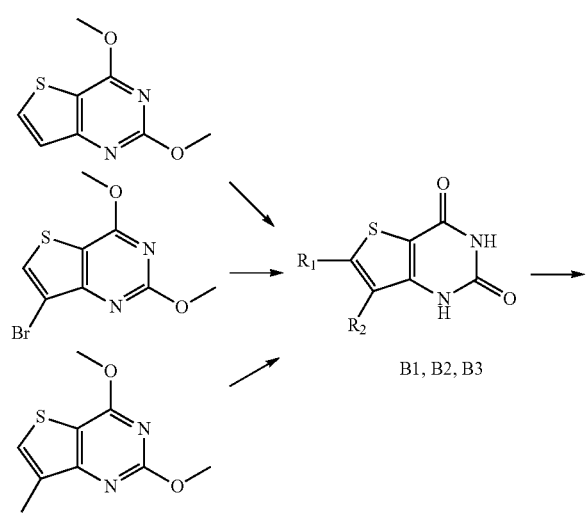

B1, B2, B3

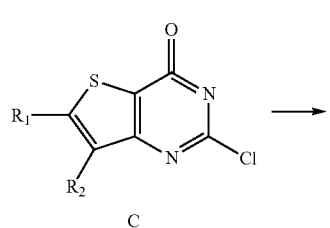

C

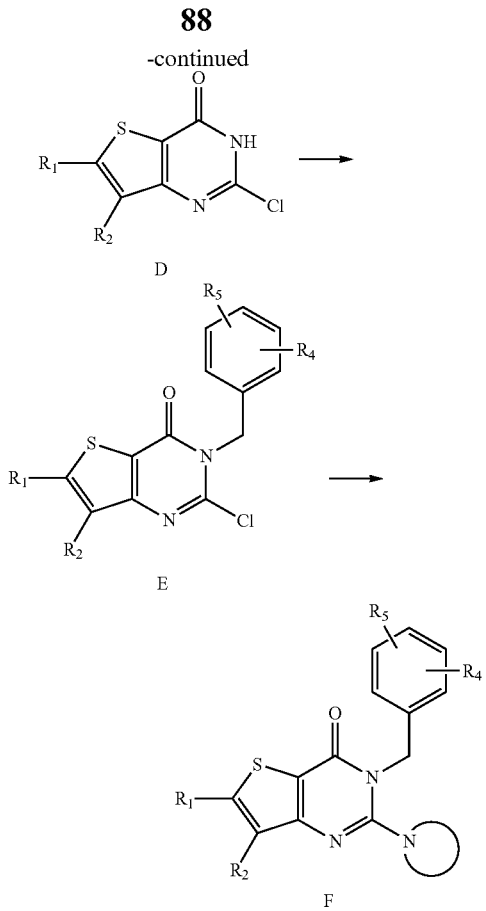

Specific synthesis steps are listed as follows:

1) Synthesis of 6,7-substituted-thieno[3,2-d]pyrimidin-2,4-dione compound B1, B2 and B3

2,4-dimethoxythieno[3,2-d]pyrimidine, 7-bromo-2,4-dimethoxythieno[3,2-d]pyrimidine or 7-methyl-2,4-dimethoxythieno[3,2-d]pyrimidine is dissolved in tetrahydrofuran, substituted tetrahydrofuran or diethyl ether and stirred for 15-30 minutes at −78° C., and then 1-3 equivalents of 2.5 M n-butyl lithium solution in n-hexane is added dropwise and stirred for another 1-2 hours at −78° C., and then a substituent reagent to be added (F reagent, iodine reagent, boric acid reagent, N,N-dimethyl-formamide reagent and the like) is added dropwise. Upon addition, the reaction mixture is stirred for another 15-30 minutes and then 1 hour at room temperature. Afterwards, the reaction solution is poured into saturated $NH_4Cl$ solution, and extracted by organic solvent, and then 6,7-substituted-2,4-dimethoxythieno[3,2-d]pyrimidine compound A1, A2 or A3 is obtained by column chromatography;

6,7-substituted-2,4-dimethoxythieno[3,2-d]pyrimidine compound A1, A2 or A3 is dissolved in organic acid and 4 equivalents of iodide is added. After stirred for 1-5 hours at reflux, the reaction solution is poured into ice water and stirred for 30 minutes, a large amount of solids are precipitated. The solids are filtered by suction, washed with water and dried, thereby obtaining the product 6,7-substituted-thieno[3,2-d]pyrimidin-2,4-dione compound B1 or B2;

Specific synthesis strategy is listed as follows:

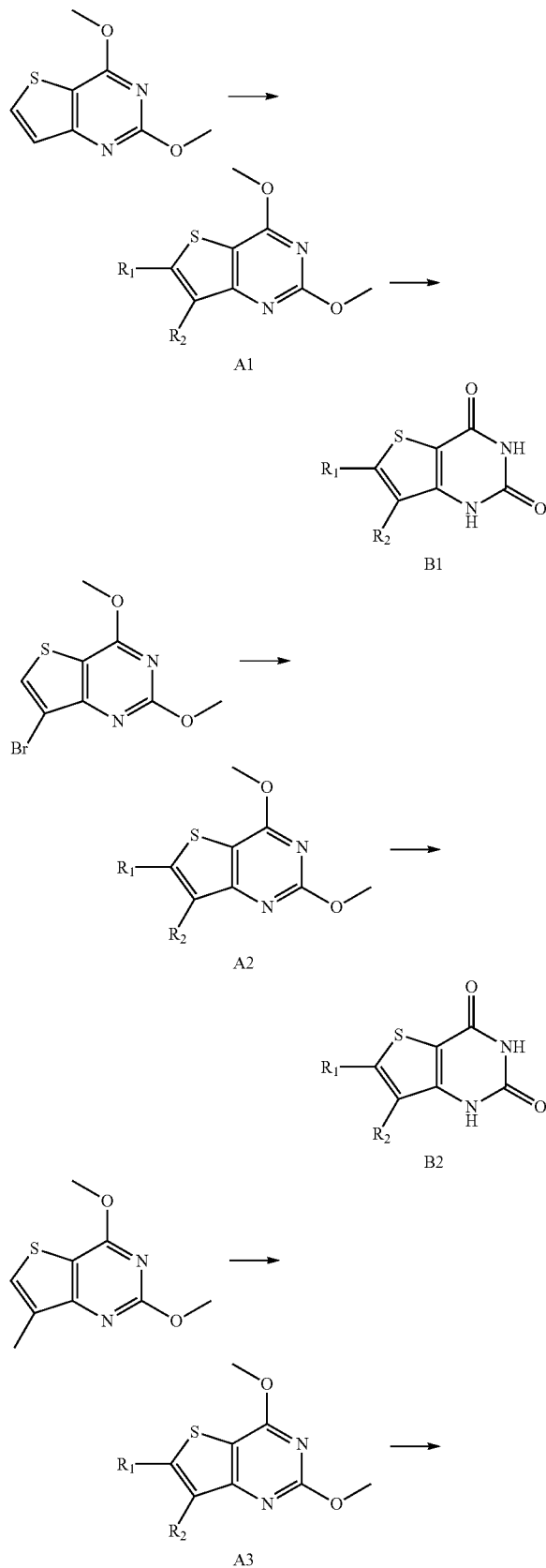

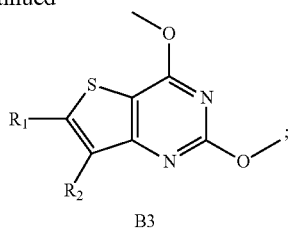

2) Synthesis of 6,7-substituted-2,4-dichlorothieno[3,2-d]pyrimidine compound C 6,7-substituted-thieno[3,2-d]pyrimidin-2,4-dione compound B1, B2 or B3 is dissolved in phosphorus oxychloride. After refluxed for 2-18 hours, the reaction solution is poured into ice water and stirred for 30 minutes, and then a large amount of solids are precipitated. The solids are filtered by suction, washed with water and dried, thereby obtaining the product 6,7-substituted-2,4-dichlorothieno[3,2-d]pyrimidine compound C;

Synthesis Strategy is Listed as Follows:

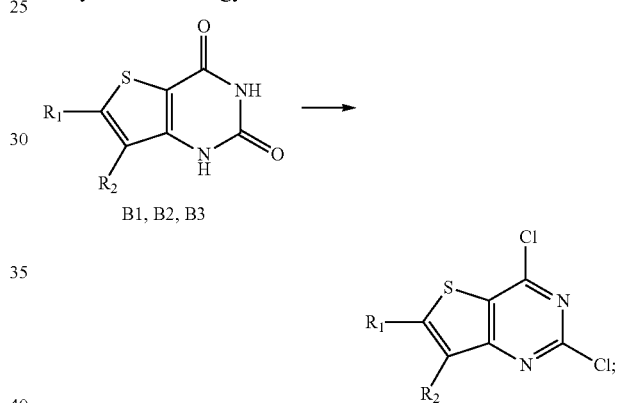

3) Synthesis of 6,7-substituted-2-chlorothieno[3,2-d]pyrimidin-4-one compound D 6,7-substituted-2,4-dichlorothieno[3,2-d]pyrimidine compound C is dissolved in organic solvent, an appropriate amount of aqueous alkali solution is added under nitrogen and stirred for 2-18 hours at room temperature. The organic solvent is evaporated from the reaction solution and an acid is added to adjust pH to neutral with stirring, and then a large amount of solids are precipitated. The solids are filtered by suction, washed with water and dried, thereby obtaining the product 6,7-substituted-2-chlorothieno[3,2-d]pyrimidin-4-one compound D;

Specific synthesis strategy is listed as follows:

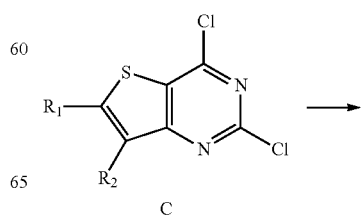

4) Synthesis of 6,7-substituted-3-substituted benzyl-2-chlorothieno[3,2-d]pyrimidin-4-one compound E

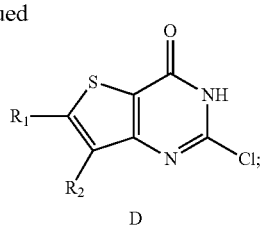

6,7-substituted-2-chlorothieno[3,2-d]pyrimidin-4-one compound D is dissolved in the mixture of glycol dimethyl ether and DMF, 60% of NaH is added at −10~5° C., then anhydrous lithium bromide is added and then substituted benzyl bromide or benzyl chloride is added and reacted for 4-18 hours at 40-100° C. After cooled, an appropriate amount of water is added, and a large amount of solids are precipitated. The solids are filtered by suction, washed with water and dried, thereby obtaining the product 6,7-substituted-3-substituted benzyl-2-chlorothieno[3,2-d]pyrimidin-4-one compound E;

Specific synthesis strategy is listed as follows:

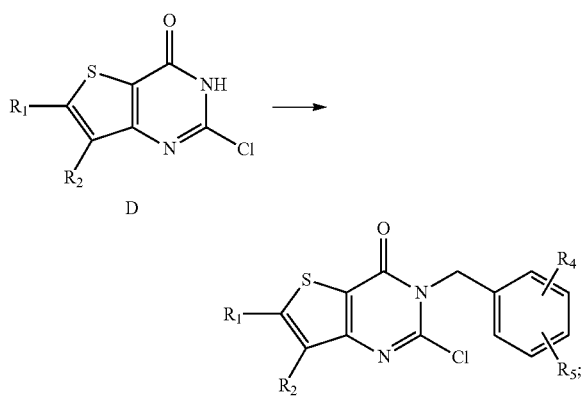

5) Synthesis of 6,7-substituted-3-substituted benzyl-2-substituted aminothieno[3,2-d]pyrimidin-4-one compound F 6,7-substituted-3-substituted benzyl-2-chlorothieno[3,2-d]pyrimidin-4-one compound E is dissolved in organic solvent and 1-4 equivalents of alkali is added, and then

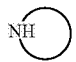

is added and reacted for 1-16 hours at 60-130° C. The reaction solution is exacted, and 6,7-substituted-3-substituted benzyl-2-substituted aminothieno[3,2-d]pyrimidin-4-one compound F is obtained by column chromatography;

Specific synthesis strategy is listed as follows:

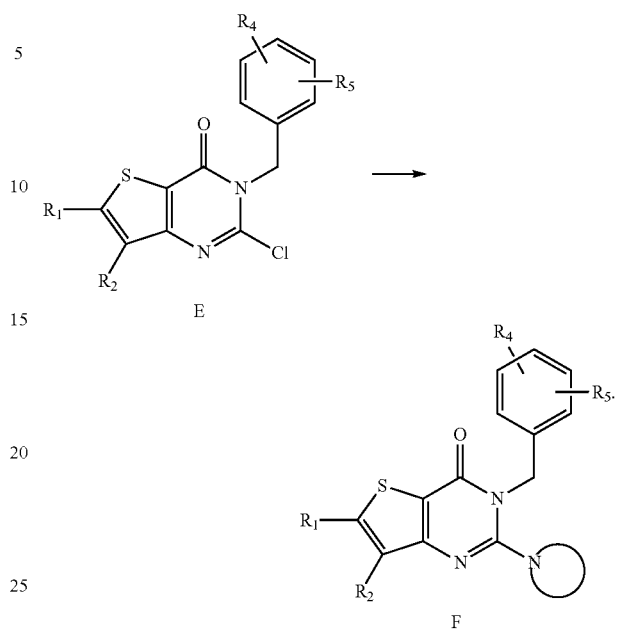

In the above preparation methods, the acid used in each step can be organic acid or inorganic acid, the organic acid can be acetic acid, trifluoroacetic acid, or formic acid, the inorganic acid can be hydrochloric acid, sulfuric acid or phosphoric acid; the alkali can be inorganic alkali or organic alkali, the inorganic alkali is selected from sodium carbonate, potassium carbonate, cesium carbonate, sodium bicarbonate, potassium phosphate, potassium dihydrogen phosphate, sodium hydroxide, lithium hydroxide and potassium hydroxide, the organic alkali is selected from triethylamine, pyridine, diazabicyclo (DBU) and N,N-diisopropylethylamine (DIPEA); the organic solvent in step 3) and step 5) can be selected from THF (tetrahydrofunan), acetonitrile, acetone, 1,4-dioxane, alcohols, diethyl ether, N,N-dimethylformamide, glycol dimethyl ether, N,N-dimethylformamide and dimethyl sulfoxide; the F reagent in step 1) can be DAST (diethylaminosulphur trifluoride), the iodine reagent can be iodine or NIS (N-iodosuccinimide); and the boric acid reagent can be triethyl borate.

Another aspect of the present invention relates to a pharmaceutical composition for treating diabetes, and the pharmaceutical composition contains the thenyl[3,2-d]pyrimidin-4-one compound of formula (I), or a pharmaceutically acceptable salts thereof and at least one pharmaceutically acceptable carrier, and can be used in treatment in vivo and has biocompatibility. The pharmaceutical composition can be prepared into various forms based on different administration routes. The pharmaceutical composition according to the present invention can be used to treat diabetes.

The pharmaceutical composition provided in the present invention can be in various forms, such as tablet, capsule, granule, syrup, solution, suspension, aerosol, and the like, and can be present in suitable solid or liquid carrier or diluent and suitable sterilized means for injection or drip. The pharmaceutical composition can also contain odorant, fragrance agent, etc., and the ideal proportion thereof is that formula (I) compound as active ingredient is more than 65% by total weight and the rest is 0.5-40%, or preferably 1-20%, or the most preferably 1-10% of pharmaceutically acceptable carrier, diluent or solution or salt solution by total weight.

Structure formula (I) compound described above can be clinically used in mammal including human and animal, and administrated through mouth, nose, skin, lungs, or gastrointestinal tract, preferably through mouth. Preferably, daily dose is 0.01-200 mg/kg body weight with one-time use, or 0.01-100 mg/kg body weight in divided dose. No matter what kind of administration route, the best dose for individual should be determined based on specific treatment. Usually, the most suitable dose is determined by gradually increasing dose from small dose.

Formula (I) compound can achieve the purpose of the treatment of type 2 diabetes by inhibiting the activity of DPPIV, indirectly increasing the content of GLP-1 in vivo and inducing a series of physiological actions in vivo.

DETAILED DESCRIPTION

Figure 1:
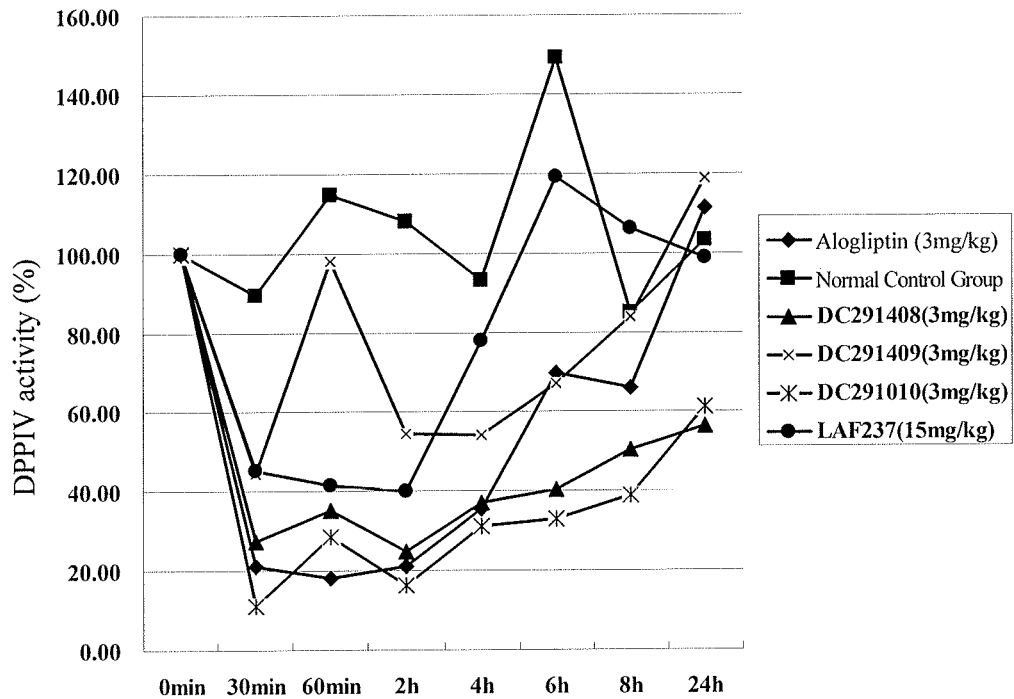
FIG. 1-FIG. 6 show the DPP IV activity in plasma of the ICR mouse after administrated once according to the embodiments of the present invention.
Figure 2:
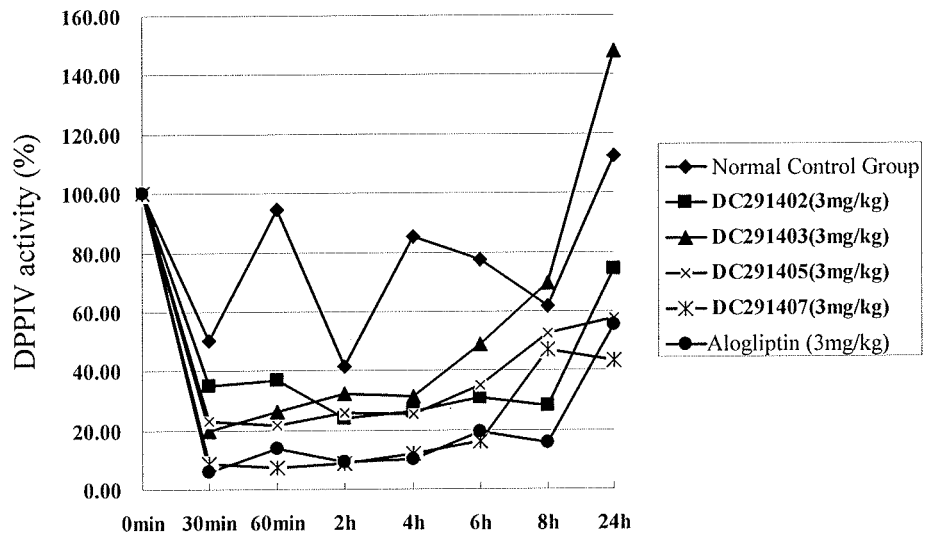
Figure 3:
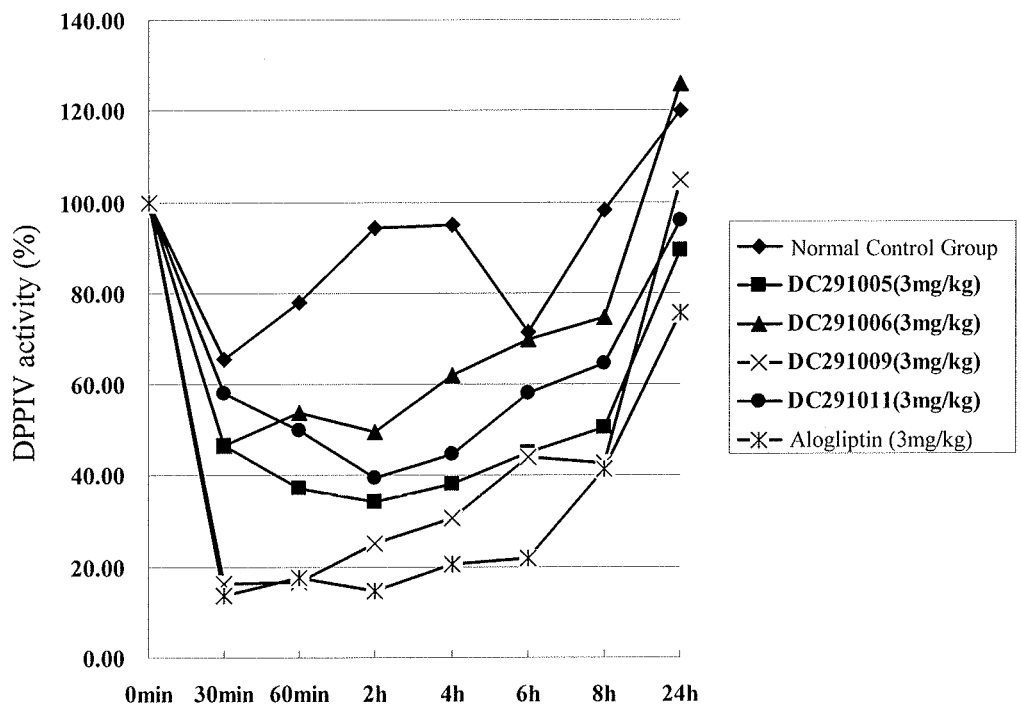
Figure 4:
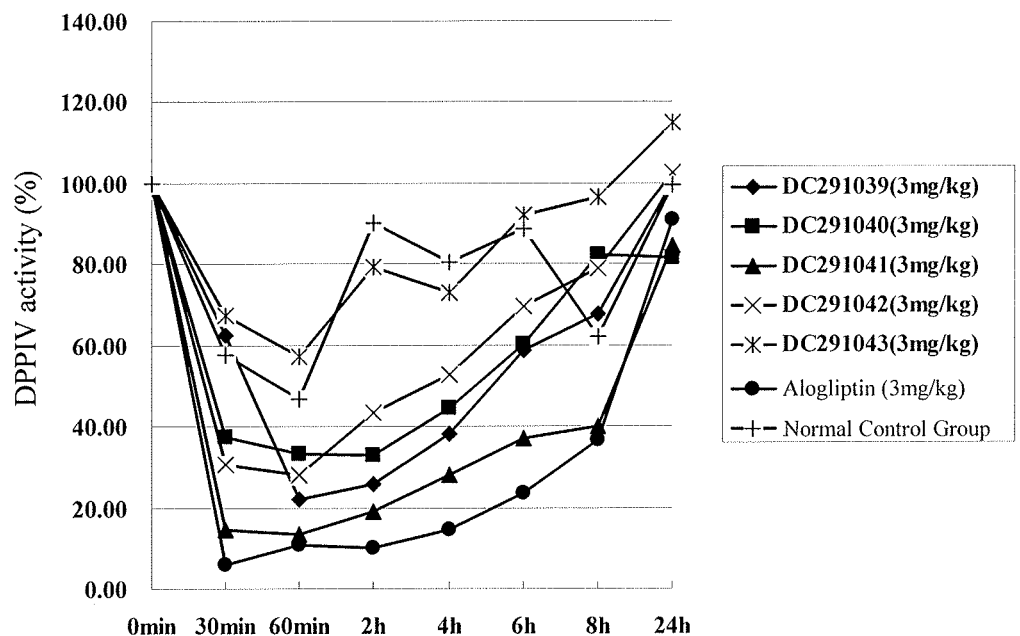
Figure 5:
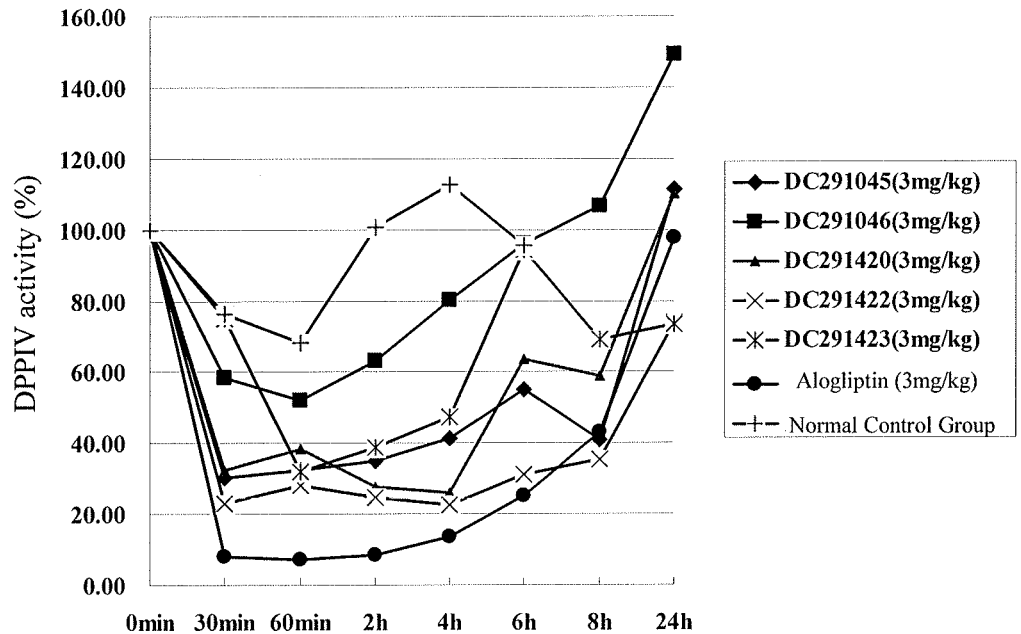
Figure 6:
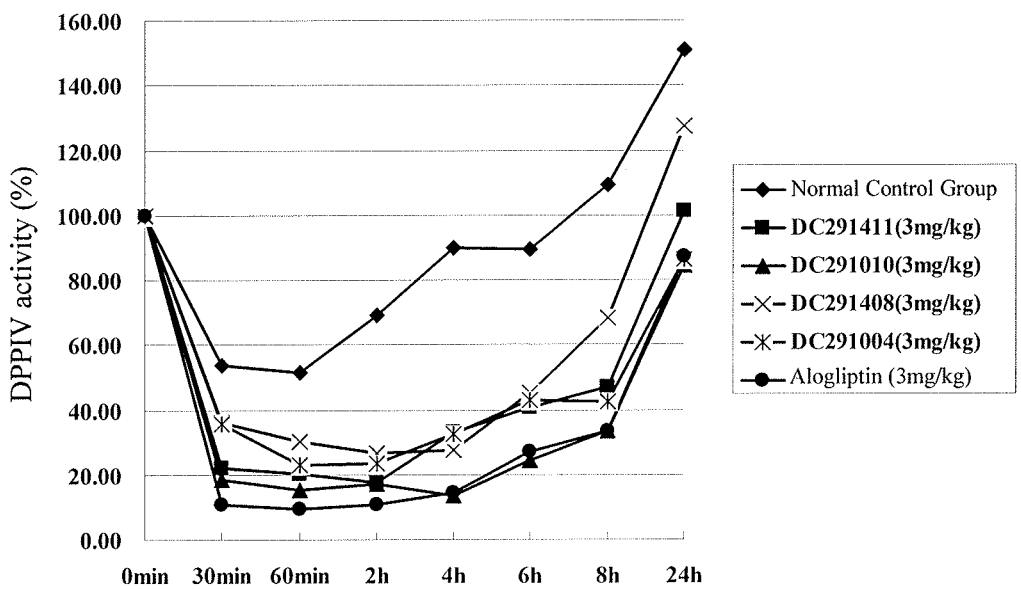
Figure 7:
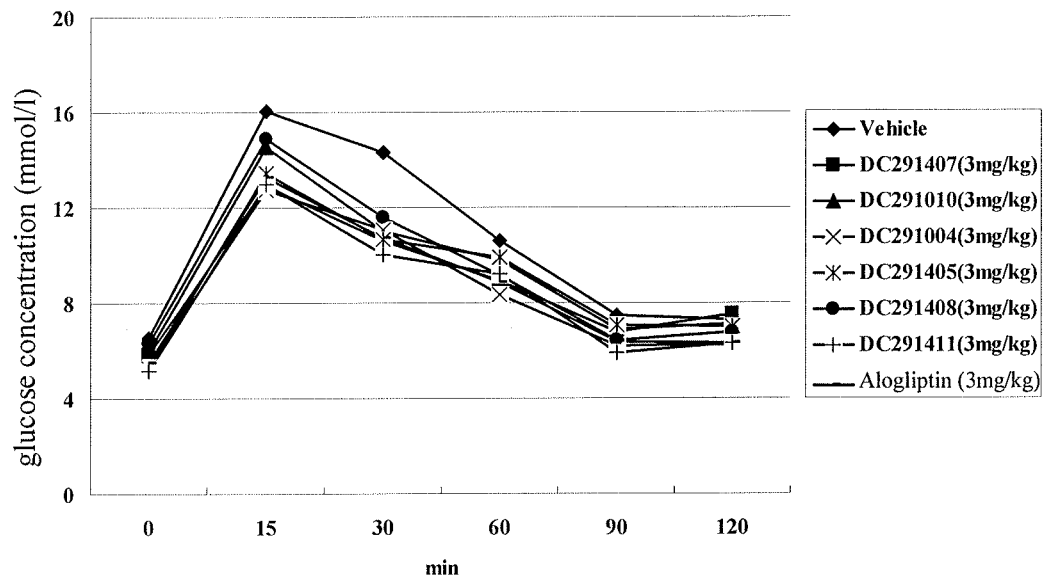
FIG. 7-FIG. 10 show oral glucose tolerance curve and the area under the curve after administrated once according to the embodiments of the present invention.
Figure 7:
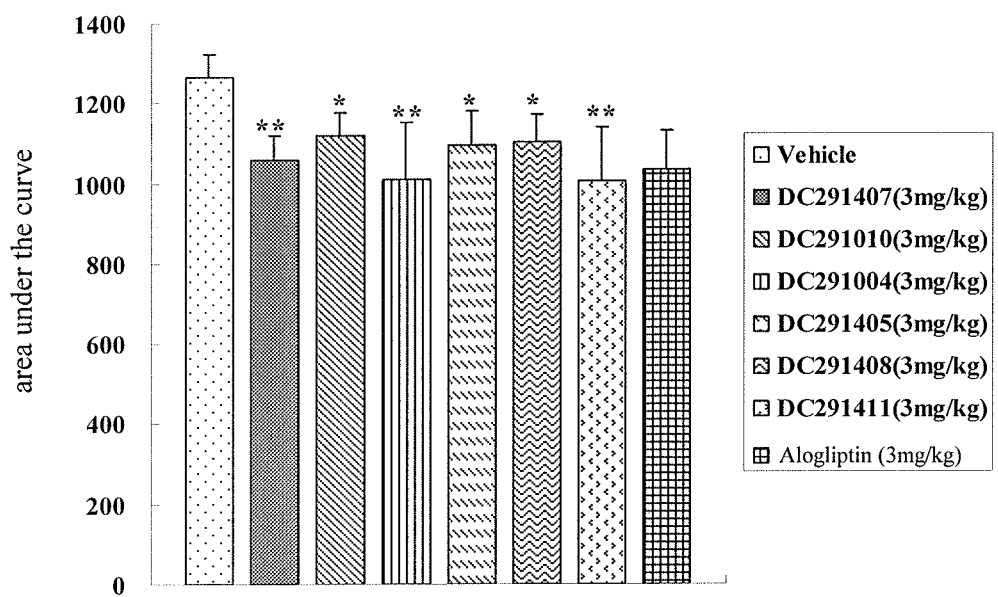
Figure 8:
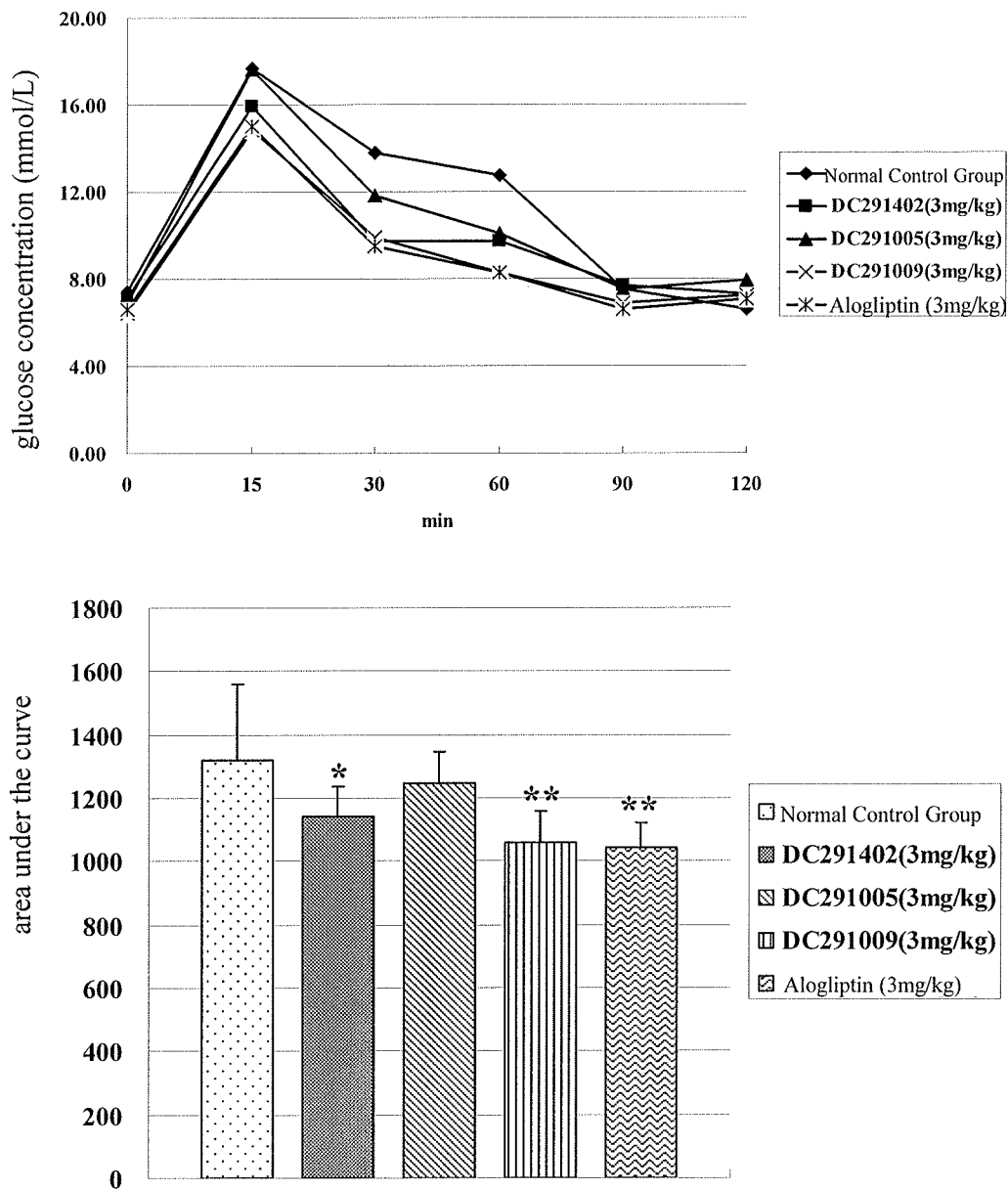
Figure 9:
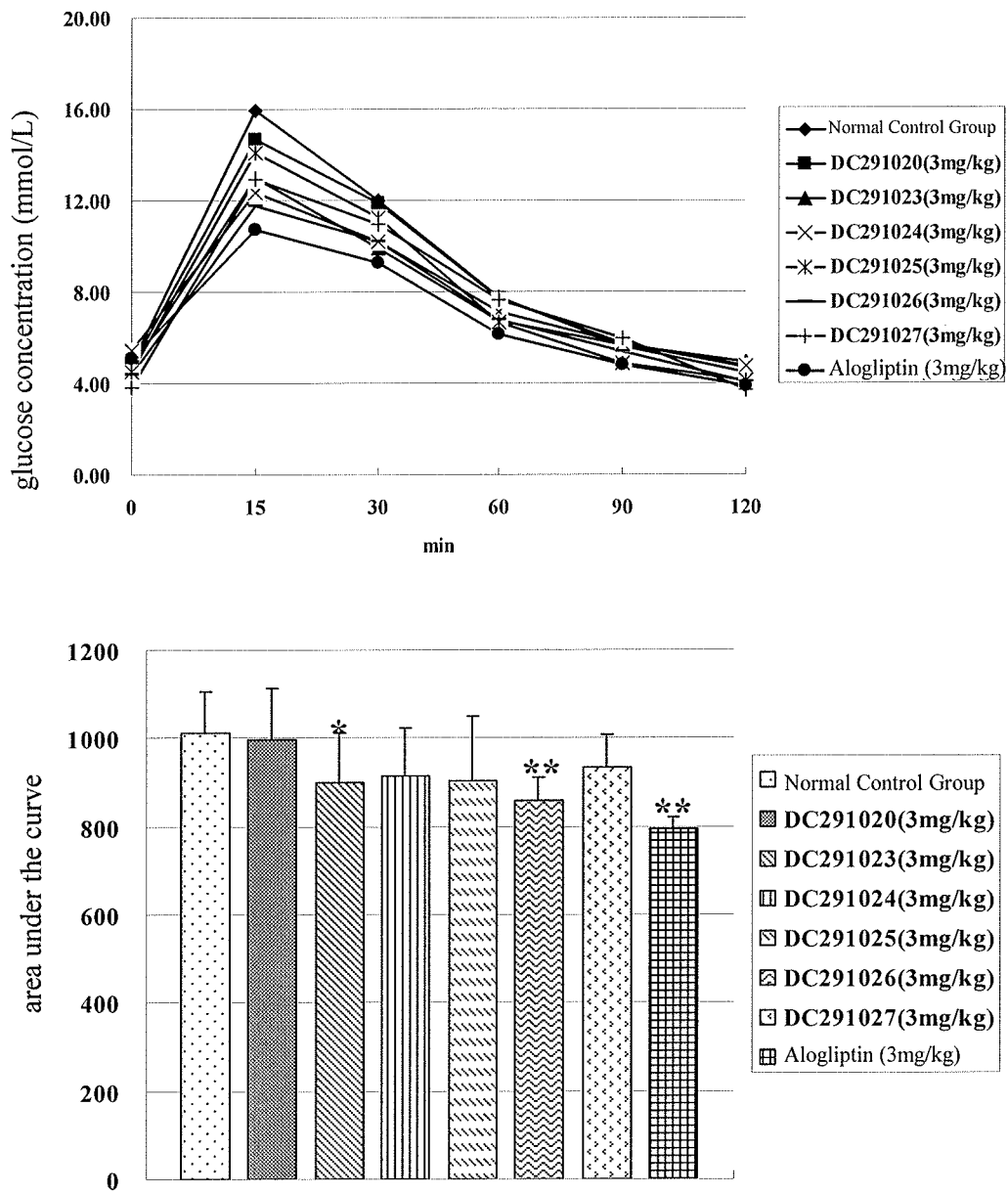
Figure 10:
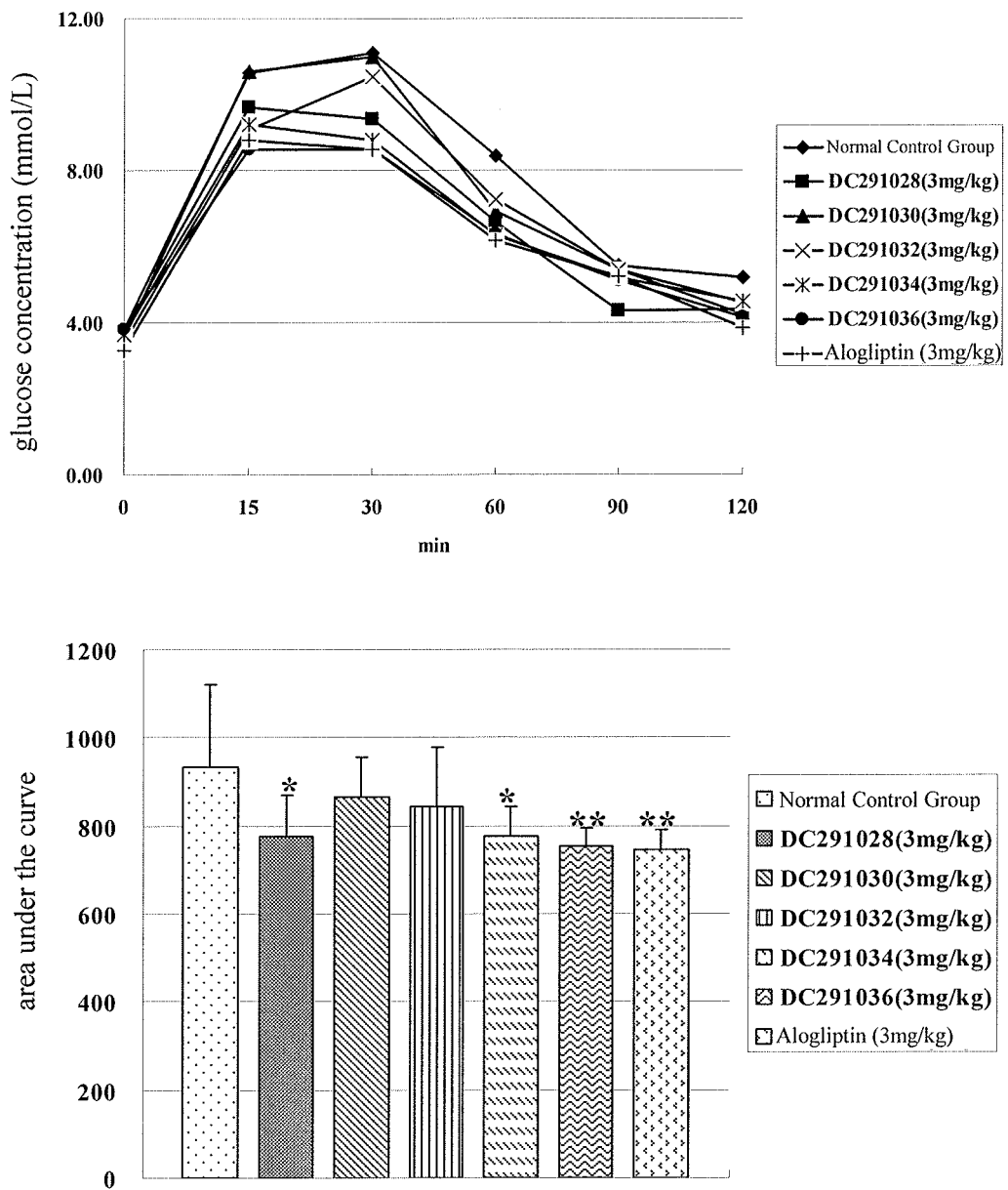

The present invention will be further illustrated in the following examples. These examples are intended to illustrate the invention, but not limit the invention in any way. All parameters of the examples as well as the rest of the description are described based on the weight unless otherwise indicated.

The analysis data for the samples were determined by the following apparatuses, wherein the nuclear magnetic resonance data were determined on GEMINI-300, Bruker AMX-400 or INVOA-600 Nuclear Magnetic Resonance Spectrometer by using TMS (tetramethylsilane) as internal standard, wherein the unit of chemical shift was ppm and that of coupling constant was Hz; and the mass spectrometric data were determined on Finnigan MAT-711, MAT-95 and LCQ-DECA mass spectrometer or IonSpec 4.7 Tesla mass spectrometer.

200-300 mesh of silica gels (Qindao Haiyang Chemical Co.) was used in the column chromatography. TLC silica gel plate was HSGF-254 thin layer chromatography prefabricated plate produced by Yantai Chemical Co. The boiling range of petroleum ether is 60-90° C. The UV light was used and iodine was used to develop the color. The normal reagents and medicaments used in the examples were purchased from CHINA National Medicines Co., LTD unless otherwise stated. The reagents and solvents used in the experiments were determined based on the specific reaction.

Example 1

Synthesis of Compound 1

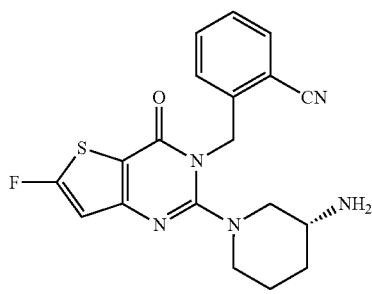

Synthesis route:

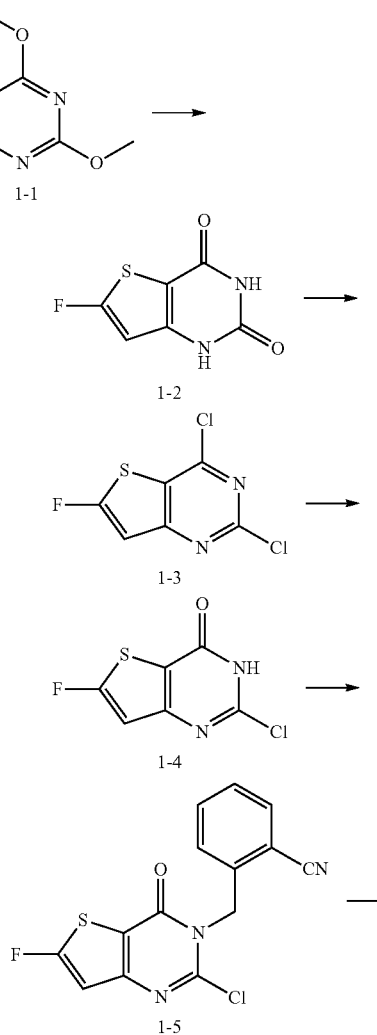

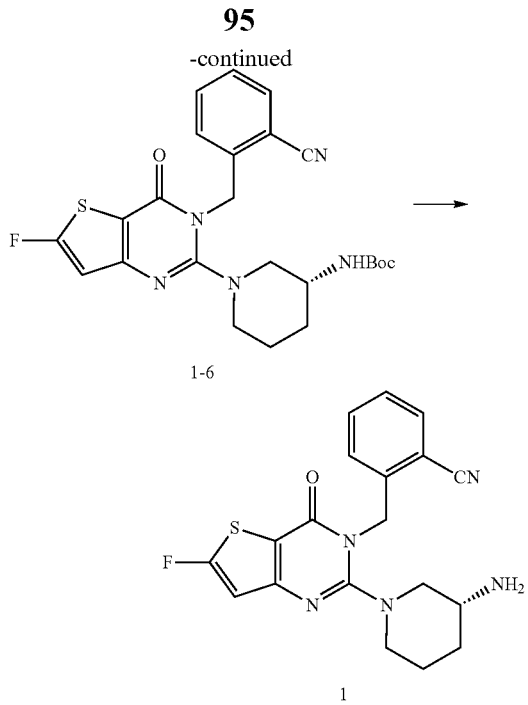

1-6

1

Synthesis of Compound 1-2

Compound 1-1 (2 g, 10.2 mmol) was dissolved in 50 ml THF and stirred for 15 minutes at −78□ under nitrogen. 6.1 ml 2.5 M (15.3 mmol) of n-butyllithium in n-hexane was added dropwise and stirred for 1 hour at −78□. NFSI (N-fluorobenzenesulfonimide, 6.42 g, 20.4 mmol) solution in THF (10 ml) was added dropwise, stirred for 15 minutes at −78□ and then stirred for 30 minutes at room temperature. 50 ml of saturated ammonium chloride solution was added. The extraction was performed by using ethyl acetate. 1.56 g of white solid was obtained by column chromatography.

The white solid was dissolved in 40 ml glacial acetic acid, and NaI (4.3 g, 29 mmol) was added. The reaction was carried out for 2 hours at 80 □. The reaction solution was poured into ice water and stirred for 30 minutes. A large amount of solids was precipitated. The solids were filtered by suction, washed with water and dried, thereby obtaining the product 1-2 (1.34 g) in 71% yield. MS: 187.0[M+H]$^+$.

Synthesis of Compound 1-3

Compound 1-2 (1.34 g, 7.2 mmol) was dissolved in 20 ml phosphorus oxychloride and refluxed overnight. The reaction solution was poured into 200 ml ice water and stirred for 30 minutes. A large amount of solids was precipitated. The solids were filtered by suction, washed with water and dried, thereby obtaining the product 1-3 (1.12 g) in 69.7% yield. MS: 224.9 [M+H]+.

Synthesis of Compound 1-4

Compound 1-3 (1.12 g, 5.0 mmol) was dissolved in 20 ml THF. 25 ml of 1M sodium hydroxide solution was added and stirred under nitrogen overnight. THF was removed by evaporation and pH value was adjusted to 7 by adding 1M hydrochloric acid solution. A large amount of solids was precipitated. The solids were filtered by suction, washed with water and dried, thereby obtaining the product 1-4 (0.97 g) in 95% yield. MS:MS: 206.9[M+H]$^+$.

Synthesis of Compound 1-5

Compound 1-4 (0.97 g, 4.75 mmol) was dissolved in 40 ml the mixture of DME and DMF (2:1, v/v). At 0 □,60% of NaH (0.247 g, 6.18 mmol) was added and stirred for 30 minutes. 1 g of anhydrous lithium bromide was added and stirred for 15 minutes at room temperature. And then 1 g of 2-cyanobenzyl bromide was added and the reaction was carried out at 70□ overnight. 100 ml of water was added and a large amount of solids were precipitated. The solids were filtered by suction, washed with water and dried, thereby obtaining the product 1-5 (1.37 g) in 90% yield. MS: 322.0[M+H]+.

Synthesis of Compound 1-6

Compound 1-5 (1.37 g, 4.3 mmol) was dissolved in 1,4-dioxane, and (R)-3Boc aminopiperidine (0.946 g, 4.73 mmol) was added. 1.5 ml of DIPEA (N,N-diisopropyl ethylamine) (0.946 g, 4.73 mmol) was added and stirred for 1 hour at 120□. The extraction was carried out by using ethyl acetate and then the solvent was removed by rotary evaporation. Compound 1-6 (1.87 g) was obtained by column chromatography in 90% yield. MS: 322.0[M+H]+.

Synthesis of Compound 1

Compound 1-6 (1.87 g, 3.87 mmol) was dissolved in 40 ml of DCM. 15 ml of TFA was added and stirred for 4 hours at room temperature. The solvent was removed by rotary evaporation and the residue was dissolved in 50 ml ethyl acetate. The mixture was washed with saturated potassium carbonate solution, and then washed with saturated sodium chloride solution. The solvent was removed by rotary evaporation and then Compound 1 (1.32 g) was obtained by column chromatography (DCM: CH$_3$OH=5: 1) in 90% yield. MS: 384.1[M+H]$^+$. $^1$H-NMR(400 Hz, CDCl$_3$): δ1.25(1H, m), 1.67(1H, m), 1.76(1H, m), 1.96(1H, m), 2.67(1H, m), 2.88(2H, m), 3.21 (1H, m), 3.39(1H, m), 5.52(2H, s), 7.03(1H, d, J=8), 7.20(1H, d, J=8.2), 7.31(1H, t, J=8), 7.46(1H, t, J=8), 7.62(1H, d, J=7.2).

Example 2

Synthesis of Compound 2

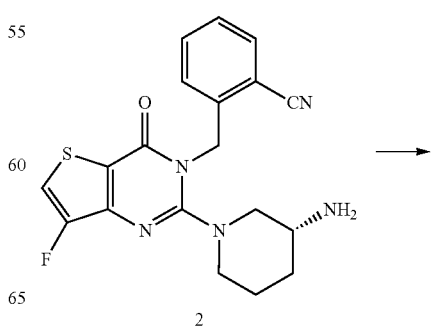

2

97

-continued

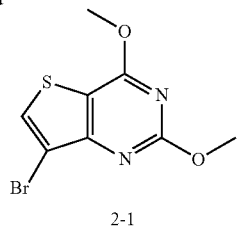

2-1

Compound 2 was synthesized according to the synthesis method in Example 1, wherein compound 2-1 was used instead of compound 1-1 in Example 1. MS: 384.1[M+H]⁺. ¹H-NMR(400 Hz, CDCl₃): δ1.25(1H, m), 1.67(1H, m), 1.76 (1H, m), 1.96(1H, m), 2.67(1H, m), 2.88(2H, m), 3.21(1H, m), 3.39(1H, m), 5.52(2H, s), 7.03(1H, d, J=8), 7.31(1H, t, J=8), 7.46(1H, t, J=8), 7.62(1H, d, J=7.2), 7.75(1H, d, J=8.2).

Example 3

Synthesis of Compound 3

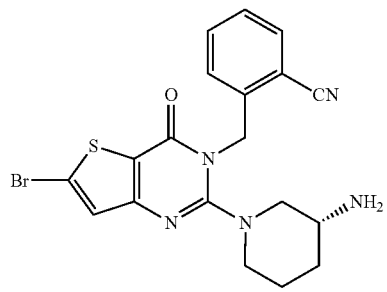

3

Compound 3 was synthesized according to the synthesis method in Example 1, wherein NBS (N-bromosuccinimide) was used instead of NFSI used in the synthesis of compound 1-2 in example 1. MS: 446.0[M+H]⁺. ¹H-NMR (400 Hz, CDCl₃): δ1.25(1H, m), 1.67(1H, m), 1.76(1H, m), 1.96(1H, m), 2.67(1H, m), 2.88(2H, m), 3.21(1H, m), 3.39(1H, m), 5.52(2H, s), 7.03(1H, d, J=8), 7.14(1H, s), 7.31(1H, t, J=8), 7.46(1H, t, J=8), 7.62(1H, d, J=7.2).

Example 4

Synthesis of Compound 4

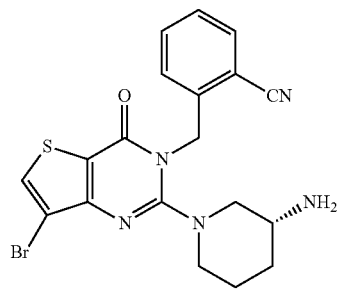

4

98

Synthesis route:

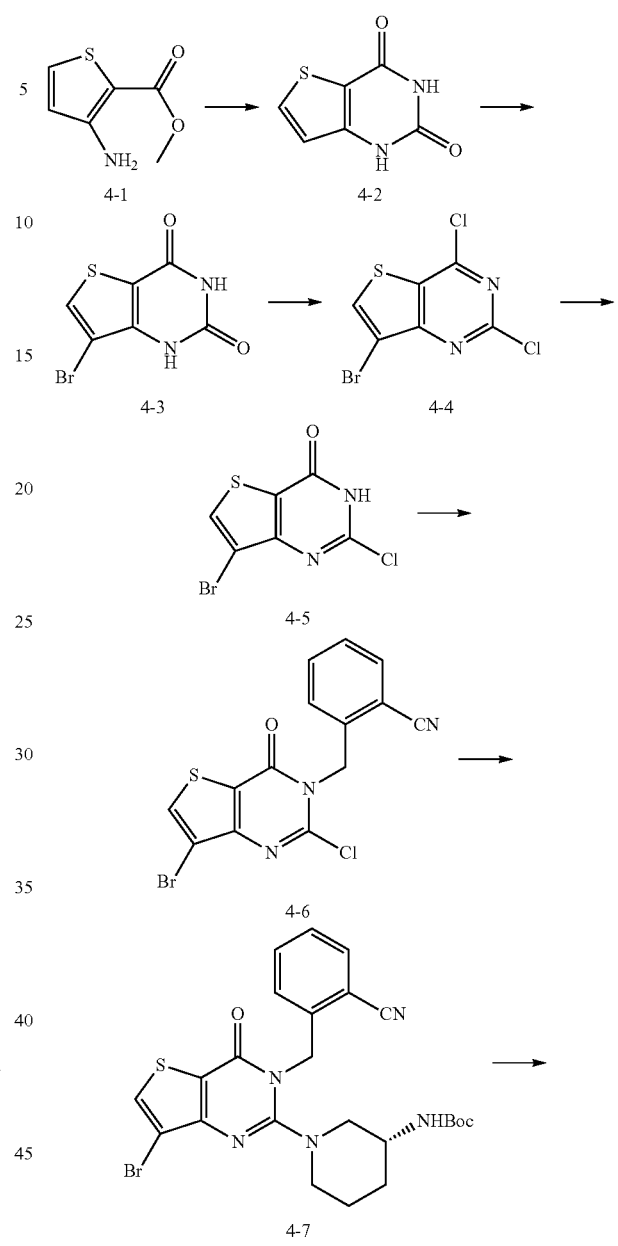

Synthesis of 4-2

Compound 4-1 (4 g) and urea (10 g) were loaded into 100 ml eggplant-shaped flask and mixed uniformly. The mixture was heated to 180° C. for 4 hours and 100 ml of water was added. A large amount of solids was precipitated. The solids were filtered by suction, washed with water and dried, thereby obtaining the product 4-2 (3.5 g) in 81.7% yield. MS: 169.0 [M+H]$^+$.

Synthesis of 4-3

3.5 g of compound 4-2 was dissolved in 60 ml glacial acetic acid. 6.66 g of bromine was added and refluxed for 24 hours. The reaction solution was poured into ice water and a large amount of solids was precipitated. The solids were filtered by suction, washed with water and dried, thereby obtaining the product 4-3 (4.1 g) in 80% yield. MS: 248.9[M+H]$^+$.

Compound 4 was synthesized from compound 4-4 according to the synthesis method in Example 1. MS: 446.0[M+H]$^+$. $^1$H-NMR(400 Hz, CDCl$_3$): δ1.25(1H, m), 1.67(1H, m), 1.76 (1H, m), 1.96(1H, m), 2.67(1H, m), 2.88(2H, m), 3.21(1H, m), 3.39(1H, m), 5.52(2H, s), 7.03(1H, d, J=8), 7.31(1H, t, J=8), 7.46(1H, t, J=8), 7.62(1H, d, J=7.2), 7.68(1H, s).

Example 5

Synthesis of Compound 5

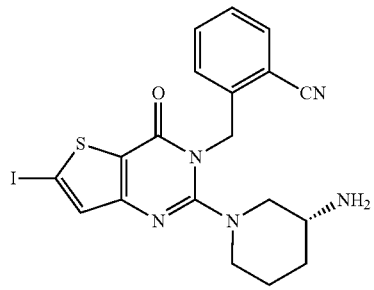

Compound 5 was synthesized according to the synthesis method in Example 1, wherein iodine was used instead of NFSI used in the synthesis of compound 1-2 in example 1. MS: 492.0[M+H]$^+$. $^1$H-NMR(400 Hz, CDCl$_3$): δ1.25 (1H, m), 1.67(1H, m), 1.76(1H, m), 1.96(1H, m), 2.67(1H, m), 2.88(2H, m), 3.21(1H, m), 3.39(1H, m), 5.52(2H, s), 7.03 (1H, d, J=8), 7.16(1H, s), 7.31(1H, t, J=8), 7.46(1H, t, J=8), 7.62(1H, d, J=7.2).

Example 6

Synthesis of Compound 6

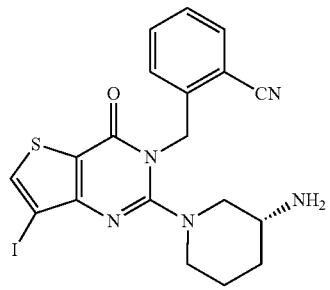

Synthesis route:

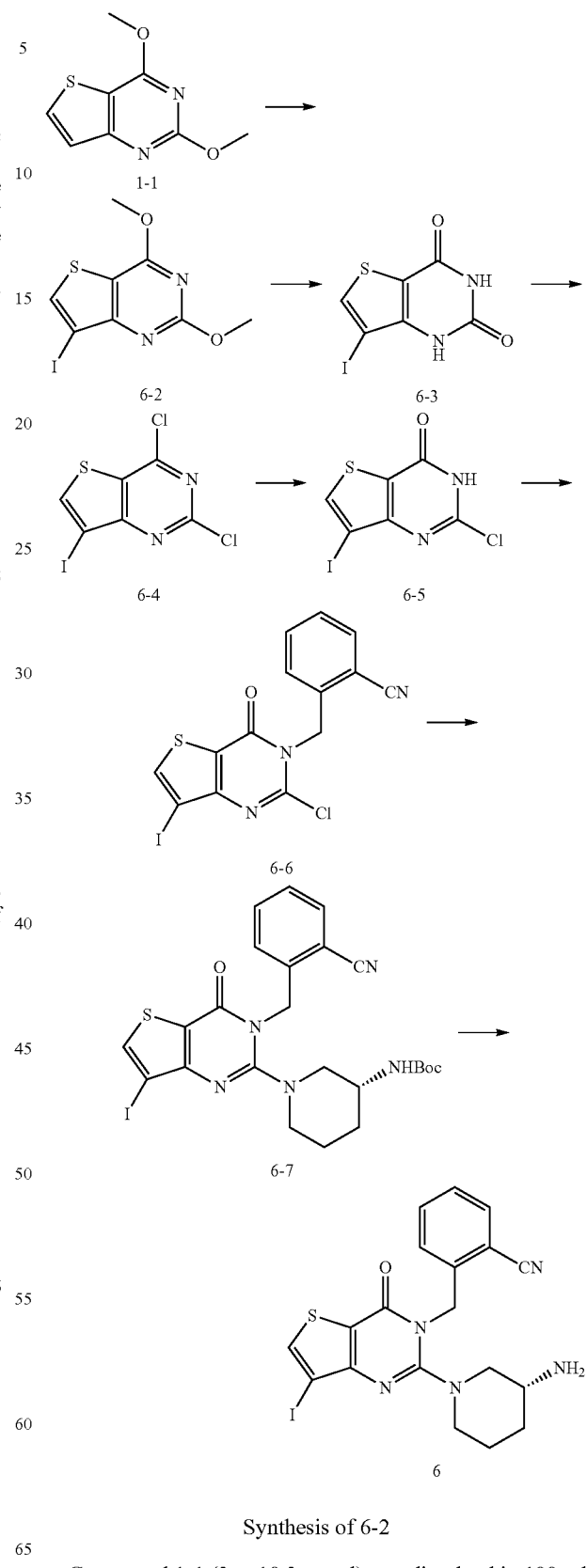

Synthesis of 6-2

Compound 1-1 (2 g, 10.2 mmol) was dissolved in 100 ml CCl$_4$. Bis(trifluoroacetoxy)iodobenzene (5.2 g, 12.2 mmol)

and iodine (5.7 g, 22.4 mmol) were added and stirred at room temperature overnight. The solvent was removed by rotary evaporation and compound 7-2 (1.2 g) was obtained by column chromatography in 36.7% yield. MS: 322.9 [M+H]+.

Compound 6 was synthesized from compound 6-3 according to Example 1. MS: 492.0 [M+H+]. $^1$H-NMR(400 Hz, CDCl$_3$): δ1.25(1H, m), 1.67(1H, m), 1.76(1H, m), 1.96(1H, m), 2.67(1H, m), 2.88(2H, m), 3.21(1H, m), 3.39(1H, m), 5.52(2H, s), 7.03(1H, d, J=8), 7.31(1H, t, J=8), 7.46(1H, t, J=8), 7.62(1H, d, J=7.2), 7.69(1H, s).

Example 7

Synthesis of Compound 7

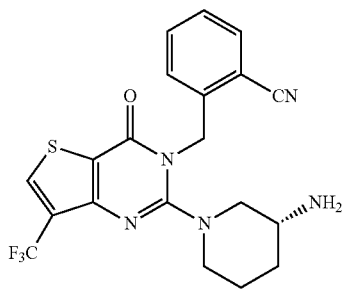

7

Synthesis route:

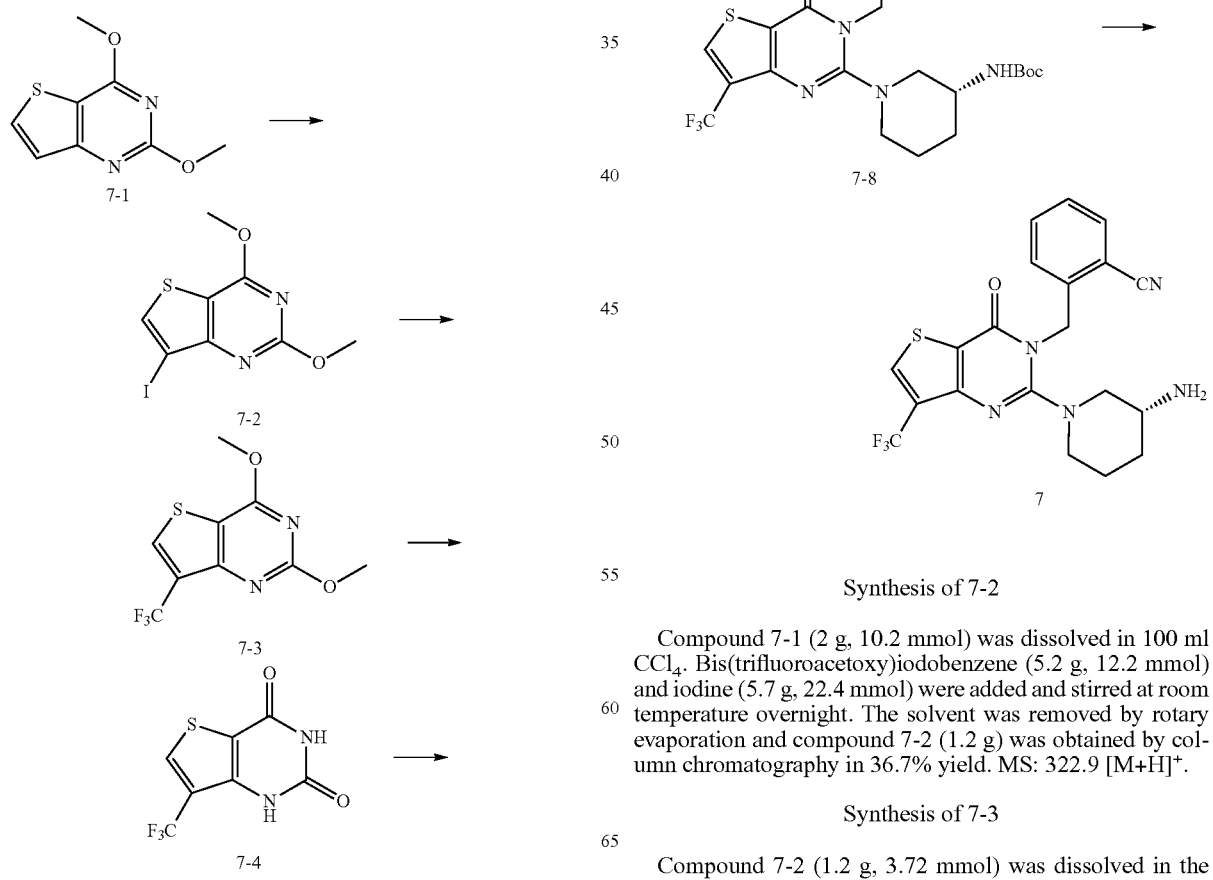

Synthesis of 7-2

Compound 7-1 (2 g, 10.2 mmol) was dissolved in 100 ml CCl$_4$. Bis(trifluoroacetoxy)iodobenzene (5.2 g, 12.2 mmol) and iodine (5.7 g, 22.4 mmol) were added and stirred at room temperature overnight. The solvent was removed by rotary evaporation and compound 7-2 (1.2 g) was obtained by column chromatography in 36.7% yield. MS: 322.9 [M+H]+.

Synthesis of 7-3

Compound 7-2 (1.2 g, 3.72 mmol) was dissolved in the mixture of NMP and DMF (25 ml, 1:1). 10% of CuI, 10% of phenanthroline and KF (0.42 g, 0.745 mmol) were added. The reaction was carried out at 60° C. for 24 hours. Compound 7-3 (0.68 g) was obtained by extraction and column chromatography in 69% yield. MS: 265.0[M+H]+.

Compound 7 was synthesized from compound 7-4 according to the synthesis method in Example 1. MS: 434.1[M+H]+. 1H-NMR(400 Hz, CDCl3): 31.25(1H, m), 1.67(1H, m), 1.76 (1H, m), 1.96(1H, m), 2.67(1H, m), 2.88(2H, m), 3.21(1H, m), 3.39(1H, m), 5.52(2H, s), 7.03(1H, d, J=8), 7.31(1H, t, J=8), 7.46(1H, t, J=8), 7.62(1H, d, J=7.2), 7.76(1H, s).

Example 8

Synthesis of Compound 8

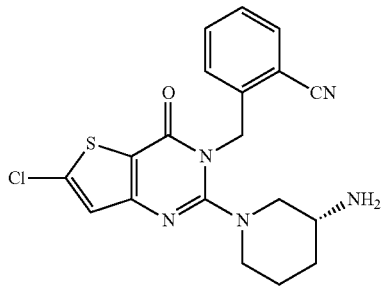

Synthesis route:

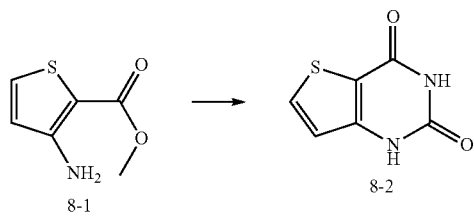

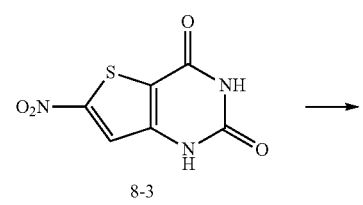

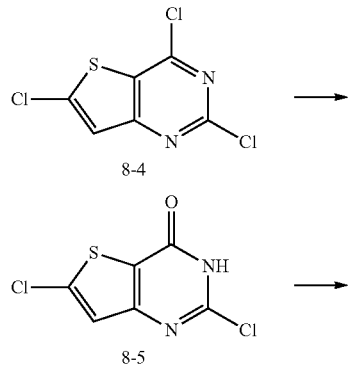

Synthesis of 8-2

Compound 8-2 was synthesized according to the synthesis of compound 4-2.

Synthesis of 8-3

Compound 8-2 (10 g, 59.5 mmol) was added into 30 ml mixture of sulfuric acid and nitric acid (1:1) at 0° C. The reaction was carried out at 0□ for 30 minutes and stirred at room temperature for 2 hours. The reaction solution was poured into ice water and stirred for 30 minutes. A large amount of solids was precipitated. The solids were filtered by suction, washed with water and dried, thereby obtaining the product 8-3 (6.8 g) in 53.6% yield. MS: 213.9[M+H]+.

Synthesis of 8-4

Compound 8-3 (6.8 g, 31.9 mmol) was dissolved in 40 ml phenyl phosphorylcholine and reacted at 180° C. for 4 hours. The reaction solution was poured into ice water and stirred for 30 minutes. A large amount of solids was precipitated. The solids were filtered by suction, and the product 8-4 (3 g) was obtained in 39.3% yield by column chromatography. MS: 238.9[M+H]+.

Compound 8 was synthesized from compound 8-5 according to the synthesis method in Example 1. MS: 400.0[M+H]+. 1H-NMR(400 Hz, CDCl3): δ1.25(1H, m), 1.67(1H, m), 1.76 (1H, m), 1.96(1H, m), 2.67(1H, m), 2.88(2H, m), 3.21(1H, m), 3.39(1H, m), 5.52(2H, s), 7.03(1H, d, J=8), 7.15(1H, s), 7.31(1H, t, J=8), 7.46(1H, t, J=8), 7.62(1H, d, J=7.2).
Example 9
Synthesis of Compound 9
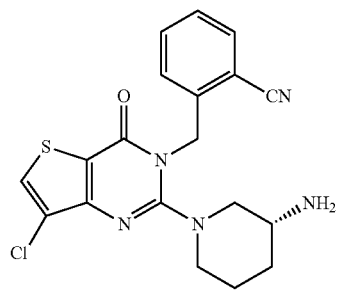
Synthesis route:
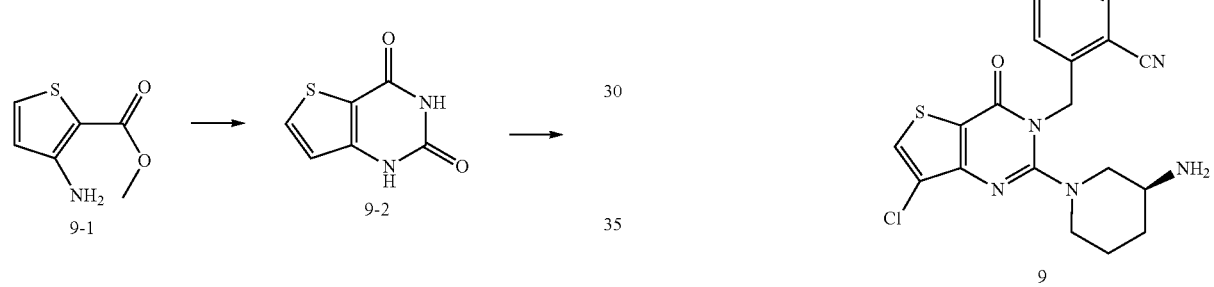
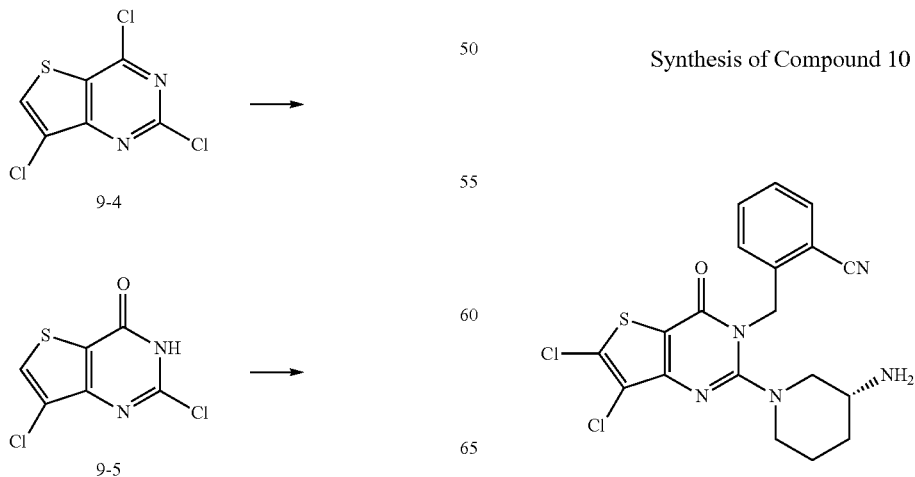
Compound 9 was synthesized according to the synthesis of compound 8. MS: 400.0[M+H]+. 1H-NMR(400 Hz, CDCl3): δ1.25(1H, m), 1.67(1H, m), 1.76(1H, m), 1.96(1H, m), 2.67(1H, m), 2.88(2H, m), 3.21(1H, m), 3.39(1H, m), 5.52(2H, s), 7.03(1H, d, J=8), 7.31(1H, t, J=8), 7.46(1H, t, J=8), 7.62(1H, d, J=7.2), 7.68(1H, s).
Example 10
Synthesis of Compound 10

Synthesis route:
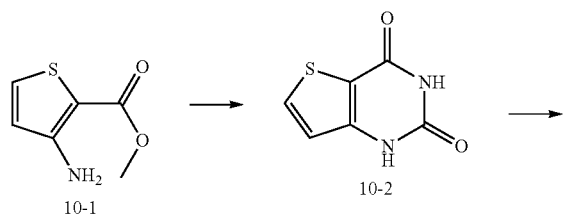
10-1    10-2
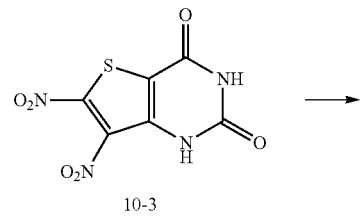
10-3
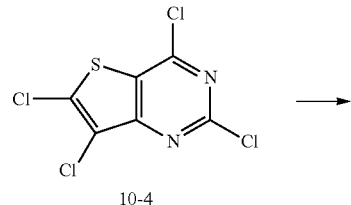
10-4
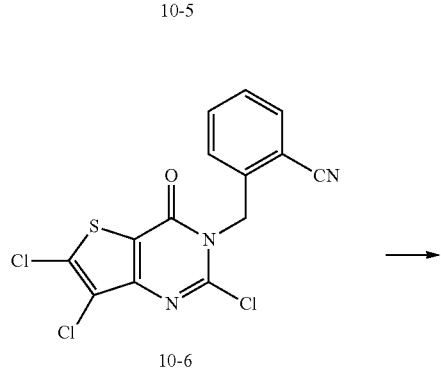
10-5
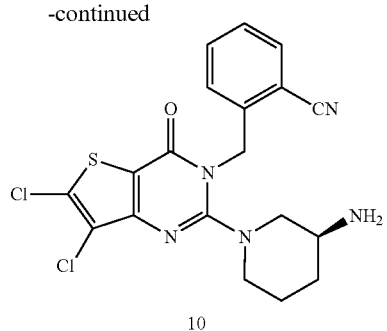
10
Compound 10 was synthesized according to the synthesis of compound 8. MS: 434.0[M+H]⁺. ¹H-NMR(400 Hz, CDCl₃): δ1.25(1H, m), 1.67(1H, m), 1.76(1H, m), 1.96(1H, m), 2.67(1H, m), 2.88(2H, m), 3.21(1H, m), 3.39(1H, m), 5.52(2H, s), 7.03(1H, d, J=8), 7.31(1H, t, J=8), 7.46(1H, t, J=8), 7.62(1H, d, J=7.2).
Example 11
Synthesis of Compound 11
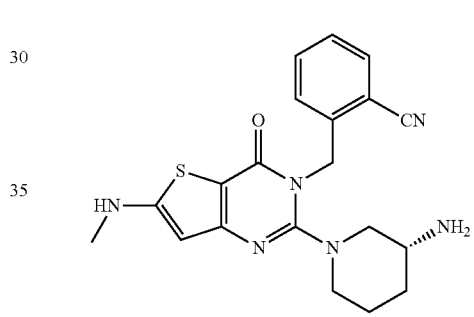
11
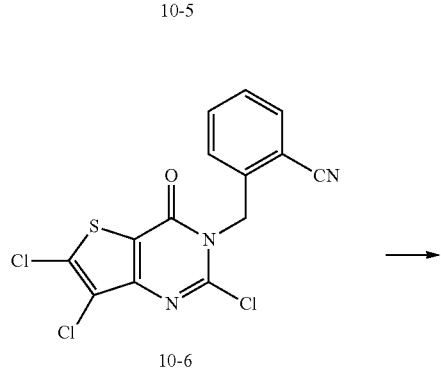
10-6
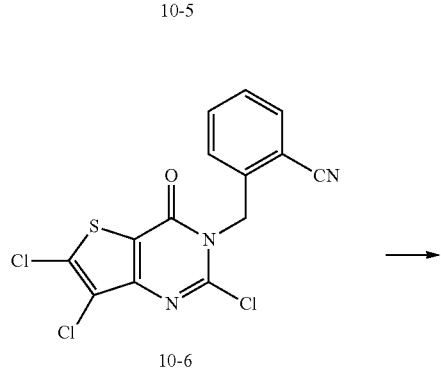
10-7
Synthesis route:
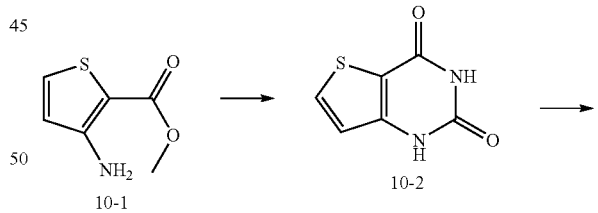
10-1    10-2
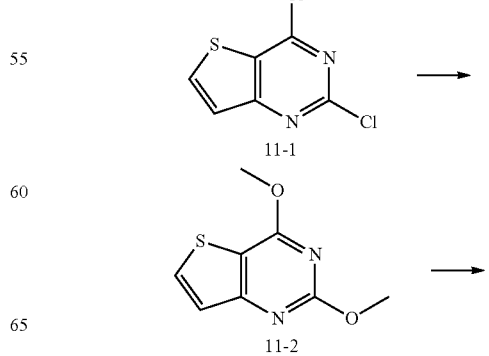
11-1
11-2

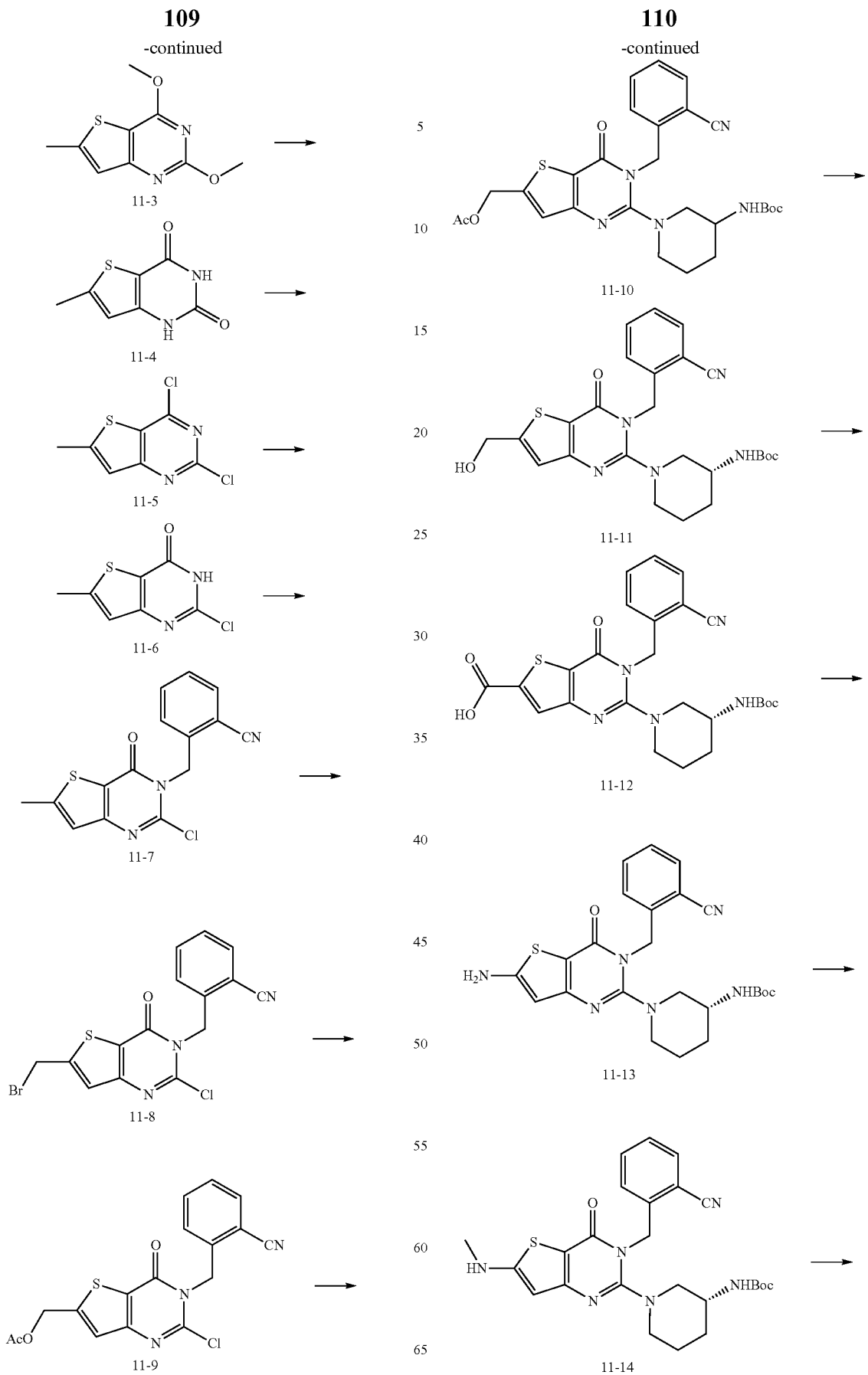

-continued

11

Synthesis of Compound 11-2

Compound 11-1 (1 g, 4.9 mmol) was dissolved in 30 ml absolute methanol. 4 equivalents of NaOMe was added and refluxed for 2 hours. When the reaction was completed, 30 ml of water was added and a large amount of solids was precipitated. Compound 11-2 was obtained by sunction filtration in 99% yield. MS: 197.1[M+H]$^+$.

Compound 11-3 was synthesized according to the synthesis of compound 1-2, wherein iodomethane was used instead of replace NFSI.

Compound 11-7 was synthesized according to the synthesis of compound 1-5.

Synthesis of Compound 11-8

Compound 11-7 (500 mg, 1.6 mmol) was dissolved in 20 ml CCl$_4$. 1.5 equivalent of NBS (N-bromosuccinimide) and catalytic amount of benzoyl peroxide were added and refluxed overnight. When the reaction was completed, extraction was performed using dichloromethane. After washed with water, compound 11-8 (250 mg) was obtained by column chromatography in 40% yield. MS: 393.9[M+H]$^+$.

Synthesis of Compound 11-9

Above compound 11-8 was dissolved in acetonitrile. 2 eq of sodium acetate and catalytic amount of 18-crown ether were added and refluxed for 5 hours. After extracted by ethyl acetate, washed with water, and isolated by column chromatography, a white solid (compound 11-9, 170 mg) was obtained in 72% yield. MS: 374.1[M+H]$^+$.

Synthesis of Compound 11-10

Refer to the synthesis of compound 1-6.

Synthesis of Compound 11-11

Compound 11-10 (200 mg 0.372 mmol) was dissolved in methanol. 2 equivalents of 10% aqueous sodium hydroxide solution was added and stirred for 10 minutes. After extracted with ethyl acetate and evaporated to dryness, a foam-like solid 11-11 (180 mg) was obtained in 98% yield. MS: 496.2 [M+H]$^+$.

Synthesis of Compound 11-12

Compound 11-11 (180 mg) was dissolved in 20 ml of acetone and 2.5 equivalents of 2.7 M Jones reagent was added dropwise in ice-bath. Upon the addition, the mixture was stirred at room temperature for 1 hour. After extracted with ethyl acetate, washed with water and evaporated to dryness, a foam-like solid (compound 11-12, 166 mg) was obtained in 90% yield. MS: 510.2 [M+H]$^+$.

Synthesis of Compound 11-13

Compound 11-12 (166 mg) was dissolved in 20 ml of toluene. 1.5 equivalents of diphenylphosphoryl azide was added and refluxed for 1 hour. 5 ml of water was added and refluxed for another 1 hour. After extracted with ethyl acetate, and isolated by column chromatography, compound 11-13 (109 mg) was obtained in 70% yield. MS: 481.2[M+H]$^+$.

Synthesis of Compound 11-14

Compound 11-13 (109 mg) was dissolved in 5 ml of DMF. 1.5 equivalents of iodomethane and 2 equivalents of cesium carbonate was added and stirred overnight at room temperature. After extracted with ethyl acetate, washed with water and evaporated to dryness, compound 11-14 (96 mg) was obtained in 85% yield. MS: 495.2[M+H]$^+$.

Compound 11 was synthesized according to the synthesis of compound 1. MS: 395.1[M+H]$^+$. $^1$H-NMR(400 Hz, CDCl$_3$): δ1.25(1H, m), 1.67(1H, m), 1.76(1H, m), 1.96(1H, m), 2.67(1H, m), 2.73(3H, s), 2.88(2H, m), 3.21(1H, m), 3.39(1H, m), 5.52(2H, s), 6.50(1H, s), 7.03(1H, d, J=8), 7.31 (1H, t, J=8), 7.46(1H, t, J=8), 7.62(1H, d, J=7.2).

Example 12

Synthesis of Compound 12

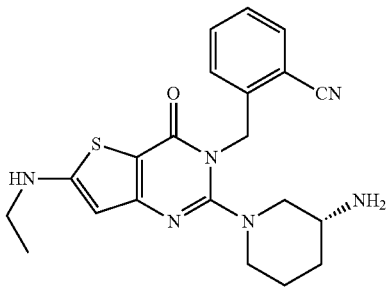

12

Compound 12 was synthesized according to the synthesis of compound 11, wherein iodoethane was used instead of iodomethane. MS: 409.1[M+H]$^+$. $^1$H-NMR(400Hz, CDCl$_3$): δ1.14(3H, t), 1.25(1H, m), 1.67(1H, m), 1.76(1H, m), 1.96 (1H, m), 2.67(1H, m), 2.75(2H, m), 2.88(2H, m), 3.21(1H, m), 3.39(1H, m), 5.52(2H, s), 6.50(1H, s), 7.03(1H, d, J=8), 7.31(1H, t, J=8), 7.46(1H, t, J=8), 7.62(1H, d, J=7.2).

Example 13

Synthesis of Compound 13

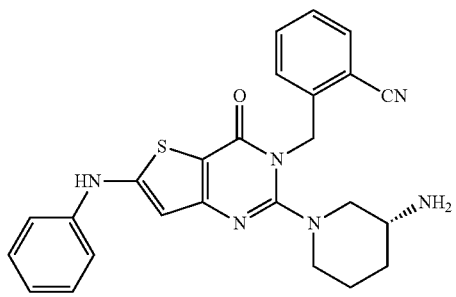

Compound 13 was synthesized according to the synthesis of compound 11, wherein iodobenzene was used instead of iodomethane, and a catalytic amount of Pd$_2$(dba)$_3$ (tris(dibenzylideneacetone)dipalladium), Xantphos (4,5-bis(diphenylphosphino)-9,9-di-methylxanthene) and 2 equivalents of CsCO$_3$ were added in to the reaction solution. MS: 457.0[M+H]$^+$. $^1$H-NMR(400 Hz, CDCl$_3$): δ1.25(1H, m), 1.67(1H, m), 1.76(1H, m), 1.96(1H, m), 2.67(1H, m), 2.88(2H, m), 3.21(1H, m), 3.39(1H, m), 5.52(2H, s), 6.60(1H, s), 7.03(9H, m).

Example 14

Synthesis of Compound 14

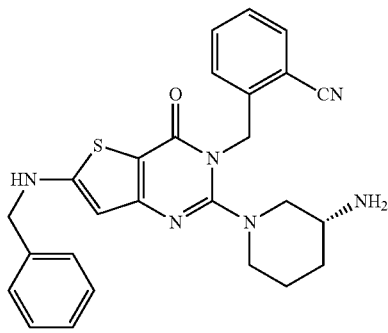

Compound 14 was synthesized according to the synthesis of compound 11, wherein benzyl bromide was used instead of iodomethane. MS: 470.1[M+H]$^+$. $^1$H-NMR(400 Hz, CDCl$_3$): δ1.25(1H, m), 1.67(1H, m), 1.76(1H, m), 1.96(1H, m), 2.67 (1H, m), 2.88(2H, m), 3.21(1H, m), 3.39(1H, m), 4.98(2H, s), 5.52(2H, s), 6.60(1H, s), 7.03(9H, m).

Example 15

Synthesis of Compound 15

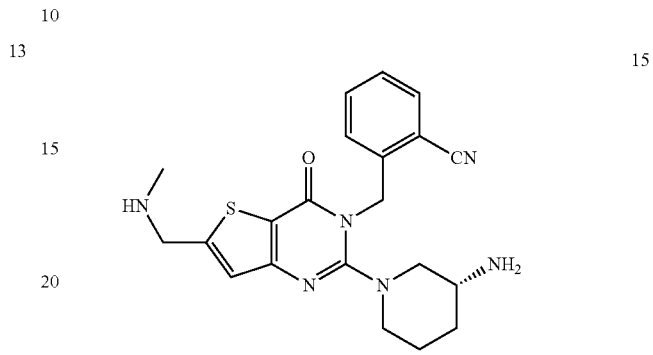

Synthesis route:

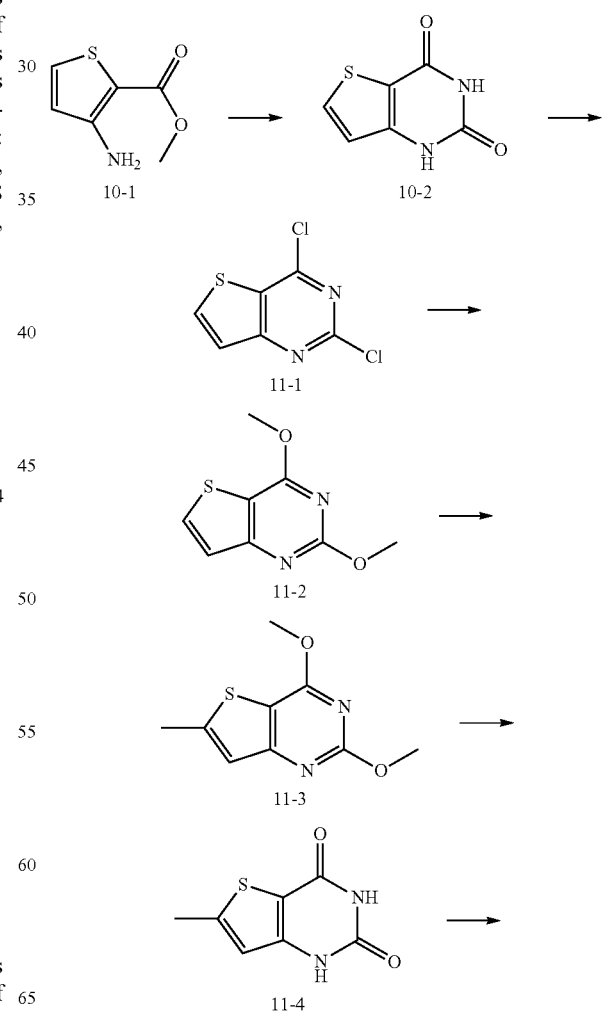

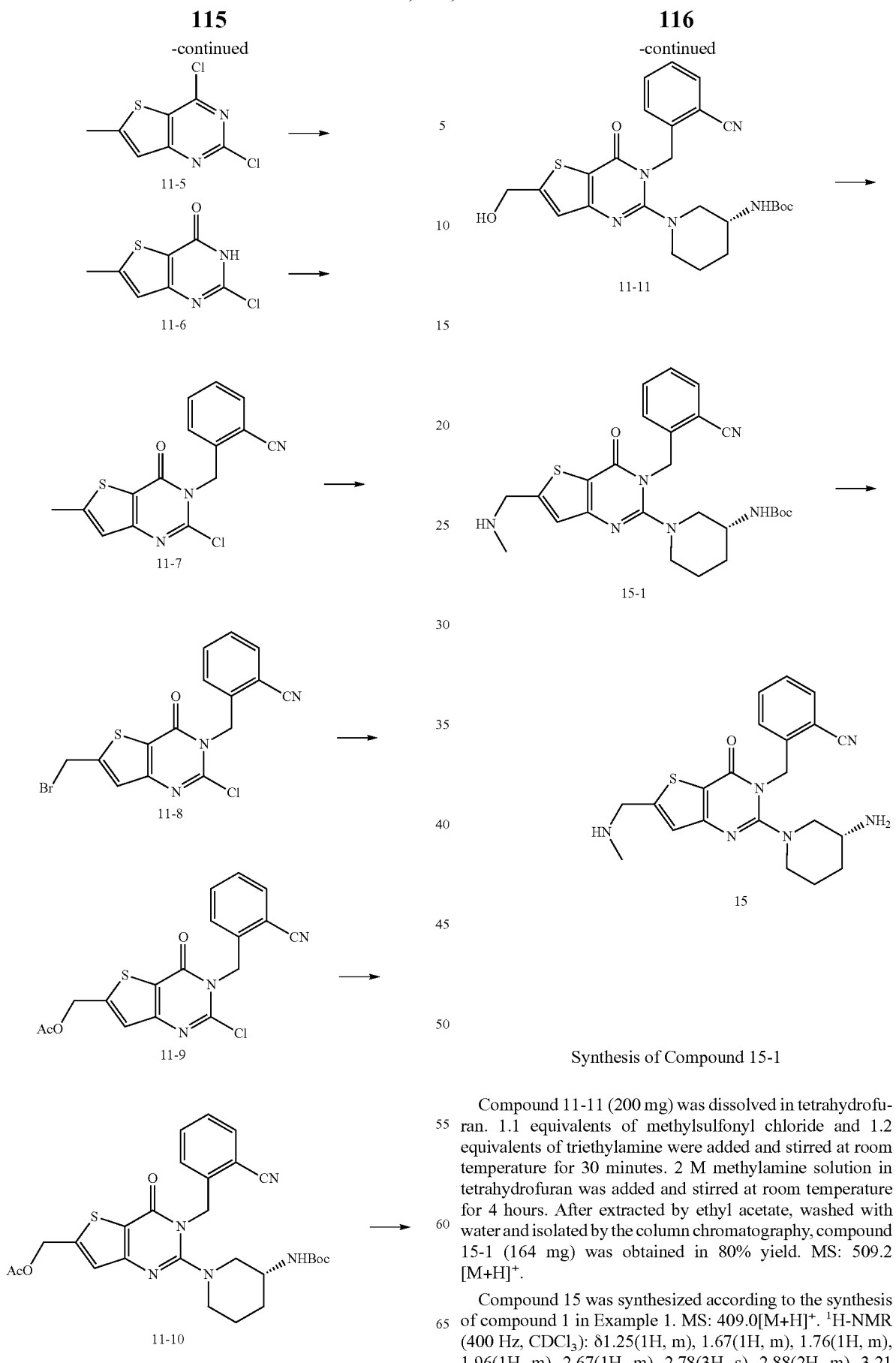

Synthesis of Compound 15-1

Compound 11-11 (200 mg) was dissolved in tetrahydrofuran. 1.1 equivalents of methylsulfonyl chloride and 1.2 equivalents of triethylamine were added and stirred at room temperature for 30 minutes. 2 M methylamine solution in tetrahydrofuran was added and stirred at room temperature for 4 hours. After extracted by ethyl acetate, washed with water and isolated by the column chromatography, compound 15-1 (164 mg) was obtained in 80% yield. MS: 509.2 [M+H]$^+$.

Compound 15 was synthesized according to the synthesis of compound 1 in Example 1. MS: 409.0[M+H]$^+$. $^1$H-NMR (400 Hz, CDCl$_3$): δ1.25(1H, m), 1.67(1H, m), 1.76(1H, m), 1.96(1H, m), 2.67(1H, m), 2.78(3H, s), 2.88(2H, m), 3.21

(1H, m), 3.39(1H, m), 3.52(2H, s), 5.52(2H, s), 6.50(1H, s), 7.03(1H, d, J=8), 7.31(1H, t, J=8), 7.46(1H, t, J=8), 7.62(1H, d, J=7.2).

(2H, m), 3.21(1H, m), 3.39(1H, m), 3.52(2H, s), 4.98(2H, s), 5.52(2H, s), 6.60(1H, s), 7.03(9H, m).

Example 16

Synthesis of Compound 16

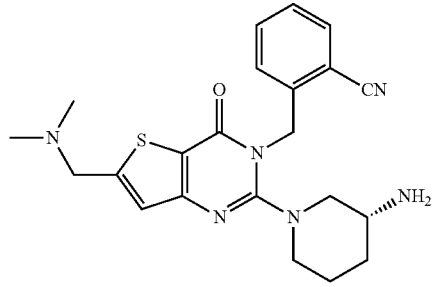

16

Compound 16 was synthesized according to the synthesis method of compound 15, wherein dimethylamine hydrochloride was used instead of methylamine solution in tetrahydrofuran. MS: 423.0[M+H]$^+$. $^1$H-NMR(400 Hz, CDCl$_3$): δ1.25 (1H, m), 1.67(1H, m), 1.76(1H, m), 1.96(1H, m), 2.67(1H, m), 2.78(6H, s), 2.88(2H, m), 3.21(1H, m), 3.39(1H, m), 3.52(2H, s), 5.52(2H, s), 6.50(1H, s), 7.03(1H, d, J=8), 7.31 (1H, t, J=8), 7.46(1H, t, J=8), 7.62(1H, d, J=7.2).

Example 17

Synthesis of Compound 17

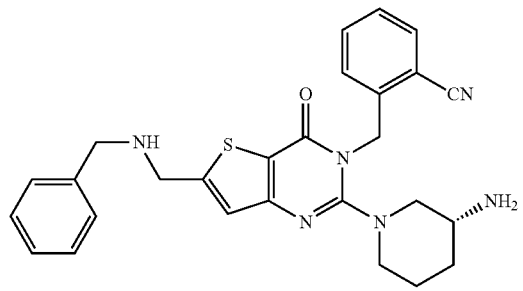

17

Compound 17 was synthesized according to the synthesis method of compound 15, wherein benzylamine was used instead of methylamine solution in tetrahydrofuran. MS: 485.0[M+H]$^+$. $^1$H-NMR(400 Hz, CDCl$_3$): δ1.25(1H, m), 1.67(1H, m), 1.76(1H, m), 1.96(1H, m), 2.67(1H, m), 2.88

Example 18

Synthesis of Compound 18

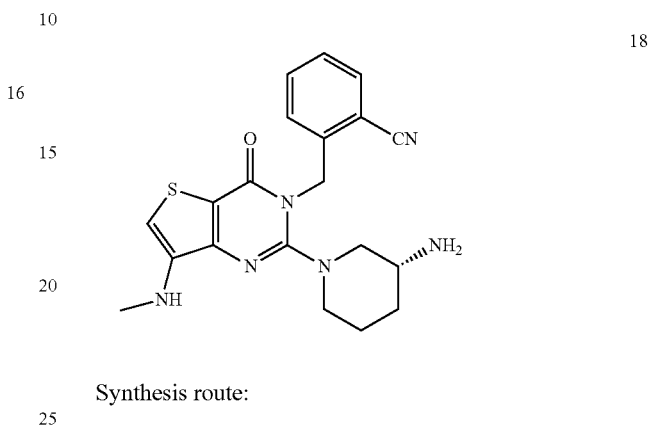

18

Synthesis route:

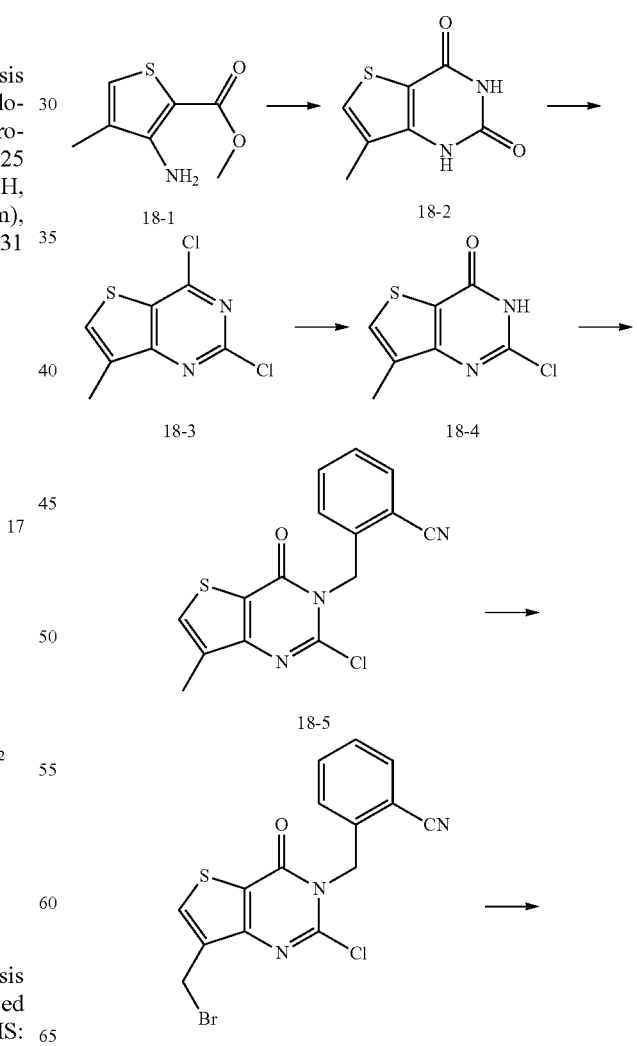

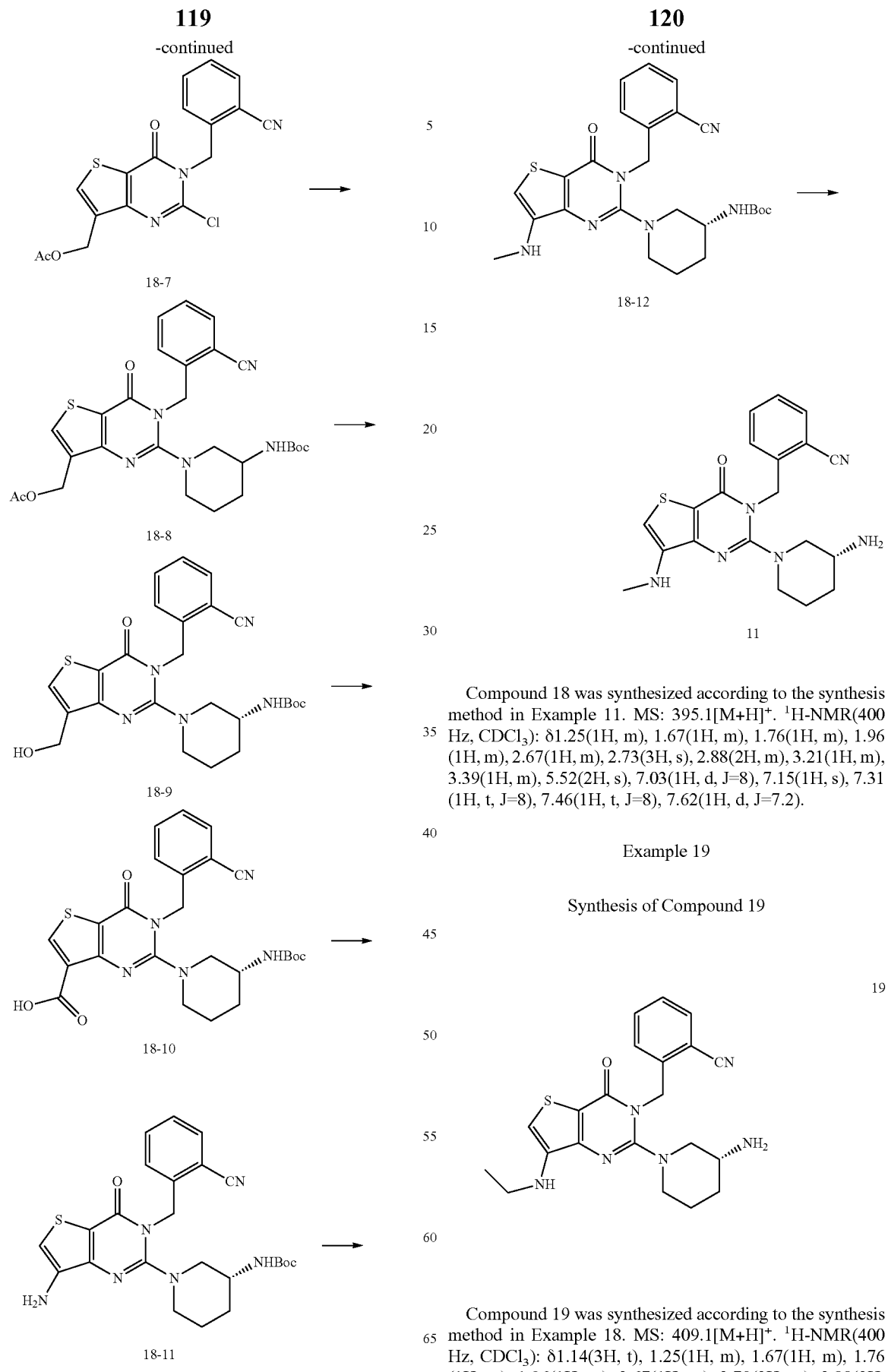
Compound 18 was synthesized according to the synthesis method in Example 11. MS: 395.1[M+H]+. 1H-NMR(400 Hz, CDCl3): δ1.25(1H, m), 1.67(1H, m), 1.76(1H, m), 1.96 (1H, m), 2.67(1H, m), 2.73(3H, s), 2.88(2H, m), 3.21(1H, m), 3.39(1H, m), 5.52(2H, s), 7.03(1H, d, J=8), 7.15(1H, s), 7.31 (1H, t, J=8), 7.46(1H, t, J=8), 7.62(1H, d, J=7.2).
Example 19
Synthesis of Compound 19
Compound 19 was synthesized according to the synthesis method in Example 18. MS: 409.1[M+H]+. 1H-NMR(400 Hz, CDCl3): δ1.14(3H, t), 1.25(1H, m), 1.67(1H, m), 1.76 (1H, m), 1.96(1H, m), 2.67(1H, m), 2.70(2H, m), 2.88(2H, m), 3.21(1H, m), 3.39(1H, m), 5.52(2H, s), 7.03(1H, d, J=8), 7.15(1H, s), 7.31(1H, t, J=8), 7.46(1H, t, J=8), 7.62(1H, d, J=7.2).

Example 20

Synthesis of Compound 20

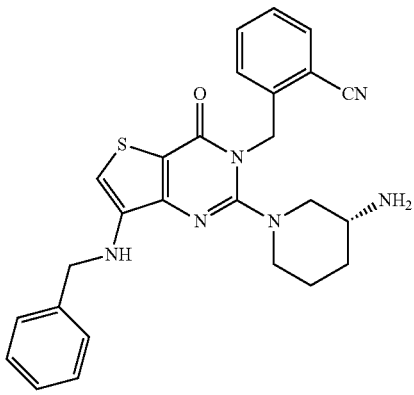

Compound 20 was synthesized according to the synthesis method in Example 18. MS: 470.1[M+H]+. 1H-NMR(400 Hz, CDCl3): δ1.25(1H, m), 1.67(1H, m), 1.76(1H, m), 1.96(1H, m), 2.67(1H, m), 2.88(2H, m), 3.21(1H, m), 3.39(1H, m), 4.98(2H, s), 5.52(2H, s), 7.13(10H, m).

Example 21

Synthesis of Compound 21

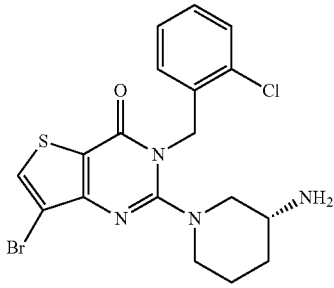

Compound 21 was synthesized according to the synthesis method of compound 4, wherein o-chlorobenzyl bromide was used instead of o-cyanobenzyl bromide. MS: 455.0[M+H]+. 1H-NMR(400 Hz, CDCl3): δ1.25(1H, m), 1.67(1H, m), 1.76(1H, m), 1.96(1H, m), 2.67(1H, m), 2.88(2H, m), 3.21(1H, m), 3.39(1H, m), 5.52(2H, s), 7.13(1H, d, J=5.6), 7.21(1H, t, J=5.6), 7.36(1H, t, J=5.6), 7.52(1H, d, J=4.8), 7.68(1H, s).

Example 22

Synthesis of Compound 22

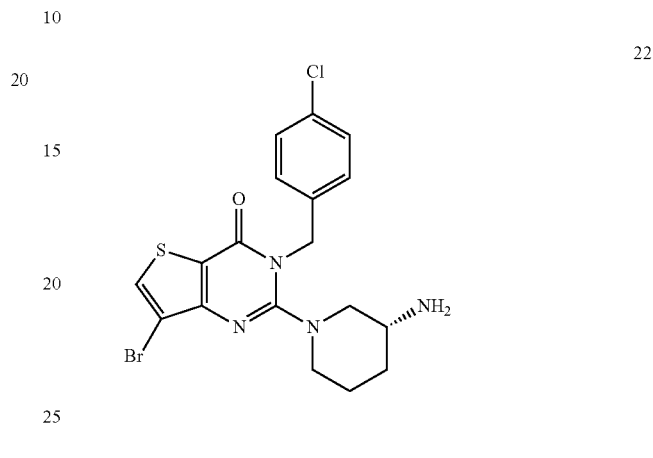

Compound 22 was synthesized according to the synthesis method of compound 4, wherein p-chlorobenzyl bromide was used instead of o-cyanobenzyl bromide. MS: 455.0[M+H]+. 1H-NMR(400 Hz, CDCl3): δ1.25(1H, m), 1.67(1H, m), 1.76(1H, m), 1.96(1H, m), 2.67(1H, m), 2.88(2H, m), 3.21(1H, m), 3.39(1H, m), 5.52(2H, s), 7.3(4H, m), 7.70(1H, s).

Example 23

Synthesis of Compound 23

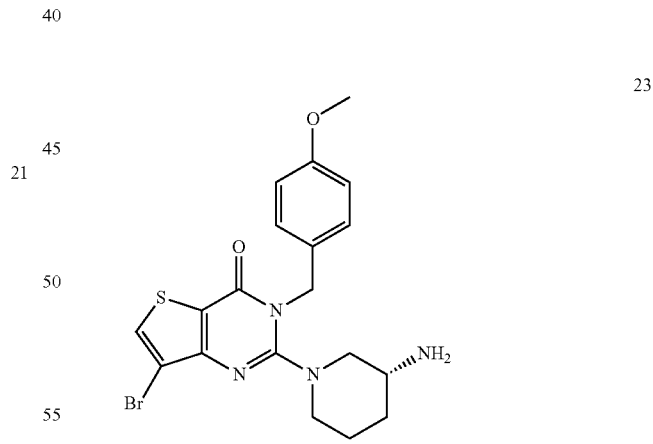

Compound 23 was synthesized according to the synthesis method of compound 4, wherein p-methoxybenzyl bromide was used instead of o-cyanobenzyl bromide. MS: 451.0[M+H]+. 1H-NMR(400 Hz, CDCl3): δ1.25(1H, m), 1.67(1H, m), 1.76(1H, m), 1.96(1H, m), 2.67(1H, m), 2.88(2H, m), 3.21(1H, m), 3.39(1H, m), 3.62(3H, s), 5.52(2H, s), 6.8(2H, d, J=3.6), 7.2(2H, d, J=3.6), 7.70(1H, s).

Example 24

Synthesis of Compound 24

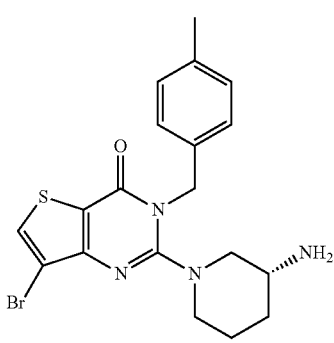

24

Compound 24 was synthesized according to the synthesis method of compound 4, wherein p-methylbenzyl bromide was used instead of o-cyanobenzyl bromide. MS: 435.0[M+H]+. 1H-NMR(400 Hz, CDCl3): δ1.25(1H, m), 1.67(1H, m), 1.76(1H, m), 1.96(1H, m), 2.34(3H, s), 2.67(1H, m), 2.88(2H, m), 3.21(1H, m), 3.39(1H, m), 5.52(2H, s), 7.1(4H, m), 7.80(1H, s).

Example 25

Synthesis of Compound 25

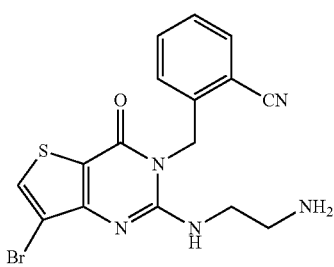

25

Compound 25 was synthesized according to the synthesis method of compound 4, wherein 2-Boc aminoethylamine was used instead of R-3Boc aminopiperidine. MS: 406.0[M+H]+. 1H-NMR(400 Hz, CDCl3): δ2.76(2H, t), 3.1(2H, t), 5.52(2H, s), 7.03(1H, d, J=8), 7.31(1H, t, J=8), 7.46(1H, t, J=8), 7.62(1H, d, J=7.2), 7.68(1H, s).

Example 26

Synthesis of Compound 26

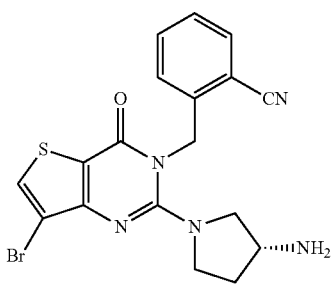

26

Compound 26 was synthesized according to the synthesis method of compound 4, wherein R-3Boc aminopyrrolidine was used instead of R-3Boc aminopiperidine. MS: 432.0[M+H]+. 1H-NMR(400 Hz, CDCl3): δ1.69(1H, m), 1.94(1H, m), 2.52(1H, m), 2.65(1H, m), 2.75(2H, m), 3.1(1H, m), 5.52(2H, s), 7.03(1H, d, J=8), 7.31(1H, t, J=8), 7.46(1H, t, J=8), 7.62(1H, d, J=7.2), 7.68(1H, s).

Example 27

Synthesis of Compound 27

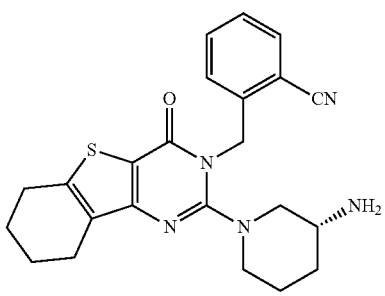

27

Synthesis route:

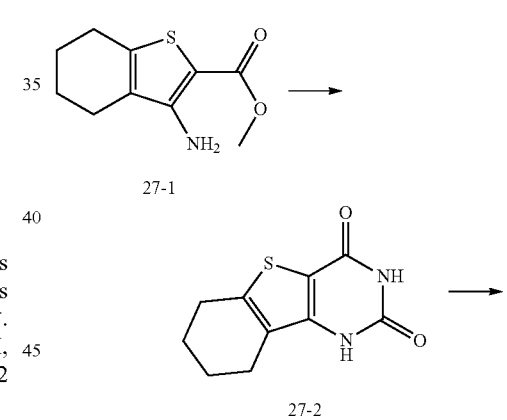

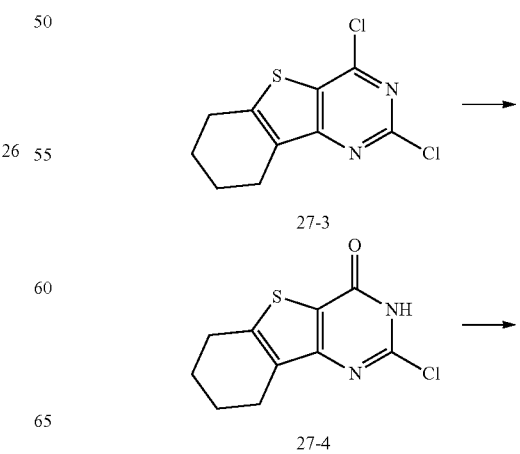

-continued
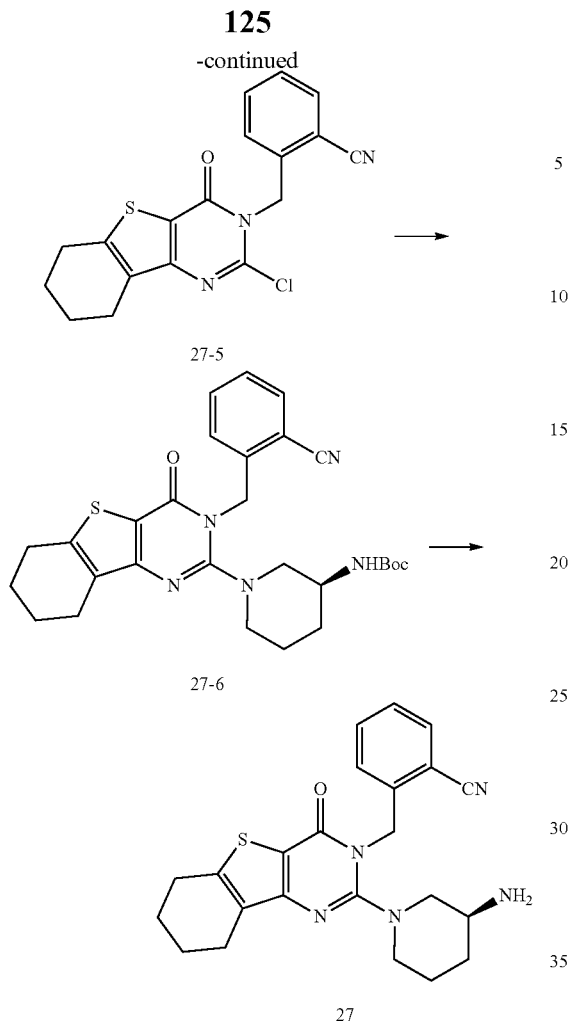
Compound 27-1 was used to replace compound 4-1 in Example 4, and compounds 27-2, 27-3, 27-4, 27-5, 27-6 and 27 were synthesized according to the synthesis methods of compounds 4-2, 4-4, 4-5, 4-6, 4-7, and 4, respectively, thereby obtaining compound 27. MS: 420.1[M+H]$^+$. $^1$H-NMR(400 MHz, CDCl$_3$): δ 7.69-7.60 (m, 2H), 7.52-7.31 (m, 2H), 5.56-5.52 (m, 1H), 5.44-5.40 (m, 1H), 3.35-3.25 (m, 3H), 3.02-2.85 (m, 5H), 2.74-2.68 (m, 3H), 2.21 (t, J=7.6 Hz, 1H), 2.02-1.97 (m, 2H), 1.64-1.58 (m, 3H).
Example 28
Synthesis of Compound 28
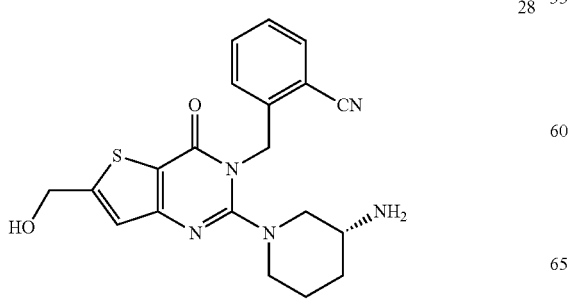
Synthesis route:
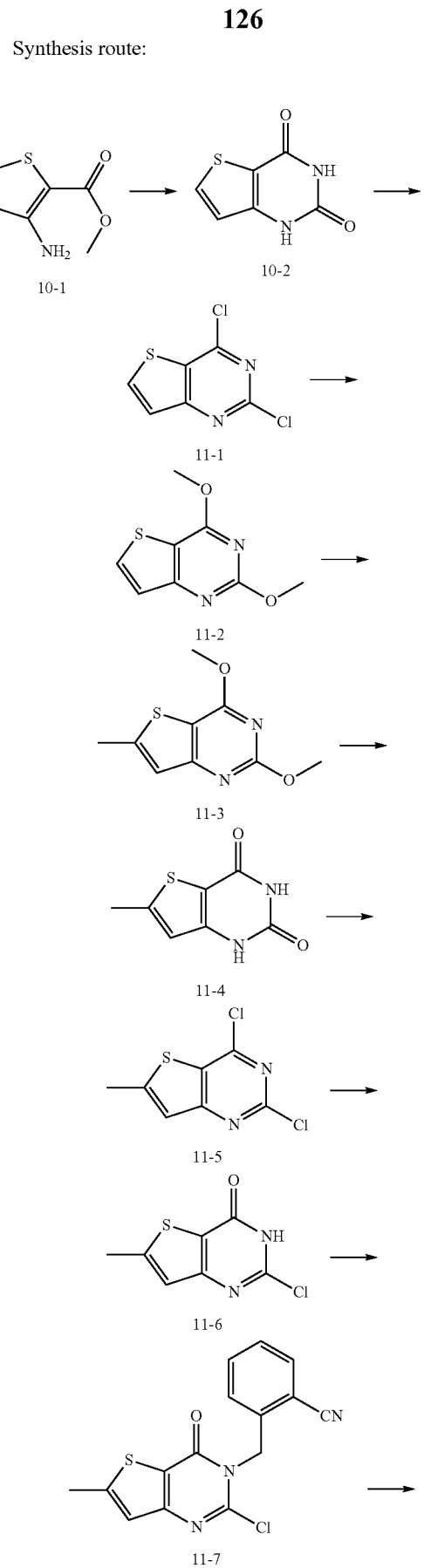

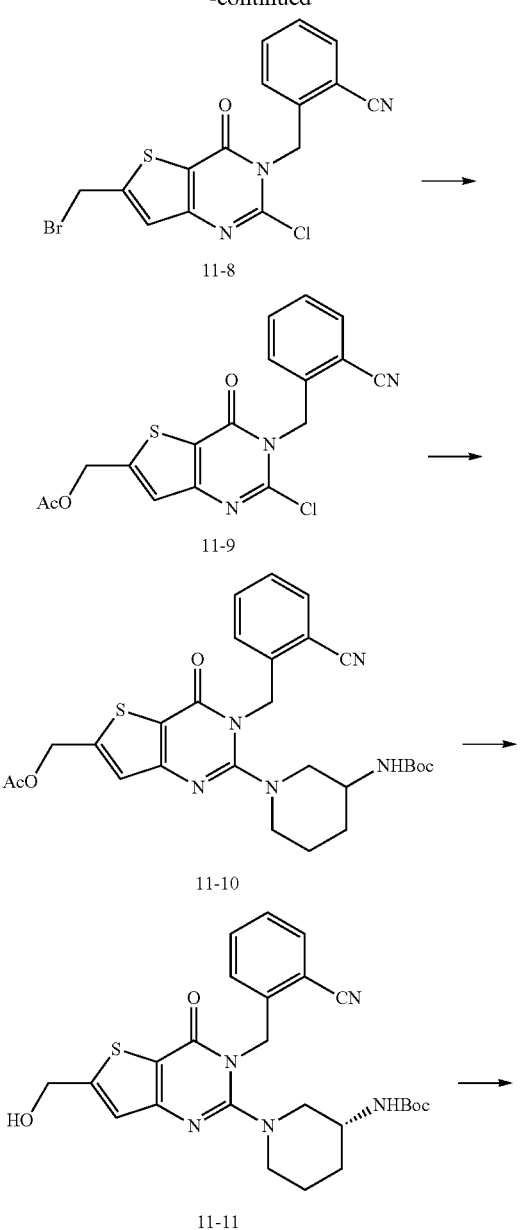

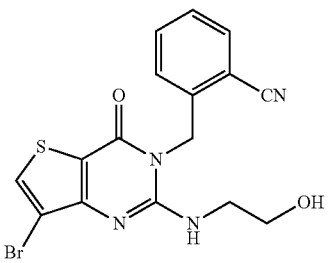

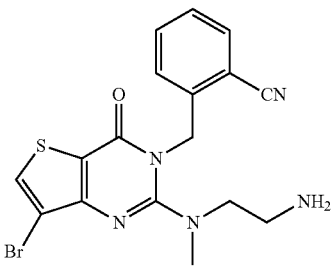

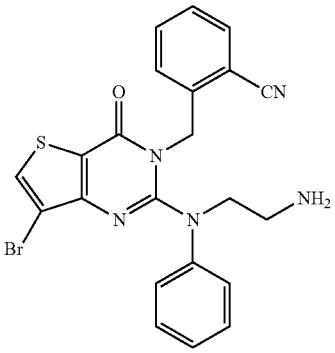

Compound 28 was synthesized from compound 11-11 according to the synthesis of compound 1 from the reaction of compound 1-6. MS: 396.0[M+H]⁺. ¹H-NMR(400 Hz, CDCl₃): δ1.25(1H, m), 1.67(1H, m), 1.76(1H, m), 1.96(1H, m), 2.67(1H, m), 2.88(2H, m), 3.21(1H, m), 3.39(1H, m), 3.89(2H, s), 5.52(2H, s), 6.50(1H, s), 7.03(1H, d, J=8), 7.31(1H, t, J=8), 7.46(1H, t, J=8), 7.62(1H, d, J=7.2).

Example 29

Synthesis of Compound 29

Compound 29 was synthesized according to the synthesis method of compound 4, wherein 2-aminoethanol was used instead of R-3Boc aminopiperidine. MS: 406.9[M+H]⁺.

Example 30

Synthesis of Compound 30

Compound 30 was synthesized according to the synthesis method of compound 4, wherein N¹-methyl-N²—BOC ethylenediamine was used instead of R-3Boc aminopiperidine. MS: 420.0[M+H]⁺.

Example 31

Synthesis of Compound 31

Compound 31 was synthesized according to the synthesis method of compound 4, wherein [(2-aminophenyl)ethyl]-carbamic acid tert-butyl ester was used instead of R-3Boc aminopiperidine. MS: 482.0[M+H]⁺.

Example 32

Synthesis of Compound 32

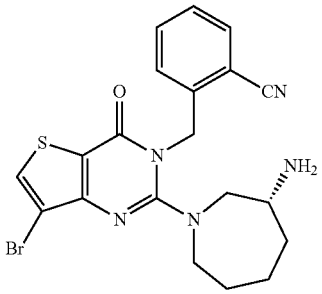

Compound 32 was synthesized according to the synthesis method of compound 4, wherein R-3-Boc amino-cycloheptylamine was used instead of R-3Boc aminopiperidine. MS: 460.0[M+H]⁺.

Example 33

Synthesis of Compound 33

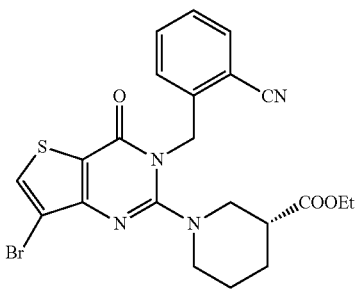

Compound 33 was synthesized according to the synthesis method of compound 4, wherein ethyl 3-piperidinecarboxylate was used instead of R-3Boc aminopiperidine. MS: 503.0 [M+H]⁺.

Example 34

Synthesis of Compound 34

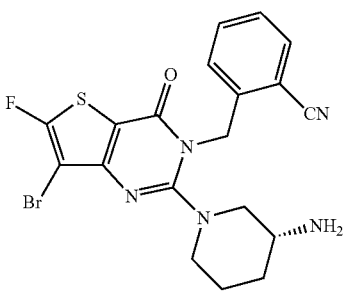

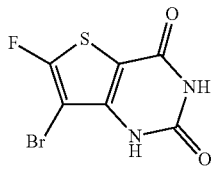

Compound 34 was synthesized according to the synthesis method of compound 1, wherein compound 34-2 was used instead of compound 1-2. MS: 464.0[M+H]⁺. ¹H-NMR(400 Hz, CDCl₃): δ1.25(1H, m), 1.67(1H, m), 1.76(1H, m), 1.96 (1H, m), 2.67(1H, m), 2.88(2H, m), 3.21(1H, m), 3.39(1H, m), 5.52(2H, s), 7.03(1H, d, J=8), 7.31(1H, t, J=8), 7.46(1H, t, J=8), 7.62(1H, d, J=7.2).

Example 35

Synthesis of Compound 35

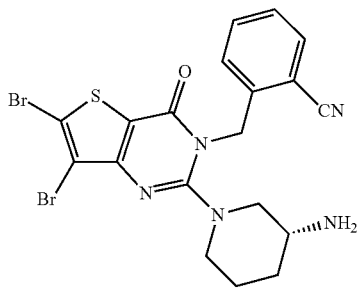

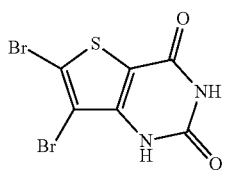

Compound 35 was synthesized according to the synthesis method of compound 1, wherein compound 35-2 was used instead of compound 1-2. MS: 523.9[M+H]⁺. ¹H-NMR(400 Hz, CDCl₃): δ1.25(1H, m), 1.67(1H, m), 1.76(1H, m), 1.96 (1H, m), 2.67(1H, m), 2.88(2H, m), 3.21(1H, m), 3.39(1H, m), 5.59(2H, s), 7.08(1H, d, J=8), 7.36(1H, t, J=8), 7.42(1H, t, J=8), 7.67(1H, d, J=7.2).

Example 36

Synthesis of Compound 36

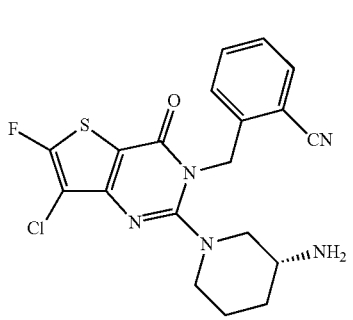

-continued

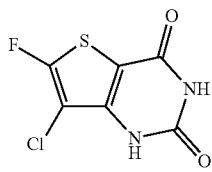

36-2

Compound 36 was synthesized according to the synthesis method of compound 1, wherein compound 36-2 was used instead of compound 1-2. MS: 418.0[M+H]$^+$. $^1$H-NMR(400 Hz, CDCl$_3$): δ1.25(1H, m), 1.67(1H, m), 1.76(1H, m), 1.96(1H, m), 2.67(1H, m), 2.88(2H, m), 3.21(1H, m), 3.39(1H, m), 5.59(2H, s), 7.04(1H, d, J=8), 7.33(1H, t, J=8), 7.40(1H, t, J=8), 7.61(1H, d, J=7.2).

Example 37

Synthesis of Compound 37

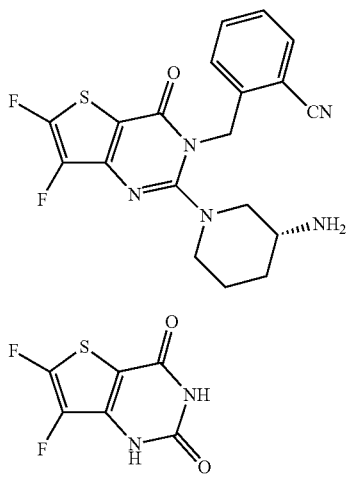

37

37-2

Compound 37 was synthesized according to the synthesis method of compound 1, wherein compound 37-2 was used instead of compound 1-2. MS: 402.1[M+H]$^+$. $^1$H-NMR(400 Hz, CDCl$_3$): δ1.25(1H, m), 1.67(1H, m), 1.76(1H, m), 1.96(1H, m), 2.67(1H, m), 2.88(2H, m), 3.21(1H, m), 3.39(1H, m), 5.59(2H, s), 7.07(1H, d, J=8), 7.35(1H, t, J=8), 7.42(1H, t, J=8), 7.65(1H, d, J=7.2).

Example 38

Synthesis of Compound 38

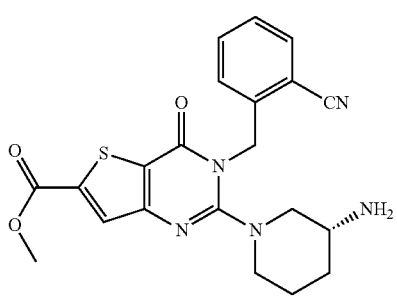

38

Synthesis route:

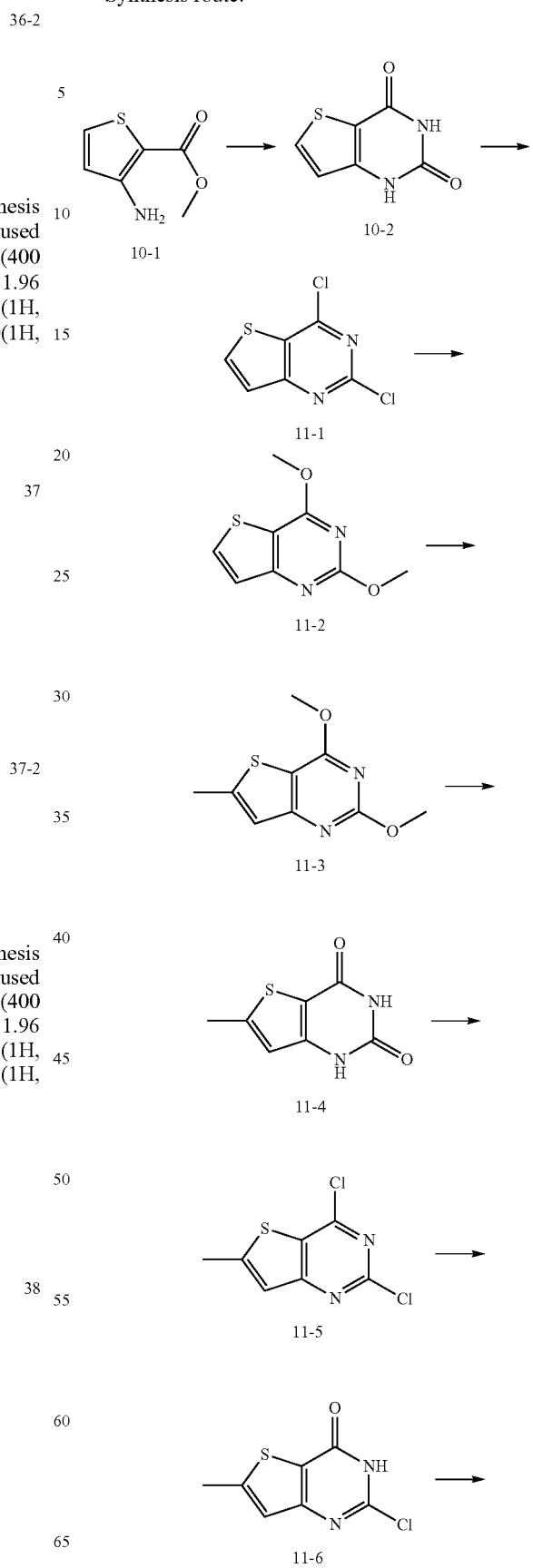

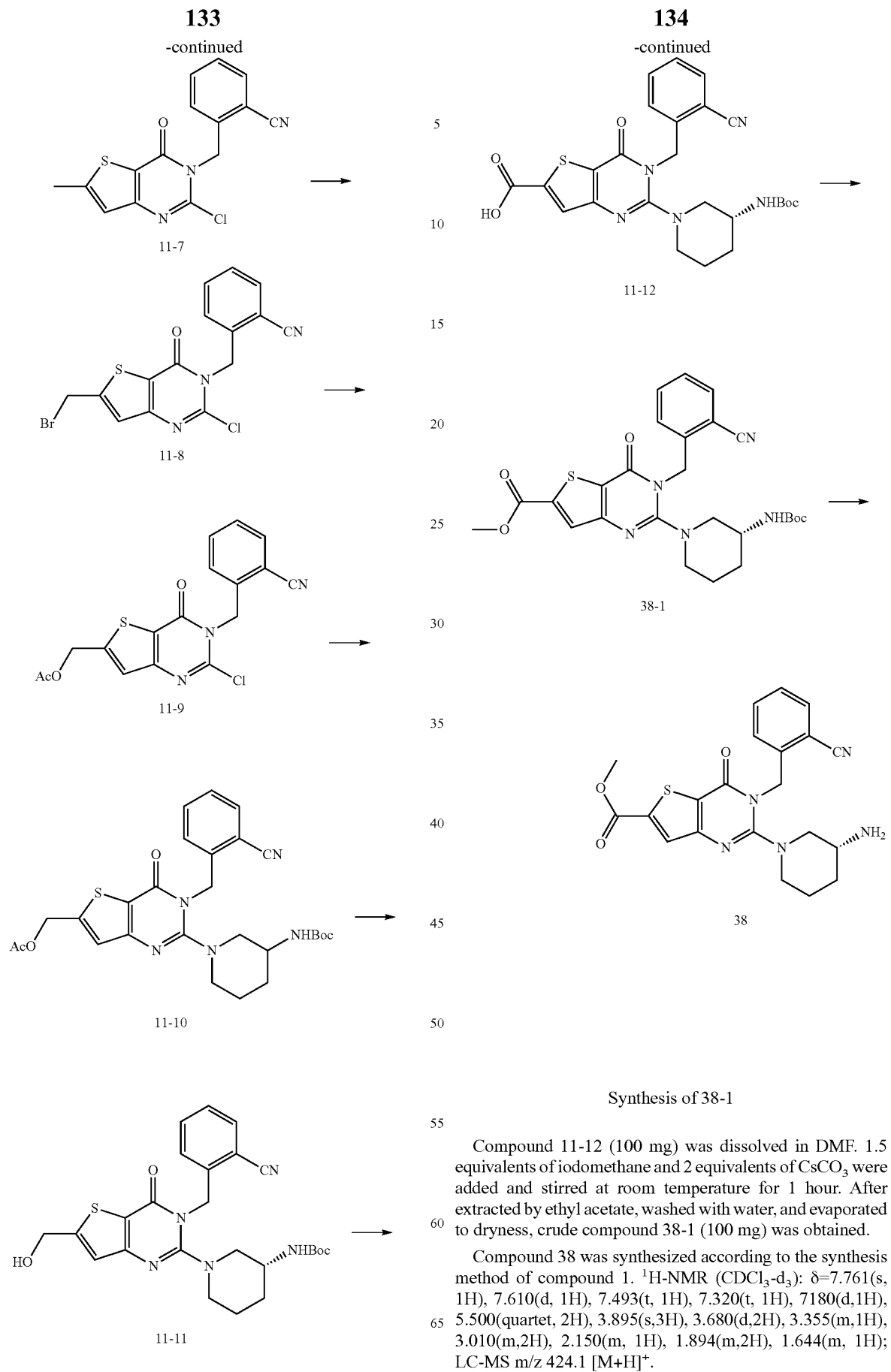

Synthesis of 38-1

Compound 11-12 (100 mg) was dissolved in DMF. 1.5 equivalents of iodomethane and 2 equivalents of CsCO$_3$ were added and stirred at room temperature for 1 hour. After extracted by ethyl acetate, washed with water, and evaporated to dryness, crude compound 38-1 (100 mg) was obtained.

Compound 38 was synthesized according to the synthesis method of compound 1. $^1$H-NMR (CDCl$_3$-d$_3$): δ=7.761(s, 1H), 7.610(d, 1H), 7.493(t, 1H), 7.320(t, 1H), 7180(d,1H), 5.500(quartet, 2H), 3.895(s,3H), 3.680(d,2H), 3.355(m,1H), 3.010(m,2H), 2.150(m, 1H), 1.894(m,2H), 1.644(m, 1H); LC-MS m/z 424.1 [M+H]$^+$.

Example 39
Synthesis of Compound 39
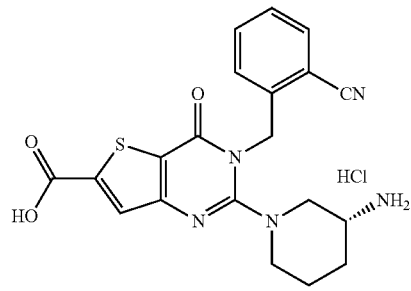
Synthesis route:
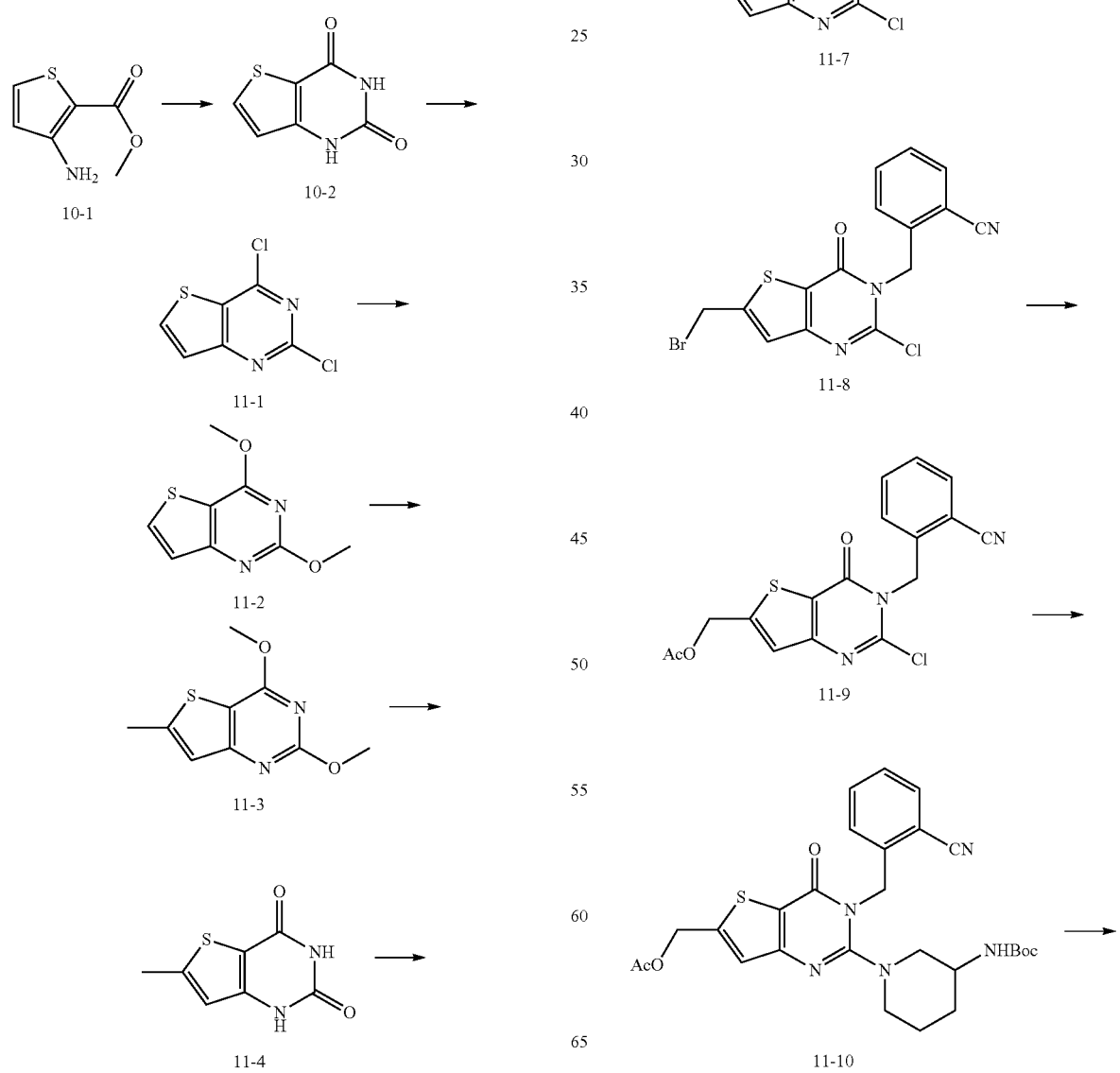

-continued
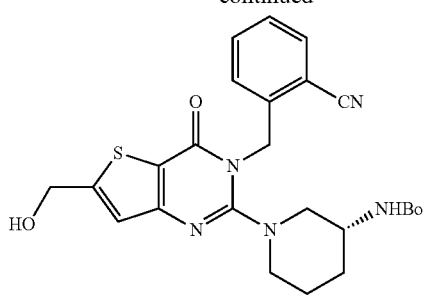
11-11
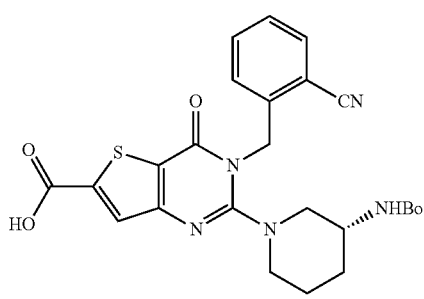
11-12
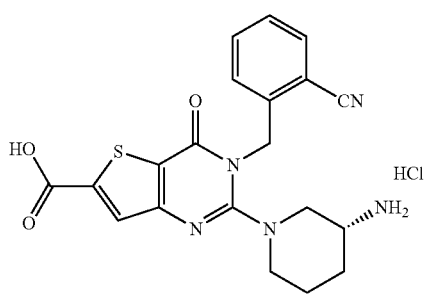
39
Compound 11-12 (100 mg, 0.237 mmol) was dissolved in 20 ml HCl in diethyl ether and stirred at room temperature for 1 hour. After evaporated to dryness, compound 39 (70 mg) was obtained in 80% yield. MS: 410.1[M+H]⁺.
Example 40
Synthesis of Compound 40
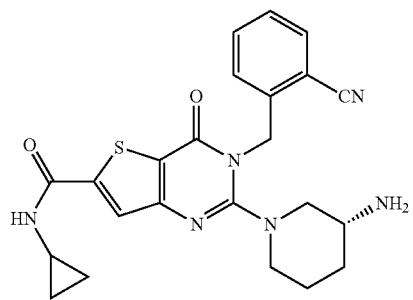
40
Synthesis route:
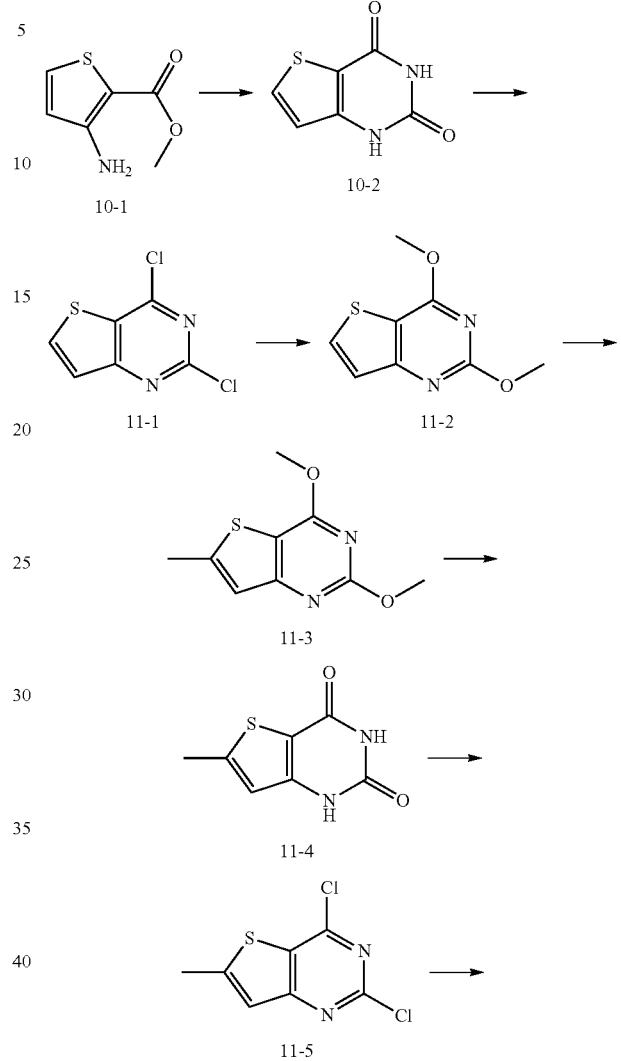
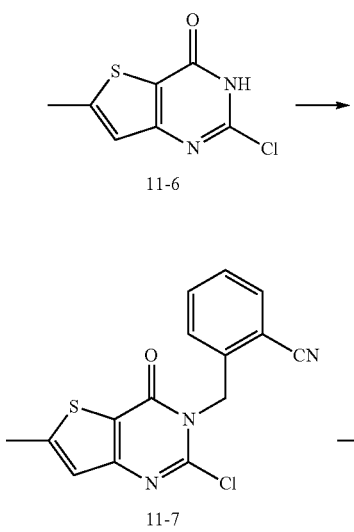

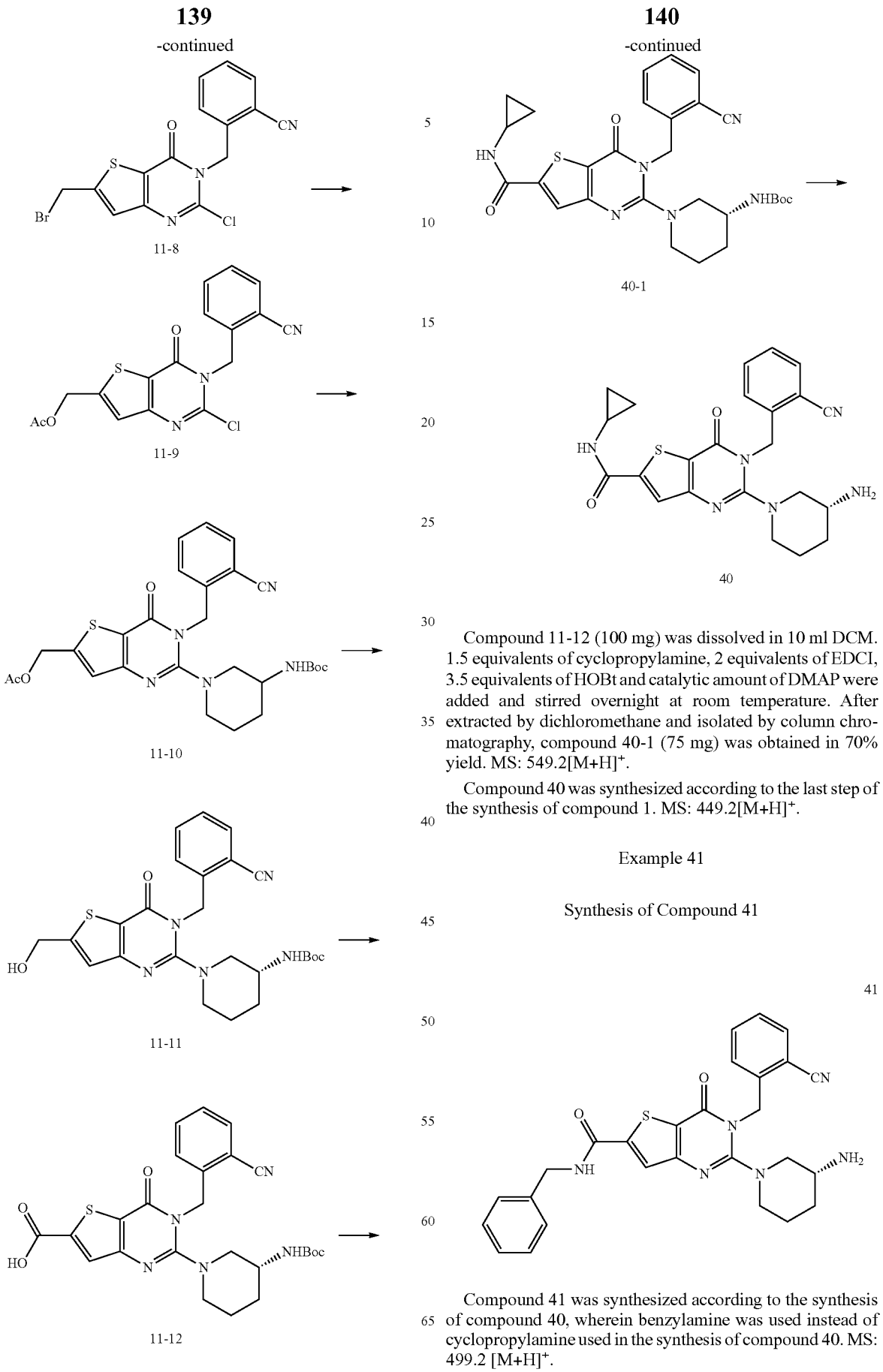

Compound 11-12 (100 mg) was dissolved in 10 ml DCM. 1.5 equivalents of cyclopropylamine, 2 equivalents of EDCI, 3.5 equivalents of HOBt and catalytic amount of DMAP were added and stirred overnight at room temperature. After extracted by dichloromethane and isolated by column chromatography, compound 40-1 (75 mg) was obtained in 70% yield. MS: 549.2[M+H]$^+$.

Compound 40 was synthesized according to the last step of the synthesis of compound 1. MS: 449.2[M+H]$^+$.

Example 41

Synthesis of Compound 41

Compound 41 was synthesized according to the synthesis of compound 40, wherein benzylamine was used instead of cyclopropylamine used in the synthesis of compound 40. MS: 499.2 [M+H]$^+$.

141
Example 42
Synthesis of Compound 42
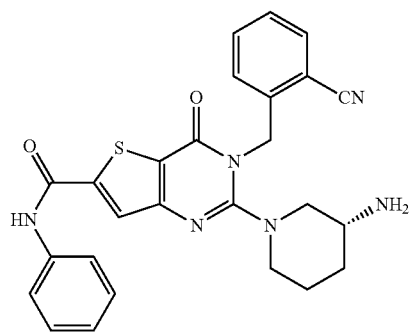
Compound 41 was synthesized according to the synthesis of compound 40, wherein phenylamine was used instead of cyclopropylamine used in the synthesis of compound 40. MS: 485.1[M+H]$^+$.
Example 43
Synthesis of Compound 43
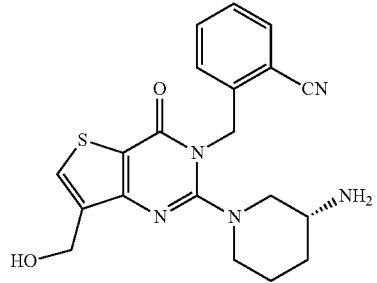
Synthesis route:
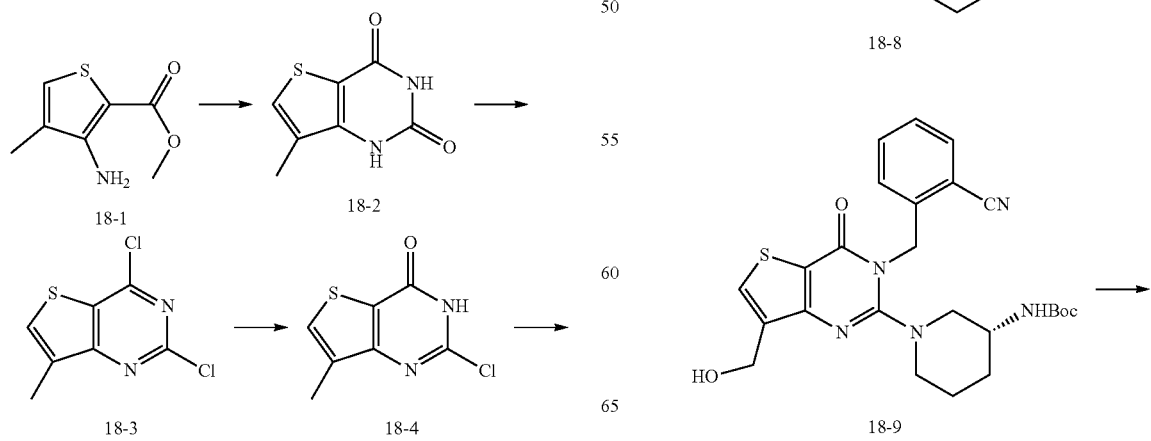

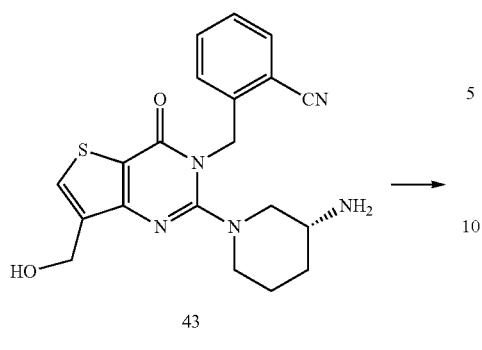
43
Compound 43 was obtained according to the synthesis of compound 28. $^1$H NMR(CDCl$_3$): δ7.64(m, 2H), 7.52(t, J=7.6 HZ, 1H), 7.37(t, J=7.6 HZ, 1H), 7.23(m, 1H), 5.25-5.72(m, 2H), 4.72(m, 2H), 3.51(m, 2H), 3.31(m, 3H), 1.95(m, 2H), 1.75(m, 1H), 1.56(m, 1H); LC-MS m/z 396.1 [M+H]$^+$.
Example 44
Synthesis of Compound 44
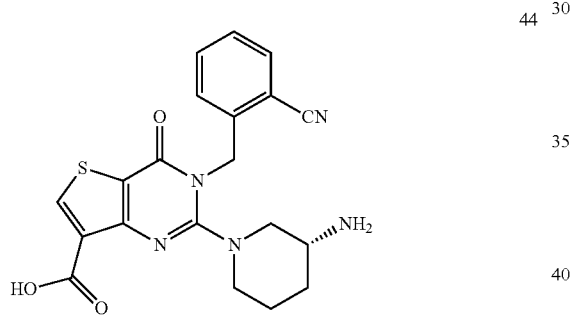
44
Synthesis route:
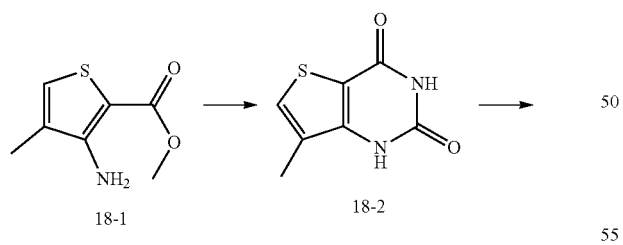
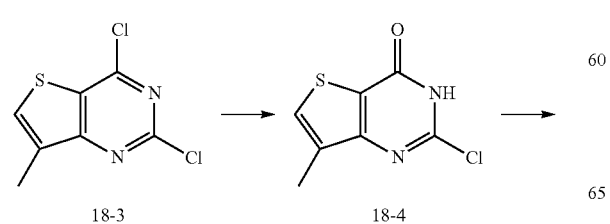
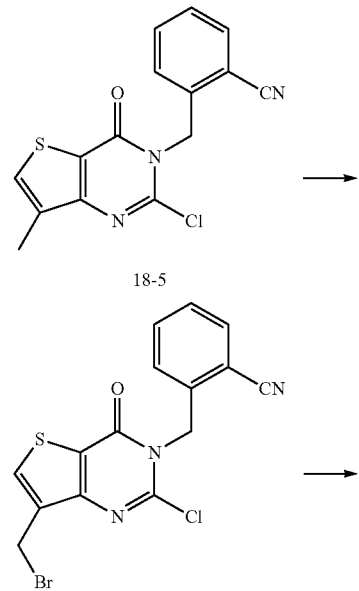
18-5
18-6
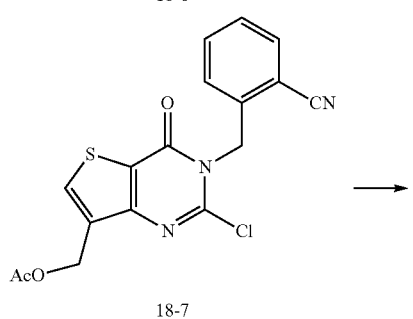
18-7
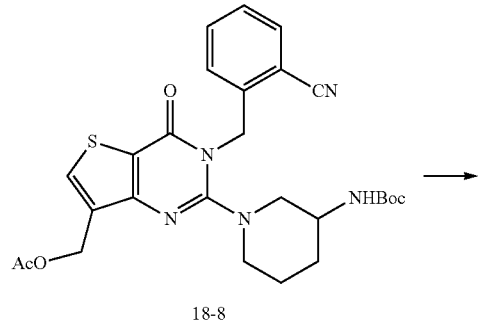
18-8
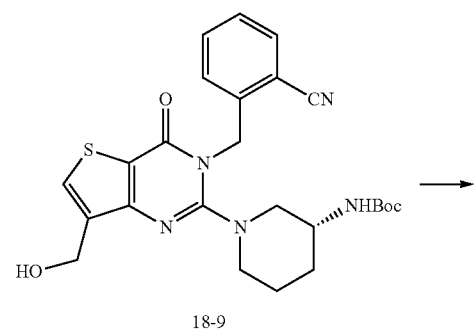
18-9

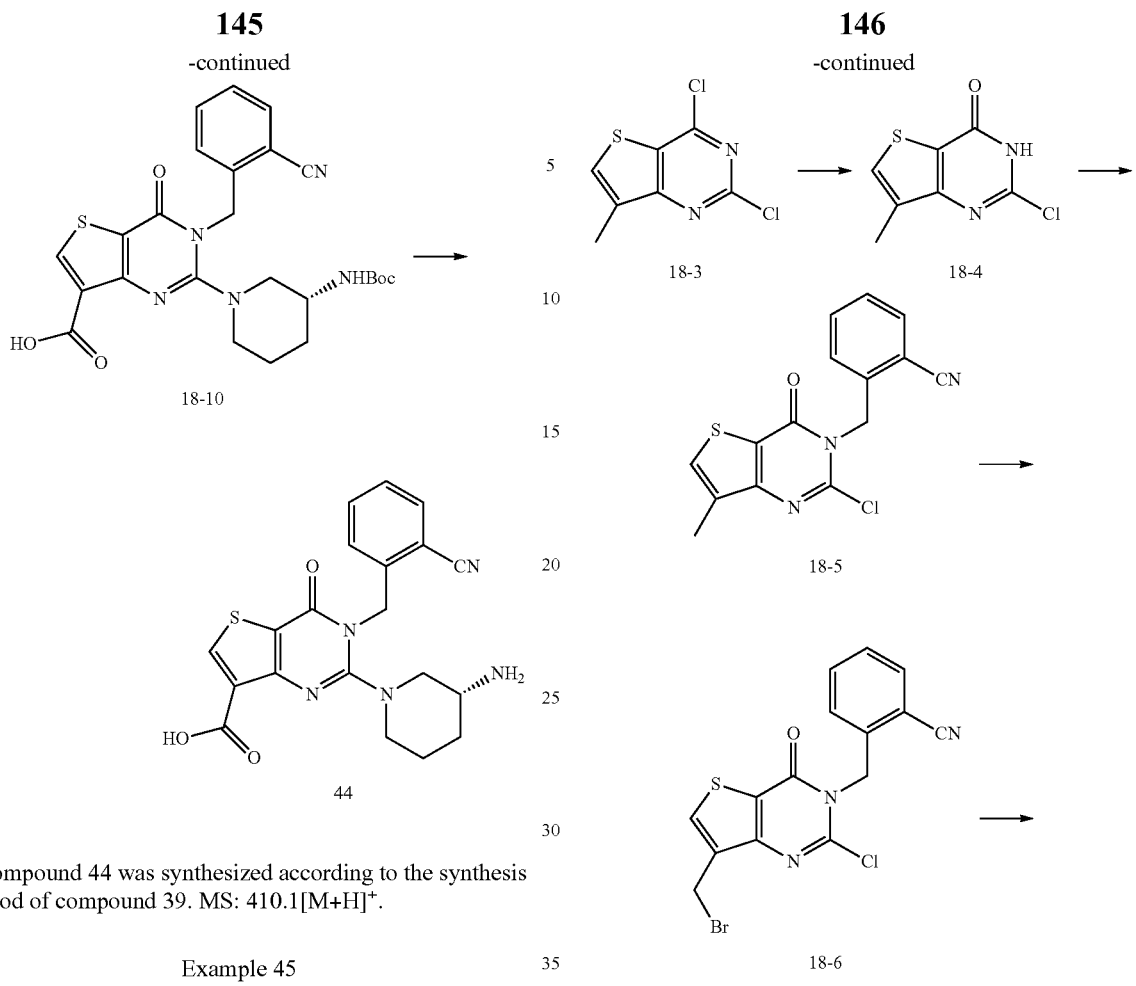
Compound 44 was synthesized according to the synthesis method of compound 39. MS: 410.1[M+H]⁺.
Example 45
Synthesis of Compound 45
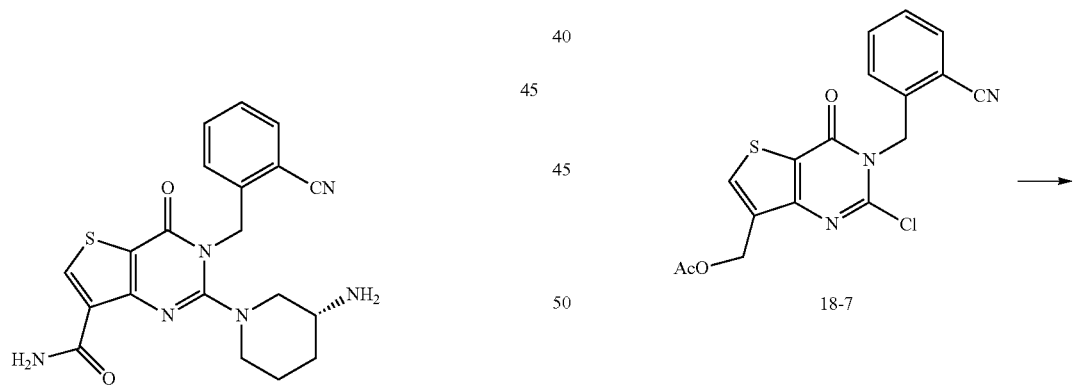
Synthesis route:
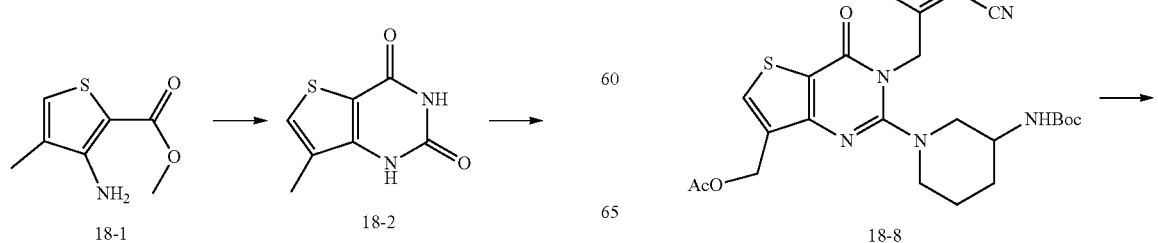

-continued

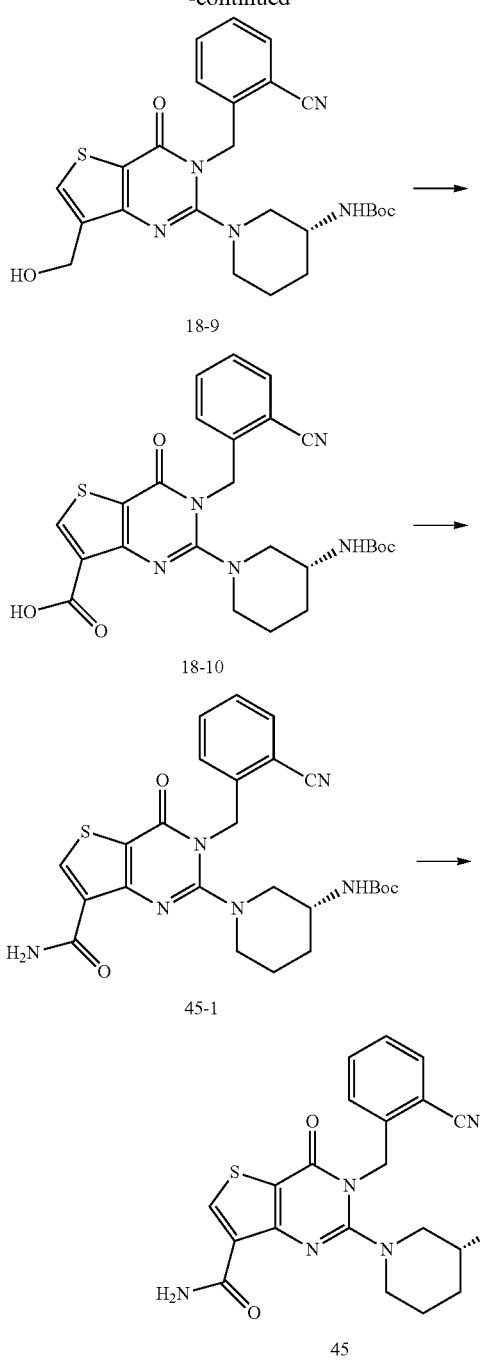

Synthesis of 45-1

Compound 18-10 (100 mg) was dissolved in 20 ml acetonitrile. 1.5 equivalents of di-tert-butyl dicarbonate, 1.5 equivalents of ammonium carbonate and 1.5 equivalents of pyridine were added and stirred overnight at room temperature. After extracted by ethyl acetate, washed with 1M hydrochloric acid, washed with water, evaporated to dryness and isolated by the column chromatography, a white foam-like solid 45-1 (80 mg) was obtained in 81% yield. MS: 509.1[M+H]$^+$.

Compound 45 was synthesized according to the synthesis method of compound 1. MS: 409.1 [M+H]$^+$.

Example 46

Synthesis of Compound 46

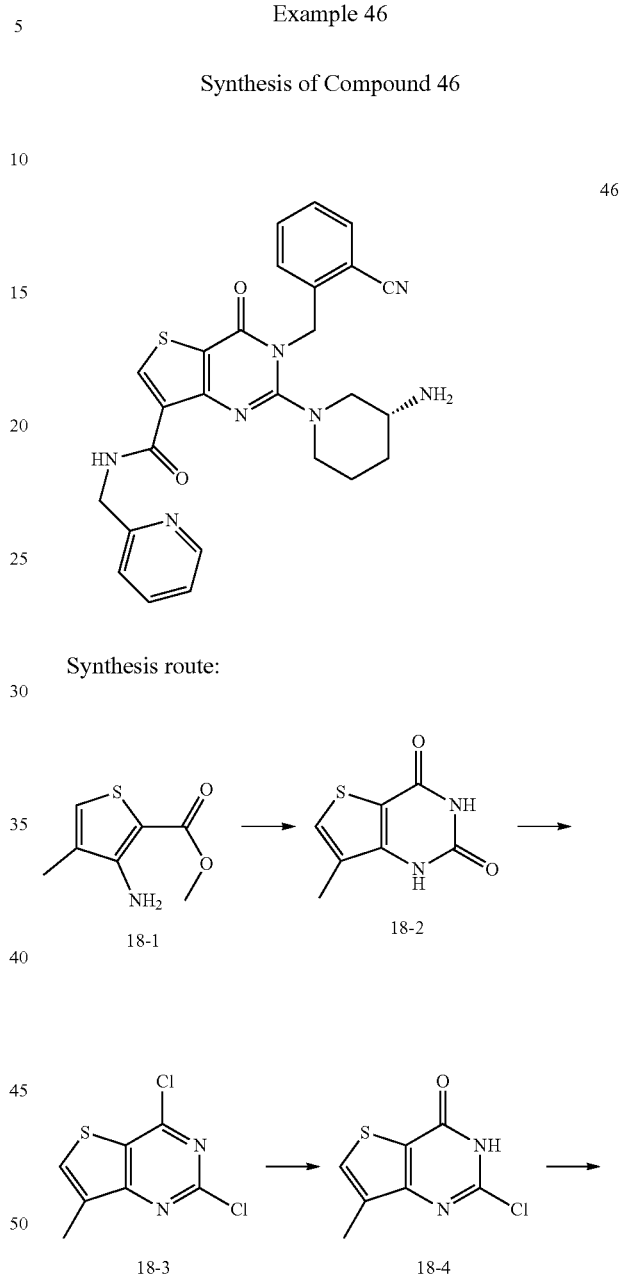

Synthesis route:

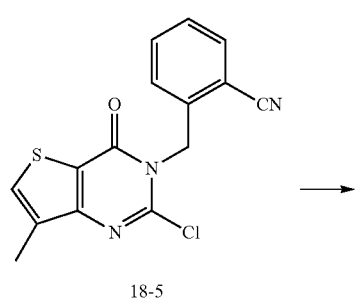

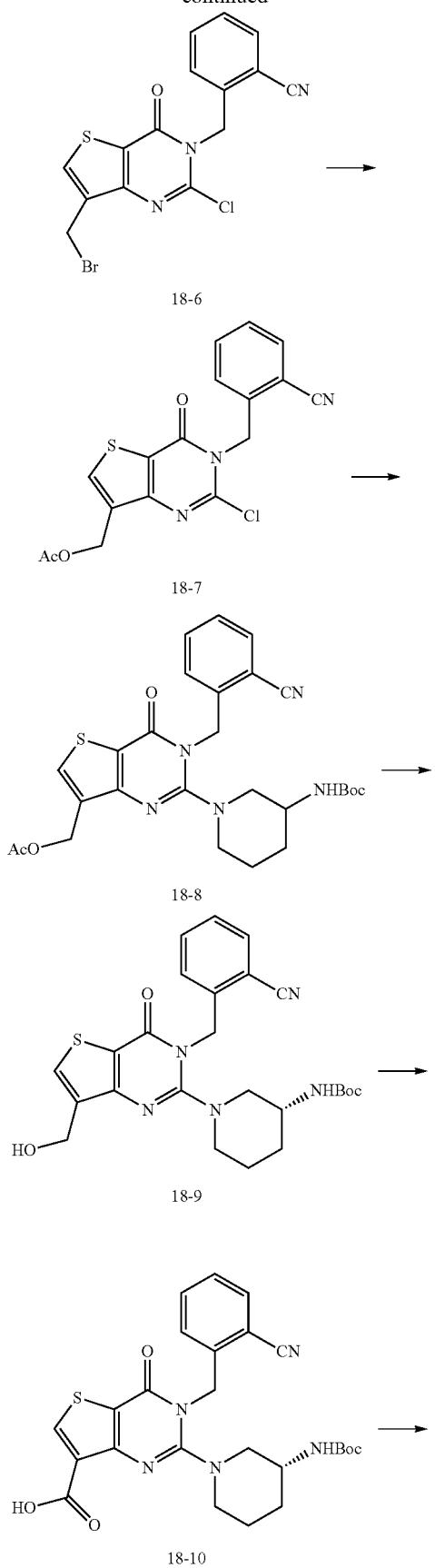
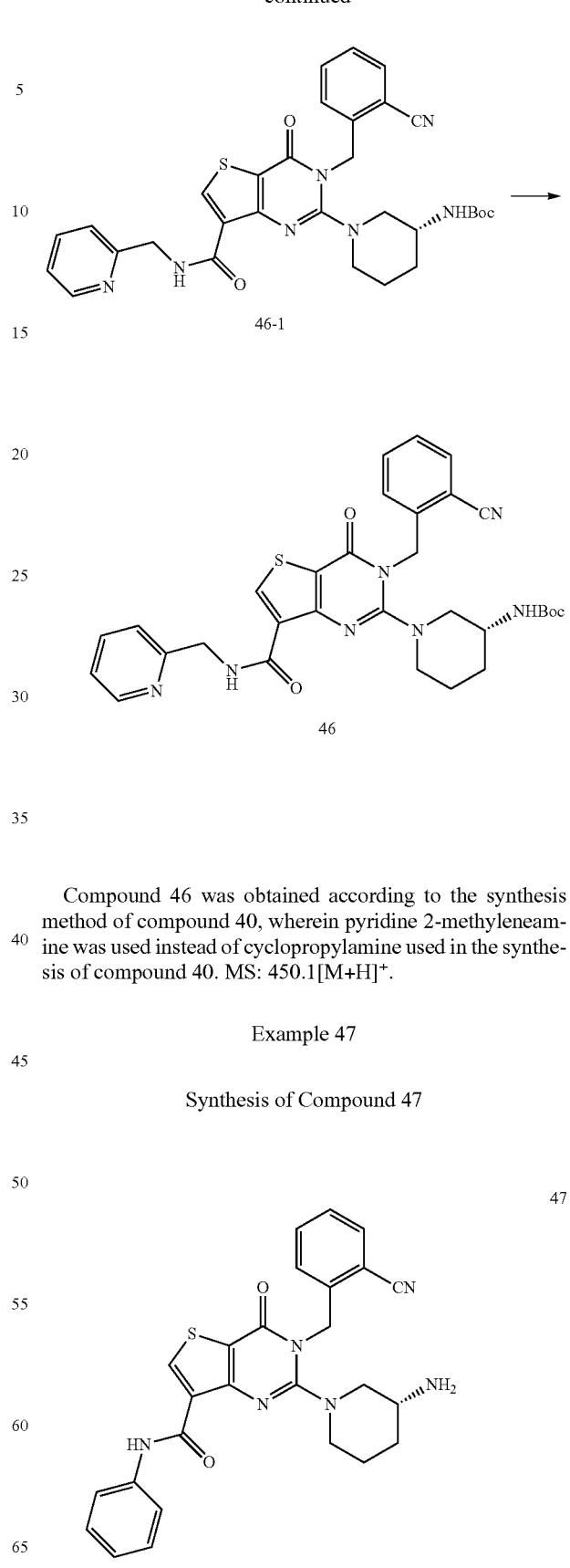
Compound 46 was obtained according to the synthesis method of compound 40, wherein pyridine 2-methyleneamine was used instead of cyclopropylamine used in the synthesis of compound 40. MS: 450.1[M+H]⁺.
Example 47
Synthesis of Compound 47

Compound 47 was synthesized according to the synthesis of compound 46, wherein phenylamine was used instead of pyridine 2-methyleneamine used in the synthesis of compound 46. MS: 484.2[M+H]⁺.

Example 48

Synthesis of Compound 48

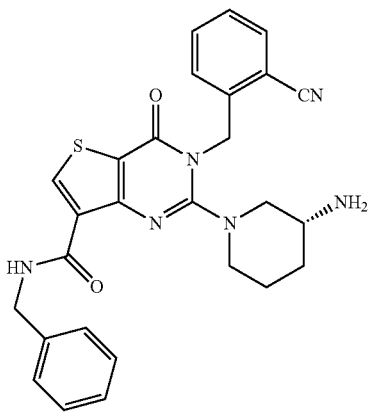
48

Compound 48 was synthesized according to the synthesis of compound 46, wherein benzylamine was used instead of pyridine 2-methyleneamine used in the synthesis of compound 46. MS: 499.2[M+H]⁺.

Example 49

Synthesis of Compound 49

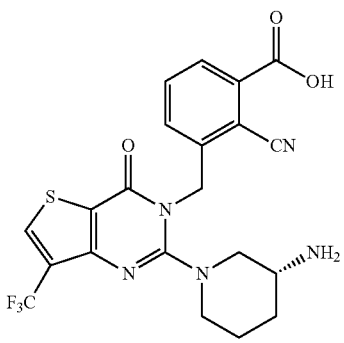
49

Compound 49 was obtained according to the synthesis of compound 7, wherein 3-bromomethyl-2cyano benzoic acid was used instead of 2-bromomethyl benzonitrile used in the synthesis of compound 7. MS: 478.1[M+H]⁺.

Example 50

Synthesis of Compound 50

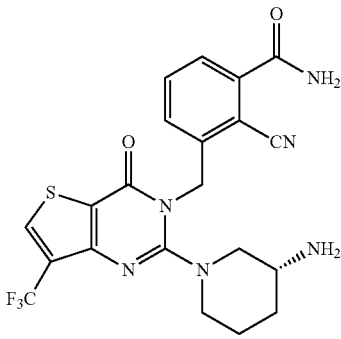
50

Compound 50 was obtained according to the synthesis of compound 7, wherein 3-bromomethyl-2cyano benzamide was used instead of 2-bromomethyl benzonitrile used in the synthesis of compound 7. MS: 477.1[M+H]⁺.

Example 51

Synthesis of Compound 51

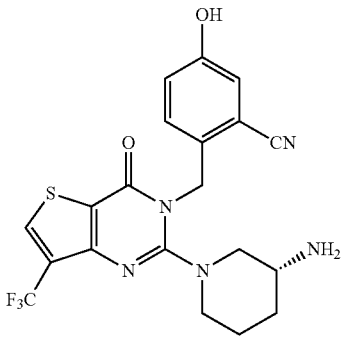
51

Compound 51 was obtained according to the synthesis of compound 7, wherein 2-bromomethyl-5-hydroxy benzonitrile was used instead of 2-bromomethyl benzonitrile used in the synthesis of compound 7. MS: 450.1[M+H]⁺.

Example 52

Synthesis of Compound 52

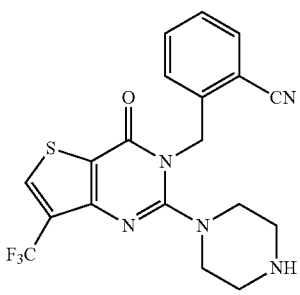
52

Compound 52 was obtained according to the synthesis of compound 7, wherein 4-Boc piperazine was used instead of R-3Boc aminopiperidinel used in the synthesis of compound 7. MS: 420.1 [M+H]⁺.

Example 53

Synthesis of Compound 53

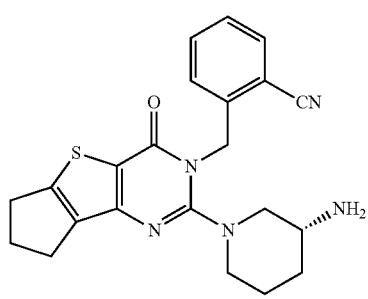

53

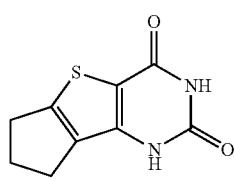

53-2

Compound 53 was synthesized according to the synthesis method of compound 27, wherein compound 53-2 was used instead of compound 27-2. MS: 406.2[M+H]⁺.

Example 54

Synthesis of Compound 54

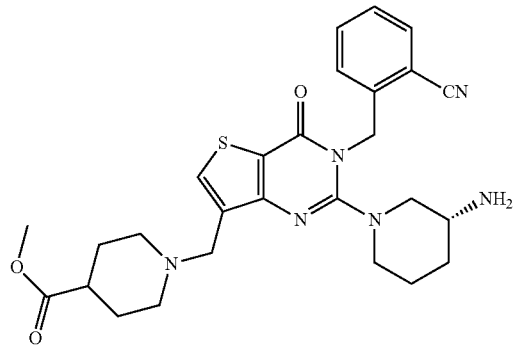

54

Compound 54 was obtained according to the synthesis of compound 18, wherein methyl piperidine-4-carboxylate was used instead of methylamine solution in tetrahydrofuran in the synthesis of compound 18. MS: 521.2[M+H]⁺.

Example 55

Synthesis of Compound 55

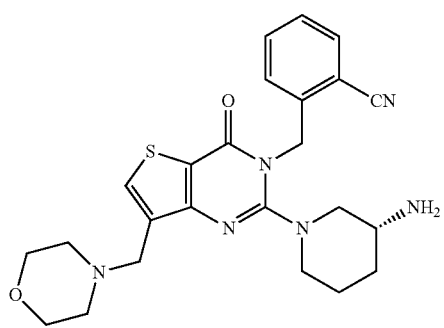

55

Compound 55 was synthesized according to the synthesis of compound 18, wherein morpholine was used instead of methylamine solution in tetrahydrofuran in the synthesis of compound 18. MS: 465.2[M+H]⁺.

Example 56

Synthesis of Compound 56

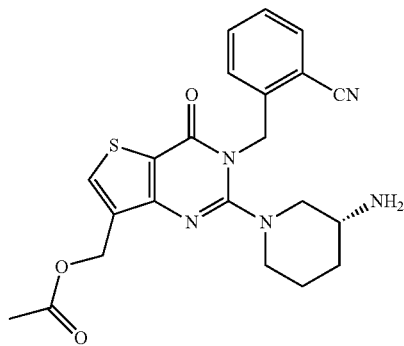

56

Synthesis route:

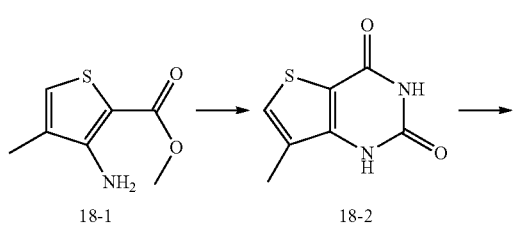

18-1  18-2

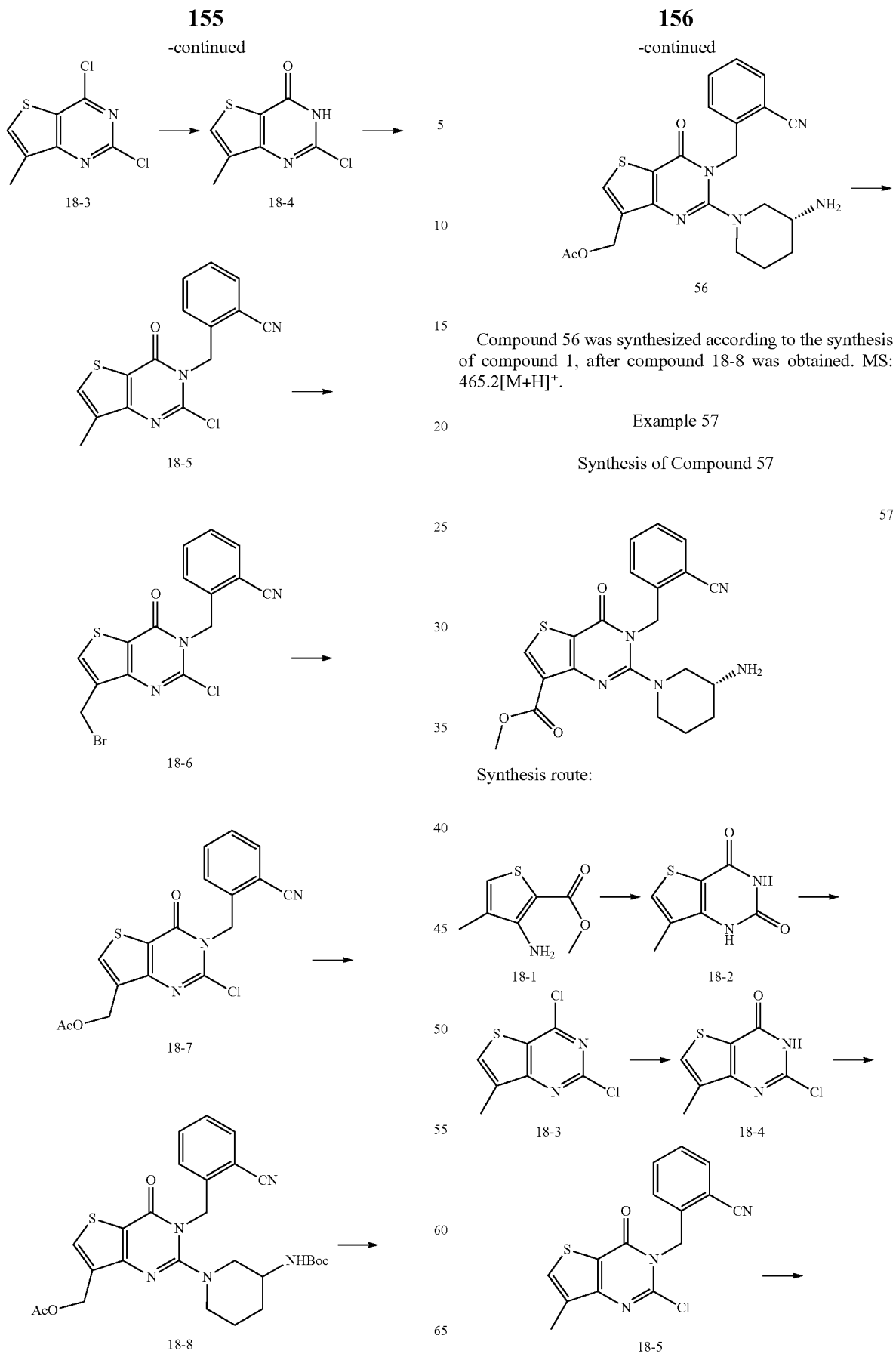
Compound 56 was synthesized according to the synthesis of compound 1, after compound 18-8 was obtained. MS: 465.2[M+H]$^+$.
Example 57
Synthesis of Compound 57
Synthesis route:

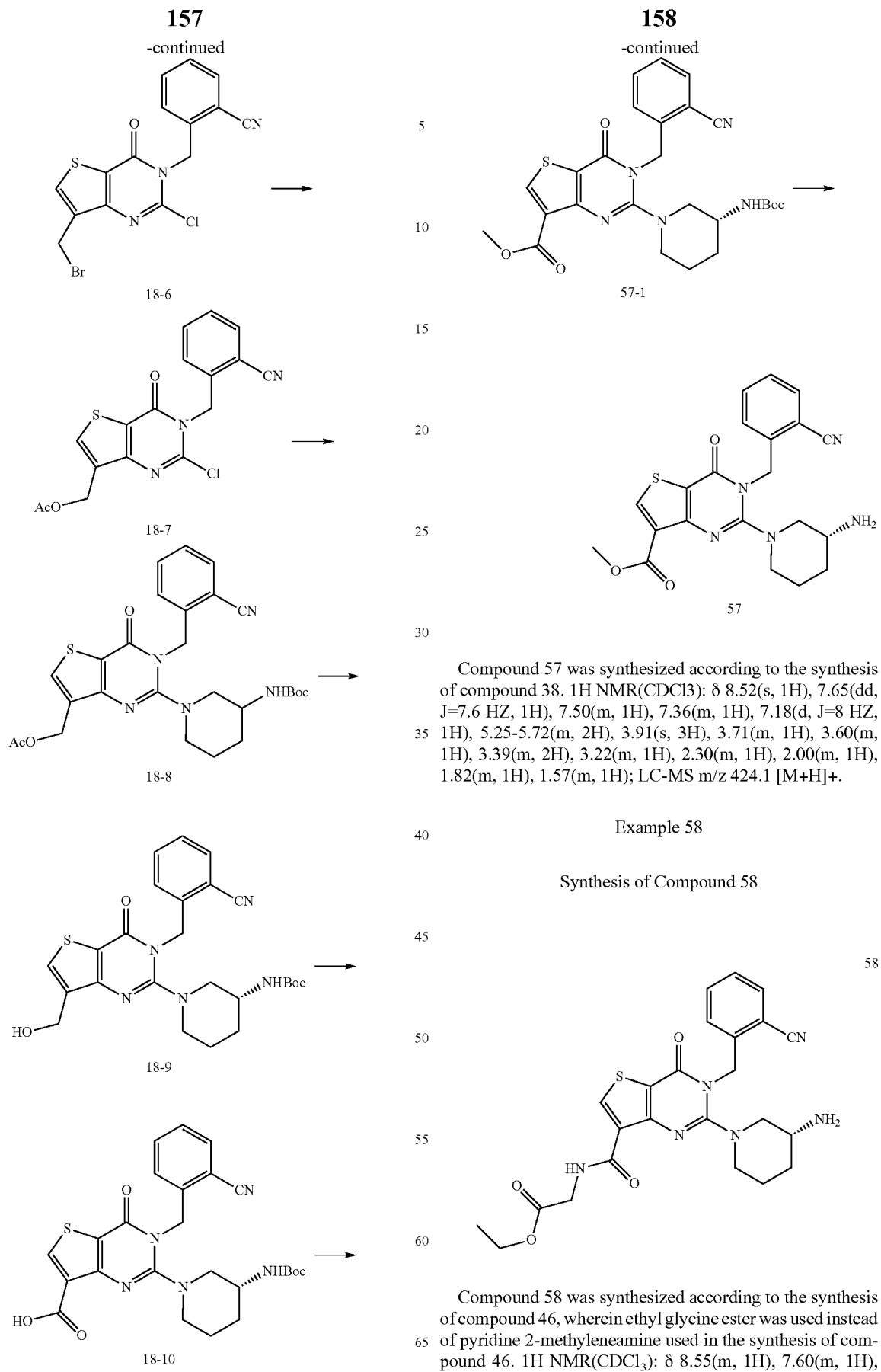

Compound 57 was synthesized according to the synthesis of compound 38. 1H NMR(CDCl3): δ 8.52(s, 1H), 7.65(dd, J=7.6 HZ, 1H), 7.50(m, 1H), 7.36(m, 1H), 7.18(d, J=8 HZ, 1H), 5.25-5.72(m, 2H), 3.91(s, 3H), 3.71(m, 1H), 3.60(m, 1H), 3.39(m, 2H), 3.22(m, 1H), 2.30(m, 1H), 2.00(m, 1H), 1.82(m, 1H), 1.57(m, 1H); LC-MS m/z 424.1 [M+H]+.

Example 58

Synthesis of Compound 58

Compound 58 was synthesized according to the synthesis of compound 46, wherein ethyl glycine ester was used instead of pyridine 2-methyleneamine used in the synthesis of compound 46. 1H NMR(CDCl$_3$): δ 8.55(m, 1H), 7.60(m, 1H), 7.48(m, 1H), 7.32(m, 1H), 7.12(m, 1H), 5.43(m, 2H), 4.20(m, 4H), 3.20(m, 2H), 3.05(m, 1H), 2.87(m, 2H), 2.00(m, 1H), 1.76(m, 1H), 1.65(m, 1H), 1.35(m, 1H), 1.26(m, 3H); LC-MS m/z 495.2 [M+H]30.

2H), 3.3(m, 2H), 3.12(m, 2H), 2.80(m, 1H), 2.05(m, 1H), 1.72(m, 2H), 1.52(m, 1H); LC-MS m/z 453.2 [M+H]+.

Example 59

Synthesis of Compound 59

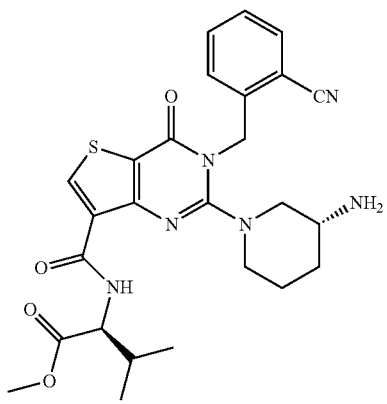

59

Compound 59 was synthesized according to the synthesis of compound 58, wherein methyl valine ester was used instead of ethyl glycine ester used in the synthesis of compound 58. 1H NMR(CDCl3): δ 9.42(d, J=8.8 HZ, 1H), 8.61 (s, 1H), 7.66(dd, J=7.6 HZ, 1H), 7.53(m, 1H), 7.37(m, 1H), 7.16(d, J=8 HZ, 1H), 5.55(m, 2H), 4.88(m, 1H), 3.76(s, 3H), 3.55(m, 1H), 3.25(m, 2H), 2.98(m, 2H), 2.05(m, 1H), 1.90(m, 1H), 1.66(m, 1H), 1.50(m, 1H), 1.01(m, 6H); LC-MS m/z 523.2 [M+H]+.

Example 60

Synthesis of Compound 60

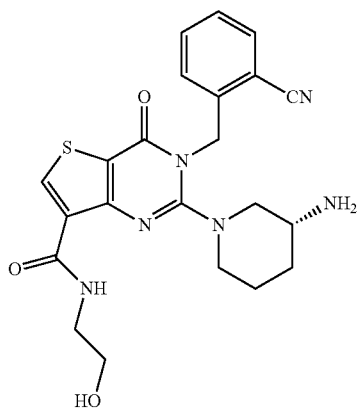

60

Compound 60 was synthesized according to the synthesis of compound 58, wherein ethanol amine was used instead of ethyl glycine ester used in the synthesis of compound 58. 1H NMR(CDCl3): δ 8.57(m, 1H), 7.62(m, 1H), 7.51(m, 1H), 7.35(m, 1H), 7.17(m, 1H), 5.43(m, 2H), 3.75(m, 2H), 3.60(m,

Example 61

Synthesis of Compound 61

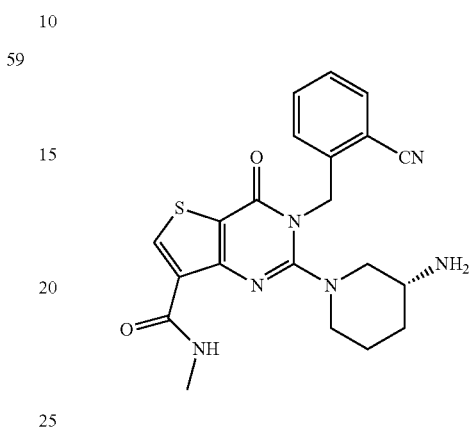

61

Compound 61 was synthesized according to the synthesis of compound 58, wherein methylamine hydrochloride was used instead of ethyl glycine ester used in the synthesis of compound 58. 1H NMR(CDCl3): δ 8.56(m, 1H), 7.62(m, 1H), 7.51(m, 1H), 7.35(m, 1H), 7.17(m, 1H), 5.45(m, 2H), 3.48(m, 1H), 3.33(m, 1H), 3.19(m, 2H), 2.99(s, 3H), 2.86(m, 1H), 2.03(m, 1H), 1.86(m, 1H), 1.70(m, 1H), 1.491(m, 1H); LC-MS m/z 423.2 [M+H]+.

Example 62

Synthesis of Compound 62

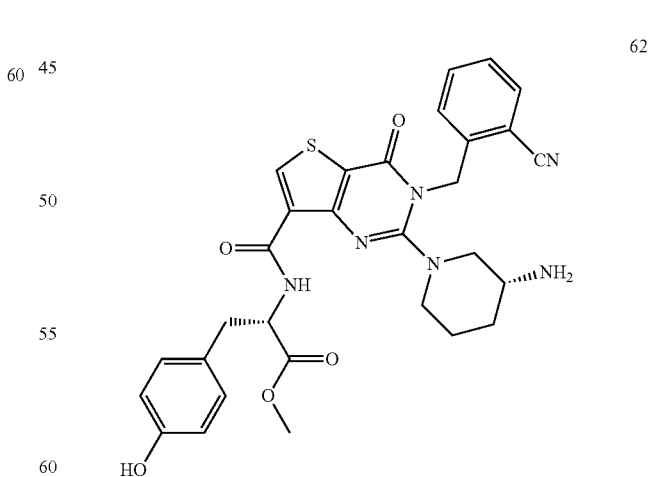

62

Compound 62 was synthesized according to the synthesis of compound 58, wherein methyl tyrosine ester was used instead of ethyl glycine ester used in the synthesis of compound 58. 1H NMR(CDCl3): δ 9.32(m, 1H), 8.57(m, 1H), 7.50(m, 2H), 7.31(m, 1H), 7.14(m, 1H), 6.75(m, 4H), 5.30(m, 3H), 3.73(m, 3H), 3.20(m, 6H), 2.86(m, 1H), 1.98(m, 1H), 1.65(m, 2H), 1.44(m, 1H); LC-MS m/z 587.2 [M+H]+.

Example 63

Synthesis of Compound 63

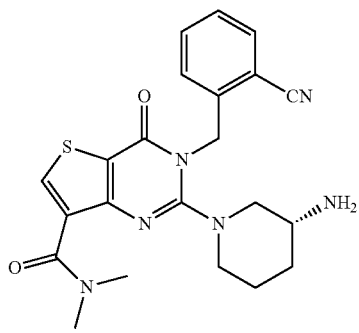

Compound 63 was synthesized according to the synthesis of compound 58, wherein dimethylamine hydrochloride was used instead of ethyl glycine ester used in the synthesis of compound 58. MS: 437.2 [M+H]+.

Example 64

Synthesis of Compound 64

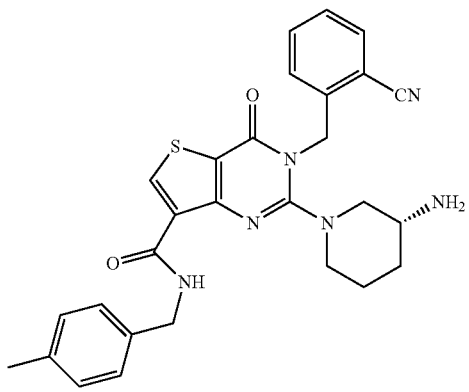

Compound 64 was synthesized according to the synthesis of compound 58, wherein 4-methylbenzylamine was used instead of ethyl glycine ester used in the synthesis of compound 58. 1H NMR(CDCl3): δ 9.19(m, 1H), 8.62(m, 1H), 7.63(m, 1H), 7.50(m, 1H), 7.30(m, 3H), 7.15(m, 3H), 5.49(s, 2H), 4.60(d, J=6.4 HZ, 2H), 3.02(m, 2H), 2.85(m, 1H), 2.55 (m, 2H), 1.85(m, 1H), 1.65(m, 1H), 1.50(m, 1H), 1.33(m, 1H); LC-MS m/z 499.2 [M+H]+.

Example 65

Synthesis of Compound 65

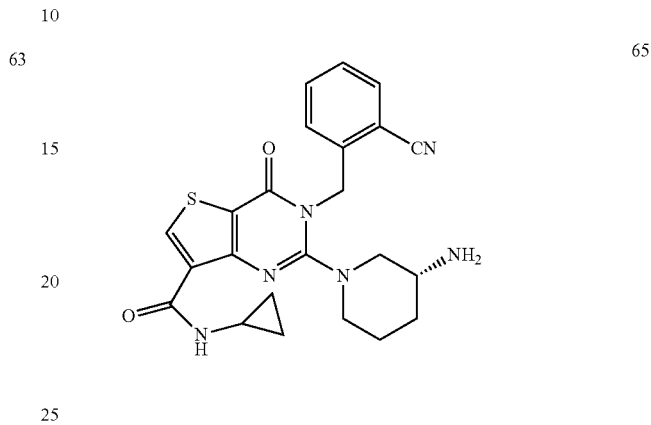

Compound 65 was synthesized according to the synthesis of compound 58, wherein cyclopropylamine was used instead of ethyl glycine ester used in the synthesis of compound 58. MS: 449.2 [M+H]+.

Example 66

Synthesis of Compound 66

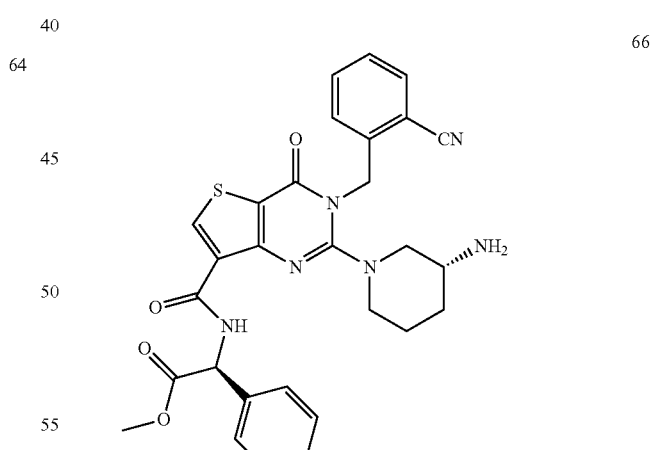

Compound 66 was synthesized according to the synthesis of compound 58, wherein methyl 2-phenylglycine ester was used instead of ethyl glycine ester used in the synthesis of compound 58. 1H NMR(CDCl3): δ 9.85(d, J=6.6 HZ, 1H), 8.58(s, 1H), 7.64(d, J=7.8 HZ, 1H), 7.50(m, 3H), 7.35(m, 4H), 7.16(m, J=6.9 HZ, 1H), 5.54(m, 2H), 5.29(m, 1H), 3.76

(s, 3H), 3.46(m, 1H), 3.20(m, 1H), 3.01(m, 1H), 2.85(m, 2H), 1.98(m, 1H), 1.81(m, 1H), 1.55(m, 2H); LC-MS m/z 557.2 [M+H]+.

Example 67

Synthesis of Compound 67

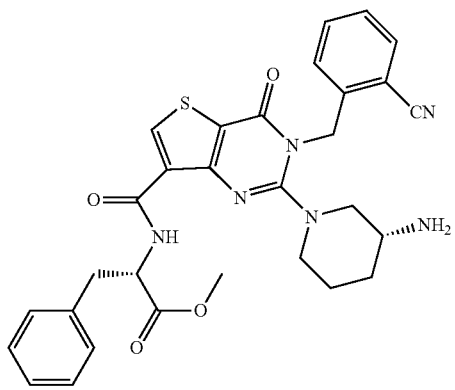

Compound 67 was synthesized according to the synthesis of compound 58, wherein methyl phenylalanine ester was used instead of ethyl glycine ester used in the synthesis of compound 58. 1H NMR(CDCl3): δ 9.31(m, 1H), 8.62(m, 1H), 7.51(m, 2H), 7.29(m, 5H), 7.07(m, 2H), 5.46(m, 2H), 5.28(m, 1H), 3.79(m, 3H), 3.22(m, 4H), 3.02(m, 1H), 2.91(m, 2H), 1.92(m, 3H), 1.47(m, 1H); LC-MS m/z 571.2 [M+H]+.

Example 68

Synthesis of Compound 68

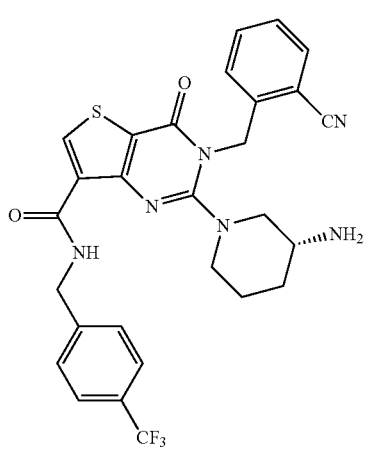

Compound 68 was synthesized according to the synthesis of compound 58, wherein p-trifluoromethyl benzylamine was used instead of ethyl glycine ester used in the synthesis of compound 58. 1H NMR(CDCl3): δ 9.31(m, 1H), 8.62(m, 1H), 7.51(m, 6H), 7.35(m, 1H), 7.14(m, 1H), 5.50(m, 2H), 4.75(m, 2H), 3.11(m, 2H), 2.90(m, 1H), 2.66(m, 2H), 1.85(m, 1H), 1.65(m, 1H), 1.55(m, 1H), 1.36(m, 1H); LC-MS m/z 567.2 [M+H]+.

Example 69

Synthesis of Compound 69

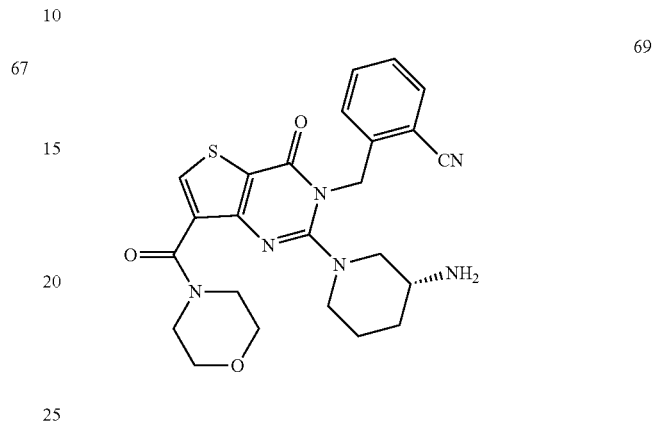

Compound 69 was synthesized according to the synthesis of compound 58, wherein morpholine was used instead of ethyl glycine ester used in the synthesis of compound 58. 1H NMR(CDCl3): δ 7.91(s, 1H), 7.62(d, J=7.6 HZ, 1H), 7.53(m, 1H), 7.35(m, 1H), 7.23(d, J=7.6 HZ, 1H), 5.50(m, 2H), 3.6 (m, 11H), 3.07(m, 1H), 2.95(m, 1H), 2.10(m, 1H), 1.83(m, 2H), 1.61(m, 1H); LC-MS m/z 479.2 [M+H]+.

Example 70

Synthesis of Compound 70

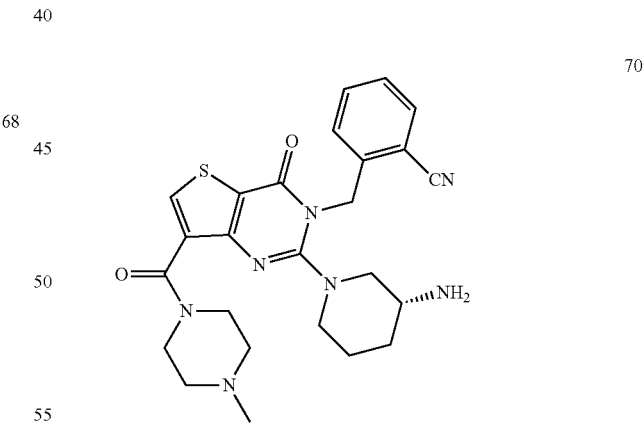

Compound 70 was synthesized according to the synthesis of compound 58, wherein 4-methylpiperazine was used instead of ethyl glycine ester used in the synthesis of compound 58. 1H NMR(CDCl3): δ 7.96(s, 1H), 7.59(d, J=7.6 HZ, 1H), 7.51(m, 1H), 7.34(m, 1H), 7.24(d, J=8.0 HZ, 1H), 5.40(m, 2H), 3.30(m, 10H), 3.07(m, 2H), 2.82(m, 1H), 2.54 (s, 3H), 2.02(m, 1H), 1.78(m, 2H), 1.62(m, 1H); LC-MS m/z 492.2 [M+H]+.

Example 71

Synthesis of Compound 71

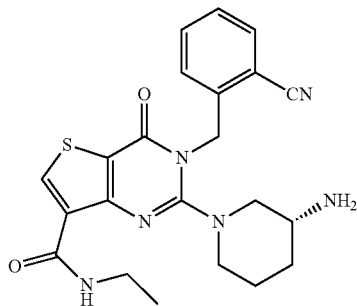

Compound 71 was synthesized according to the synthesis of compound 58, wherein ethylamine hydrochloride was used instead of ethyl glycine ester used in the synthesis of compound 58. MS: 437.2 [M+H]⁺.

Example 72

Synthesis of Compound 72

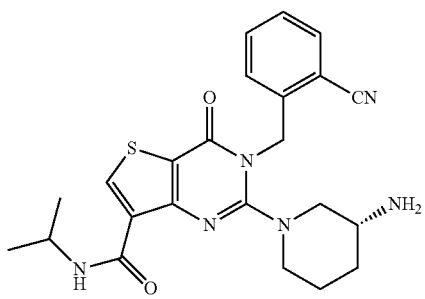

Compound 72 was synthesized according to the synthesis of compound 58, wherein isopropylamine was used instead of ethyl glycine ester used in the synthesis of compound 58. MS: 451.2 [M+H]⁺.

Example 73

Synthesis of Compound 73

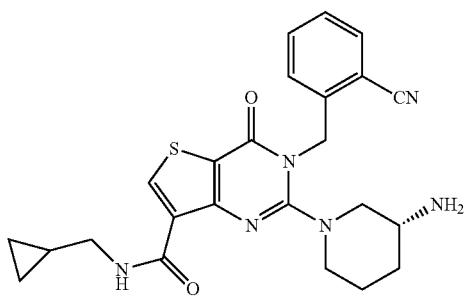

Compound 73 was synthesized according to the synthesis of compound 58, wherein cyclopropylmethylamine was used instead of ethyl glycine ester used in the synthesis of compound 58. MS: 463.2 [M+H]⁺.

Example 74

Synthesis of Compound 74

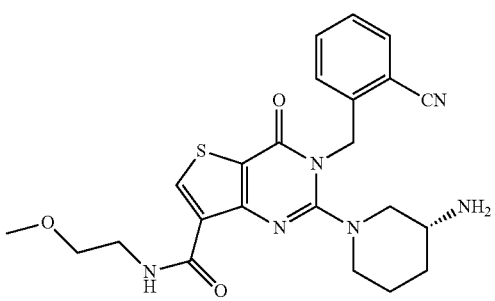

Compound 74 was synthesized according to the synthesis of compound 58, wherein 2-methoxyl ethylamine was used instead of ethyl glycine ester used in the synthesis of compound 58. MS: 467.2 [M+H]⁺.

Example 75

Synthesis of Compound 75

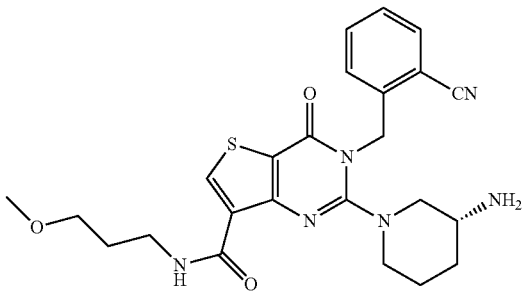

Compound 75 was synthesized according to the synthesis of compound 58, wherein 3-methoxyl propylamine was used instead of ethyl glycine ester used in the synthesis of compound 58. 1H NMR(CDCl3): δ 8.98(m, 1H), 8.60(m, 1H), 7.68(m, 1H), 7.55(m, 1H), 7.38(m, 1H), 7.16(m, 1H), 5.54(s, 2H), 3.52(m, 4H), 3.41(m, 1H), 3.34(m, 3H), 3.21(m, 1H), 3.12(m, 1H), 2.91(m, 1H), 2.78(m, 1H), 2.04(m, 1H), 1.85(m, 1H), 1.36(m, 1H); LC-MS m/z 481.2 [M+H]+.

Example 76

Synthesis of Compound 76

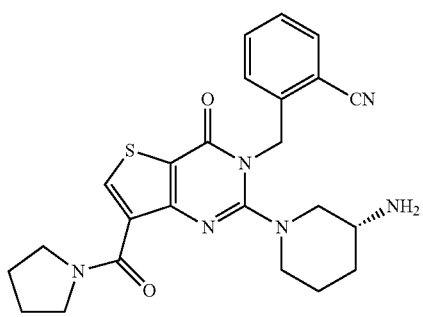

Compound 76 was synthesized according to the synthesis of compound 58, wherein pyrrolidine was used instead of ethyl glycine ester used in the synthesis of compound 58. MS: 463.2 [M+H]$^+$.

Example 77

Synthesis of Compound 77

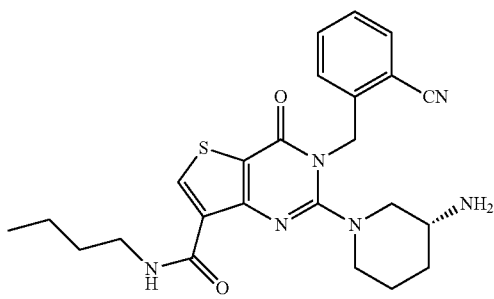 [SMILES: CCCCNC(=O)c1csc2c(=O)n(Cc3ccccc3C#N)c(N3CCC[C@@H](N)C3)nc12]

Compound 77 was synthesized according to the synthesis of compound 58, wherein n-butylamine was used instead of ethyl glycine ester used in the synthesis of compound 58. 1H NMR(CDCl3): δ 8.84(m, 1H), 8.60(m, 1H), 7.66(m, 1H), 7.53(m, 1H), 7.38(m, 1H), 7.16(m, 1H), 5.56(s, 2H), 3.50(m, 3H), 3.20(m, 2H), 2.92(m, 2H), 2.01(m, 2H), 1.63(m, 3H), 1.45(m, 3H), 0.96(m, 3H); LC-MS m/z 465.2 [M+H]+.

Example 78

Synthesis of Compound 78

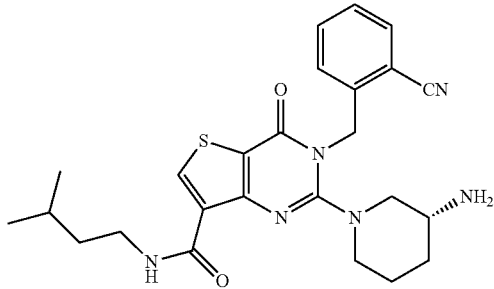 [SMILES: CC(C)CCNC(=O)c1csc2c(=O)n(Cc3ccccc3C#N)c(N3CCC[C@@H](N)C3)nc12]

Compound 78 was synthesized according to the synthesis of compound 58, wherein isopentylamine was used instead of ethyl glycine ester used in the synthesis of compound 58. 1H NMR(CDCl3): δ 8.85(m, 1H), 8.60(m, 1H), 7.66(m, 1H), 7.53(m, 1H), 7.38(m, 1H), 7.16(m, 1H), 5.55(m, 2H), 3.52(m, 2H), 3.35(m, 1H), 3.15(m, 2H), 2.91(m, 1H), 2.77(m, 1H), 2.01(m, 1H), 1.85(m, 1H), 1.71(m, 2H), 1.54(m, 2H), 1.40(m, 1H), 0.95(m, 614); LC-MS m/z 479.2 [M+H]+.

Example 79

Synthesis of Compound 79

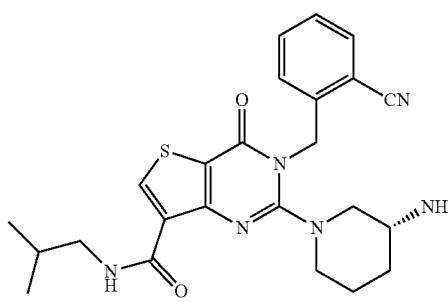

Compound 79 was synthesized according to the synthesis of compound 58, wherein iso-butylamine was used instead of ethyl glycine ester used in the synthesis of compound 58. MS: 465.2 [M+H]+.

Example 80

Synthesis of Compound 80

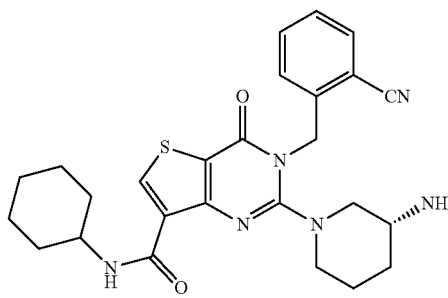

Compound 80 was synthesized according to the synthesis of compound 58, wherein cyclohexylamine was used instead of ethyl glycine ester used in the synthesis of compound 58. 1H NMR(CDCl3): δ 8.82(d, J=8.1 HZ, 1H), 8.58(s, 1H), 7.66(d, J=7.5 HZ, 1H), 7.53(m, 1H), 7.38(m, 1H), 7.14(d, J=7.5 HZ, 1H), 5.55(m, 2H), 3.98(m, 1H), 3.40(m, 1H), 3.19 (m, 2H), 2.91(m, 2H), 2.05(m, 4H), 1.75(m, 4H), 1.45(m, 3H), 1.25(m, 3H); LC-MS m/z 491.2 [M+H]+.

Example 81

Synthesis of Compound 81

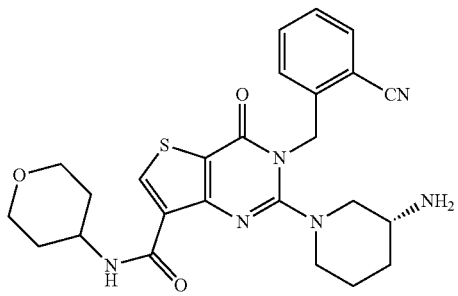

Compound 81 was synthesized according to the synthesis of compound 58, wherein 4-amino hexahydropyran was used instead of ethyl glycine ester used in the synthesis of compound 58. MS: 493.2 [M+H]+.

Example 82

Synthesis of Compound 82

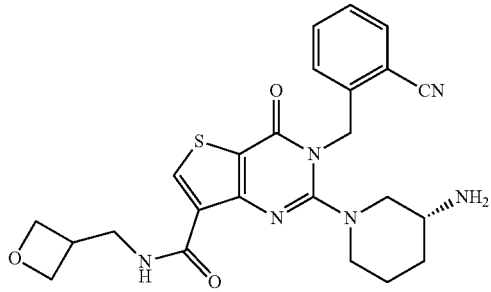

Compound 82 was synthesized according to the synthesis of compound 58, wherein 3-aminomethyl epoxypropane was used instead of ethyl glycine ester used in the synthesis of compound 58. MS: 479.2 [M+H]+.

Example 83

Synthesis of Compound 83

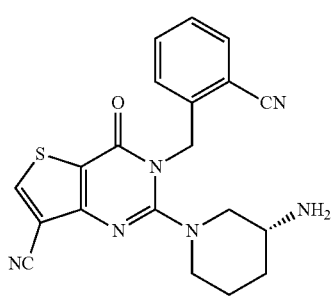

Synthesis route:

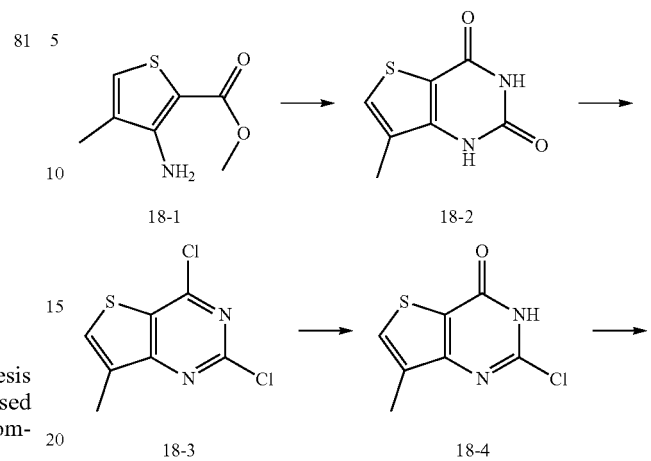

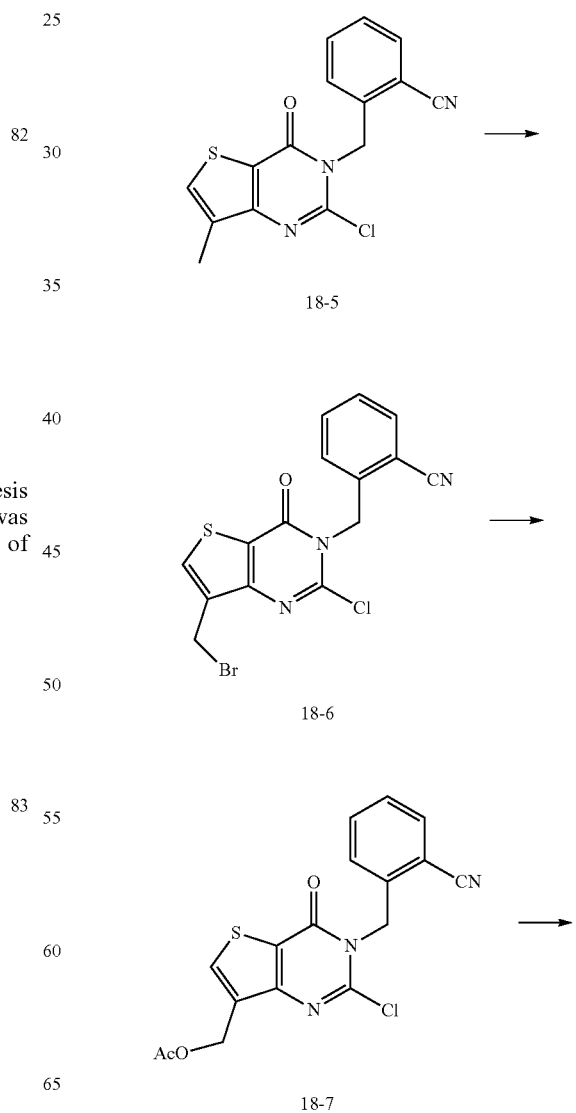

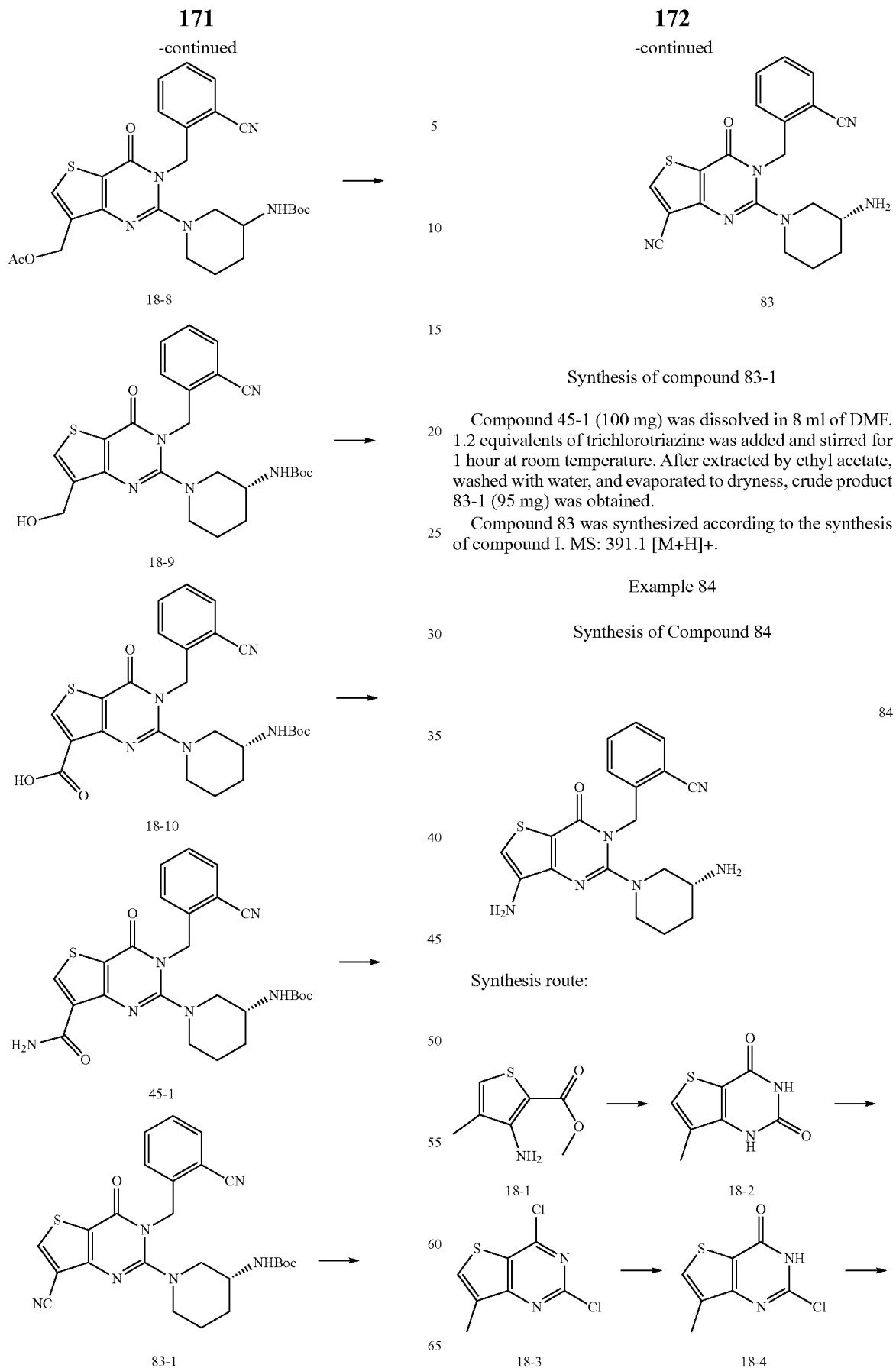

Synthesis of compound 83-1

Compound 45-1 (100 mg) was dissolved in 8 ml of DMF. 1.2 equivalents of trichlorotriazine was added and stirred for 1 hour at room temperature. After extracted by ethyl acetate, washed with water, and evaporated to dryness, crude product 83-1 (95 mg) was obtained.

Compound 83 was synthesized according to the synthesis of compound I. MS: 391.1 [M+H]+.

Example 84

Synthesis of Compound 84

Synthesis route:

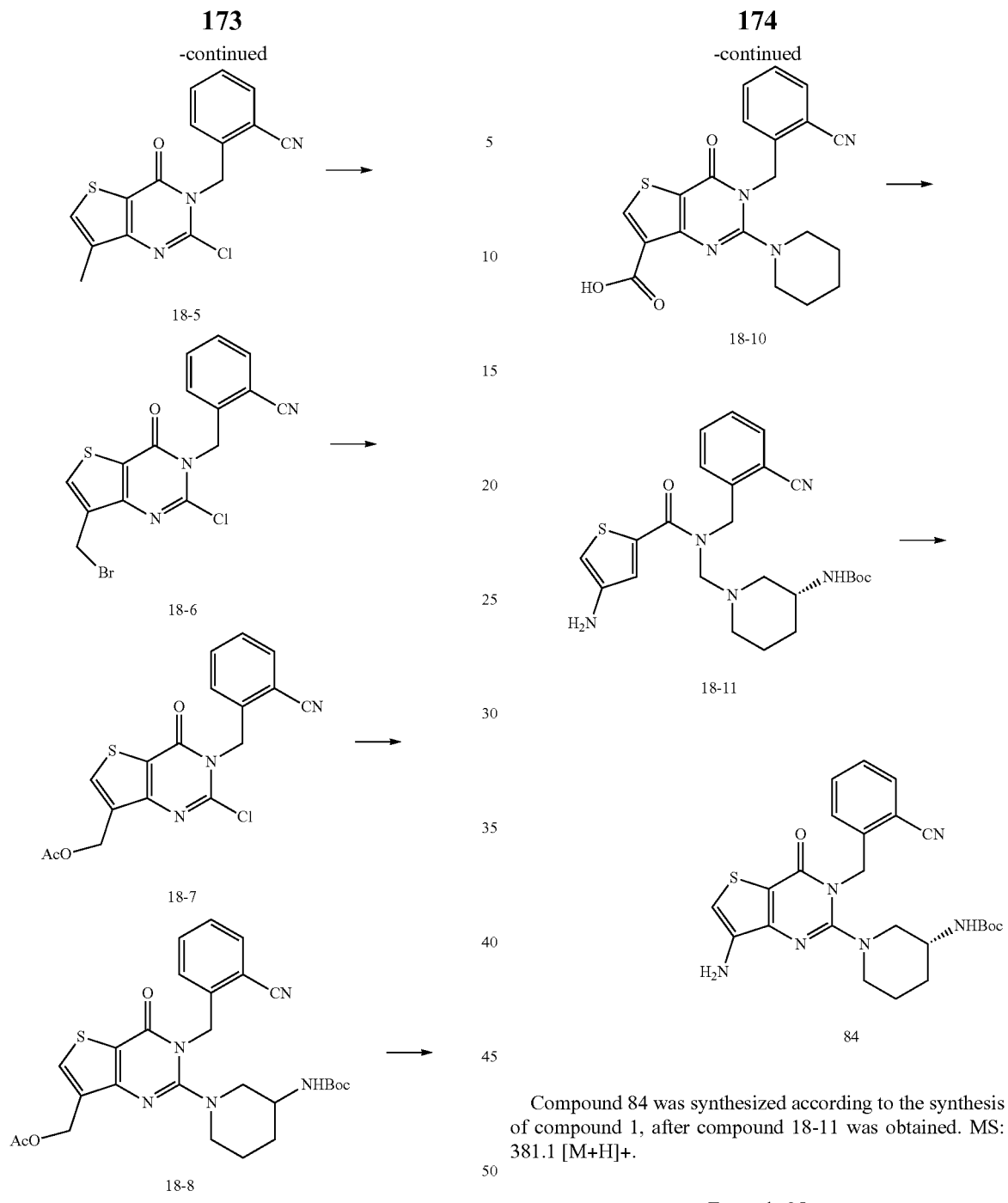
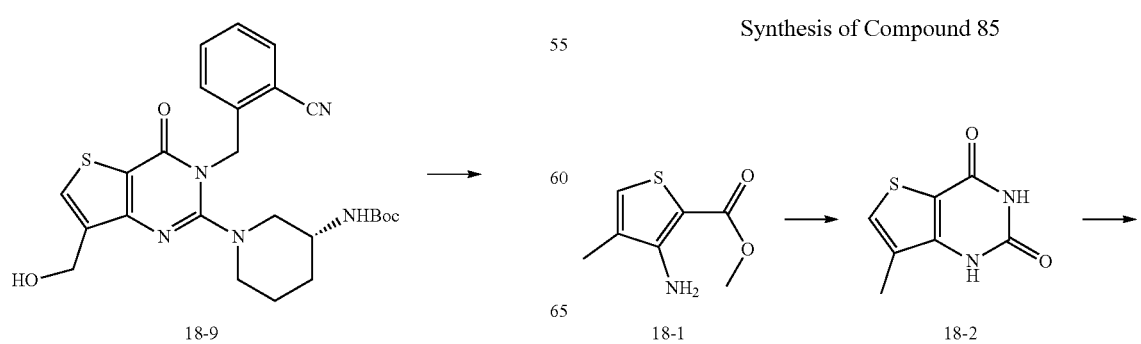
Compound 84 was synthesized according to the synthesis of compound 1, after compound 18-11 was obtained. MS: 381.1 [M+H]+.
Example 85
Synthesis of Compound 85

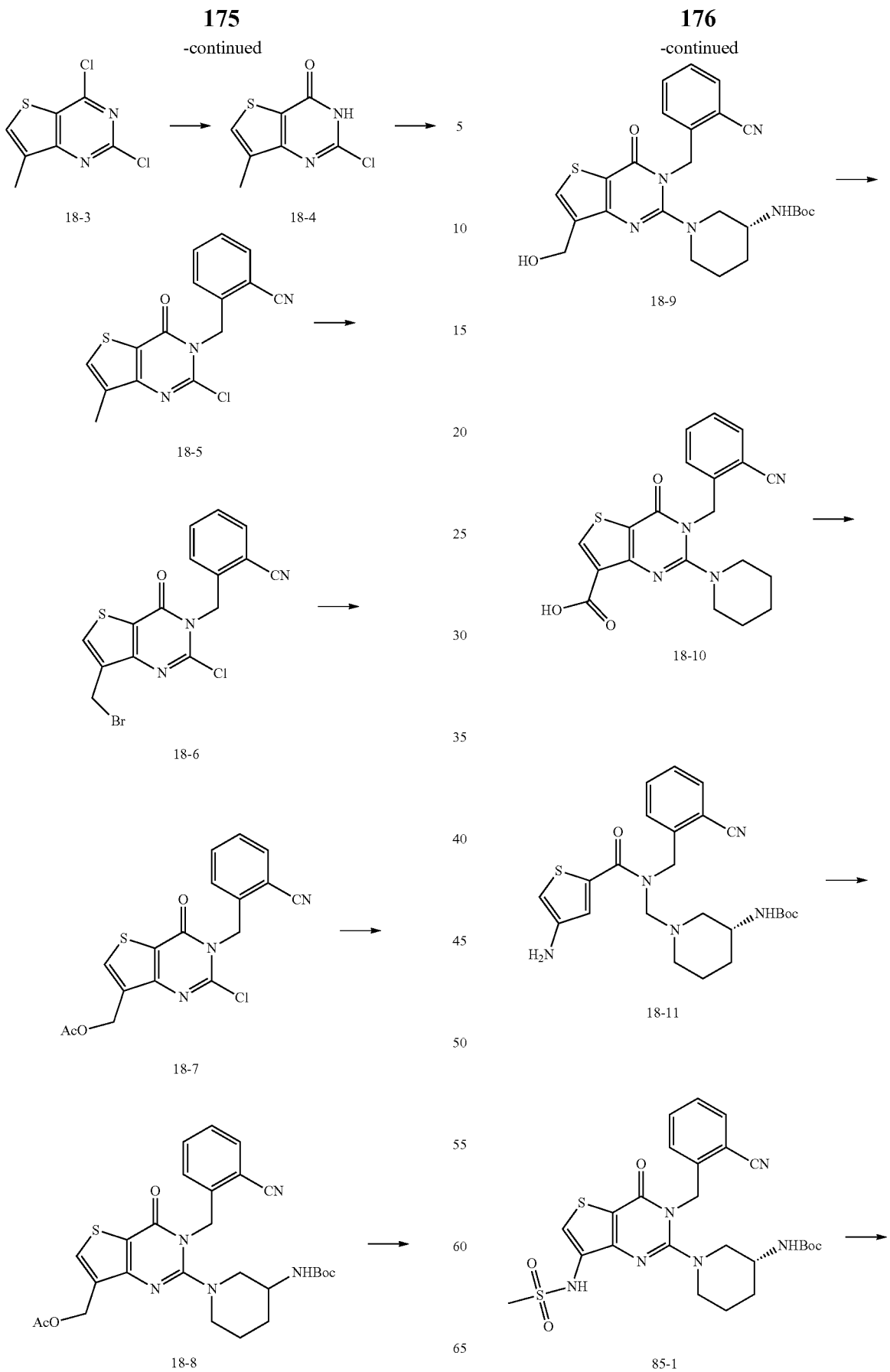

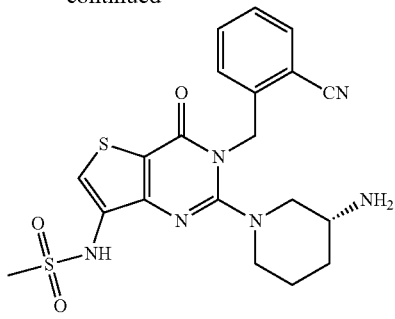

85

Synthesis of Compound 85-1

Compound 18-11 (100 mg) was dissolved in tetrahydrofuran. 1.1 equivalents of methylsulfonyl chloride and 1.2 equivalents of triethylamine were added and stirred for 1 hour at room temperature. After extracted by ethyl acetate, washed with water, and evaporated to dryness, 95 mg of crude product 85-1 was obtained.

Compound 85 was synthesized according to the synthesis of compound 1. MS: 459.1 [M+H]+.

Example 86

Synthesis of Compound 86

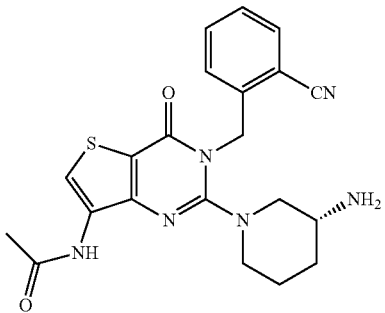

86

Compound 86 was synthesized according to the synthesis of compound 85, wherein acetyl chloride was used instead of methylsulfonyl chloride used in the synthesis of compound 85-1. MS: 423.2[M+H]+.

Example 87

Synthesis of Compound 87

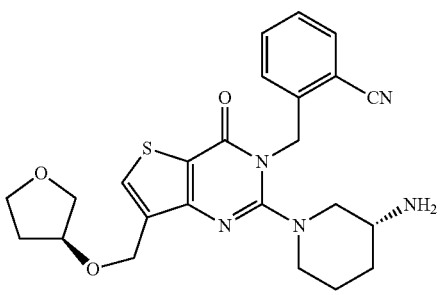

87

Synthesis route:

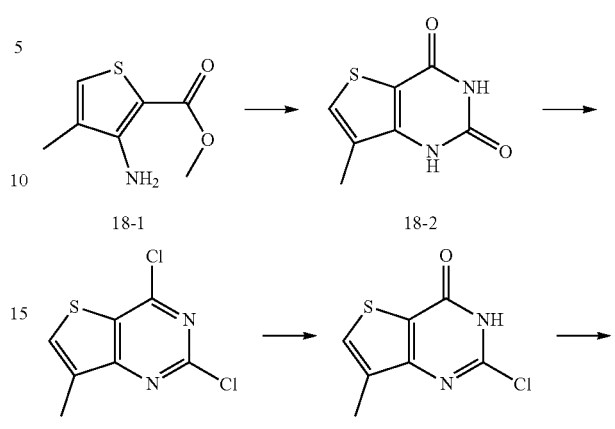

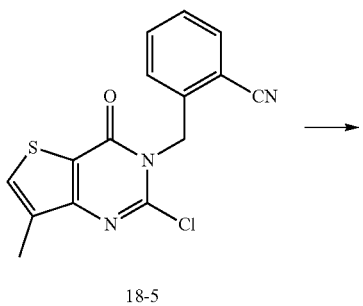

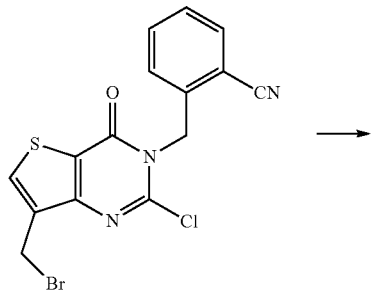

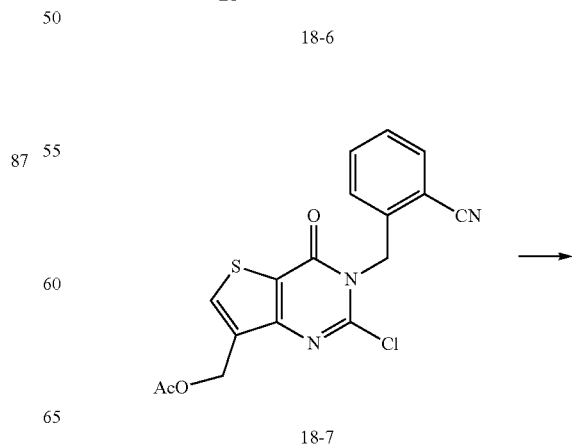

179
-continued

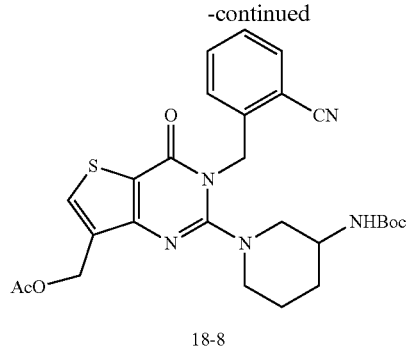

18-8

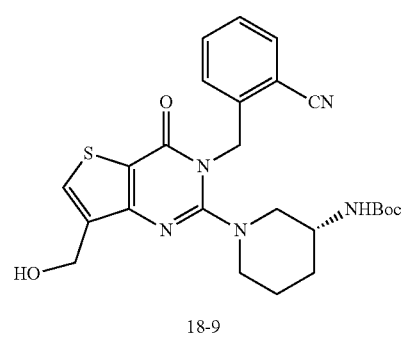

18-9

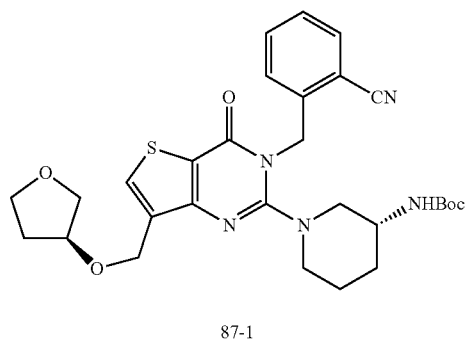

87-1

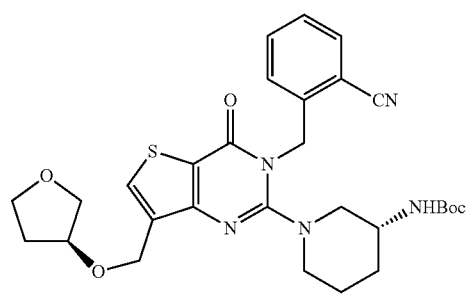

87

Compound 87 was synthesized according to the synthesis of compound 15, wherein S-3-hydroxytetrahydrofuran was used instead of methylamine solution in tetrahydrofuran. MS: 466.2[M+H]⁺.

180

Example 88

Synthesis of Compound 88

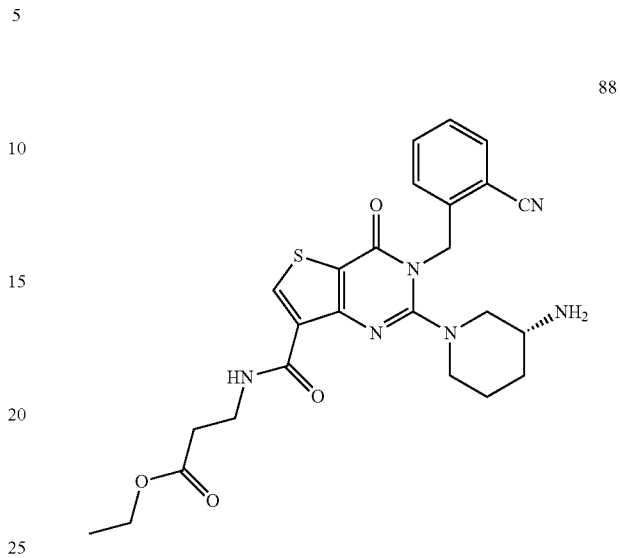

88

Compound 88 was synthesized according to the synthesis of compound 58, wherein ethyl alanine ester was used instead of ethyl glycine ester used in the synthesis of compound 58. MS: 509.2 [M+H]⁺.

Example 89

Synthesis of Compound 89

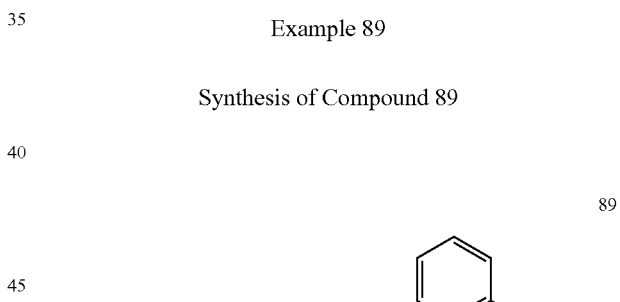

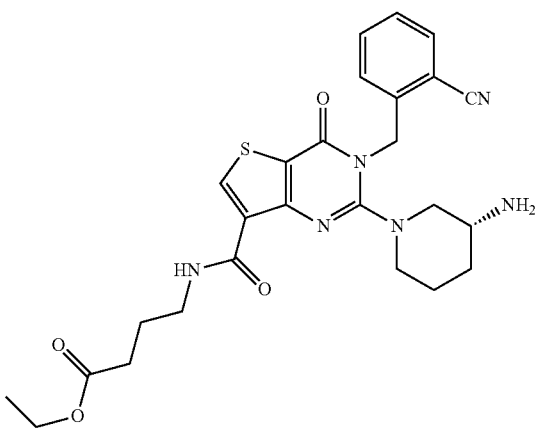

89

Compound 89 was synthesized according to the synthesis of compound 58, wherein ethyl 4-amino butanoate was used instead of ethyl glycine ester used in the synthesis of compound 58. MS: 523.2 [M+H]⁺.

Example 90

Synthesis of Compound 90

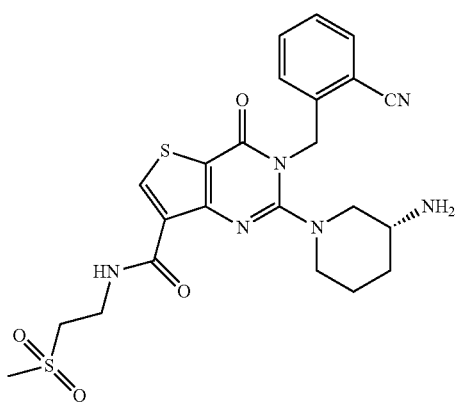

Compound 90 was synthesized according to the synthesis of compound 58, wherein 4-mesyl ethylamine was used instead of ethyl glycine ester used in the synthesis of compound 58. MS: 515.2 [M+H]$^+$.

Example 91

Synthesis of Compound 91

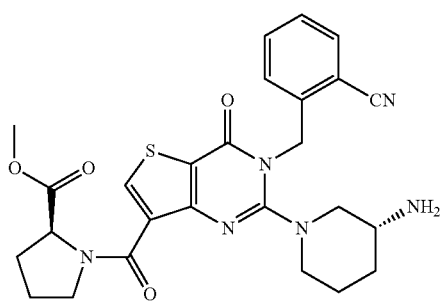

Compound 91 was synthesized according to the synthesis of compound 58, wherein methyl proline ester was used instead of ethyl glycine ester used in the synthesis of compound 58. MS: 521.2 [M+H]$^+$.

Example 92

Synthesis of Compound 92

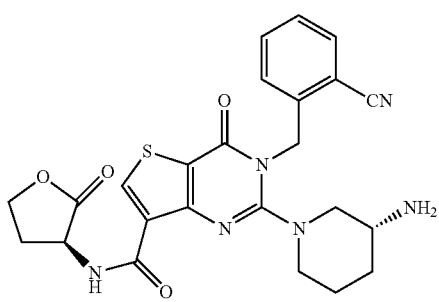

Compound 92 was synthesized according to the synthesis of compound 58, wherein S-2-carbonyl-4-aminotetrahydrofuran was used instead of ethyl glycine ester used in the synthesis of compound 58. MS: 493.2 [M+H]+.

Example 93

Synthesis of Compound 93

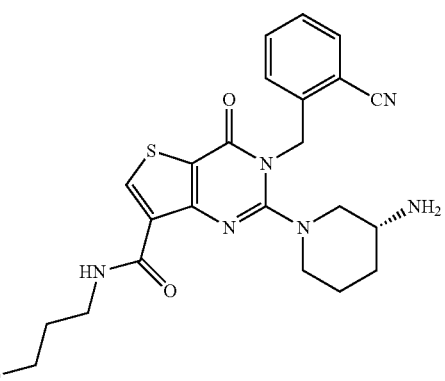

Compound 93 was synthesized according to the synthesis of compound 58, wherein 3-hydroxypropylamine was used instead of ethyl glycine ester used in the synthesis of compound 58. MS: 467.2 [M+H]+.

Example 94

Synthesis of Compound 94

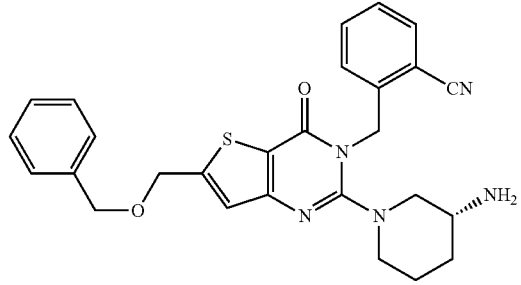

Compound 94 was synthesized according to the synthesis of compound 15, wherein benzyl alcohol was used instead of methylamine solution in tetrahydrofuran used in the synthesis of compound 15-1. MS: 486.2[M+H]+.

Example 95

Synthesis of Compound 95

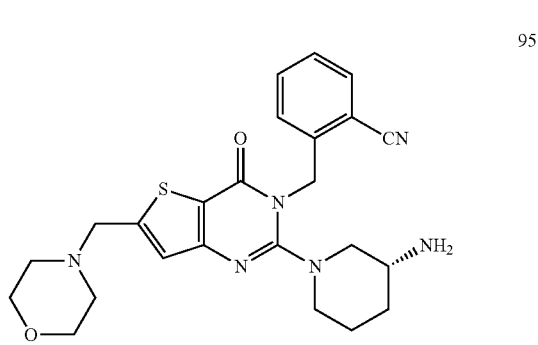

Compound 95 was synthesized according to the synthesis of compound 15, wherein morpholine was used instead of methylamine solution in tetrahydrofuran used in the synthesis of compound 15-1. MS: 465.2[M+H]+.
Example 96
Synthesis of Compound 96
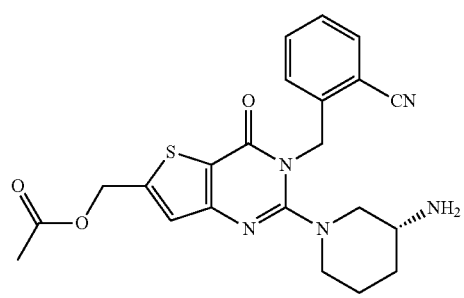
96
Synthesis route:
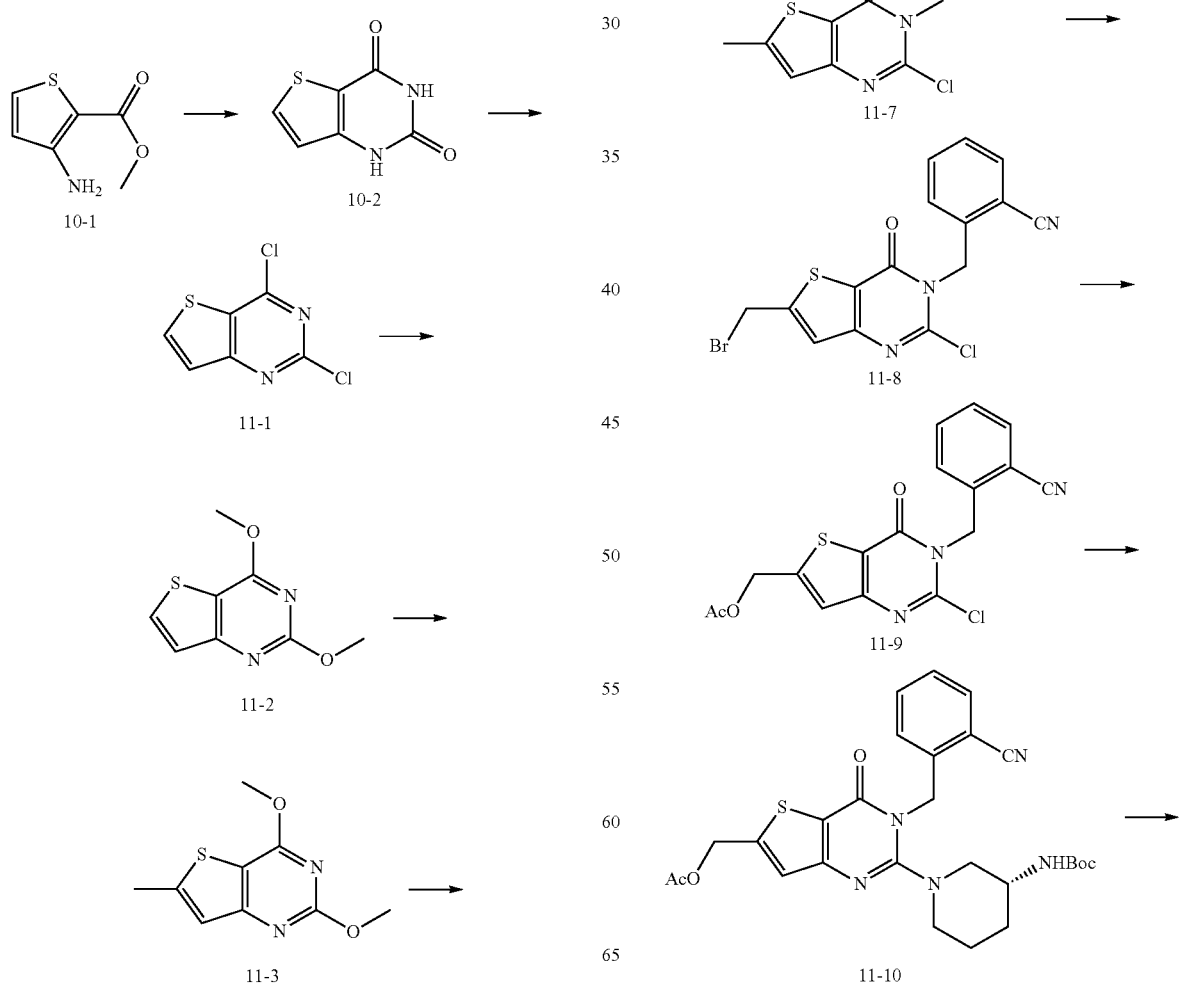

185
-continued
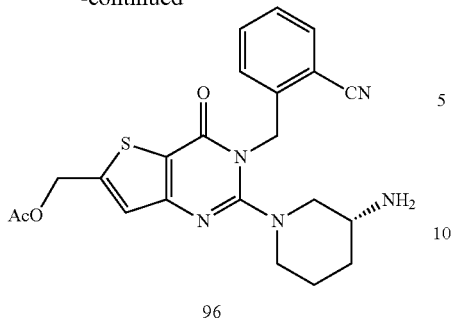
96
Compound 96 was synthesized according to the synthesis of compound 56. 1H-NMR (CDCl3-d3): δ=7.632(d, 1H), 7.482(t, 1H), 7.327(t, 1H), 7.167(s, 1H), 7.080(d,1H), 5.515 (quartet, 2H), 5.267(s,2H), 3.365(t,1H), 3.204(s,1H), 3.055 (m,1H), 2.893(m, 1H), 2.357(m,1H), 2.108(s, 3H), 2.022(m, 1H), 1.781(m,1H), 1.576(m,2H); LC-MS ink 438.2[M+H]+.
Example 97
Synthesis of Compound 97
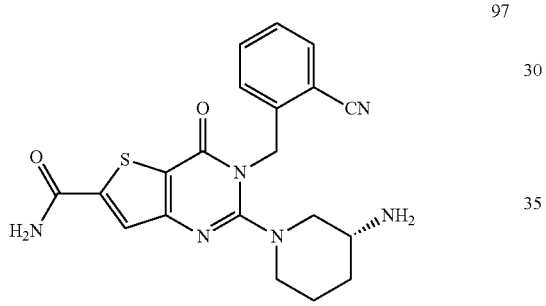
97
Synthesis route:
186
-continued
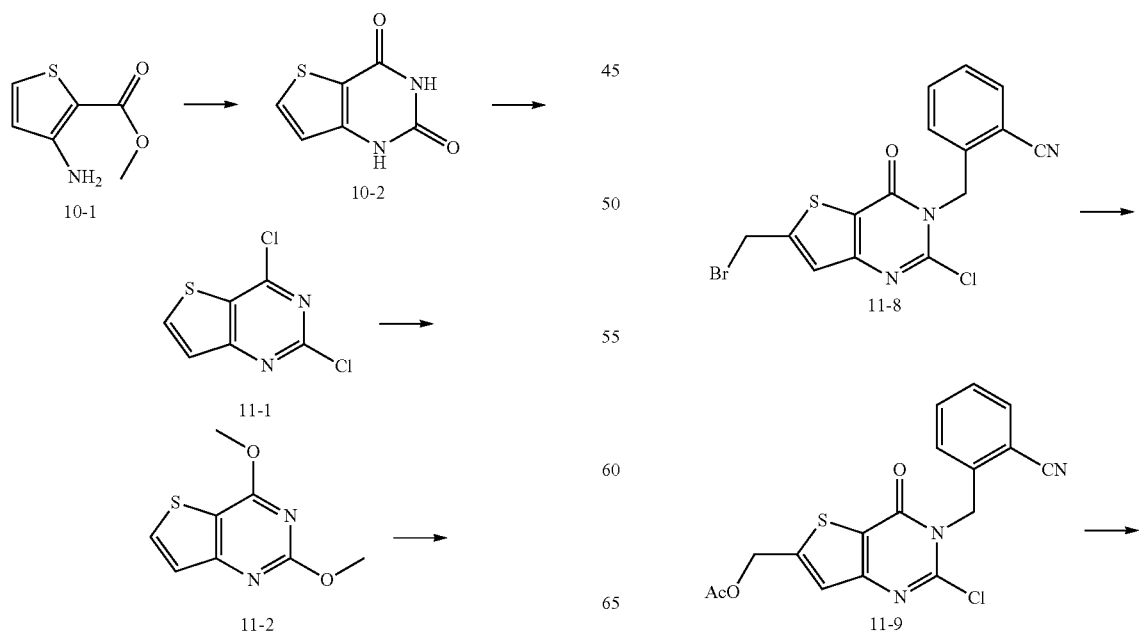

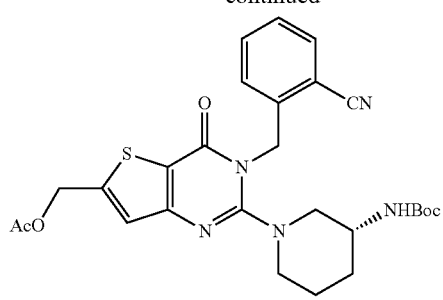
11-10
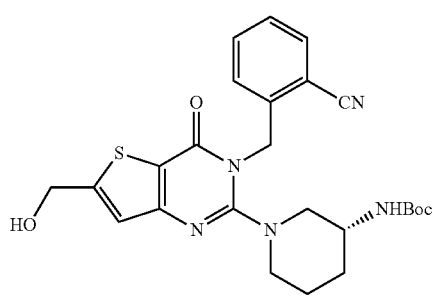
11-11
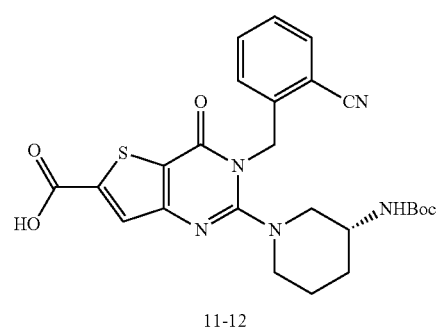
11-12
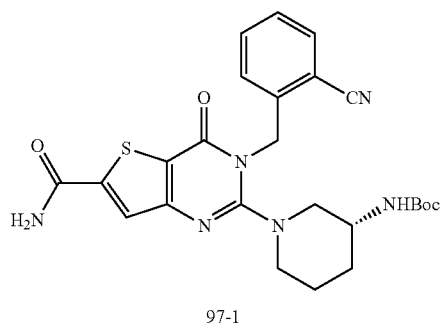
97-1
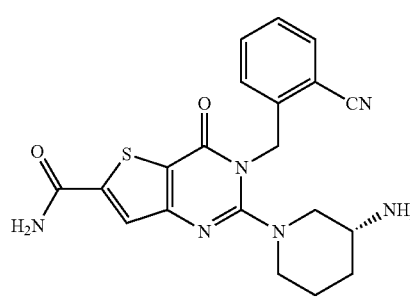
97
Compound 97 was synthesized according to the synthesis of compound 45. MS: 409.1[M+H]$^+$.
Example 98
Synthesis of Compound 98
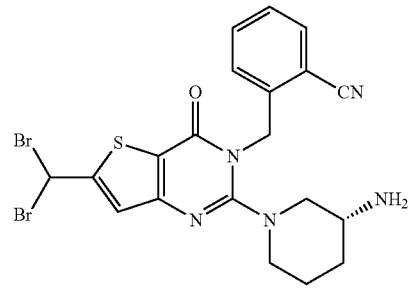
98
Synthesis route:
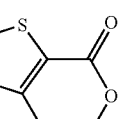
10-1
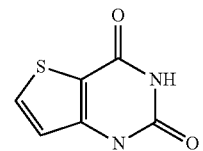
10-2
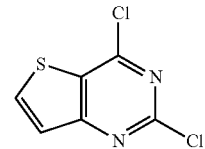
11-1
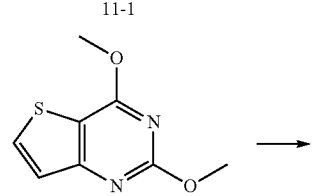
11-2
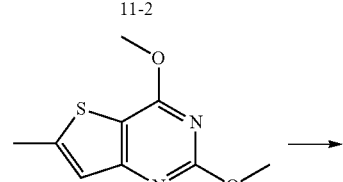
11-3

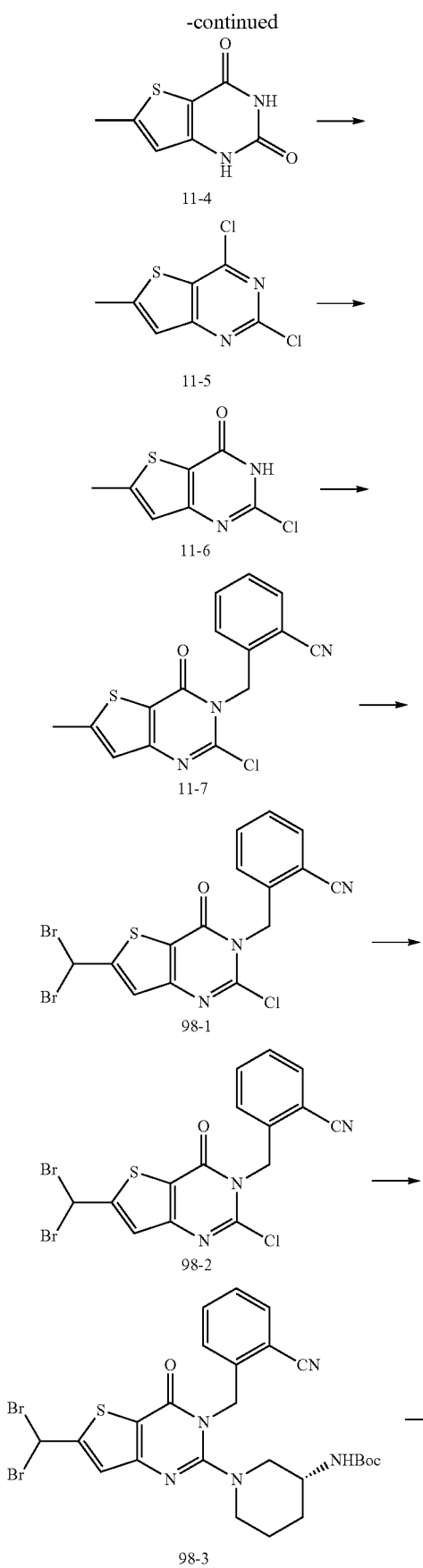

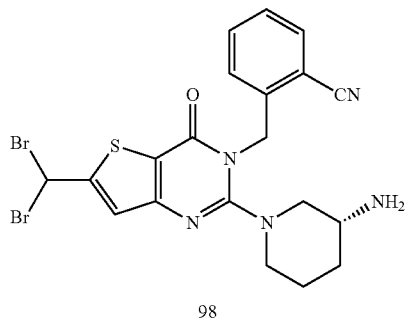

98

Synthesis of compound 98-1

Compound 11-7 (1 g) was dissolved in CCl$_4$. 2.5 equivalent of NBS (N-bromosuccinimide) and catalytic amount of benzoyl peroxide were added and refluxed overnight. After extracted by dichloromethane, washed with water, compound 98-1 (740 mg) was obtained by column chromatography in 51% yield. MS: 471.8[M+H]+.

Compound 98 was synthesized according to the synthesis of compound 1. 1H-NMR (CDCl3-d3): δ=7.603(m, 1H), 7.499(m, 1H), 7.369(s, 1H), 7.324(t, 1H), 7.184(d, 1H), 6.820 (m, 1H), 5.485(quartet, 2H), 5.293(s, 1H), 3.594(m, 2H), 3.270(m, 1H), 3.022(m, 1H), 2.908(m,2H), 2.105(m, 1H), 1.825(m, 2H), 1.603(m, 1H); LC-MS m/z 538.0[M+H]+.

Example 99

Synthesis of Compound 99

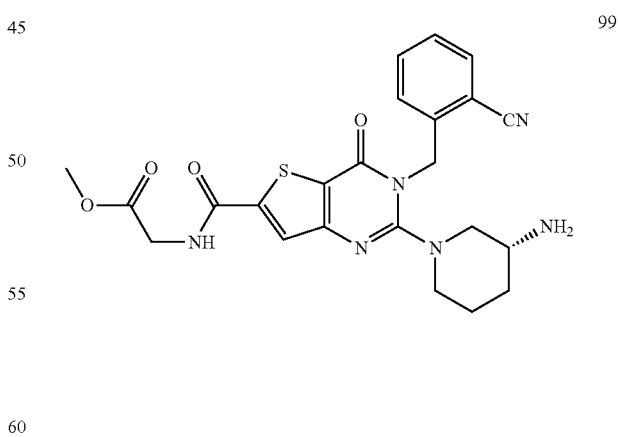

99

Compound 99 was obtained according to the synthesis of compound 40, wherein methyl glycine ester was used instead of cyclopropylamine used in the synthesis of compound 40. 1H-NMR(CDCl3-d3): δ=7.756(s, 1H), 7.630(d, 1H), 7.537 (t, 1H), 7.368(t, 1H), 7.218(d, 1H), 5.442(quartet, 2H), 4.114 (s, 2H), 3.730(s, 3H), 3.590(d, 1H), 3.493(d, 1H), 3.323(d, 1H), 3.180(m, 2H), 2.958(m, 1H), 2.096(s, 1H), 1.820(d, 1H), 1.690(d. 1H); LC-MS m/z 481.2[M+H]+.

Example 100

Synthesis of Compound 100

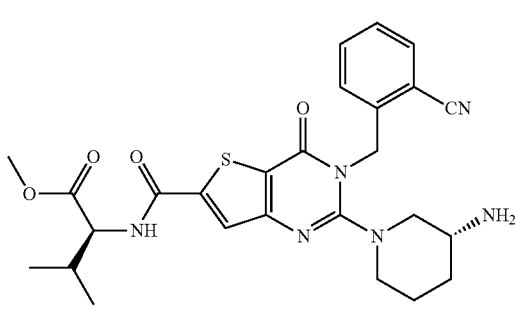

Compound 100 was synthesized according to the synthesis of compound 99, wherein methyl valine ester was used instead of methyl glycine ester used in the synthesis of compound 99. 1H-NMR(CDCl3-d3): δ=7.812(s, 1H), 7.540(d, 1H), 7.469(t, 1H), 7.277(t, 1H), 7.194(d, 1H), 5.450(quartet, 2H), 4.593(quartet, 1H), 3.723(s, 3H), 3.608(d, 1H), 3.344(d, 1H), 3.000(m, 2H), 2.280(m, 1H), 2.100(s, 1H), 1.880(d, 1H), 1.910(m, 1H); 1.797(s, 1H), 0.980(t, 6H), 0.900(d, 1H); LC-MS m/z 523.2 [M+H]+.

Example 101

Synthesis of Compound 101

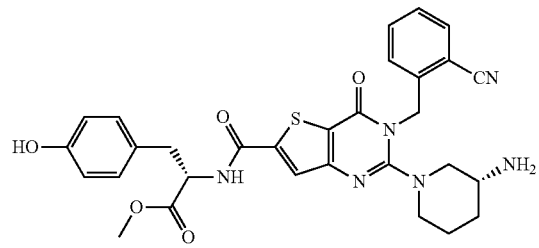

Compound 101 was synthesized according to the synthesis of compound 99, wherein methyl tyrosine ester was used instead of methyl glycine ester used in the synthesis of compound 99. 1H-NMR(CDCl3-d3): δ=7.580(d, 1H), 7.548(s, 1H), 7.479(t, 1H), 7.315(t, 1H), 7.258(s, 1H), 7.153(d,1H), 6.940(d,2H), 6.710(d,2H), 5.400(quartet, 2H), 4.861(quartet, 1H), 3.711(s, 3H), 3.495(d, 1H), 3.410(s, 1H), 3.200(m, 2H), 3.100(m, 2H), 2.946(m,1H), 2.028(s,1H), 1.742(s,2H); 1.600 (s, 1H); LC-MS m/z 587.2 [M+H]+.

Example 102

Synthesis of Compound 102

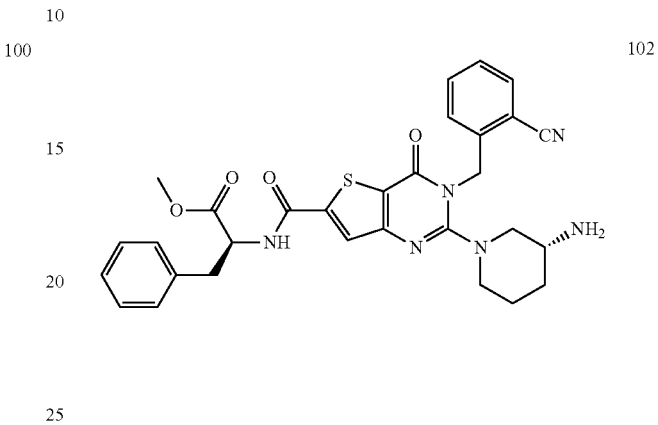

Compound 102 was synthesized according to the synthesis of compound 99, wherein methyl phenylalanine ester was used instead of methyl glycine ester used in the synthesis of compound 99. 1H-NMR(CDCl3-d3): δ=7.733(s, 1H), 7.540 (d, 1H), 7.439(t, 1H), 7.214(m, 7H), 5.410(quartet, 2H), 4.930(quartet, 1H), 3.677(s, 3H), 3.620(d, 2H), 3.390(s, 1H), 3.210(m, 2H), 3.007(s, 1H), 2.941(s,1H), 2.071(s,1H), 1.947 (s,1H); 1.771(s,1H), 1.538(s,1H); LC-MS m/z 571.2 [M+H]+.

Example 103

Synthesis of Compound 103

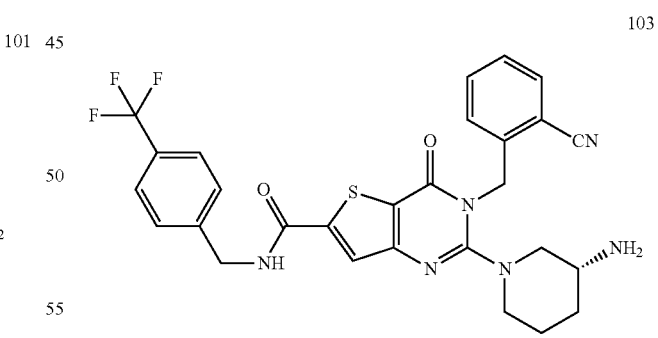

Compound 103 was synthesized according to the synthesis of compound 99, wherein p-trifluoromethyl benzylamine was used instead of methyl glycine ester used in the synthesis of compound 99. 1H-NMR(CDCl3-d3): δ=7.792(s, 1H), 7.528 (d, 1H), 7.445(m, 5H), 7.260(t, 1H), 7.154(d,1H), 5.354 (quartet, 2H), 4.549(s, 2H), 3.518(s, 2H), 3.340(s. 1H), 3.014

(s, 1H), 2.889(s, 1H), 2.009(s, 1H), 1.830(s, 1H), 1.717(s, 1H), 1.532(s,1H); LC-MS m/z 567.2[M+H]+.

Example 104

Synthesis of Compound 104

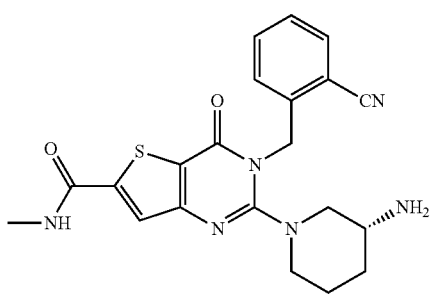

104

Compound 104 was synthesized according to the synthesis of compound 99, wherein methylamine hydrochloride was used instead of methyl glycine ester used in the synthesis of compound 99. 1H-NMR(CDCl3-d3): δ=7.684(s, 1H), 7.625 (d, 1H), 7.530(t, 1H), 7.363(t, 1H), 7.210(d, 1H), 5.440(quartet, 2H), 3.587(d, 1H), 3.471(m, 1H), 3.305(m, 1H), 3.177(m, 2H), 2.912(s,3H), 2.105(d, 1H), 1.789(m, 1H), 1.680(m,2H); LC-MS m/z 423.2[M+H]+.

Example 105

Synthesis of Compound 105

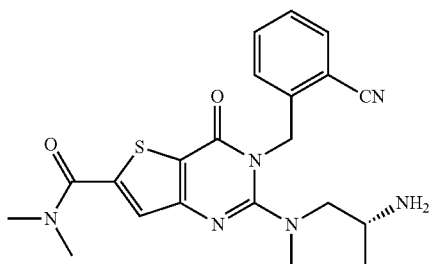

105

Compound 105 was synthesized according to the synthesis of compound 99, wherein dimethylamine hydrochloride was used instead of methyl glycine ester used in the synthesis of compound 99. 1H-NMR(CDCl3-d3): δ=7.600(d, 1H), 7.484 (t, 1H), 7.403(s, 1H), 7.314(t, 1H), 7.161(d, 1H), 5.490(quartet, 2H), 3.538(d, 2H), 3.279(m, 1H), 3.140(d, 6H), 3.026(s, 1H), 2.948(t,1H), 2.069(s, 1H), 1.850(s, 2H), 1.600(m,1H); LC-MS m/z 437.2[M+H]+.

Example 106

Synthesis of Compound 106

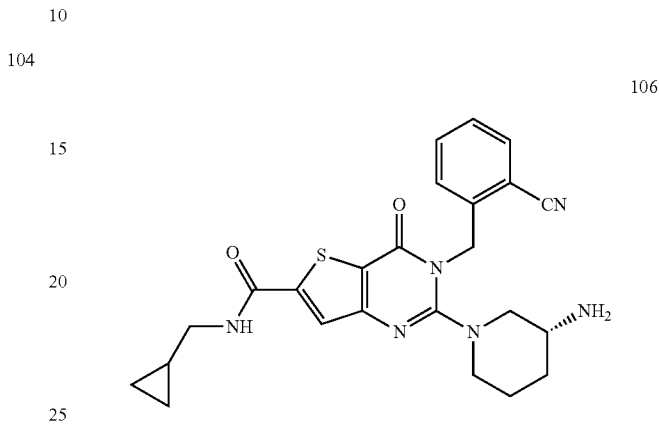

106

Compound 106 was synthesized according to the synthesis of compound 99, wherein cyclopropylmethylamine was used instead of methyl glycine ester used in the synthesis of compound 99. 1H-NMR(CDCl3-d3): δ=7.710(s, 1H), 7.650(d, 1H), 7.535(t, 1H), 7.374(t, 1H), 7.170(d, 1H), 5.487(quartet, 2H), 3.450(d, 2H), 3.274(d, 2H), 3.160(s, 1H), 2.987(m,1H), 2.902(t,1H), 2.036(s, 1H), 1.794(s,1H), 1.667(m,1H), 1.553 (d,1H), 1.084(s, 1H), 0.540(m,2H), 0.278(m,2H); LC-MS m/z 463.2[M+H]+.

Example 107

Synthesis of Compound 107

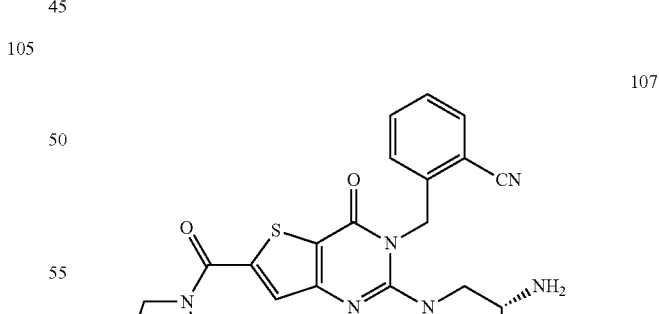

107

Compound 107 was synthesized according to the synthesis of compound 99, wherein pyrrolidine was used instead of methyl glycine ester used in the synthesis of compound 99. 1H-NMR(CDCl3-d3): δ=7.620(d, 1H), 7.529(s, 1H), 7.492 (t, 1H), 7.327(t, 1H), 7.121(d, 1H), 5.495(t, 2H), 3.740(t, 3H), 3.450(d, 1H), 3.264(m, 1H), 3.084(d,1H), 2.962(t,1H), 2.872

(m,1H), 2.864(t, 1H), 1.970(m, 5H), 1.790(m,1H), 1.600(m, 2H); LC-MS m/z 463.2[M+H]+.

Example 108

Synthesis of Compound 108

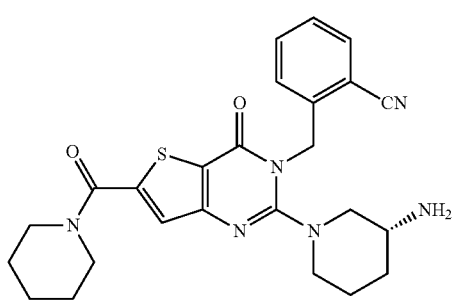
108

Compound 108 was synthesized according to the synthesis of compound 99, wherein piperidine was used instead of methyl glycine ester used in the synthesis of compound 99. 1H-NMR(CDCl3-d3): δ=7.644(d, 1H), 7.504(t, 1H), 7.344(t, 1H), 7.310(s, 1H), 7.116(d, 1H), 5.523(quartet, 2H), 3.630(s, 4H), 3.390(d, 1H), 3.249(s, 1H), 3.088(d,1H), 2.940(m,2H), 2.013(m,1H), 1.824(s, 1H), 1.650(d, 8H); LC-MS m/z 477.2 [M+H]+.

Example 109

Synthesis of Compound 109

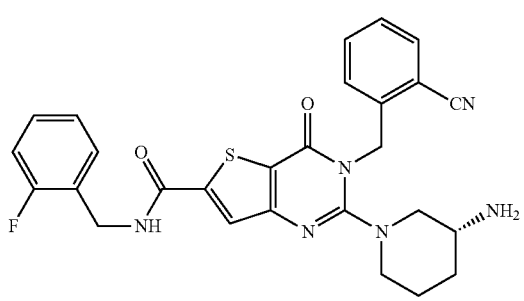
109

Compound 109 was synthesized according to the synthesis of compound 99, wherein 2-fluorobenzylamine was used instead of methyl glycine ester used in the synthesis of compound 99. 1H-NMR(CDCl3-d3): δ=7.632(s, 1H), 7.572(d, 1H), 7.453(t, 1H), 7.385(t, 1H), 7.298(t, 1H), 7.192(m,1H), 7.094(t,1H), 7.035(t,1H), 6.966(t,1H), 5.542(t, 2H), 4.595(d, 2H), 3.436(d, 1H), 3.253(s, 1H), 3.012(m, 2H), 2.815(d,1H), 1.991(s,1H), 1.719(s, 1H), 1.566(s, 2H); LC-MS m/z 517.2 [M+H]+.

Example 110

Synthesis of Compound 110

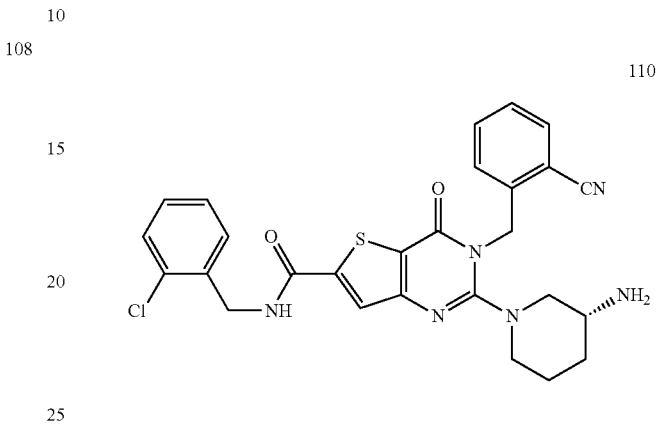
110

Compound 110 was synthesized according to the synthesis of compound 99, wherein 2-chlorobenzylamine was used instead of methyl glycine ester used in the synthesis of compound 99. 1H-NMR(CDCl3-d3): δ=7.666(s, 1H), 7.584(d, 1H), 7.440(m, 2H), 7.308(m, 2H), 7.179(m, 2H), 7.105(d, 1H), 5.442(t, 2H), 4.635(d, 2H), 3.409(d, 1H), 3.203(s, 1H), 3.052(d, 1H), 2.928(t,1H), 2.824(t,1H), 1.967(s,1H), 1.717(s, 1H), 1.532(m,2H); LC-MS m/z 533.1 [M+H]+.

Example 111

Synthesis of Compound 111

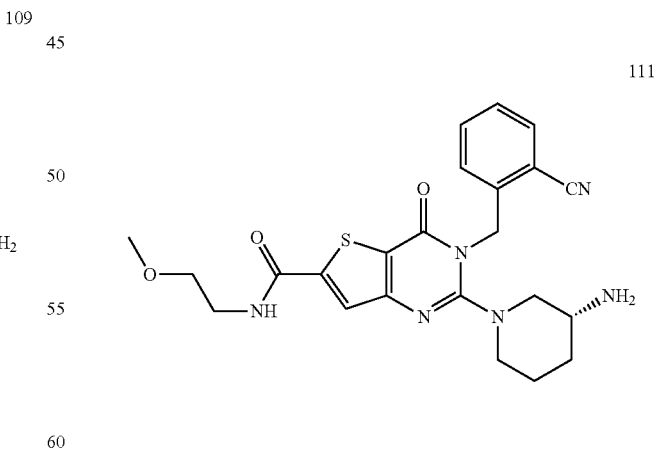
111

Compound III was synthesized according to the synthesis of compound 99, wherein 2-methoxylethylamine was used instead of methyl glycine ester used in the synthesis of compound 99. 1H-NMR(CDCl3-d3): δ=7.590(d, 2H), 7.458(t, 1H), 7.303(t, 1H), 7.058(d, 1H), 5.421(s, 2H), 3.497(m,3H), 3.309(m, 5H), 3.040(m, 2H), 2.755(m, 2H), 1.927(m, 1H), 1.710(m, 1H), 1.589(m, 1H), 1.341(m, 1H); LC-MS m/z 467.2[M+H]+.

Example 112

Synthesis of Compound 112

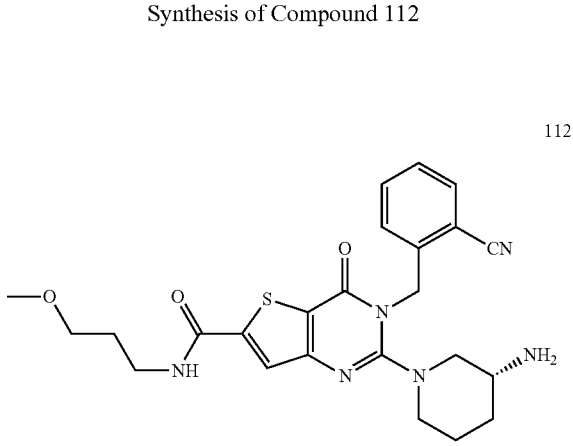

112

Compound 112 was synthesized according to the synthesis of compound 99, wherein 3-methoxylpropylamine was used instead of methyl glycine ester used in the synthesis of compound 99. 1H-NMR(CDCl3-d3): δ=7.695(d, 1H), 7.646(s, 1H), 7.568(t, 1H), 7.411(t, 1H), 7.178(d, 1H), 5.525 (s, 2H), 3.567(m, 5H), 3.406(m, 3H), 3.169(m, 2H), 2.903(m, 2H), 2.045(m, 1H), 1.918(m, 2H), 1.816(m, 1H), 1.699(m, 1H), 1.481(m, 1H); LC-MS m/z 481.2[M+H]+.

Example 113

Synthesis of Compound 113

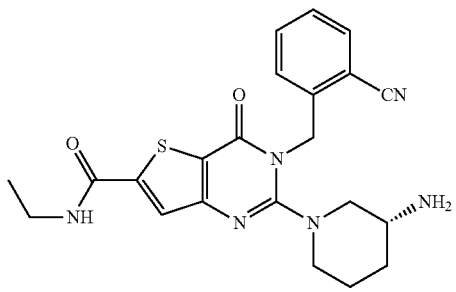

113

Compound 113 was synthesized according to the synthesis of compound 99, wherein ethylamine hydrochloride was used instead of methyl glycine ester used in the synthesis of compound 99. 1H-NMR(CDCl3-d3): δ=7.697(t, 2H), 7.570(t, 1H), 7.568(t, 1H), 7.413(t, 1H), 7.175(d, 1H), 5.521(s, 2H), 3.416(m, 3H), 3.157(m, 2H), 2.889(m, 2H), 2.040(m, 1H), 1.811(m,1H), 1.682(m,1H), 1.445(m,1H), 1.270(s, 3H); LC-MS m/z 437.2 [M+H]+.

Example 114

Synthesis of Compound 114

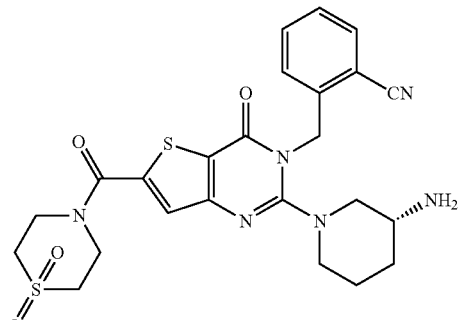

114

Compound 114 was synthesized according to the synthesis of compound 99, wherein 1,1-di-O-thiomorpholine was used instead of methyl glycine ester used in the synthesis of compound 99. 1H-NMR(CDCl3-d3): δ=7.664(d, 1H), 7.542(t, 1H), 7.422(s, 1H), 7.384(t, 1H), 7.172(d, 1H), 5.495 (t, 2H), 4.192(s,4H), 3.425(d, 1H), 3.079(m,5H), 2.903(m, 3H), 2.021(m,1H), 1.811(m,1H), 1.670(m,1H), 1.491(m,1H); LC-MS m/z 527.1 [M+H]+.

Example 115

Synthesis of Compound 115

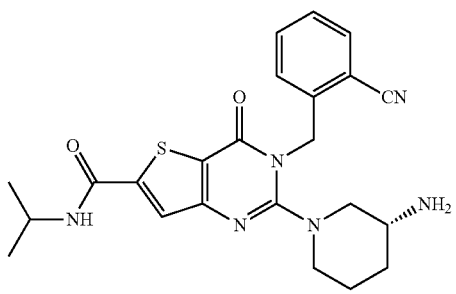

115

Compound 115 was synthesized according to the synthesis of compound 99, wherein isopropylamine was used instead of methyl glycine ester used in the synthesis of compound 99. MS: 451.2 [M+H]+.

Example 116

Synthesis of Compound 116

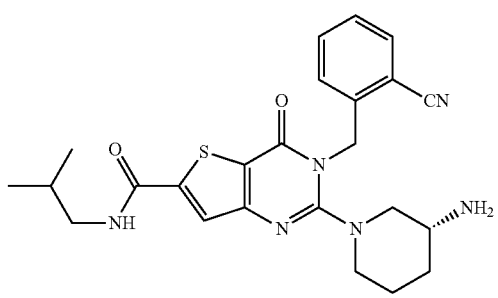

116

Compound 116 was synthesized according to the synthesis of compound 99, wherein isobutylamine was used instead of methyl glycine ester used in the synthesis of compound 99. 1H-NMR(CDCl3-d3): δ=7.713(s, 1H), 7.555(d, 1H), 7.473 (t, 1H), 7.296(t, 1H), 7.158(d,1H), 5.426(t, 2H), 3.576(d,1H), 3.482(s, 1H), 3.201(m,3H), 3.020(m, 1H), 2.854(m,1H), 2.82 (m,1H), 1.905(m,1H), 1.762(s,2H), 1.583(s,1H), 0.915(d, 6H); LC-MS m/z 465.2[M+H]+.

Example 117

Synthesis of Compound 117

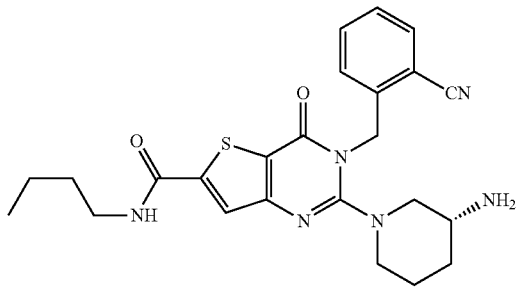

117

Compound 117 was synthesized according to the synthesis of compound 99, wherein n-butylamine was used instead of methyl glycine ester used in the synthesis of compound 99. 1H-NMR (CDCl3-d3): δ=7.713(s, 1H), 7.564(d, 1H), 7.483 (t, 1H), 7.307(t, 1H), 7.183(d, 1H), 5.434 (quartet, 2H), 3.577 (m,2H), 3.373(m, 3H), 3.044(m,1H), 2.898(m, 1H), 2.092(s, 1H), 1.833(d,2H), 1.587(m,3H), 1.354(m,2H), 0.881(t,3H); LC-MS m/z 465.2[M+H]+.

Example 118

Synthesis of Compound 118

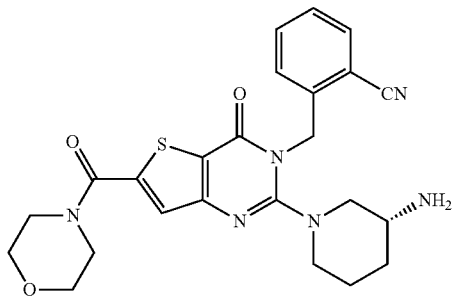

118

Compound 118 was synthesized according to the synthesis of compound 99, wherein morpholine was used instead of methyl glycine ester used in the synthesis of compound 99. 1H-NMR(CDCl3-d3): δ=7.620(d, 1H), 7.505(t, 1H), 7.368 (s, 1H), 7.340(t, 1H), 7.172(d,1H), 5.498 (quartet, 2H), 3.721 (s,8H), 3.486(m, 2H), 3.197(m,1H), 3.064(m, 1H), 2.954(m, 1H), 2.058(m,1H), 1.821(m,2H), 1.616(m,1H); LC-MS m/z 479.2[M+H]+.

Example 119

Synthesis of Compound 119

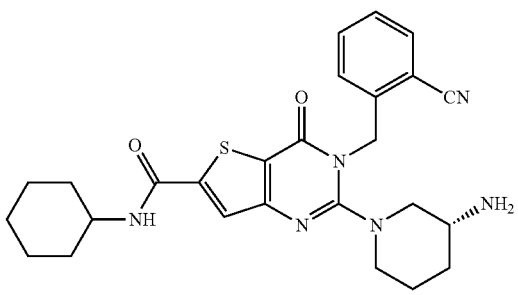

119

Compound 119 was synthesized according to the synthesis of compound 99, wherein cyclohexane was used instead of methyl glycine ester used in the synthesis of compound 99. 1H-NMR(CDCl3-d3): δ=7.673(s, 1H), 7.568(d, 1H), 7.483 (t, 1H), 7.304(t, 1H), 7.169(d,1H), 5.446 (quartet, 2H), 3.864 (s,1H), 3.540(m, 2H), 3.261(m,1H), 3.026(s, 1H), 2.877(m, 1H), 2.060(m,1H), 1.948(s,2H), 1.789(m,4H), 1.610(d,2H), 1.338(m,4H), 1.162(m,1H); LC-MS m/z 491.2 [M+H]+.

Example 120

Synthesis of Compound 120

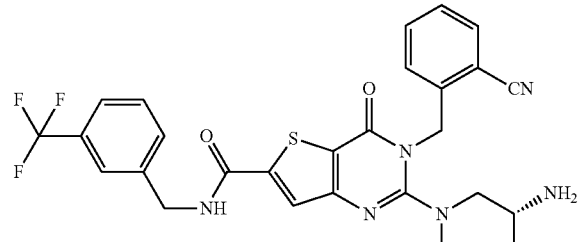

120

Compound 120 was synthesized according to the synthesis of compound 99, wherein 3-trifluoromethylbenzylamine was used instead of methyl glycine ester in the synthesis of compound 99. 1H-NMR(CDCl3-d3): δ=7.693(s, 1H), 7.597 (s, 1H), 7.520(d, 2H), 7.425(t, 2H), 7.332(t,1H), 7.284(d,1H), 7.140(d,2H), 5.368(m, 2H), 4.576(s,1H), 3.522(s,2H), 3.292

(s, 1H), 2.987(s,1H), 2.853(s, 1H), 2.010(s,1H), 1.761(d,1H), 1.519(s,1H); LC-MS m/z 567.2[M+H]+.

Example 121

Synthesis of Compound 121

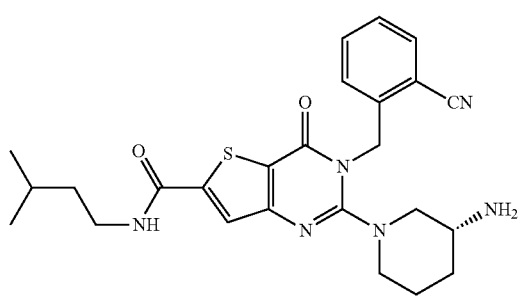

Compound 121 was synthesized according to the synthesis of compound 99, wherein isopentylamine was used instead of methyl glycine ester used in the synthesis of compound 99. 1H-NMR(CDCl3-d3): δ=7.673(s, 1H), 7.572(d, 1H), 7.483 (t, 1H), 7.310(t, 1H), 7.168(d,1H), 5.442 (quartet, 2H), 3.501 (m,2H), 3.410(quartet, 2H), 3.219(s, 1H), 3.047(s, 1H), 2.872 (s, 1H), 2.067(s, 1H), 1.773(s, 2H), 1.610(m, 2H), 1.500 (quartet, 2H), 0.890(d, 6H); LC-MS m/z 479.2 [M+H]+.

Example 122

Synthesis of Compound 122

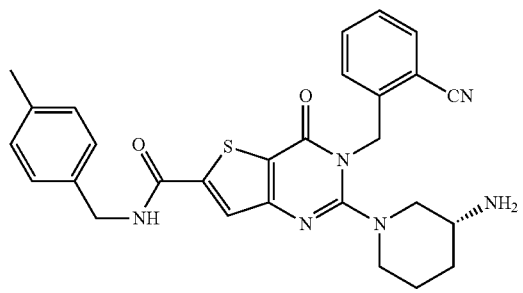

Compound 122 was synthesized according to the synthesis of compound 99, wherein 4-methylbenzylamine was used instead of methyl glycine ester used in the synthesis of compound 99. 1H-NMR(CDCl3-d3): δ=7.645(s, 1H), 7.520(d, 1H), 7.420(t, 1H), 7.264(t, 1H), 7.194(d, 2H), 7.110(d, 1H), 7.010(d, 2H), 5.390(quartet, 2H), 4.469(s, 2H), 3.482(m, 2H), 3.244(m, 1H), 2.936(s, 1H), 2.828(s, 1H), 2.218(s, 3H), 2.004(s, 1H), 1.738(m, 2H), 1.510(s, 1H); LC-MS m/z 513.2 [M+H]+.

Example 123

Synthesis of Compound 123

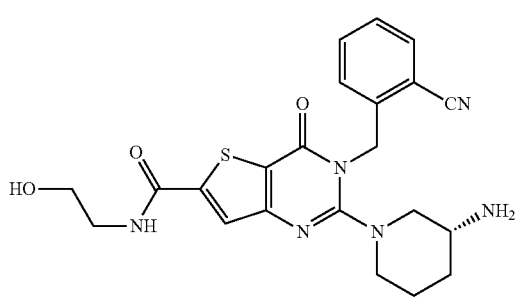

Compound 123 was synthesized according to the synthesis of compound 99, wherein 2-hydroxyethylamine was used instead of methyl glycine ester used in the synthesis of compound 99. 1H-NMR(CDCl3-d3): δ=7.580(d, 2H), 7.459(t, 1H), 7.288(t, 1H), 7.080(d, 1H), 5.400 (quartet, 2H), 3.669 (m, 2H), 3.452(m, 2H), 3.317(m, 1H), 3.094(m, 2H), 2.845 (quartet, 2H), 1.923(m, 1H), 1.705(s, 1H), 1.575(m, 1H), 1.401(m, 1H); LC-MS m/z 453.2[M+H]+.

Example 124

Synthesis of Compound 124

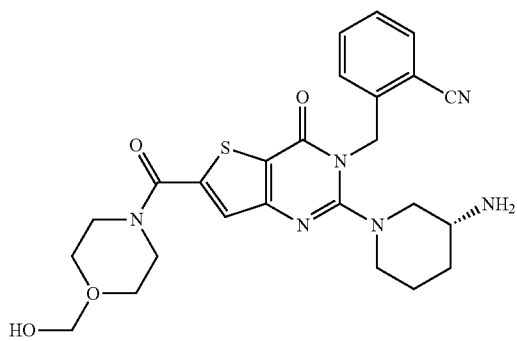

Compound 124 was synthesized according to the synthesis of compound 99, wherein 4-hydroxymethyl piperidine was used instead of methyl glycine ester used in the synthesis of compound 99. 1H-NMR(CDCl3-d3): δ=7.690(d, 1H), 7.580 (m, 1H), 7.417(t, 1H), 7.328(s, 1H), 7.231(d, 1H), 5.524 (quartet, 2H), 4.130(quartet, 1H), 3.794(s, 5H), 3.500(m, 1H), 3.354(m, 1H), 3.164(m, 1H), 3.068(quartet, 1H), 2.940

(t, 1H), 2.106(m, 1H), 1.856(m, 4H), 1.680(m, 2H), 1.271(m, 3H); LC-MS m/z 507.2 [M+H]+.

Example 125

Synthesis of Compound 125

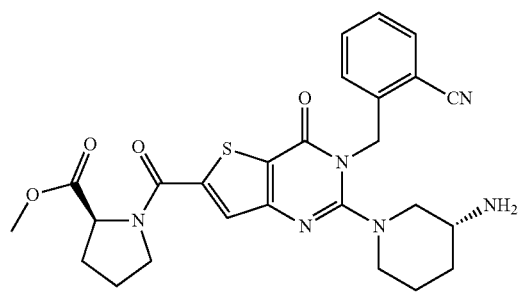

125

Compound 125 was synthesized according to the synthesis of compound 99, wherein methyl L-proline ester was used instead of methyl glycine ester used in the synthesis of compound 99. 1H-NMR(CDCl3-d3): δ=7.600(d, 2H), 7.490(m, 1H), 7.321(t, 1H), 7.139(d, 1H), 5.484(t, 2H), 4.637(quartet, 1H), 3.900(m, 2H), 3.735(s, 3H), 3.535(d, 1H), 3.392(m, 1H), 3.084(m, 2H), 2.917(t, 1H), 2.280(m, 1H), 2.078(m, 4H), 1.800(m, 1H), 1.623(m, 2H); LC-MS m/z 521.2[M+H]+.

Example 126

Synthesis of Compound 126

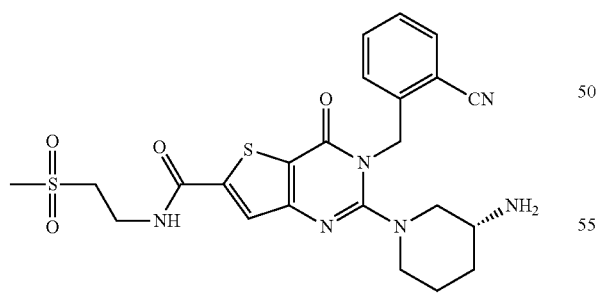

126

Compound 126 was synthesized according to the synthesis of compound 99, wherein 2-mesyl ethylamine was used instead of methyl glycine ester used in the synthesis of compound 99. 1H-NMR(CDCl3-d3): δ=7.705(s, 1H), 7.680(d, 1H), 7.570(t, 1H), 7.402(t, 1H), 7.221(d, 1H), 5.494 (quartet, 2H), 3.918(t, 2H), 3.452(m, 4H), 3.377(m, 1H), 3.171(m, 2H), 3.057(s, 3H), 3.078(d, 1H), 1.849(m, 1H), 1.696(m,2H); LC-MS m/z 515.1 [M+H]+.

Example 127

Synthesis of Compound 127

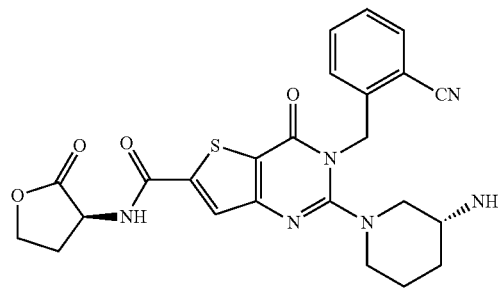

127

Compound 127 was synthesized according to the synthesis of compound 99, wherein S-2-carbonyl-4-amino tetrahydrofuran was used instead of methyl glycine ester used in the synthesis of compound 99. MS: 493.2 [M+H]+.

Example 128

Synthesis of Compound 128

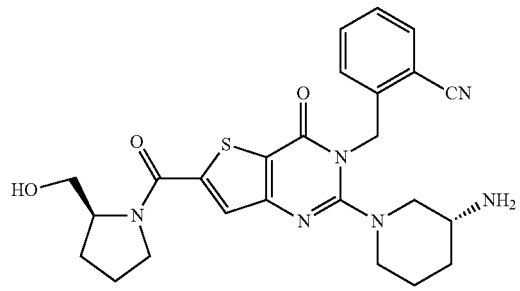

128

Compound 128 was synthesized according to the synthesis of compound 99, wherein L-proline was used instead of methyl glycine ester used in the synthesis of compound 99. 1H-NMR(CDCl3-d3): δ=7.638(d, 1H), 7.554(s, 1H), 7.510 (t, 1H), 7.348(t, 1H), 7.145(d, 1H), 5.494 (quartet, 2H), 4.402 (s, 1H), 3.736(m, 5H), 3.410(d, 1H), 3.289(s, 1H), 3.137(m, 1H), 3.000(m, 2H), 2.068(m, 3H), 1.834(m, 3H), 1.633(s, 2H); LC-MS m/z 493.2[M+H]+.

Example 129

Synthesis of Compound 129

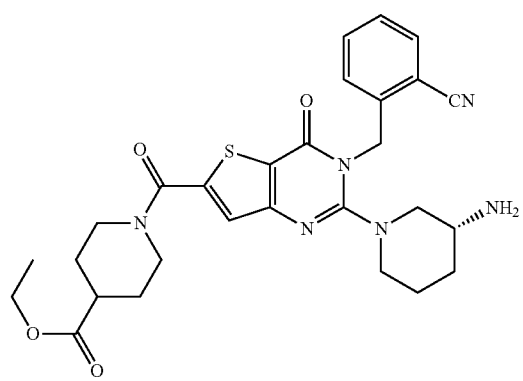

129

Compound 129 was synthesized according to the synthesis of compound 99, wherein methyl piperidine-4-carboxylate was used instead of methyl glycine ester used in the synthesis of compound 99. 1H-NMR(CDCl3-d3): δ=7.628(d, 1H), 7.500(t, 1H), 7.337(m, 2H), 7.145(d, 1H), 5.506 (quartet, 2H), 4.143(quartet, 2H), 3.454(m, 2H), 3.373(s, 1H), 3.093 (m, 4H), 2.934(m, 1H), 2.590(m, 1H), 2.009(m, 3H), 1.743 (m, 5H), 1.251(t, 3H); LC-MS m/z 549.2206[M+H]+.

Example 130

Synthesis of Compound 130

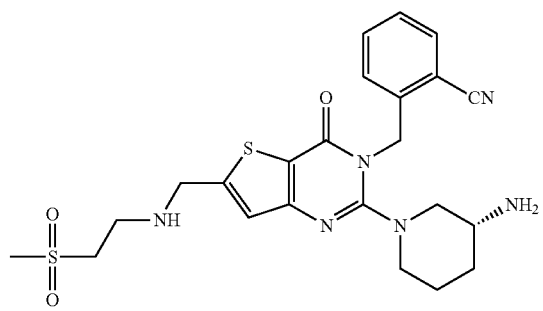

130

Compound 130 was synthesized according to the synthesis of compound 15, wherein 2-mesyl ethylamine was used instead of methylamine solution in tetrahydrofuran used in the synthesis of compound 15-1. MS: 501.2[M+H]+.

Example 131

Synthesis of Compound 131

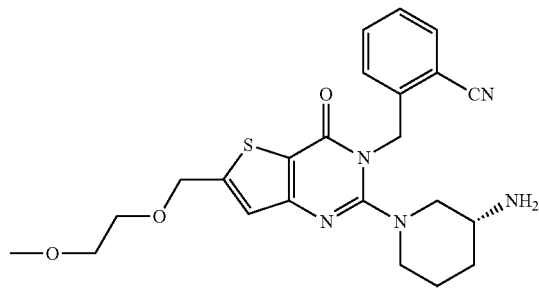

131

Compound 131 was synthesized according to the synthesis of compound 15, wherein 2-methoxyl-ethanol was used instead of methylamine solution in tetrahydrofuran used in the synthesis of compound 15-1. MS: 454.2[M+H]+.

Example 132

Synthesis of Compound 132

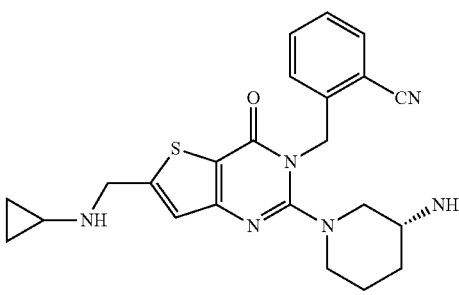

132

Compound 132 was synthesized according to the synthesis of compound 15, wherein cyclopropylamine was used instead of methylamine solution in tetrahydrofuran used in the synthesis of compound 15-1. MS: 435.2[M+H]+.

Example 133

Synthesis of Compound 133

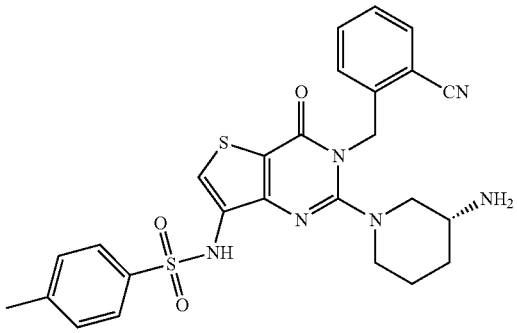

133

Compound 133 was synthesized according to the synthesis of compound 85, wherein p-toluensulfonyl chloride was used instead of methylsulfonyl chloride. MS: 535.2[M+H]+.

Example 134

Synthesis of Compound 134

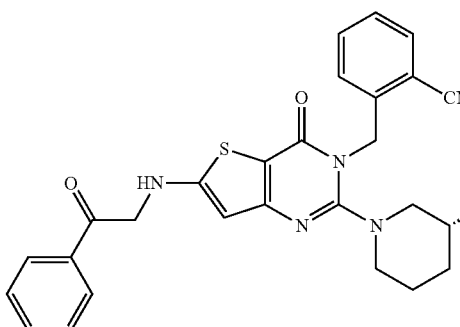

134

Compound 134 was synthesized according to the synthesis of compound 11, wherein bromo-acetophenone was used instead of iodomethane used in the synthesis of compound 11. MS: 499.2 [M+H]+.
Example 135
Synthesis of Compound 135
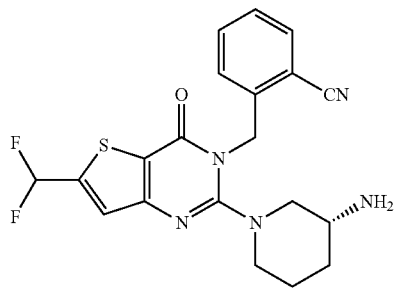
135
Synthesis route:
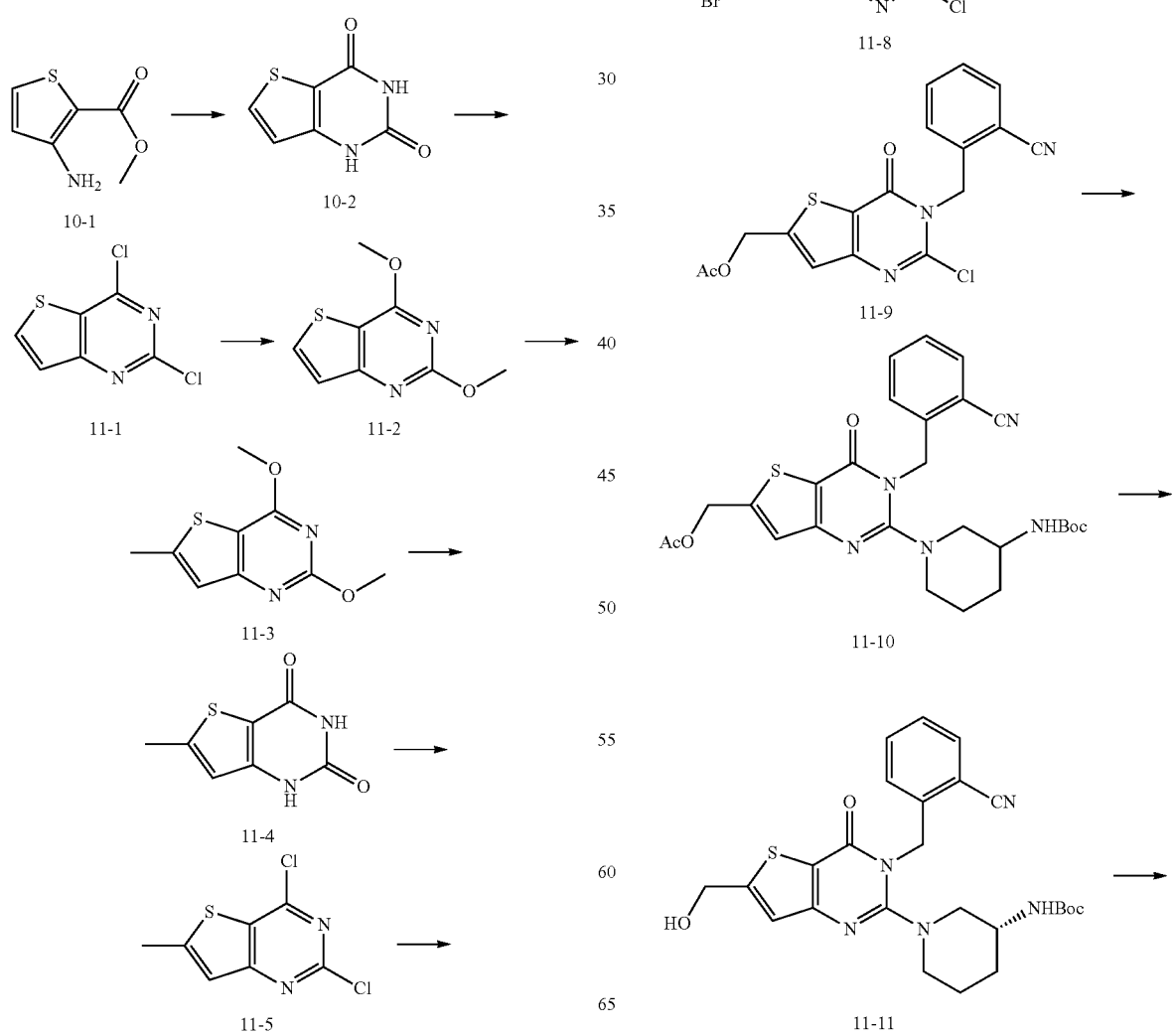

Compound 135 was synthesized according to the synthesis of compound 1. MS: 416.1 [M+H]+.

Example 136

Synthesis of Compound 136

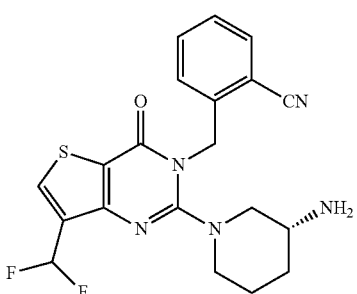

Synthesis route:

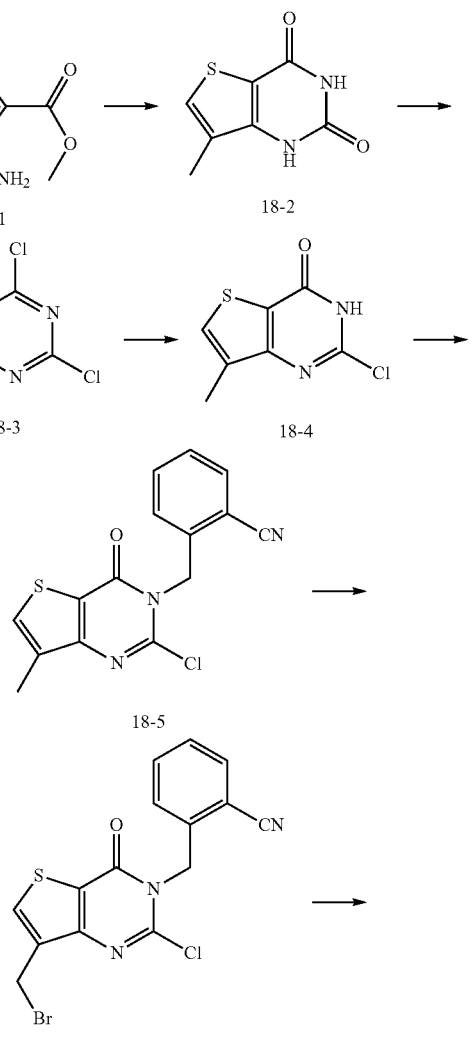

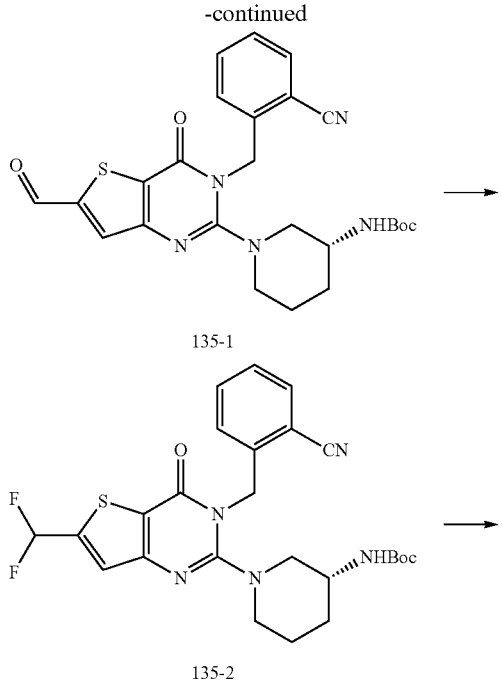

Synthesis of Compound 135-1

Compound 11-11 (100 mg) was dissolved in 10 ml dichloromethane. 1.1 equivalents of Dess-Martin Periodinane was added and stirred at room temperature for 2 hours. After extracted by dichloromethane, washed with water and evaporated to remove the solvent, compound 135-1 (80 mg) was obtained by column chromatography in 80% yield. MS: 494.2[M+H]+.

Synthesis of Compound 135-2

Compound 135-1 (80 mg) was dissolved in dichloromethane, and biethylaminosulphur trifluoride was added at −78° C. under nitrogen. The mixture was heated to room temperature and stirred overnight. The reaction solution was poured into saturated and ice-cooled sodium bicarbonate solution and stirred for 15 minutes. After extracted by dichloromethane, and washed with water, compound 135-2 (56 mg) was obtained by column chromatography in 67% yield. MS: 516.2 [M+H]+.

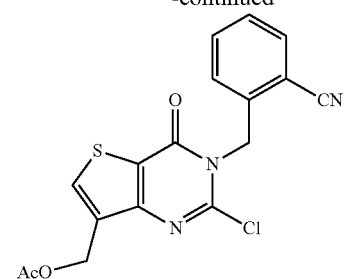

18-7

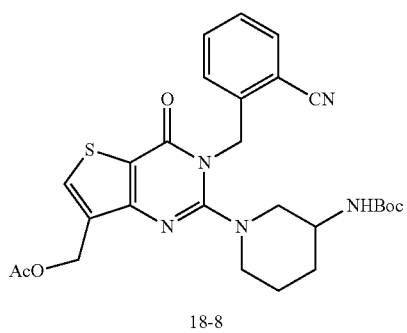

18-8

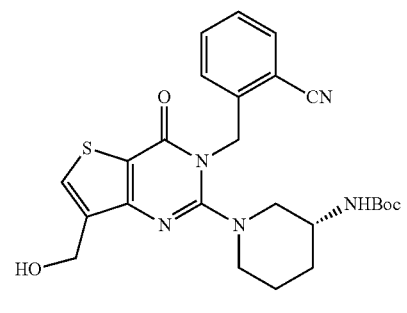

18-9

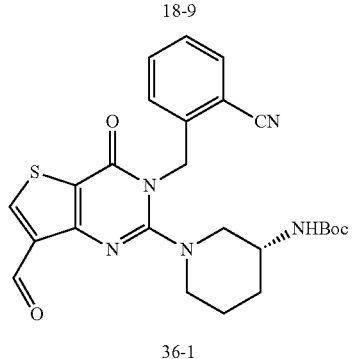

36-1

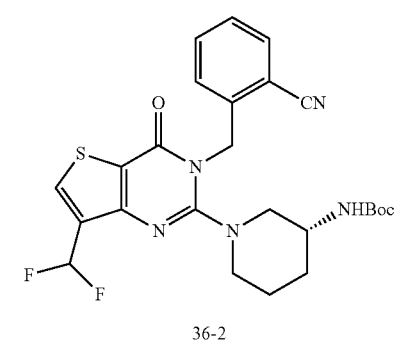

36-2

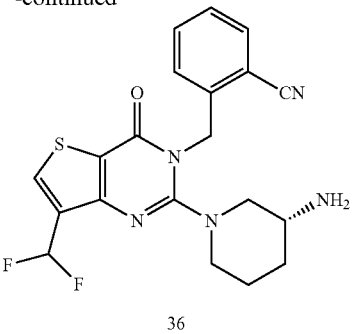

36

Compound 136 was synthesized according to the synthesis of compound 135. 1H NMR(CDCl3): δ 8.05(s, 1H), 7.66(m, 1H), 7.51(m, 1H), 7.36(m, 1H), 6.85-7.13(m, 2H), 5.52(m, 2H), 3.42(m, 1H), 3.26(m, 1H), 3.15(m, 1H), 2.96(m, 2H), 2.01(m, 1H), 1.79(m, 1H), 1.62(m, 2H); LC-MS m/z 416.1 [M+H]+.

Example 137

Synthesis of Compound 137

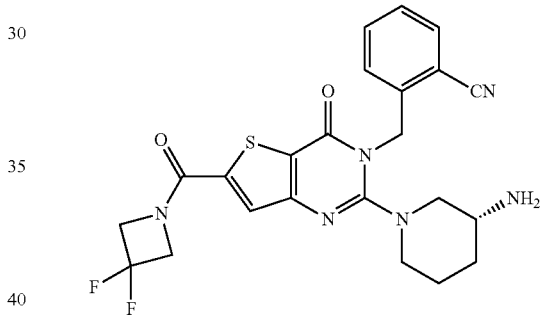

137

Synthesis route:
Compound 137 was synthesized according to the synthesis of compound 99, wherein 3,3-difluoroazetidine was used instead of methyl glycine ester used in the synthesis of compound 99. LC-MS m/z 485.1 [M+H]+.

Example 138

Synthesis of Compound 138

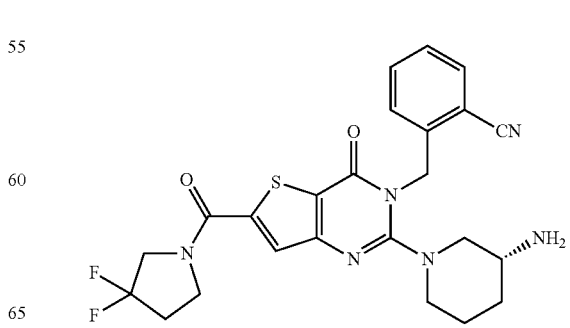

138

Synthesis route:

Compound 138 was synthesized according to the synthesis of compound 99, wherein 3,3-difluorotetrahydropyrrolidine was used instead of methyl glycine ester used in the synthesis of compound 99. LC-MS m/z 499.2[M+H]$^+$.

Example 139

Synthesis of Compound 139

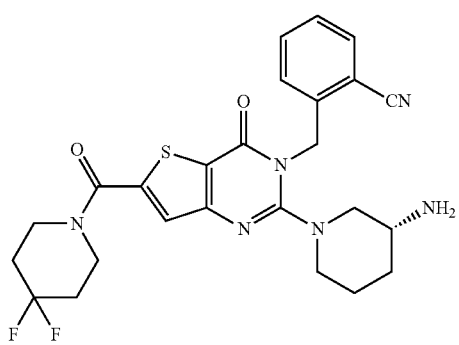

Synthesis route:

Compound 139 was synthesized according to the synthesis of compound 99, wherein 4,4-difluoropiperidine was used instead of methyl glycine ester used in the synthesis of compound 99. LC-MS m/z 513.2[M+H]+.

Example 140

Synthesis of Compound 140

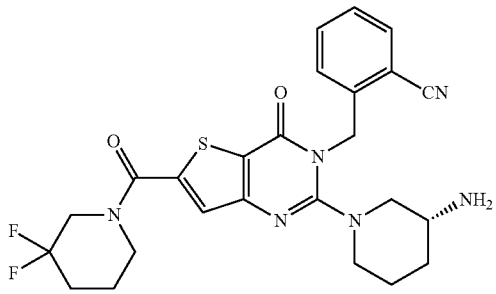

Synthesis route:

Compound 140 was synthesized according to the synthesis of compound 99, wherein 3,3-difluoropiperidine was used instead of methyl glycine ester used in the synthesis of compound 99. LC-MS m/z 513.2[M+H]+.

Example 141

Synthesis of Compound 141

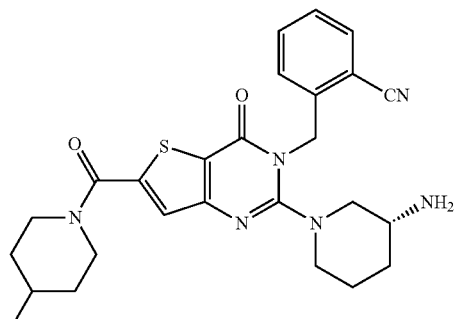

Synthesis route:

Compound 141 was synthesized according to the synthesis of compound 99, wherein 4-fluoropiperidine was used instead of methyl glycine ester used in the synthesis of compound 99. LC-MS m/z 495.2[M+H]+.

Example 142

Synthesis of Compound 142

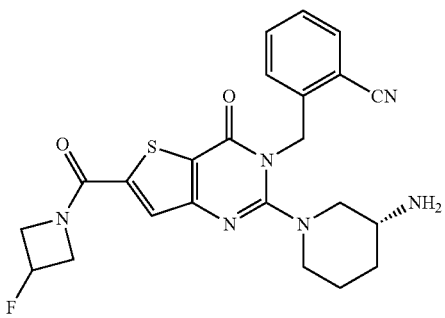

Synthesis route:

Compound 142 was synthesized according to the synthesis of compound 99, wherein 3-fluoroazetidine was used instead of methyl glycine ester used in the synthesis of compound 99. LC-MS m/z 467.2[M+H]+.

Example 143

Synthesis of Compound 143

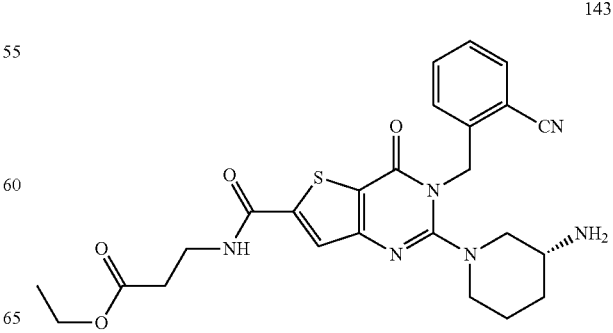

Synthesis route:
Compound 143 was synthesized according to the synthesis of compound 99, wherein ethyl alanine ester was used instead of methyl glycine ester used in the synthesis of compound 99. LC-MS m/z 509.2[M+H]+.

Example 144

Synthesis of Compound 144

144

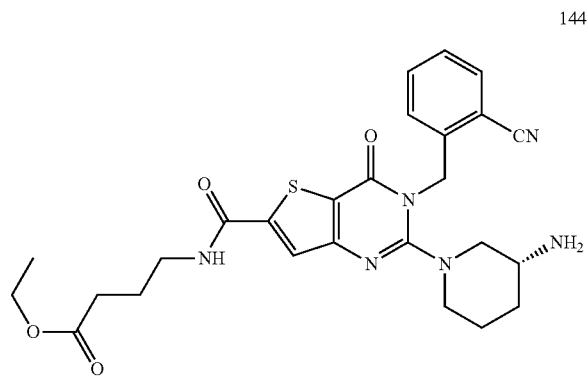

Synthesis route:
Compound 143 was synthesized according to the synthesis of compound 99, wherein ethyl 4-aminobutanoate was used instead of methyl glycine ester used in the synthesis of compound 99. LC-MS m/z 523.2[M+H]+.

EXPERIMENTAL EXAMPLE

Example 1

Activity Tests in vitro

Screening method: dipeptidyl peptidase IV (DPP IV) activity screening, dipeptidyl peptidase 7 (DPP 7), dipeptidyl peptidase 8 (DPP 8) activity screening, and dipeptidyl peptidase 9 (DPP 9) activity screening.
Instruments: Microplate Reader (PerkinElmer, USA).
Materials: human DPP IV, obtained extracellular fragment of protease DPP IV (aa29-766), was expressed and purified by our laboratory using baculovirus expression system Bac-to-Bac (purchased from GIBCO company) in accordance with the conventional experimental technology; human DPP 8 was obtained in insect cells by our laboratory using baculovirus expression system Bac-to-Bac (purchased from GIBCO company) in accordance with the conventional experimental technology; Human DPP 9 was obtained in insect cells by our laboratory using baculovirus expression system Bac-to-Bac (purchased from GIBCO company) in accordance with the conventional experimental technology; and the substrate Ala-Pro-AMC was synthesized by GL Biochem (Shanghai) Ltd.
Principle of Activity test: DPP IV, DPP 8 and DPP 9 can specifically hydrolyze the substrate Ala-Pro-AMC to form product AMC, and AMC is excited by 355 nm of UV light to generate 460 nm of emission light. The linear change of fluorescence value at 460 nm in unit time was dynamically measured and DPP IV activity was obtained by calculation. Sitagliptin (CAS: 486460-32-6, synthesized according to the conventional experimental technique in the art, see: Journal of Medicinal Chemistry 48 (2005) 141-151.), positive medicament Alogliptin (3 mg/kg, CAS: 850649-62-6, synthesized according to the conventional experimental technique in the art, see: Journal of Medicinal Chemistry 50 (2007) 2297-2300.), and positive medicament LAF237 (15 mg/kg, Vildagliptin, CAS: 274901-16-5, synthesized according to the conventional experimental technique in the art, see: Journal of Medicinal Chemistry 46 (2003) 2774-2789.) were used as control compound in the experiment.

Sample treatment: the sample was dissolved in DMSO and stored in low temperature. The concentration of DMSO in the final system was controlled so that the detected activity was not affected.

The activity of sample was tested under the selected single concentration from preliminary screening, for example, 20 μg/mL. For the sample which showed activity in a certain condition, for example, inhibition rate (% Inhibition) was more than 50, the dependent relationship between activity and dose, i.e. $IC_{50}$ value was determined by nonlinear fitting sample activity over sample concentration. The software for calculation was Graphpad Prism 4 and the model used for fitting was sigmoidal dose-response (variable slope). For most inhibitor screening models, the bottom and top of the fitting curve were set to 0 and 100. In general, each sample in the test was set in duplication or more (n≥2) and the results were represented by Standard Deviation (SD) or Standard Error (SE).

Experimental Results:
The results of the activities of the compounds were shown in table 1, and showed that the compounds of the invention have good DPPIV inhibitory activity.

TABLE 1

The detection results of activities in vitro of the compounds

| No. | DC No. | DPP IV $IC_{50}$ (nM) | DPP 7 $IC_{50}$ (μM) | DPP 8 $IC_{50}$ (μM) | DPP 9 $IC_{50}$ (μM) | FAP $IC_{50}$ (μM) |
|---|---|---|---|---|---|---|
| 1 | | 34.70 | | | | |
| 4 | | 8.78 | | | | |
| 8 | | 45.63 | | | | |
| 9 | | 36.81 | | | | |
| 10 | | 90.00 | | | | |
| 27 | | 35.50 | | | | |
| 28 | DC291408 | 10.16 | N.I. | 27.03 | 35.22 | 85.86 |
| 38 | DC291407 | 11.52 | N.I. | N.I. | N.I. | N.I. |
| 39 | DC291410 | 28.30 | N.I. | N.I. | N.I. | N.I. |
| 40 | DC291419 | 18.33 | N.I. | N.I. | 266.19 | 213.40 |
| 43 | DC291004 | 18.90 | N.I. | N.I. | N.I. | N.I. |
| 44 | DC291002 | 9.76 | 39.22 | N.I. | N.I. | N.I. |
| 45 | DC291011 | 3.57 | N.I. | N.I. | N.I. | N.I. |
| 54 | DC291003 | 238.07 | 39.22 | N.I. | N.I. | N.I. |
| 55 | DC291005 | 17.76 | N.I. | N.I. | N.I. | N.I. |
| 56 | DC291006 | 11.26 | N.I. | N.I. | N.I. | N.I. |
| 57 | DC291009 | 20.02 | 69.53 | N.I. | N.I. | N.I. |
| 58 | DC291010 | 8.72 | N.I. | 14.35 | N.I. | N.I. |
| 59 | DC291012 | 26.6 | N.I. | 34.98 | 187.42 | 49.52 |
| 60 | DC291013 | 13.28 | N.I. | 36.76 | 109.99 | 57.06 |
| 61 | DC291014 | 13.87 | N.I. | 45.94 | 253.61 | 30.28 |
| 62 | DC291015 | 49.16 | N.I. | 12.28 | 54.78 | 37.38 |
| 63 | DC291016 | 27.48 | N.I. | 47.86 | 189.23 | 169.82 |
| 64 | DC291017 | 33.2 | 52.02 | 5.81 | 39.74 | 9.38 |
| 65 | DC291018 | 30.21 | N.I. | 44.79 | 137.47 | 75.54 |
| 66 | DC291019 | 35.85 | N.I. | 14.39 | 47.14 | 18.81 |
| 67 | DC291020 | 13.75 | N.I. | 24.87 | 53.04 | 28.09 |
| 68 | DC291021 | 22.96 | 144.79 | 8.16 | 100.40 | 8.78 |
| 69 | DC291022 | 32.1 | N.I. | N.I. | N.I. | N.I. |
| 70 | DC291023 | 18.65 | N.I. | 38.89 | 94.49 | 135.64 |
| 71 | DC291024 | 14.27 | 144.21 | 26.79 | 237.68 | 52.15 |
| 72 | DC291025 | 15.14 | N.I. | 30.15 | 149.02 | 39.38 |
| 73 | DC291026 | 8.92 | 158.79 | 9.08 | 66.81 | 14.58 |
| 74 | DC291027 | 10.64 | N.I. | 18.44 | 92.92 | 30.56 |

TABLE 1-continued

The detection results of activities in vitro of the compounds

| No. | DC No. | DPP IV $IC_{50}$ (nM) | DPP 7 $IC_{50}$ (μM) | DPP 8 $IC_{50}$ (μM) | DPP 9 $IC_{50}$ (μM) | FAP $IC_{50}$ (μM) |
|---|---|---|---|---|---|---|
| 75 | DC291028 | 8.15 | N.I. | 22.97 | 91.67 | 28.33 |
| 76 | DC291029 | 81.58 | N.I. | N.I. | N.I. | N.I. |
| 77 | DC291030 | 11.14 | 29.99 | 49.42 | N.I. | 45.18 |
| 78 | DC291031 | 28.78 | 27.10 | 60.41 | 406.53 | 64.28 |
| 79 | DC291032 | 15.10 | 357.22 | 46.98 | 226.43 | 40.92 |
| 80 | DC291033 | 25.96 | N.I. | 25.72 | 115.15 | 28.72 |
| 81 | DC291034 | 20.16 | N.I. | 59.36 | 347.95 | 44.01 |
| 82 | DC291035 | 65.93 | N.I. | 18.12 | N.I. | 16.48 |
| 83 | DC291036 | 16.14 | 38.23 | 316.54 | N.I. | 160.11 |
| 84 | DC291037 | 24.19 | N.I. | 62.04 | N.I. | 91.34 |
| 85 | DC291038 | 37.12 | N.I. | 338.54 | N.I. | 255.04 |
| 86 | DC291039 | 20.85 | N.I. | 317.81 | N.I. | 120.83 |
| 87 | DC291040 | 26.49 | N.I. | N.I. | N.I. | |
| 88 | DC291041 | 14.81 | N.I. | 54.91 | N.I. | |
| 89 | DC291042 | 14.28 | N.I. | 39.43 | N.I. | |
| 90 | DC291043 | 14.27 | N.I. | 102.21 | N.I. | |
| 91 | DC291044 | 36.35 | N.I. | 88.0 | N.I. | |
| 92 | DC291045 | 21.70 | N.I. | 76.66 | N.I. | |
| 93 | DC291046 | 14.76 | N.I. | 60.69 | N.I. | |
| 94 | DC291402 | 10.43 | N.I. | 34.25 | 55.05 | 96.77 |
| 95 | DC291404 | 59.17 | N.I. | N.I. | N.I. | N.I. |
| 96 | DC291405 | 11.56 | N.I. | N.I. | N.I. | N.I. |
| 97 | DC291409 | 20.40 | N.I. | N.I. | N.I. | N.I. |
| 98 | DC291411 | 9.95 | N.I. | 27.03 | 35.22 | 85.86 |
| 99 | DC291412 | 24.73 | N.I. | 65.96 | 179.17 | 177.53 |
| 100 | DC291413 | 28.30 | N.I. | 43.13 | 117.17 | 118.53 |
| 101 | DC291414 | 30.59 | N.I. | 13.46 | 14.85 | 42.04 |
| 102 | DC291415 | 38.43 | N.I. | 27.84 | 32.63 | 68.49 |
| 103 | DC291416 | 53.79 | N.I. | N.I. | 86.84 | 144.79 |
| 104 | DC291417 | 17.11 | N.I. | N.I. | 254.20 | 239.43 |
| 105 | DC291418 | 26.98 | N.I. | N.I. | 257.03 | 200.44 |
| 106 | DC291420 | 18.29 | N.I. | 76.18 | 127.30 | 116.63 |
| 107 | DC291421 | 24.06 | N.I. | 39.70 | 122.13 | 98.59 |
| 108 | DC291422 | 11.84 | N.I. | 15.15 | 111.14 | 26.97 |
| 109 | DC291423 | 15.63 | N.I. | 62.07 | 91.80 | 101.36 |
| 110 | DC291424 | 24.78 | N.I. | 80.58 | 51.20 | 132.81 |
| 111 | DC291425 | 18.93 | N.I. | 112.49 | 131.25 | N.I. |
| 112 | DC291426 | 23.85 | N.I. | 69.06 | 158.57 | 213.42 |
| 113 | DC291427 | 18.75 | N.I. | 165.95 | 303.38 | 172.58 |
| 114 | DC291428 | 22.24 | N.I. | 56.17 | 307.25 | 52.18 |
| 115 | DC291429 | 14.48 | N.I. | 181.24 | 167.21 | 145.63 |
| 116 | DC291430 | 18.62 | N.I. | 95.27 | N.I. | 126.16 |
| 117 | DC291431 | 15.99 | N.I. | 63.23 | 78.51 | 118.29 |
| 118 | DC291432 | 18.45 | N.I. | 83.57 | N.I. | 80.18 |
| 119 | DC291433 | 20.62 | N.I. | 94.03 | N.I. | 112.53 |
| 120 | DC291434 | 28.56 | N.I. | 53.79 | 49.74 | 87.44 |
| 121 | DC291435 | 26.85 | N.I. | N.I. | N.I. | N.I. |
| 122 | DC291436 | 26.25 | N.I. | N.I. | 53.11 | N.I. |
| 123 | DC291437 | 19.83 | N.I. | 222.51 | N.I. | |
| 124 | DC291438 | 26.87 | N.I. | 43.89 | N.I. | |
| 125 | DC291439 | 33.84 | N.I. | 15.51 | 171.59 | |
| 126 | DC291440 | 20.07 | N.I. | 55.91 | N.I. | |
| 127 | DC291441 | 24.58 | N.I. | 52.67 | N.I. | |
| 128 | DC291442 | 30.66 | N.I. | 39.04 | N.I. | |
| 129 | DC291443 | 33.86 | N.I. | 16.29 | N.I. | |
| | Sitagliptin | 25.92 | 160.96 | 25.22 | 39.15 | 31.24 |
| | Vildagliptin | 66.79 | N.I. | 1.96 | 0.20 | 3.72 |
| | Alogliptin | 16.30 | N.I. | 274.97 | 1328.28 | 863.55 |

N.I.: No Inhibition.

Example 2

Study on DPP IV Inhibitory Activity in vivo

Animals: ICR mouse (8-10 weeks old; sex: male; 25 g-30 g of body weight, purchased from Shanghai SLAC Laboratory Animal Center).

Step: ICR mouse fasted overnight and was administrated with the tested compound (3 mg/kg), positive medicament Alogliptin (3 mg/kg), or positive medicament LAF237 (3 mg/kg) through mouth. Meanwhile the solvent group was used as blank control. The blood was taken from orbital venous plexus of the mouse before administration, and 30, 60, 2 h, 4 h, 6 h, 8 h and 240 h after administration, respectively and loaded into Eppendorf tube (Qizhong Industrial (Shanghai) co., Ltd.) treated by anticoagulant. The plasma was obtained by centrifugation and DPP IV activity was determined.

Results: 23 compounds were selected for DPP IV activity experiment of ICR mouse in vivo according to the test results of DPP IV activity and selectivity in vitro. The test results were shown in FIG. 1, FIG. 2, FIG. 3, FIG. 4, FIG. 5 and FIG. 6. After single dose, DC derivatives can significantly reduce DPP IV activity of ICR mouse plasma, wherein the hypoglycemic ability in vivo of 11 compounds including DC291004, DC291005, DC291009, DC291010, DC291402, DC291405, DC291407, DC291408, DC291411, DC291041 and DC291422 (3 mg) is comparable to that of Alogliptin (3 mg), and better than that of Vildagliptin (LAF237, 15 mg).

Example 3

Hypoglycemic Effect in vivo

Acute hypoglycemic effect of single dose through mouth on the normal ICR mouse

Animal: ICR mouse (8-10 weeks old, sex: male, weight: 25-30 g, purchased from Shanghai SLAC Laboratory Animal Center).

Step:

1. Two days before the experiment, the food consumption was recorded and the daily food consumption of each animal was calculated;

2. The animals fasted overnight (⅓ of daily food consumption was provided, about 2 g);

3. The blood glucose was measured on the second day. According to the blood glucose, the animals were randomly divided into 4 groups with 8 mice in each group: the solvent control group (0.5% methylcellulose, MC), the compound test group (3 mg/kg), the control group of positive medicament Alogliptin (3 mg/kg), the control group of positive medicament LAF237 (15 mg/kg);

4. The medicament was administrated through gavage (1 mouse/min). After 6 hours, the blood glucose was measured. Glucose was administrated through gavage according to the body weight (2.5 g/kg). The blood glucose value was monitored at 30 min, 60 min, 90 min, and 120 min after administration.

Figure 11:
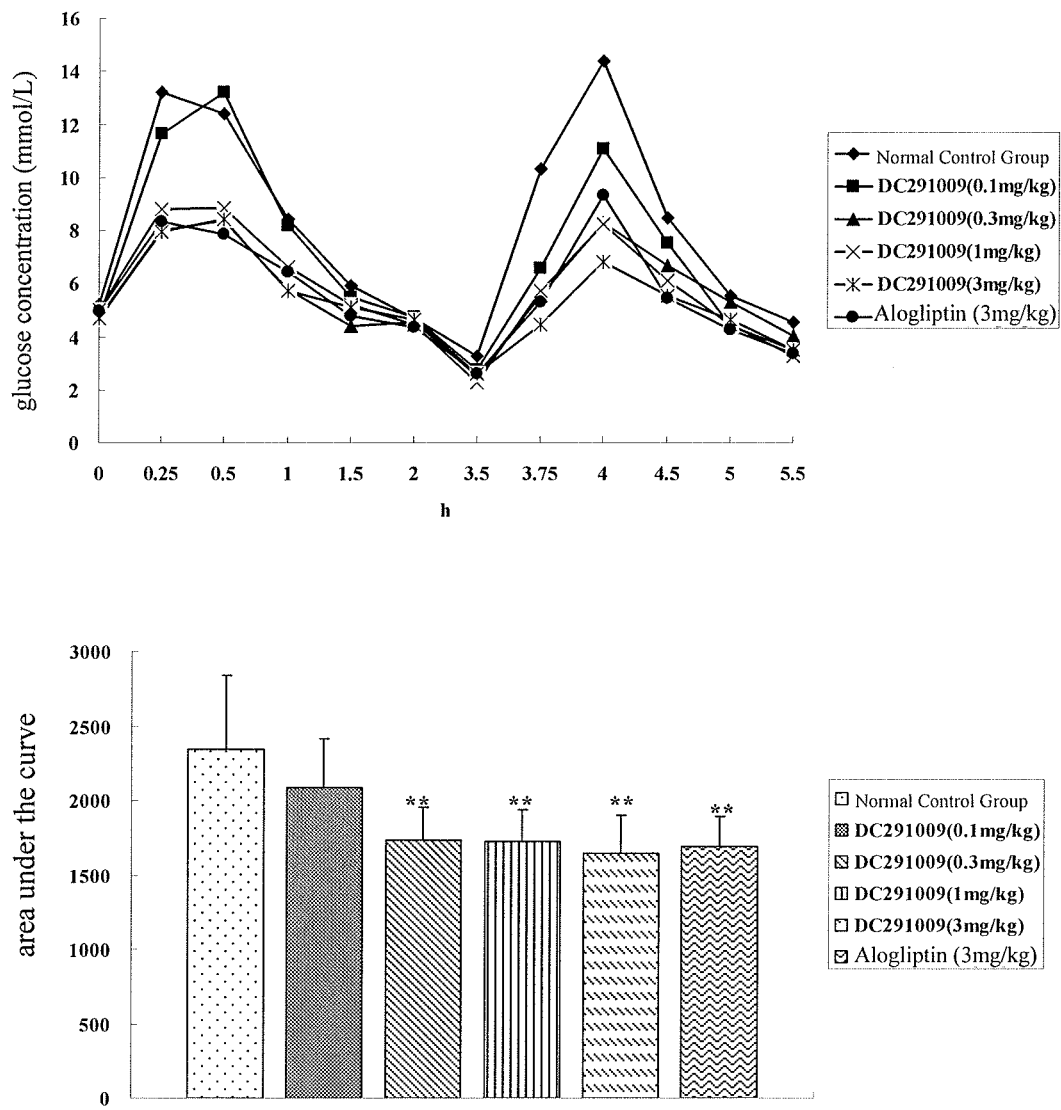
FIG. 11-FIG. 12 show oral glucose tolerance curve and the area under the curve after DC291009 was administrated once with multiple doses according to the embodiments of the present invention.
Figure 12:
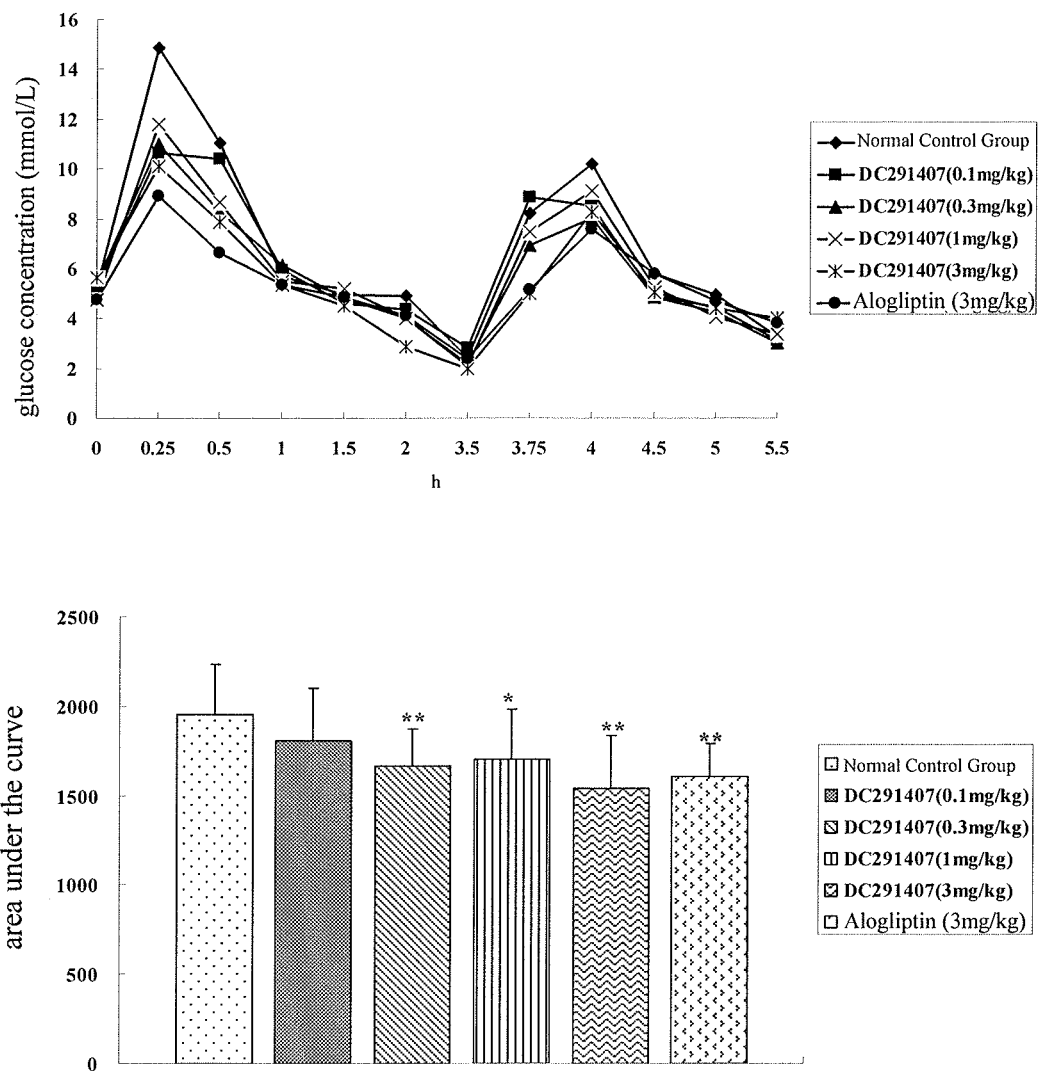

Results: 20 compounds were selected for oral glucose tolerance test (OGTT) in vivo of ICR mouse according to the results of DPP IV activities of ICR mouse plasma and the test results were shown in FIG. 7, FIG. 8, FIG. 9, FIG. 10, FIG. 11 and FIG. 12. After single dose, DC derivatives can dose-dependently significantly improve the glucose tolerance of ICR mouse, wherein the hypoglycemic ability in vivo of 7 compounds including DC291004, DC291009, DC291402, DC291407, DC291411, DC291034 and DC291036 is comparable to that of Alogliptin (FIGS. 7-10). Moreover, oral glucose tolerance tests were performed for compounds DC291009 and DC291407 after multiple single-dose administration. The results showed that the hypoglycemic ability in vivo of compound DC291009 or compound DC291407 is comparable to that of Alogliptin (FIGS. 11-12).

Example 4

Experimental Method for Safety Evaluation

Male normal ICR mice, 28-34 g of body weight (purchased from Shanghai SLAC Laboratory Animal Center), were randomly divided into model group and drug group according to the body weight with 4 mice each group. After grouping, each compound was administered once through gavage according to the dose of 100 mg/kg at the same time. After that, the mice in each group were observed in succession for one week, and the food consumption and weight of the mouse were monitored. The experimental results were as follows.

TABLE 2

The effect of single dose on the body weight (g) of normal ICR mouse

| Group | Before administration | After administration | | | | | | |
|---|---|---|---|---|---|---|---|---|
| | | 1 d | 2 d | 3 d | 4 d | 5 d | 6 d | 7 d |
| Normal Control Group | 31 ± 1.2 | 31.3 ± 1.1 | 32.1 ± 1.1 | 32.3 ± 1.2 | 32.8 ± 1.3 | 32.9 ± 1.3 | 33.3 ± 1.4 | 33.6 ± 1.3 |
| DC291407 (100 mg/kg) Group | 29.7 ± 1.8 | 30.0 ± 1.6 | 30.0 ± 1.7* | 29.7 ± 1.9* | 30.0 ± 1.5* | 30.5 ± 1.5* | 30.4 ± 1.8* | 30.6 ± 1.9* |
| DC291004 (100 mg/kg) Group | 30.2 ± 0.7 | 30.3 ± 1.0 | 30.8 ± 0.9 | 31.0 ± 1.2 | 31.6 ± 1.2 | 32.0 ± 1.6 | 32.0 ± 1.2 | 32.5 ± 1.3 |
| DC291009 (100 mg/kg) Group | 30.8 ± 2.2 | 31.3 ± 2.0 | 31.5 ± 2.3 | 31.8 ± 2.3 | 32.3 ± 2.2 | 32.4 ± 2.5 | 32.6 ± 2.6 | 33 ± 2.6 |
| DC291411 (100 mg/kg Group | 30 ± 1.5 | 30.5 ± 1.6 | 31.2 ± 1.6 | 31.0 ± 1.7 | 31.5 ± 1.9 | 31.8 ± 1.5 | 31.6 ± 1.8 | 32.1 ± 1.7 |

*$p < 0.05$ versus model group.

It can be seen from table 2 that compared with the normal control group, the weight of the ICR mouse began to show significant statistical difference ($p<0.05$) relative to the control group from the second day after single dose of DC291407 (100 mg/kg), which lasted until 7 days after administration (i.e. at the end of the experiment). However, the body weight was not consistently decreased during this period and retained around 30.0 g which did not significantly differ from the weights of the normal control group and other drug groups. Therefore, it was speculated that DC291407 possibly had no effect on body weight. There were no significant statistical differences between other groups and the normal control group.

TABLE 3

The effect of single dose on the food consumption (g · $day^{-1}$ · $cage^{-1}$) of normal ICR mouse

| Administration dosage | Before administration | After administration | | | | | | |
|---|---|---|---|---|---|---|---|---|
| | | 1 d | 2 d | 3 d | 4 d | 5 d | 6 d | 7 d |
| Normal Control Group | 22.3 | 19.6 | 20.4 | 21.5 | 20.2 | 20.9 | 21.9 | 21.5 |
| DC291407 (100 mg/kg) Group | 21.4 | 18.4 | 18.5 | 19.0 | 19.4 | 22.3 | 22.6 | 23.5 |
| DC291004 (100 mg/kg) Group | 22.5 | 18.7 | 21.0 | 21.1 | 21.5 | 21.9 | 21.5 | 24.1 |
| DC291009 (100 mg/kg) Group | 23.3 | 21.2 | 21.3 | 22.6 | 22.8 | 22.2 | 21.9 | 23.8 |
| DC291411 (100 mg/kg) Group | 20.8 | 19.3 | 21.3 | 18.8 | 18.3 | 17.7 | 20.5 | 21.9 |

It can be seen form table 3 that because of high dose of administrated medicament, the food consumption of mouse in each group decreased significantly from one day after administration, and then began to restore and substantially restored to the level of pre-administration at 7 days after administration.

TABLE 4

The effect of single dose on the important viscera index (%) of normal ICR mouse

| Group | Liver index | Kidney index | Spleen index |
|---|---|---|---|
| Normal Control Group | 4.9 ± 0.3 | 1.5 ± 0.0 | 0.3 ± 0.1 |
| DC291407 (100 mg/kg) Group | 5.3 ± 0.4 | 1.5 ± 0.2 | 0.4 ± 0.0* |

TABLE 4-continued

The effect of single dose on the important viscera index (%) of normal ICR mouse

| Group | Liver index | Kidney index | Spleen index |
|---|---|---|---|
| DC291004 (100 mg/kg) Group | 5.3 ± 0.3 | 1.5 ± 0.1 | 0.4 ± 0.0 |
| DC291009 (100 mg/kg) Group | 5.3 ± 0.2 | 1.4 ± 0.1 | 0.4 ± 0.1 |
| DC291411 (100 mg/kg) Group | 5.0 ± 0.4 | 1.4 ± 0.1 | 0.4 ± 0.0 |

*$p < 0.05$ versus model group.

It can be seen from table 4 that on the $7^{th}$ day after administrated, the liver index and spleen index of administrated ICR mouse in each group increased to a certain extent. However, there was a statistical difference between spleen index of DC29147 group and that of normal control group, while there was no statistical difference among other groups. The kidney index of DC291407 or DC291004 group did not significantly differ from that of normal control group, and the kidney index of DC291411 or DC291009 group is slightly lower than that of normal control group. However, there was no statistical difference.

Experimental Conclusion

The test results showed that after DC291407 (100 mg/kg) was administrated, there was statistical difference between the weight from the second day after administration to the $7^{th}$ day after administration and that of the normal control group, while the value did not greatly differ from that of each other group, therefore, there was possibly no practical significance. Moreover, compared with the normal control group, the spleen index significantly increased on the $7^{th}$ day after administration, while the value did not greatly differ from that of each other group, therefore, biological significance was not obvious. For other drug groups, DC291004 (100 mg/kg), DC291009 (100 mg/kg) and DC291411 (100 mg/kg), compared with the normal control group, there was no statistical difference for both of body weight and viscera index, and the liver index and spleen index slightly increased on the $7^{th}$ day after administration. Summing up, DC291407, DC291004, DC291009 and DC291411 in this experiment did not reflect obvious acute toxicity.

Example 5

Study on Pharmacokinetics

The concentration of metabolite M1 (4071001), metabolite M2 (407002) or metabolite M3 (407003) in plasma was determined by LC-MS/MS method after DC291407 was administrated to the rats through gavage and intravenous injection.

Figure 13:
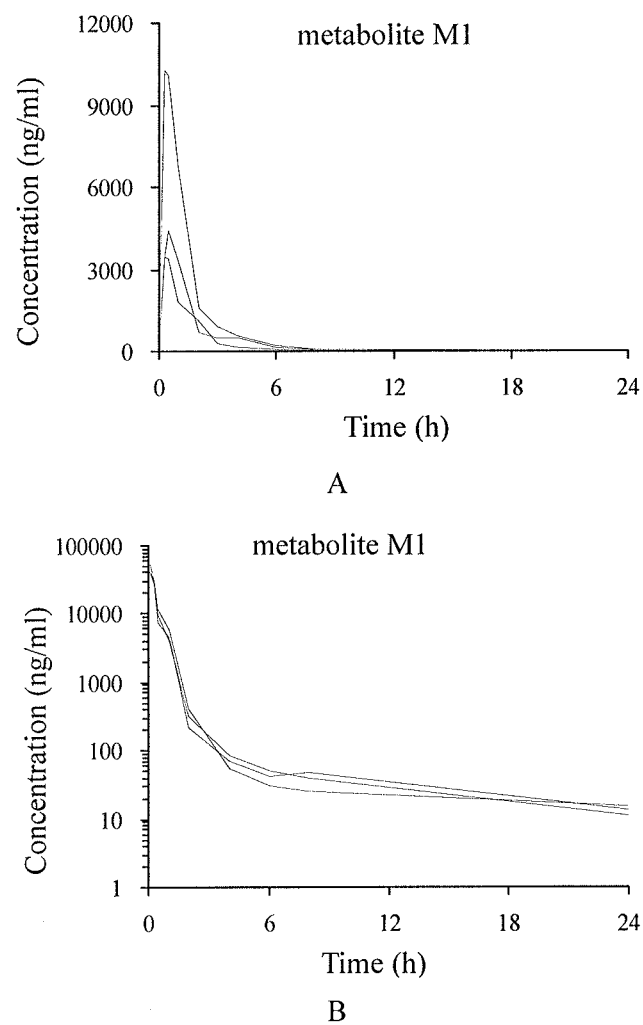
FIG. 13 shows the plasma concentration-time curve of metabolite M1 after DC291407 was administrated to the rats by gavage and by intravenous injection according to the embodiments of the present invention, wherein A is the plasma concentration-time curve of metabolite M1 after 20 mg/kg of DC291407 was administrated to the rats by gavage, and B is the plasma concentration-time curve of metabolite M1 after 10 mg/kg of DC291407 was administrated to the rats by intravenous injection.

As shown in FIG. 13, after 20 mg/kg of DC291407 was administrated to th healthy

Sprague-Dawley (SD) rats (purchased from Shanghai SLAC Laboratory Animal Center) through gavage, the plasma mainly contained hydrolysis-metabolite M1 (specially, a demethylated product from DC291407). In addition, relatively low concentration of M2 (specially, acetylizated (below 20 ng/ml) was detected in the samples collected within one hour after administration, and the prototype compound and metabolite M3 (specially, acetylizated DC291407) can not be detected in plasma.

After 10 mg/kg of DC291407 was administered to the rats through vein, the plasma mainly contained hydrolysis-metabolite M1. In addition, relatively low concentration of prototype compound and M2 were detected, and metabolite M3 can not be detected in plasma.

After normalization of the dose, the absolute bioavailability was 22.1% after 20 mg/kg of DC291407 was administered to the rats through gavage, based on AUC of metabolite M1.

The LC/MS/MS used is triple quadruple LC/MS 6460 from Agilent.

Specific administration regimen is as follows:

Six healthy male Sprague-Dawley (SD) rats with the weight of 180-220 g were randomly divided into 2 groups. The rats in each group were administrated with the tested compound by gavage or intravenous injection, respectively. Details are shown in the following table:

| Group | The number of animals | Compound | Administration route | Administration dosage (mg/kg) | Administration volume (ml/kg) |
|---|---|---|---|---|---|
| 1 | 3 | DC291407 | gavage | 20 | 10 |
| 2 | 3 | DC291407 | vein | 10 | 5.0 |

The compound was dissolved in 6.7% DMSO/6.7% Tween/86.6% normal saline.

The rats fasted for 12 h and can drink water ad libitum. 2 h after dosing, the rats were provided with food all together. The time point for collecting blood samples and the sample processing are listed as follows.

Intragastric administration: 0.25, 0.5, 1.0, 2.0, 3.0, 4.0, 6.0, 8.0 and 24 h after administration;

Intravenous administration: 5 min, 0.25, 0.5, 1.0, 2.0, 4.0, 6.0, 8.0 and 24 h after administration. At above time point, 0.3 ml venous blood was taken from retrobulbar venous plexus of the rat and loaded into heparinization tube. After centrifuged at 11000 rpm for 5 min, the plasma was separated and frozen at −20° C. in a refrigerator.

TABLE 5

Plasma concentrations (ng/mL) of metabolite M1 after 20 mg/kg of DC291407 was administered to the rats through gavage

| Animal No. | Time (h) | | | | | | | | | |
|---|---|---|---|---|---|---|---|---|---|---|
| | 0 | 0.25 | 0.5 | 1.0 | 2.0 | 3.0 | 4.0 | 6.0 | 8.0 | 24 |
| 1 | BLQ | 3454 | 4435 | 3326 | 690 | 476 | 500 | 138 | 97.1 | 13.0 |
| 2 | BLQ | 3427 | 3404 | 1771 | 1091 | 299 | 105 | 57.3 | 58.9 | 13.0 |
| 3 | BLQ | 10255 | 10087 | 6789 | 1569 | 872 | 565 | 173 | 49.5 | 14.3 |
| Average | | 5712 | 5975 | 3962 | 1117 | 549 | 390 | 123 | 68.5 | 13.4 |
| standard deviation | | 3934 | 3598 | 2569 | 440 | 293 | 249 | 59 | 25.2 | 0.7 |

BLQ: Below the lower detection limit of the measuring method (Below the lower quantification).

TABLE 6

Plasma concentrations (ng/mL) of metabolite M2 after 20 mg/kg of DC291407 was administered to the rats through gavage

| Animal | Time (h) | | | | | | | | | |
|---|---|---|---|---|---|---|---|---|---|---|
| No. | 0 | 0.25 | 0.5 | 1.0 | 2.0 | 3.0 | 4.0 | 6.0 | 8.0 | 24 |
| 1 | BLQ | 3.87 | 4.79 | 3.88 | BLQ | BLQ | BLQ | BLQ | BLQ | BLQ |
| 2 | BLQ | 3.24 | 3.94 | BLQ | BLQ | BLQ | BLQ | BLQ | BLQ | BLQ |
| 3 | BLQ | 16.3 | 16.9 | 10.7 | BLQ | BLQ | BLQ | BLQ | BLQ | BLQ |

TABLE 7

Plasma concentrations (ng/mL) of prototype compound after 10 mg/kg of DC291407 was administered to the rats through intravenous injection

| Animal | Time (h) | | | | | | | | |
|---|---|---|---|---|---|---|---|---|---|
| No. | 0.083 | 0.25 | 0.50 | 1.0 | 2.0 | 4.0 | 6.0 | 8.0 | 24 |
| 4 | 63.4 | 49.7 | 27.4 | 11.3 | 4.75 | BLQ | BLQ | BLQ | BLQ |
| 5 | 60.7 | 34.4 | 31.7 | 11.9 | 3.94 | BLQ | BLQ | BLQ | BLQ |
| 6 | 53.4 | 20.3 | 9.72 | 6.61 | 3.44 | BLQ | BLQ | BLQ | BLQ |
| Average | 59.2 | 34.8 | 23.0 | 9.9 | 4.05 | | | | |
| standard deviation | 5.2 | 14.7 | 11.7 | 2.9 | 0.66 | | | | |

TABLE 8

Plasma concentrations (ng/mL) of metabolite M1 after 10 mg/kg of DC291407 was administered to the rats through intravenous injection

| Animal | Time (h) | | | | | | | | |
|---|---|---|---|---|---|---|---|---|---|
| No. | 0.083 | 0.25 | 0.50 | 1.0 | 2.0 | 4.0 | 6.0 | 8.0 | 24 |
| 4 | 39818 | 28858 | 11784 | 5628 | 401 | 55.4 | 30.9 | 24.8 | 15.2 |
| 5 | 41730 | 29247 | 7251 | 4634 | 214 | 68.1 | 41.4 | 48.5 | 13.3 |
| 6 | 53535 | 29592 | 9426 | 3891 | 314.7 | 85.5 | 49.3 | 38.5 | 10.8 |
| Average | 45028 | 29232 | 9487 | 4717 | 310 | 69.7 | 40.5 | 37.3 | 13.1 |
| standard deviation | 7429 | 367 | 2267 | 872 | 93 | 15.1 | 9.2 | 11.9 | 2.2 |

TABLE 9

Plasma concentrations (ng/mL) of metabolite M2 after 10 mg/kg of DC291407 was administered to the rats through intravenous injection

| Animal | Time (h) | | | | | | | | |
|---|---|---|---|---|---|---|---|---|---|
| No. | 0.083 | 0.25 | 0.50 | 1.0 | 2.0 | 4.0 | 6.0 | 8.0 | 24 |
| 4 | 126 | 866 | 144 | 36.0 | BLQ | BLQ | BLQ | BLQ | BLQ |
| 5 | 209 | 132 | 153 | 30.9 | 7.18 | BLQ | BLQ | BLQ | BLQ |
| 6 | 15.0 | 20.3 | 9.39 | 3.26 | BLQ | BLQ | BLQ | BLQ | BLQ |
| Average | 117 | 339 | 102 | 23.4 | | | | | |
| standard deviation | 98 | 459 | 81 | 17.6 | | | | | |

TABLE 10

Pharmacokinetic parameters of metabolite M1 after 20 mg/kg of DC291407 was administered to the rats through gavage

| Animal No. | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) | F (%) |
|---|---|---|---|---|---|---|---|
| 1 | 0.50 | 4435 | 8191 | 8292 | 2.86 | 5.37 | |
| 2 | 0.25 | 3427 | 5758 | 5907 | 3.15 | 7.97 | |
| 3 | 0.25 | 10255 | 15633 | 15706 | 1.74 | 3.55 | |

TABLE 10-continued

Pharmacokinetic parameters of metabolite M1 after 20 mg/kg of DC291407 was administered to the rats through gavage

| Animal No. | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) | F (%) |
|---|---|---|---|---|---|---|---|
| Average | 0.33 | 6039 | 9860 | 9968 | 2.58 | 5.63 | 22.1 |
| standard deviation | 0.14 | 3686 | 5145 | 5110 | 0.75 | 2.22 | |
| CV % | 43.3 | 61.0 | 52.2 | 51.3 | 28.9 | 39.4 | |

TABLE 11

Pharmacokinetic parameters of prototype drug after 10 mg/kg of DC291407 was administered to the rats through intravenous injection

| Animal No. | $AUC_{0-t}$ (ng·h/mL) | $AUC_{0-\infty}$ (ng·h/mL) | MRT (h) | $t_{1/2}$ (h) | CL (L/h/kg) | $V_{ss}$ (L/kg) |
|---|---|---|---|---|---|---|
| 4 | 42.4 | 45.9 | 0.68 | 0.51 | 218 | 148 |
| 5 | 40.9 | 43.9 | 0.67 | 0.53 | 228 | 154 |
| 6 | 24.8 | 29.8 | 0.98 | 1.01 | 335 | 328 |
| Average | 36.0 | 39.9 | 0.78 | 0.68 | 260 | 210 |
| standard deviation | 9.7 | 8.8 | 0.17 | 0.28 | 65 | 102 |
| CV % | 27.0 | 22.0 | 22.3 | 41.3 | 25.0 | 48.7 |

TABLE 12

Pharmacokinetic parameters of metabolite M1 after 10 mg/kg of DC291407 was administered to the rats through intravenous injection

| Animal No. | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) |
|---|---|---|---|---|---|---|
| 4 | 0.083 | 39818 | 22692 | 23114 | 1.60 | 19.2 |
| 5 | 0.083 | 41730 | 20658 | 20834 | 1.01 | 9.18 |
| 6 | 0.083 | 53535 | 23472 | 23603 | 0.79 | 8.40 |
| Average | 0.083 | 45028 | 22274 | 22517 | 1.13 | 12.3 |
| standard deviation | 0.0 | 7429 | 1453 | 1478 | 0.42 | 6.0 |
| CV % | 0.0 | 16.5 | 6.5 | 6.6 | 36.9 | 49.2 |

It can be seen from table 5 to table 12, after 20 mg/kg of DC291407 was administered to the rats through gavage, the plasma mainly contained hydrolysis-metabolite M1. In addition, relatively low concentration of M2 (below 20 ng/ml) was detected in the samples collected within one hour after administration, and prototype compound and metabolite M3 can not be detected. After 10 mg/kg of DC291407 was administrated to the rats through intravenous injection, the plasma mainly contained hydrolysis-metabolite M1. Moreover, relatively low concentration of prototype compound and M2 can be detected while no metabolite M3 can be detected.

After normalizing the dosage, absolute bioavailability was 22.1%, half-life was 5.63 h and AUC was 9860 ng·h/mL after 20 mg/kg of DC291407 was administered to the rats through gavage, based on the AUC of metabolite M1.

The invention claimed is:

1. A thieno[3,2-d]pyrimidin-4-one compound of structural formula I, an enantiomer, a diastereoisomer, a racemate and mixtures thereof, and a pharmaceutically acceptable salt thereof,

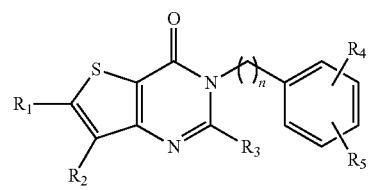

I wherein, n is an integer from 1 to 3;

$R_1$ and $R_2$ are identical or different, and not hydrogen simultaneously, and $R_1$ is H, $CBr_2H$, $CCl_2H$, $CF_2H$, a cyano, $CF_3$, an aldehyde group, $(CH_2)_mOR_6$, $(CH_2)_mNR_6R_7$,

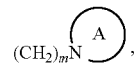

$(CH_2)_mCOOR_8$, $CONR_9R_{10}$, or

$R_2$ is H, a halogen, $CBr_2H$, $CCl_2H$, $CF_2H$, a cyano, $CF_3$, an aldehyde group, $(CH_2)_mOR_6$, $(CH_2)_mNR_6R_7$,

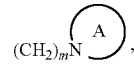

$(CH_2)_mCOOR_8$, $CONR_9R_{10}$,

or $R_1$ and $R_2$ are linked together to form C3-C6 alkylidene;

m is an integer from 0 to 3;

$R_6$ and $R_7$ are identical or different, and each of $R_6$ and $R_7$ is independently selected from H, a linear or branched saturated or unsaturated C1-C6 hydrocarbyl, a C3-C7 cyclic hydrocarbyl, a C1-C3 alkoxy, a 4-7 member heterocyclic group, a C1-C4 alkyloyl RCO, a C5-C7 aroyl ArCO, a C1-C4 alkylsulfonyl $RSO_2$, a C5-C7 arylsulfonyl $ArSO_2$, a C5-C7 aroylmethylene, a 5-7 member heteroaroylmethylene, a benzyl, a pyridinedimethylene, a C5-C7 aryl Ar or a 5-7 member heteroaryl; wherein, the linear or branched saturated or unsaturated C1-C6 hydrocarbyl is non-substituted or substituted by one or more substituents selected from a methylsulfonyl, a cyclopropyl, a hydroxy, a C1-C3 alkoxy, a C1-C3 alkoxycarbonyl, and an epoxypropyl; the heterocyclic group contains 1-3 heteroatoms selected from O, S and N, the methylene of the heterocyclic group is non-substituted or substituted by carbonyl or sulfonyl, or the heterocyclic group is non-substituted or substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a C1-C4 alkoxy carbonyl, a mercapto, a C1-C4 acyl and a C5-C7 aryl Ar; the aryl or the benzyl is non-substituted or substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the heteroaryl contains 1-3 heteroatoms selected from O, S and N, is combined with a phenyl or a C5-C7 heteroaryl, or is substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

$R_8$ is selected from H, a linear or branched saturated or unsaturated C1-C6 hydrocarbyl, a C3-C7 cyclic hydrocarbyl;

$R_9$ and $R_{10}$ are different, and each is independently selected form H,

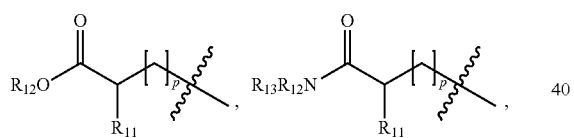

a linear or branched saturated or unsaturated C1-C6 hydrocarbyl, a C3-C7 cyclic hydrocarbyl, a C4-C7 heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched saturated or unsaturated C1-C6 hydrocarbyl is non-substituted or substituted by one or more substituents selected from a methylsulfonyl, a cyclopropyl, a hydroxy, a C1-C3 alkoxy, a C1-C3 alkoxycarbonyl, and an epoxypropyl; the heterocyclic group contains 1-3 heteroatoms selected from O, S and N, the methylene of the heterocyclic group is non-substituted or substituted by carbonyl or sulfonyl, or the heterocyclic group is non-substituted or substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the aryl or the benzyl is non-substituted or substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the heteroaryl contains 1-3 heteroatoms selected from O, S and N, is optionally combined with a phenyl or a C5-C7 heteroaryl, or is non-substituted or substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

P is an integer from 0 to 2;

$R_{11}$, $R_{12}$ and $R_{13}$ are identical or different, each of which is independently selected from H, a linear or branched saturated or unsaturated C1-C6 hydrocarbyl, a C3-C7 cyclic hydrocarbyl, a phenyl or a benzyl; wherein the phenyl or the benzyl is non-substituted or substituted by one or more substituents selected from a halogen, a linear or branched C1-C3 hydrocarbyl, a cyano, a nitro, an amino, a hydroxy, a hydroxymethyl, a trifluoromethyl, a trifluoromethoxy, a carboxyl, and a C1-C4 alkoxy;

is a 3-7 member nitrogen-containing heterocyclic group, the heterocyclic group further contains 1-3 heteroatoms selected from O, S and N, and the methylene of the heterocyclic group is non-substituted or substituted by carbonyl or sulfonyl, and the heterocyclic group is non-substituted or substituted by 1-5 substituents selected from H, a linear or branched C1-C6 hydrocarbyl, a halogen, a cyano, a nitro, an amino, a hydroxy, a hydroxymethyl, a trifluoromethyl, a trifluoromethoxy, a carboxyl, an acylamino, a carboxylate group, C1-C4 alkoxy carbonyl, a mercapto, a C1-C4 alkoxy and hydroxamino;

$R_3$ is selected from $NR_{14}R_{15}$ or

wherein $R_{14}$ and $R_{15}$ are identical or different, and each of $R_{14}$ and $R_{15}$ is independently H, a linear or branched saturated or unsaturated C1-C6 hydrocarbyl and hydrocarboxyl, a C3-C7 cyclic hydrocarbyl, a C1-C6 hydrocarbyl amino, a C1-C6 hydrocarbyl amino hydroxy, a C1-C6 hydrocarbyl amidino, a C1-C6 hydrocarbyl guanidyl, a benzyl, a C5-C7 aryl Ar or a 5-7 member heteroaryl, and the heteroaryl contains 1-3 heteroatoms selected from O, S and N, is optionally combined with a phenyl or a C5-C7 heteroaryl, or is non-substituted or substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

is a 3-7 member nitrogen-containing heterocyclic group, and the heterocyclic group further contains 1-4 heteroatoms selected from O, S and N, and is non-substituted or substituted by 1-5 substituents selected from H, a linear or branched C1-C6 hydrocarbyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, an amidino, a guanidyl and hydroxamino;

$R_4$, and $R_5$ are identical or different, and each of $R_4$ and $R_5$ is independently H, a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl, a C1-C4 sulfonyl, a C1-C4 sulfonyl amino, an aminoacyl or a C1-C4 linear or branched alkyl non-substituted or substituted sulfonyl;

the halogen is a fluoro, a chloro, a bromo or an iodo.

2. The thieno[3,2-d]pyrimidin-4-one compound, an enantiomer, a diastereoisomer, a racemate and mixtures thereof, and a pharmaceutically acceptable salt thereof according to claim 1, wherein, in general formula I:

n is 1;

$R_1$ and $R_2$ are identical or different, and not hydrogen simultaneously, and $R_1$ is H, $CBr_2H$, $CCl_2H$, $CF_2H$, a cyano, $CF_3$, an aldehyde group, $(CH_2)_mOR_6$, $(CH_2)_mNR_6R_7$,

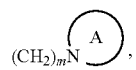

$(CH_2)_mCOOR_8$, $CONR_9R_{10}$, or

$R_2$ is H, a halogen, $CBr_2H$, $CCl_2H$, $CF_2H$, a cyano, $CF_3$, an aldehyde group, $(CH_2)_mOR_6$, $(CH_2)_mNR_6R_7$,

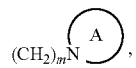

$(CH_2)_mCOOR_8$, $CONR_9R_{10}$, or

or $R_1$ and $R_2$ are linked together to form C3-C6 alkylidene;

m is an integer from 0 to 3;

$R_6$ and $R_7$ are identical or different, and each of $R_6$ and $R_7$ is independently selected from H, a linear or branched C1-C6 alkyl, a C3-C7 cycloalkyl, a C1-C3 alkoxy, a 4-7 member heterocyclic group, a C1-C4 alkyloyl RCO, a C5-C7 aroyl ArCO, a C1-C4 alkylsulfonyl $RSO_2$, a C5-C7 arylsulfonyl $ArSO_2$, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C6 alkyl is non-substituted or substituted by one or more substituents selected from a methylsulfonyl, a cyclopropyl, a hydroxy, a C1-C3 alkoxy, a C1-C3 alkoxycarbonyl, and an epoxypropyl; the heterocyclic group contains 1-3 heteroatoms selected from O, S and N; the aryl or the benzyl is non-substituted or substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the heteroaryl contains 1-3 heteroatoms selected from O, S and N, is optionally combined with a phenyl or a C5-C7 heteroaryl, or is non-substituted or substituted by one or more substituents selected from a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

$R_8$ is selected from H, a linear or branched C1-C6 alkyl;

$R_9$ and $R_{10}$ are different, each of which is independently selected from H,

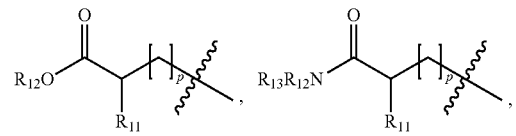

a linear or branched C1-C6 alkyl, a C3-C7 cycloalkyl, a 4-7 member heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C6 alkyl is non-substituted or substituted by one or more substituents selected from a methylsulfonyl, a cyclopropyl, a hydroxy, a C1-C3 alkoxy, a C1-C3 alkoxycarbonyl, and an epoxypropyl; the heterocyclic group contains 1-3 heteroatoms selected from O, S and N, the methylene of the heterocyclic group is non-substituted or substituted by carbonyl or sulfonyl, or the heterocyclic group is non-substituted or substituted by one or more substituents selected from a halogen, a linear or branched C1-C6 alky, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the aryl or the benzyl can be non-substituted or substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar; the heteroaryl contains 1-3 heteroatoms selected from O, S and N, is optionally combined with a phenyl or a C5-C7 heteroaryl, or is substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

p is an integer from 0 to 2;

$R_{11}$, $R_{12}$ and $R_{13}$ are identical or different, and each of $R_{11}$, $R_{12}$ and $R_{13}$ is independently selected from H, a linear or branched C1-C6 alkyl, a C3-C7 cycloalkyl, a phenyl or a benzyl; the phenyl or the benzyl is non-substituted or substituted by one or more substituents selected from a halogen, a linear or branched C1-C3 alky, a cyano, a nitro, an amino, a hydroxy, a hydroxymethyl, a trifluoromethyl, a trifluoromethoxy, a carboxyl, and a C1-C4 alkoxy;

is a 3-7 member nitrogen-containing heterocyclic group, the heterocyclic group further contains 1-3 heteroatoms selected from O, S and N, and the methylene of the heterocyclic group is non-substituted or substituted by carbonyl or sulfonyl, or is substituted by 1-5 substituents selected from H, a linear or branched C1-C6 hydrocarbyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, a C1-C4 alkoxy and hydroxamino;

$R_3$ is selected from $NR_{14}R_{15}$ or

wherein, $R_{14}$ and $R_{15}$ are identical or different, and each of $R_{14}$ and $R_{15}$ is independently H, a linear or branched C1-C6 alkyl and alkoxy, a C3-C7 cycloalkyl, a C1-C6 alkylamino, a C1-C6 alkylamino hydroxy, a C1-C6 alkyl amidino, a C1-C6 alkyl guanidyl, a benzyl, a C5-C7 aryl Ar or a 5-7 member heteroaryl, and the heteroaryl contains 1-3 heteroatoms selected from O, S and N, is combined with a phenyl or a C5-C7 heteroaryl, or is non-substituted or substituted by one or more substituents selected from a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl and a C5-C7 aryl Ar;

is a 3-7 member nitrogen-containing heterocyclic group, and the heterocyclic group further contains 1-4 heteroatoms selected from O, S and N, and is non-substituted or substituted by 1-5 substituents selected from H, a linear or branched C1-C6 alkyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, an amidino, a guanidyl and hydroxamino;

$R_4$, and $R_5$ are identical or different, and each of $R_4$ and $R_5$ is independently H, a halogen, a linear or branched C1-C6 hydrocarbyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl, a C1-C4 sulfonyl, a C1-C4 sulfonyl amino, an aminoacyl or a C1-C4 linear or branched alkyl substituted sulfonyl;

the halogen is a fluoro, a chloro, a bromo or an iodo.

3. The thieno[3,2-d]pyrimidin-4-one compound, an enantiomer, a diastereoisomer, a racemate and mixtures thereof, and a pharmaceutically acceptable salt thereof according to claim 2, wherein, in general formula I:

n=1;

$R_1$ and $R_2$ are identical or different, and not hydrogen simultaneously, and $R_1$ is H, $CBr_2H$, $CCl_2H$, $CF_2H$, a cyano, $CF_3$, an aldehyde group, $(CH_2)_mOR_6$, $(CH_2)_mNR_6R_7$,

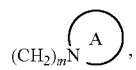

$(CH_2)_mCOOR_8$, $CONR_9R_{10}$, or

$R_2$ is H, a halogen, $CBr_2H$, $CCl_2H$, $CF_2H$, a cyano, $CF_3$, an aldehyde group, $(CH_2)_mOR_6$, $(CH_2)_mNR_6R_7$,

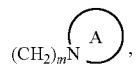

$(CH_2)_mCOOR_8$, $CONR_9R_{10}$, or

or $R_1$ and $R_2$ are linked together to form C3-C6 alkylidene;

m is an integer from 0 to 3;

$R_6$ and $R_7$ are identical or different, and each of $R_6$ and $R_7$ is independently selected from H, a linear or branched C1-C3 alkyl, a C3-C5 cycloalkyl, a C1-C3 alkoxy, a 4-7 member heterocyclic group, a C1-C3 alkyloyl RCO, a C5-C7 aroyl ArCO, a C1-C3 alkylsulfonyl $RSO_2$, a C5-C7 arylsulfonyl $ArSO_2$, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C3 alkyl is non-substituted or substituted by one or more substituents selected from a methylsulfonyl, a cyclopropyl, a hydroxy, a C1-C3 alkoxy, a C1-C3 alkoxycarbonyl, and an epoxypropyl, the heterocyclic group contains 1-3 heteroatoms selected from O, S and N; the aryl or the benzyl is non-substituted or substituted by one or more substituents selected from a halogen, a linear or branched C1-C3 alkyl, an amino, a hydroxy, a hydroxymethyl, a trifluoromethyl, and a trifluoromethoxy; the heteroaryl contains 1-3 heteroatoms selected from O, S and N;

$R_8$ is selected from H, a linear or branched C1-C3 alkyl and C3-C5 cycloalkyl;

$R_9$ and $R_{10}$ are different, each of which is independently selected from H,

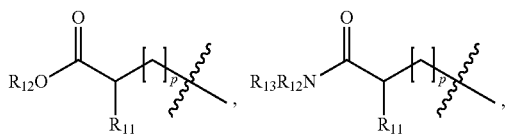

a linear or branched C1-C5 alkyl, a C3-C7 cycloalkyl, a 4-7 member heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C3 alkyl is non-substituted or substituted by one or more substituents selected from a methylsulfonyl, a cyclopropyl, a hydroxy, a C1-C3 alkoxy, a C1-C3 alkoxycarbonyl, and an epoxypropyl; the heterocyclic group contains 1-3 heteroatoms selected from O, S and N, the methylene of the heterocyclic group is non-substituted or substituted by carbonyl or sulfonyl, or the heterocyclic group is non-substituted or substituted by one or more substituents selected from a halogen, a linear or branched C1-C3 alky, an amino, a hydroxy, a hydroxymethyl, a trifluoromethyl, and a trifluoromethoxy; the aryl or the benzyl can be substituted by one or more substituents selected from a halogen, a linear or branched C1-C3 alky, an amino, a hydroxy, a hydroxymethyl, a trifluoromethyl, and a trifluoromethoxy; the heteroaryl contains 1-3 heteroatoms selected from O, S and N;

P is an integer from 0 to 2;

$R_{11}$, $R_{12}$ and $R_{13}$ are identical or different, and each of $R_{11}$, $R_{12}$ and $R_{13}$ is independently selected from H, a linear or branched C1-C3 alkyl, a C3-C7 cyclic hydrocarbyl, a phenyl or a benzyl; the phenyl or the benzyl is non-substituted or substituted by one or more substituents selected from a halogen, a linear or branched C1-C3 alky, an amino, a hydroxy, a hydroxymethyl, a trifluoromethyl, and a trifluoromethoxy;

is a 3-7 member nitrogen-containing heterocyclic group, the heterocyclic group further contains 1-3 heteroatoms selected from O, S and N, and the methylene of the heterocyclic group is non-substituted or substituted by carbonyl or sulfonyl or is substituted by 1-2 substituents selected from H, a linear or branched C1-C3 alkyl, a halogen, an amino, a hydroxy, a hydroxymethyl, a trifluoromethyl, a trifluoromethoxy, a C1-C4 alkoxy carbonyl, and a C1-C4 alkoxy;

$R_3$ is selected from $NR_{14}R_{15}$ or

wherein $R_{14}$ and $R_{15}$ are identical or different, and each of $R_{14}$ and $R_{15}$ is independently H, a linear or branched C1-C3 alkyl and alkoxy, a C3-C5 cycloalkyl, a C1-C3 alkylamino, a C1-C3 alkylamino hydroxy, a C1-C3 alkyl amidino, a C1-C3 alkyl guanidyl, a benzyl, a C5-C7 aryl Ar or a 5-7 member heteroaryl, and the heteroaryl contains 1-3 heteroatoms selected from O, S and N;

is a 3-7 member nitrogen-containing heterocyclic group, and said heterocyclic group further contains 1-4 heteroatoms selected from O, S and N, and is substituted by 1-3 substituents selected from H, a linear or branched C1-C6 alkyl, a halogen, a cyano, a nitro, an amino, a hydroxy, a hydroxymethyl, a trifluoromethyl, a trifluoromethoxy, a carboxyl, an acylamino, a carboxylate group, a C1-C4 alkoxy carbonyl, a mercapto, an amidino, a guanidyl and hydroxamino;

$R_4$, and $R_5$ are identical or different, and each of $R_4$ and $R_5$ is independently H, a halogen, a linear or branched C1-C6 alkyl, a cyano, a nitro, an amino, a hydroxy, a hydroxymethyl, a trifluoromethyl, a trifluoromethoxy, a carboxyl, a C1-C4 alkoxy, a mercapto, a C1-C4 acyl, a C1-C4 sulfonyl, a C1-C4 sulfonyl amino, an aminoacyl or a C1-C4 linear or branched alkyl substituted sulfonyl;

the halogen is a fluoro, a chloro, a bromo or an iodo.

4. The thieno[3,2-d]pyrimidin-4-one compound, an enantiomer, a diastereoisomer, a racemate and mixtures thereof, and a pharmaceutically acceptable salt thereof according to claim 3, wherein, in general formula I:

$R_3$ is $NR_{10}(CH_2)_kNH_2$, $NR_{10}(CH_2)_kOH$, $NR_{10}(CH_2)_kNH\text{-}CNHNH_2$, $NR_{10}(CH_2)_kCNHNH_2$ or $NR_{10}(CH_2)_kN\text{-}HOH$;

wherein, k is an integer from 0 to 4;

n, $R_1$, $R_2$, and $R_4\text{-}R_{15}$ are defined as claim 3.

5. The thieno[3,2-d]pyrimidin-4-one compound, an enantiomer, a diastereoisomer, a racemate and mixtures thereof, and a pharmaceutically acceptable salt thereof according to claim 3, wherein, in general formula I:

$R_3$ is

wherein

is an aziridinyl, an azacyclobutyl, a pyrrolidinyl, a piperidyl, an azacycloheptyl, a morpholinyl, a piperazinyl, a homopiperazinyl, a thiomorpholinyl, a thiomorpholinyl with S on the cycle being substituted by sulfoxide or sulphone, an imidazolidinyl, a pyrazinyl or a hexahydropyrimidinyl, and is substituted by 1-3 substituents selected from H, a linear or branched C1-C3 alky, a halogen, a cyano, a nitro, an amino, a hydroxy, a hydroxymethyl, a trifluoromethyl, a trifluoromethoxy, a carboxyl, an acylamino, a carboxylate group, a mercapto, an amidino, a guanidyl and hydroxamino;

n, $R_1$, $R_2$, and $R_4\text{-}R_{15}$ are defined as claim 3.

6. The thieno[3,2-d]pyrimidin-4-one compound, an enantiomer, a diastereoisomer, a racemate and mixtures thereof, and a pharmaceutically acceptable salt thereof according to claim 5, wherein, in general formula I:

$R_3$ is

, and is substituted by 1-3 substituents selected from H, a cyano, an amino, a hydroxy, a trifluoromethyl, an amidino, a guanidyl, a carboxylate group and hydroxamino; n, $R_1$, $R_2$,

, and $R_4$-$R_{15}$ are defined as claim 5.

7. The thieno[3,2-d]pyrimidin-4-one compound, an enantiomer, a diastereoisomer, a racemate and mixtures thereof, and a pharmaceutically acceptable salt thereof according to claim 3, wherein, in general formula I,
n=1,
$R_1$ and $R_2$ are identical or different, and not hydrogen simultaneously and $R_1$ is H, $CBr_2H$, $CCl_2H$, $CF_2H$, a cyano, $CF_3$, an aldehyde group, $(CH_2)_mOR_6$, $(CH_2)_mNR_6R_7$,

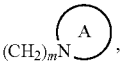, $(CH_2)_mCOOR_8$, $CONR_9R_{10}$, or

;

$R_2$ is H, a halogen, $CBr_2H$, $CCl_2H$, $CF_2H$, a cyano, $CF_3$, an aldehyde group, $(CH_2)_mOR_6$, $(CH_2)_mNR_6R_7$,

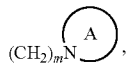, $(CH_2)_mCOOR_8$, $CONR_9R_{10}$, or

, wherein,
m is an integer from 0 to 3;
$R_6$ and $R_7$ are identical or different, and each of $R_6$ and $R_7$ is independently selected from H, a linear or branched C1-C3 alkyl, a C3-C5 cycloalkyl, a C1-C3 alkoxy, a 4-6 member heterocyclic group, a C1-C3 alkyloyl RCO, a C5-C7 aroyl ArCO, a benzyl and a C5-C7 aryl Ar; the linear or branched C1-C3 alkyl is non-substituted or substituted by one or more substituents selected from a methylsulfonyl, a C1-C3 alkoxy, and a C1-C3 alkoxycarbonyl; the heterocyclic group contains one heteroatom selected from O, S and N;

$R_8$ is selected from H, and a linear or branched C1-C3 alkyl;
$R_9$ and $R_{10}$ are different, each of which is independently selected from H,

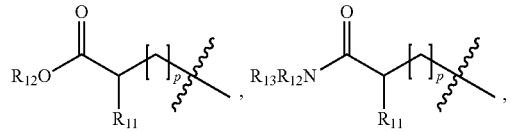

a linear or branched C1-C5 alkyl, a C3-C6 cycloalkyl, a 4-6 member heterocyclic group, a C5-C7 aroylmethylene, a 5-7 member heteroaroylmethylene, a benzyl, a pyridinedimethylene, a C5-C7 aryl Ar or a 5-7 member heteroaryl; wherein the linear or branched C1-C3 alkyl is non-substituted or substituted by one or more substituents selected from a methylsulfonyl, a cyclopropyl, a hydroxy, a C1-C3 alkoxy, a C1-C3 alkoxycarbonyl, and an epoxypropyl; the heterocyclic group contains 1-2 heteroatoms selected from O, S and N; the aryl or the benzyl can be non-substituted or substituted by one or more substituents selected from a halogen, a linear or branched C1-C3 alky, a hydroxy, a hydroxymethyl, a trifluoromethyl and a trifluoromethoxy; the heteroaryl contains 1-2 heteroatoms selected from O, S and N;
P is an integer from 0 to 2;
$R_{11}$, $R_{12}$ and $R_{13}$ are identical or different, and each of $R_{11}$, $R_{12}$ and $R_{13}$ is independently selected from H, a linear or branched C1-C3 alkyl, a phenyl or a benzyl; the phenyl or the benzyl is non-substituted or substituted by one or more substituents selected from a halogen, a linear or branched C1-C3 alky, and a hydroxyl;

is an aziridinyl, an azacyclobutyl, a pyrrolidinyl, a piperidyl, an azacycloheptyl, a morpholinyl, a piperazinyl, a homopiperazinyl, a thiomorpholinyl, a thiomorpholinyl with S on the cycle being substituted by sulfoxide or sulphone, an imidazolidinyl, a pyrazinyl, a hexahydropyrimidinyl or

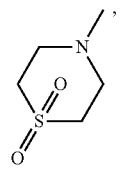

and is non-substituted or substituted by 1-2 substituents selected from H, a linear or branched C1-C3 alky, a halogen, a hydroxy, and a C1-C4 alkoxycarbonyl;
$R_4$ and $R_5$ are identical or different, and each of $R_4$ and $R_5$ is independently H, a halogen, a methyl, an ethyl, a cyano, a hydroxy, a carboxyl, a methoxyl, a ethoxyl or an aminoacyl;
the halogen is a fluoro, a chloro, a bromo or an iodo;
$R_3$ is defined as claim 4 or claim 5.

8. The thieno[3,2-d]pyrimidin-4-one compound, an enantiomer, a diastereoisomer, a racemate and mixtures thereof, and a pharmaceutically acceptable salt thereof according to claim 7, wherein, in general formula I:
n=1,
$R_1$ and $R_2$ are different, and not hydrogen simultaneously, and $R_1$ is H, $(CH_2)_m COOR_8$, $CONR_9R_{10}$, or

;

$R_2$ is H, a halogen, $(CH_2)_m COOR_8$, $CONR_9R_{10}$, or

, wherein,
m is an integer from 0 to 3;
$R_8$ is selected from H, or a linear or branched C1-C3 alkyl;
$R_9$ and $R_{10}$ are identical or different, each of which is independently selected from H, a linear or branched C1-C3 alkyl, a C3-C6 cycloalkyl, a C4-C6 heterocyclic group, a phenyl or a 5-7 member heteroaryl; wherein the linear or branched C1-C3 alkyl is non-substituted or substituted by a C1-C3 alkoxycarbonyl but not necessarily; the heterocyclic group contains one heteroatom selected from O, S and N; the heteroaryl contains one heteroatom selected from O, S and N;

is a pyrrolidinyl, a piperidyl, a morpholinyl, a piperazinyl, a homopiperazinyl, or a thiomorpholinyl, and is non-substituted or substituted by 1-2 substituents selected from H, a linear or branched C1-C3 alky, a halogen, a hydroxy, and a C1-C4 alkoxycarbonyl;
$R_3$ is a pyrrolidinyl, a piperidyl, a morpholinyl, a piperazinyl, a homopiperazinyl, or a thiomorpholinyl, and is substituted by a cyano, an amino or a hydroxyl;
$R_4$ and $R_5$ are identical or different, and each of $R_4$ and $R_5$ is independently H, a fluoro, a chloro, a bromo, a methyl, an ethyl, a cyano, or a hydroxyl.

9. The thieno[3,2-d]pyrimidin-4-one compound, an enantiomer, a diastereoisomer, a racemate and mixtures thereof, and a pharmaceutically acceptable salt thereof according to claim 8, wherein, in general formula I:
$R_1$ and $R_2$ are identical or different, and not hydrogen simultaneously, and $R_1$ is H, $(CH_2)_m COOR_8$, $CONR_9R_{10}$, or

;

$R_2$ is H, a halogen, $(CH_2)_m COOR_8$, $CONR_9R_{10}$, or

;

wherein,
m is 0;
$R_8$ is selected from H, or a linear or branched C1-C3 alkyl;
$R_9$ and $R_{10}$ are different, each of which is independently selected from H, a linear or branched C1-C3 alkyl, a cyclopropyl, a tetrahydropyran-4-yl or pyridinyl; wherein the linear or branched C1-C3 alkyl is non-substituted or substituted by a C1-C3 alkoxycarbonyl;

is a piperidyl, and is non-substituted or substituted by 1-2 substituents selected from H, a linear or branched C1-C3 alky, a halogen, a hydroxy, and a C1-C4 alkoxycarbonyl;
$R_3$ is a pyrrolidinyl, a piperidyl, a morpholinyl, or a piperazinyl, and is substituted by a cyano, an amino or a hydroxyl;
$R_4$ and $R_5$ are identical or different, and each of $R_4$ and $R_5$ is independently H, a fluoro, a chloro, a bromo, a methyl, an ethyl, a cyano, or a hydroxyl.

10. The thieno[3,2-d]pyrimidin-4-one compound of structural general formula I, an enantiomer, a diastereoisomer, a racemate and mixtures thereof, and a pharmaceutically acceptable salt thereof according to claim 1, wherein, the thieno[3,2-d]pyrimidin-4-one compound is one of the following compounds:

| Designation | Structure |
|---|---|
| (R)-2-((2-(3-aminopiperidin-1-yl)-7-fluoro-4-oxothieno[3,2-d]pyrimidin-3(4H)-yl)methyl)benzonitrile | 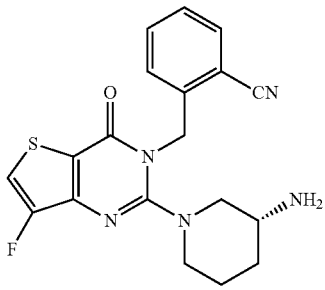 |

| Designation | Structure |
|---|---|
| (R)-2-((2-(3-aminopiperidin-1-yl)-7-bromo-4-oxothieno[3,2-d]pyrimidin-3(4H)-yl)methyl)benzonitrile | 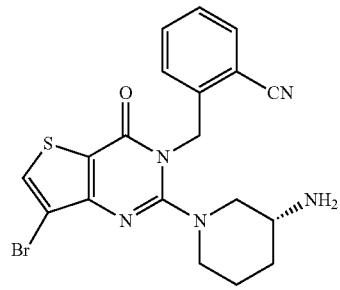<br>4 |
| (R)-2-((2-(3-aminopiperidin-1-yl)-7-iodo-4-oxothieno[3,2-d]pyrimidin-3(4H)-yl)methyl)benzonitrile | 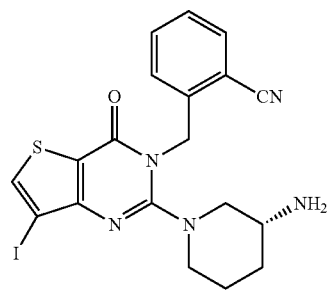<br>6 |
| (R)-2-((2-(3-aminopiperidin-1-yl)-4-oxo-7-(trifluoromethyl)thieno[3,2-d]pyrimidin-3(4H)-yl)methyl)benzonitrile | 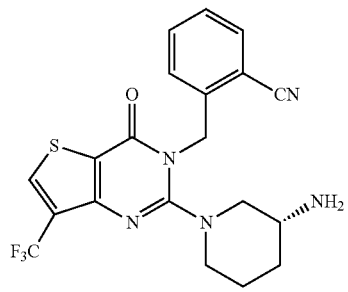<br>7 |
| (R)-2-((2-(3-aminopiperidin-1-yl)-6-chloro-4-oxothieno[3,2-d]pyrimidin-3(4H)-yl)methyl)benzonitrile | 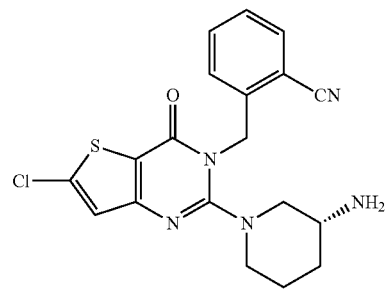<br>8 |

| Designation | Structure |
|---|---|
| (R)-2-((2-(3-aminopiperidin-1-yl)-7-chloro-4-oxothieno[3,2-d]pyrimidin-3(4H)-yl)methyl)benzonitrile | 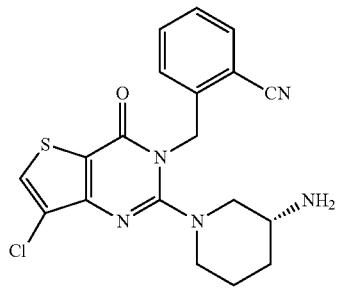<br>9 |
| (R)-2-((2-(3-aminopiperidin-1-yl)-6-(methylamino)-4-oxothieno[3,2-d]pyrimidin-3(4H)-yl)methyl)benzonitrile | 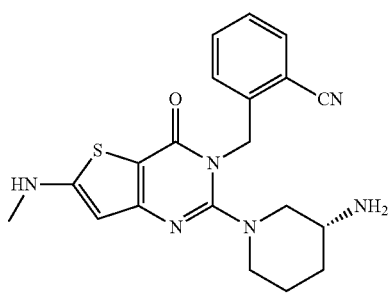<br>11 |
| (R)-2-((2-(3-aminopiperidin-1-yl)-6-(ethylamino)-4-oxothieno[3,2-d]pyrimidin-3(4H)-yl)methyl)benzonitrile | 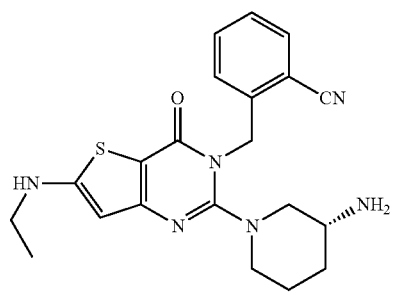<br>12 |
| (R)-2-((2-(3-aminopiperidin-1-yl)-4-oxo-6-(phenylamino)thieno[3,2-d]pyrimidin-3(4H)-yl)methyl)benzonitrile | 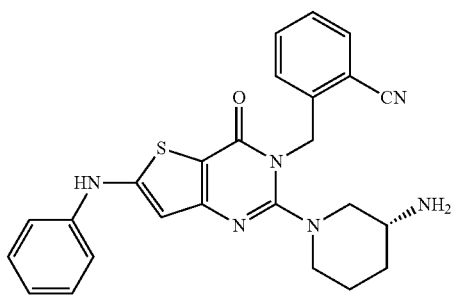<br>13 |

| Designation | Structure |
|---|---|
| (R)-2-((2-(3-aminopiperidin-1-yl)-6-(benzylamino)-4-oxothieno[3,2-d]pyrimidin-3(4H)-yl)methyl)benzonitrile | 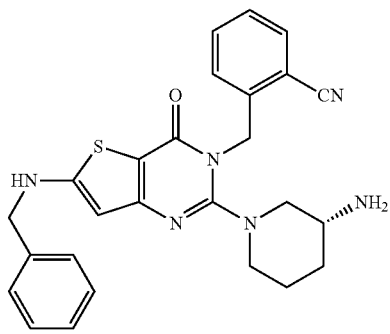<br>14 |
| (R)-2-((2-(3-aminopiperidin-1-yl)-6-((methylamino)methyl)-4-oxothieno[3,2-d]pyrimidin-3(4H)-yl)methyl)benzonitrile | 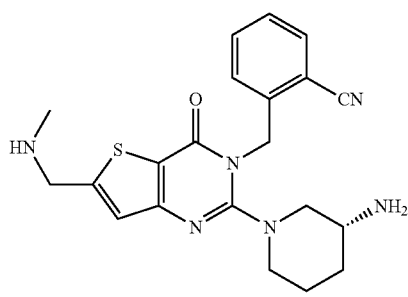<br>15 |
| (R)-2-((2-(3-aminopiperidin-1-yl)-6-((dimethylamino)methyl)-4-oxothieno[3,2-d]pyrimidin-3(4H)-yl)methyl)benzonitrile | 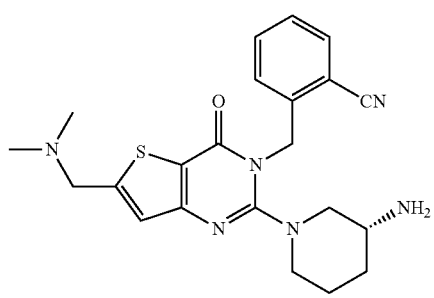<br>16 |
| (R)-2-((2-(3-aminopiperidin-1-yl)-6-((benzylamino)methyl)-4-oxothieno[3,2-d]pyrimidin-3(4H)-yl)methyl)benzonitrile | 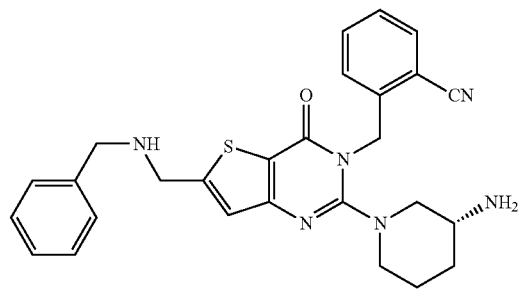<br>17 |

-continued
| Designation | Structure |
|---|---|
| (R)-2-((2-(3-aminopiperidin-1-yl)-7-(methylamino)-4-oxothieno[3,2-d]pyrimidin-3(4H)-yl)methyl)benzonitrile | 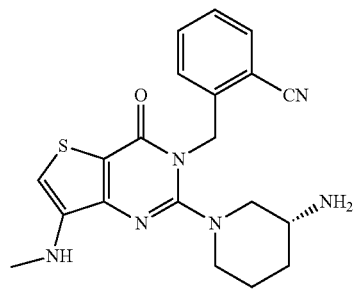<br>18 |
| (R)-2-((2-(3-aminopiperidin-1-yl)-7-(ethylamino)-4-oxothieno[3,2-d]pyrimidin-3(4H)-yl)methyl)benzonitrile | 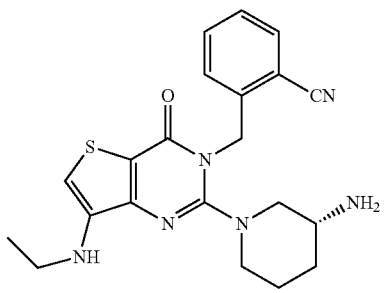<br>19 |
| (R)-2-((2-(3-aminopiperidin-1-yl)-7-(benzylamino)-4-oxothieno[3,2-d]pyrimidin-3(4H)-yl)methyl)benzonitrile | 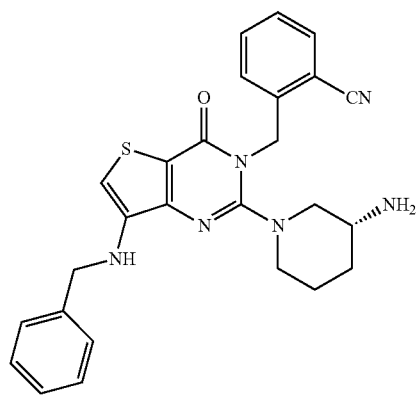<br>20 |
| (R)-2-(3-aminopiperidin-1-yl)-7-bromo-3-(2-chlorobenzyl)thieno[3,2-d]pyrimidin-4(3H)-one | 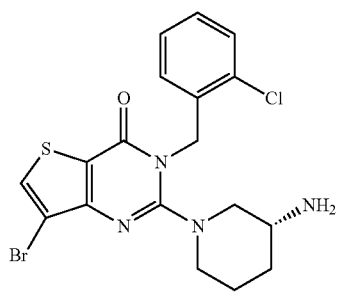<br>21 |

-continued
| Designation | Structure |
|---|---|
| (R)-2-(3-aminopiperidin-1-yl)-7-bromo-3-(4-chlorobenzyl)thieno[3,2-d]pyrimidin-4(3H)-one | 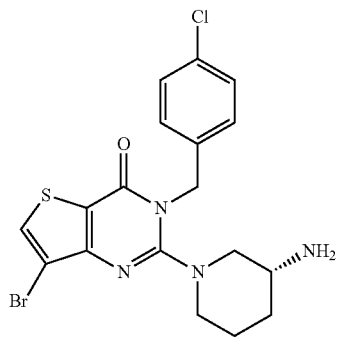<br>22 |
| (R)-2-(3-aminopiperidin-1-yl)-7-bromo-3-(4-methoxybenzyl)thieno[3,2-d]pyrimidin-4(3H)-one | 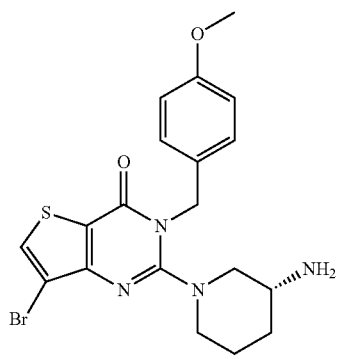<br>23 |
| (R)-2-(3-aminopiperidin-1-yl)-7-bromo-3-(4-methylbenzyl)thieno[3,2-d]pyrimidin-4(3H)-one | 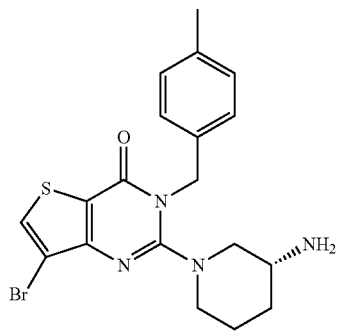<br>24 |
| 2-((2-((2-aminoethyl)amino)-7-bromo-4-oxothieno[3,2-d]pyrimidin-3(4H)-yl)methyl)benzonitrile | 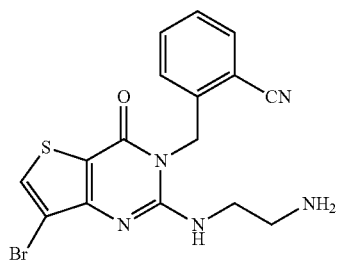<br>25 |

-continued

| Designation | Structure |
|---|---|
| (R)-2-((2-(3-aminopyrrolidin-1-yl)-7-bromo-4-oxothieno[3,2-d]pyrimidin-3(4H)-yl)methyl)benzonitrile | 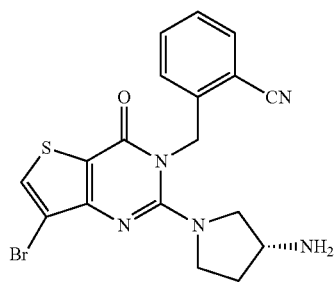<br>26 |
| (R)-2-((2-(3-aminopiperidin-1-yl)-4-oxo-6,7,8,9-tetrahydrobenzo[4,5]thieno[3,2-d]pyrimidin-3(4H)-yl)methyl)benzonitrile | 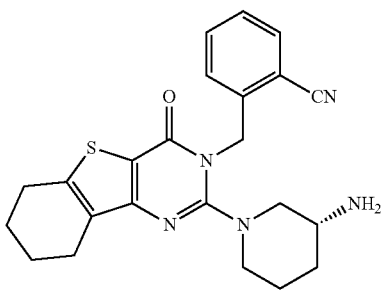<br>27 |
| (R)-2-((2-(3-aminopiperidin-1-yl)-6-(hydroxymethyl)-4-oxothieno[3,2-d]pyrimidin-3(4H)-yl)methyl)benzonitrile | 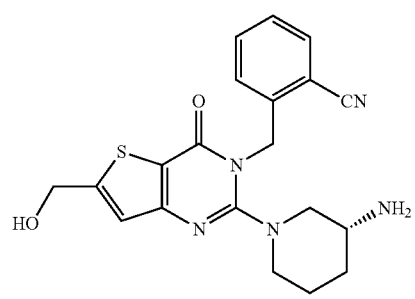<br>28 |
| 2-((7-bromo-2-((2-hydroxyethyl)amino)-4-oxothieno[3,2-d]pyrimidin-3(4H)-yl)methyl)benzonitrile | 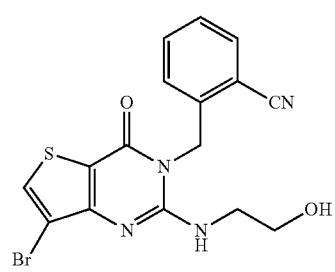<br>29 |
| 2-((2-((2-aminoethyl)(methyl)amino)-7-bromo-4-oxothieno[3,2-d]pyrimidin-3(4H)-yl)methyl)benzonitrile | 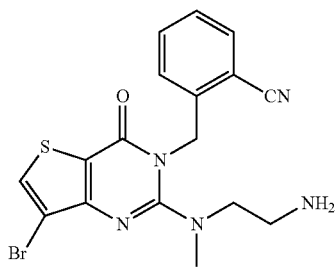<br>30 |

-continued

| Designation | Structure |
|---|---|
| 2-((2-((2-aminoethyl)(phenyl)amino)-7-bromo-4-oxothieno[3,2-d]pyrimidin-3(4H)-yl)methyl)benzonitrile | 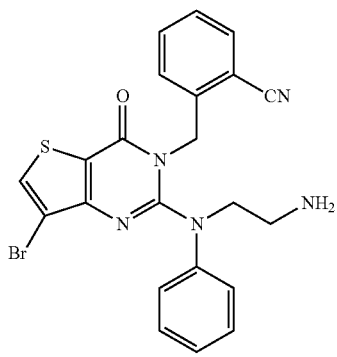<br>31 |
| (R)-2-((2-(3-aminoazepan-1-yl)-7-bromo-4-oxothieno[3,2-d]pyrimidin-3(4H)-yl)methyl)benzonitrile | 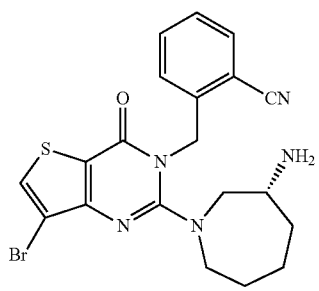<br>32 |
| (R)-ethyl 1-(7-bromo-3-(2-cyanobenzyl)-4-oxo-3,4-dihydrothieno[3,2-d]pyrimidin-2-yl)piperidine-3-carboxylate | 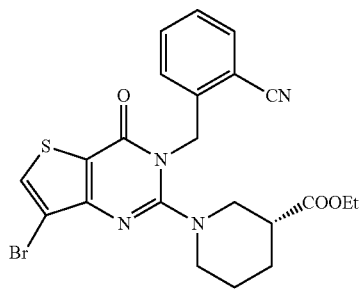<br>33 |
| (R)-methyl 2-(3-aminopiperidin-1-yl)-3-(2-cyanobenzyl)-4-oxo-3,4-dihydrothieno[3,2-d]pyrimidine-6-carboxylate | 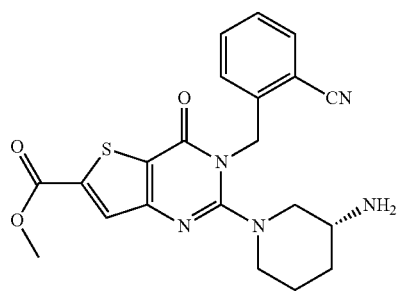<br>38 |

| Designation | Structure |
|---|---|
| (R)-2-(3-amino-1-yl)-3-(2-cyanobenzyl)-4-oxo-3,4-dihydrothieno[3,2-d]pyrimidine-6-carboxylic acid hydrochloride | 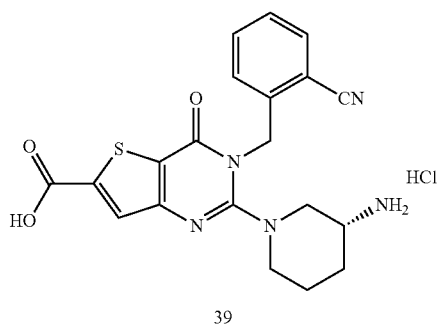<br>39 |
| (R)-2-(3-aminopiperidin-1-yl)-3-(2-cyanobenzyl)-N-cyclopropyl-4-oxo-3,4-dihydrothieno[3,2-d]pyrimidine-6-carboxamide | 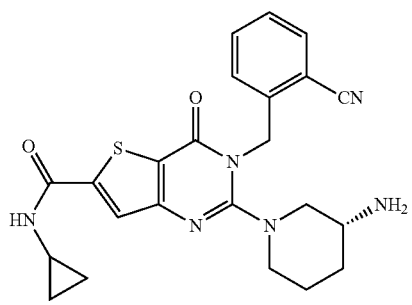<br>40 |
| (R)-2-(3-aminopiperidin-1-yl)-N-benzyl-3-(2-cyanobenzyl)-4-oxo-3,4-dihydrothieno[3,2-d]pyrimidine-6-carboxamide | 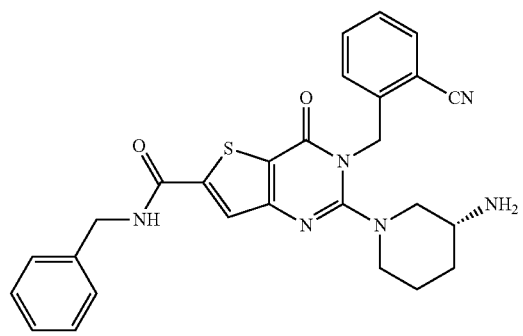<br>41 |
| (R)-2-(3-aminopiperidin-1-yl)-3-(2-cyanobenzyl)-4-oxo-N-phenyl-3,4-dihydrothieno[3,2-d]pyrimidine-6-carboxamide | 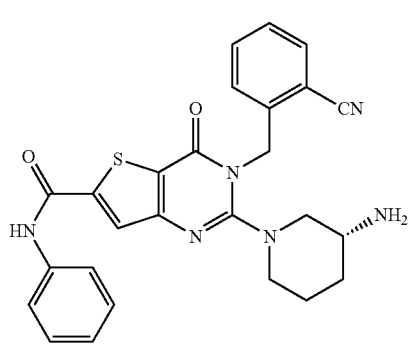<br>42 |

| Designation | Structure |
|---|---|
| (R)-2-((2-(3-aminopiperidin-1-yl)-7-(hydroxymethyl)-4-oxothieno[3,2-d]pyrimidin-3(4H)-yl)methyl)benzonitrile | 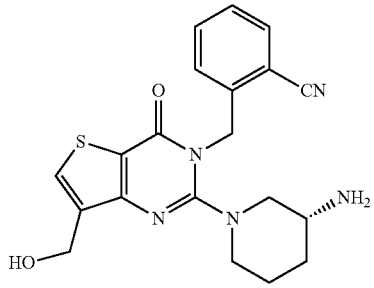<br>43 |
| (R)-2-(3-aminopiperidin-1-yl)-3-(2-cyanobenzyl)-4-oxo-3,4-dihydrothieno[3,2-d]pyrimidine-7-carboxylic acid hydrochloride | 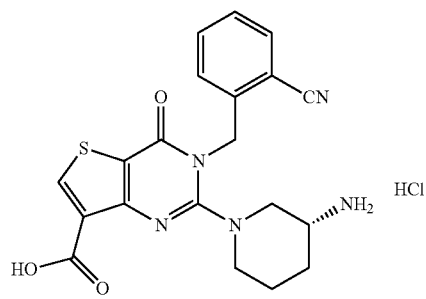<br>44 |
| (R)-2-(3-aminopiperidin-1-yl)-3-(2-cyanobenzyl)-4-oxo-N-(pyridin-2-ylmethyl)-3,4-dihydrothieno[3,2-d]pyrimidine-7-carboxamide | 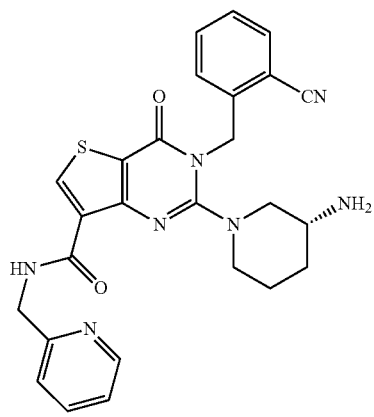<br>46 |
| (R)-2-(3-aminopiperidin-1-yl)-3-(2-cyanobenzyl)-4-oxo-N-phenyl-3,4-dihydrothieno[3,2-d]pyrimidine-7-carboxamide | 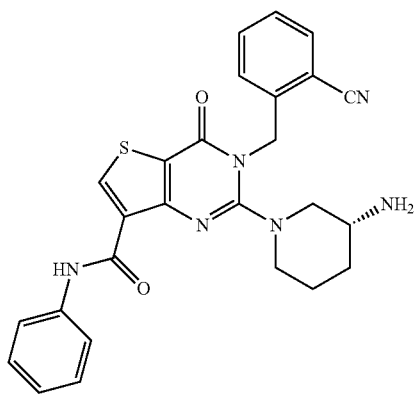<br>47 |

| Designation | Structure |
|---|---|
| (R)-2-(3-aminopiperidin-1-yl)-N-benzyl-3-(2-cyanobenzyl)-4-oxo-3,4-dihydrothieno[3,2-d]pyrimidine-7-carboxamide | 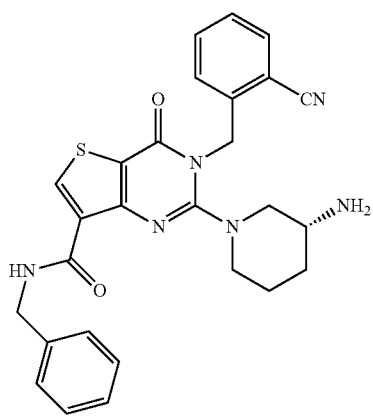<br>48 |
| (R)-3-((2-(3-aminopiperidin-1-yl)-4-oxo-7-(trifluoromethyl)thieno[3,2-d]pyrimidin-3(4H)-yl)methyl)-2-cyanobenzoic acid | 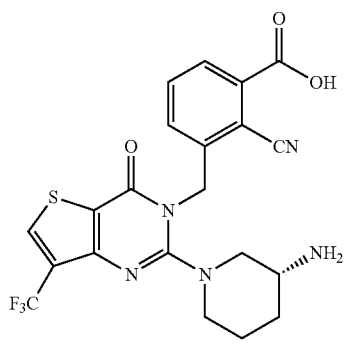<br>49 |
| (R)-3-((2-(3-aminopiperidin-1-yl)-4-oxo-7-(trifluoromethyl)thieno[3,2-d]pyrimidin-3(4H)-yl)methyl)-2-cyanobenzamide | 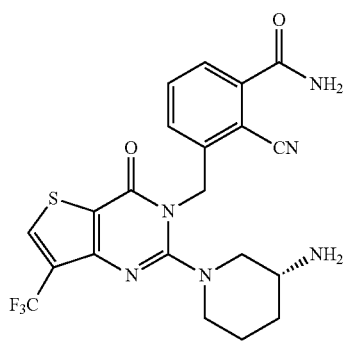<br>50 |
| (R)-2-((2-(3-aminopiperidin-1-yl)-4-oxo-7-(trifluoromethyl)thieno[3,2-d]pyrimidin-3(4H)-yl)methyl)-5-hydroxybenzonitrile | 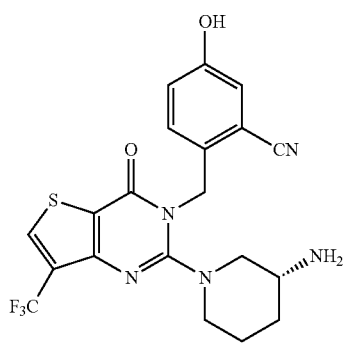<br>51 |

-continued

| Designation | Structure |
|---|---|
| 2-((4-oxo-2-(piperazin-1-yl)-7-(trifluoromethyl)thieno[3,2-d]pyrimidin-3(4H)-yl)methyl)benzonitrile | 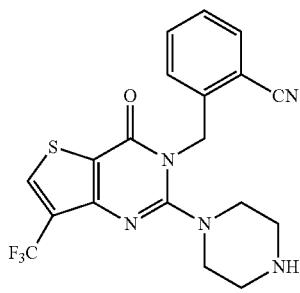<br>52 |
| (R)-2-((2-(3-aminopiperidin-1-yl)-4-oxo-4,6,7,8-tetrahydro-3H-cyclopenta[4,5]thieno[3,2-d]pyrimidin-3-yl)methyl)benzonitrile | 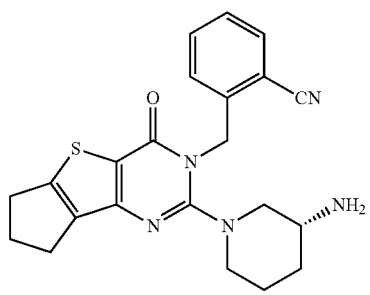<br>53 |
| (R)-methyl 1-((2-(3-aminopiperidin-1-yl)-3-(2-cyanobenzyl)-4-oxo-3,4-dihydrothieno[3,2-d]pyrimidin-7-yl)methyl)piperidine-4-carboxylate | 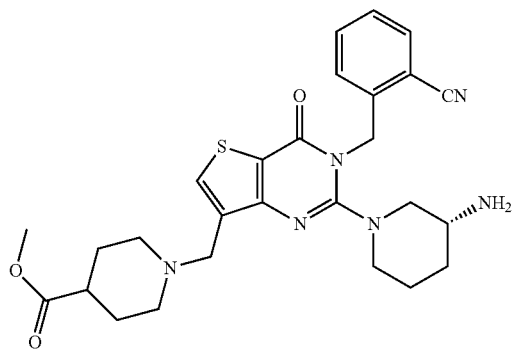<br>54 |
| (R)-2-((2-(3-aminopiperidin-1-yl)-7-(morpholinomethyl)-4-oxothieno[3,2-d]pyrimidin-3(4H)-yl)methyl)benzonitrile | 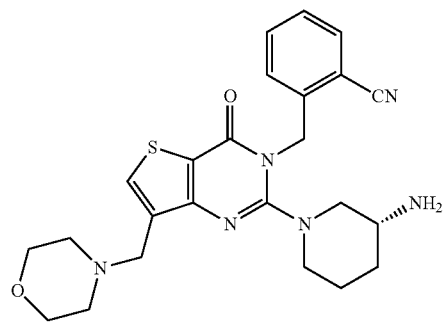<br>55 |

| Designation | Structure |
|---|---|
| (R)-(2-(3-aminopiperidin-1-yl)-3-(2-cyanobenzyl)-4-oxo-3,4-dihydrothieno[3,2-d]pyrimidin-7-yl)methyl acetate | 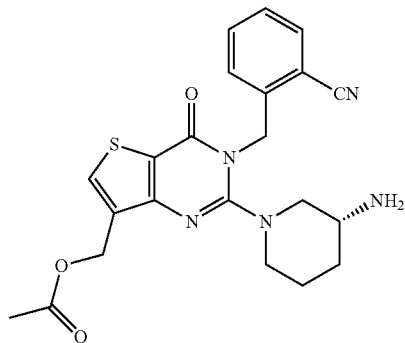<br>56 |
| (R)-methyl 2-(3-aminopiperidin-1-yl)-3-(2-cyanobenzyl)-4-oxo-3,4-dihydrothieno[3,2-d]pyrimidine-7-carboxylate | 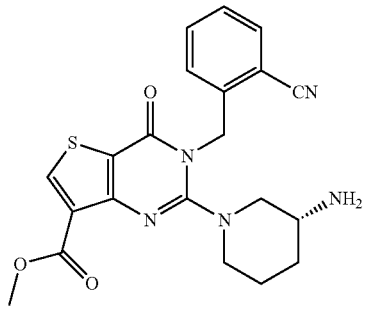<br>57 |
| (R)-ethyl 2-(2-(3-aminopiperidin-1-yl)-3-(2-cyanobenzyl)-4-oxo-3,4-dihydrothieno[3,2-d]pyrimidine-7-carboxamido)acetate | 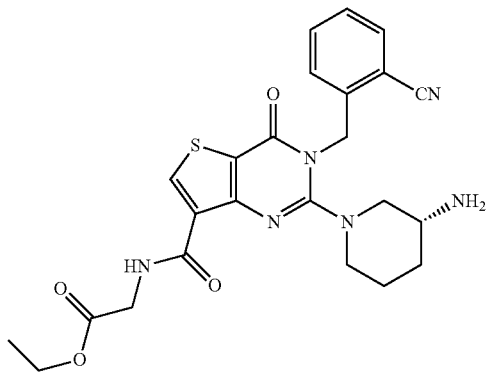<br>58 |
| (S)-methyl 2-(2-((R)-3-aminopiperidin-1-yl)-3-(2-cyanobenzyl)-4-oxo-3,4-dihydrothieno[3,2-d]pyrimidine-7-carboxamido)-3-methylbutanoate | 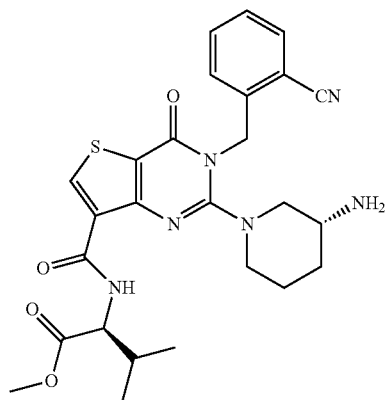<br>59 |

| Designation | Structure |
|---|---|
| (R)-2-(3-aminopiperidin-1-yl)-3-(2-cyanobenzyl)-N-(2-hydroxyethyl)-4-oxo-3,4-dihydrothieno[3,2-d]pyrimidine-7-carboxamide | 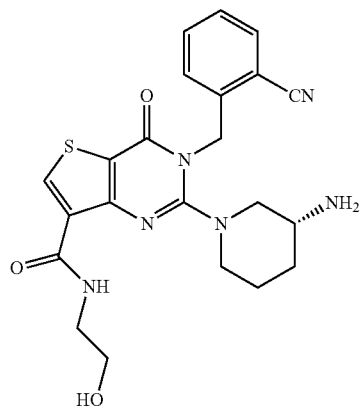 60 |
| (R)-2-(3-aminopiperidin-1-yl)-3-(2-cyanobenzyl)-N-methyl-4-oxo-3,4-dihydrothieno[3,2-d]pyrimidine-7-carboxamide | 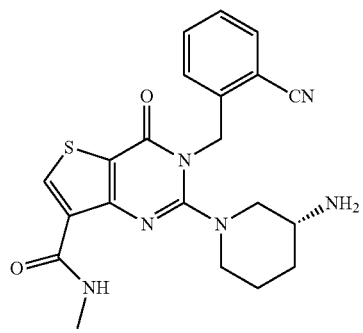 61 |
| (S)-methyl 2-(2-((R)-3-aminopiperidin-1-yl)-3-(2-cyanobenzyl)-4-oxo-3,4-dihydrothieno[3,2-d]pyrimidine-7-carboxamido)-3-(4-hydroxyphenyl)propanoate | 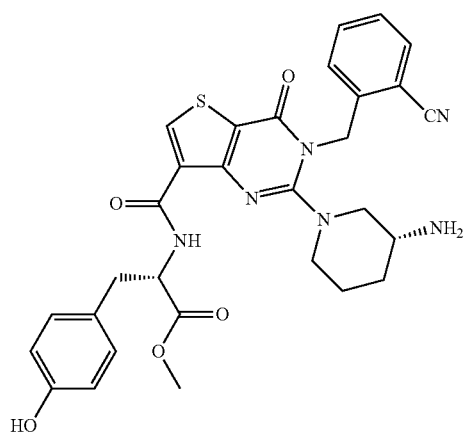 62 |

| Designation | Structure |
|---|---|
| (R)-2-(3-aminopiperidin-1-yl)-3-(2-cyanobenzyl)-N-(4-methylbenzyl)-4-oxo-3,4-dihydrothieno[3,2-d]pyrimidine-7-carboxamide | 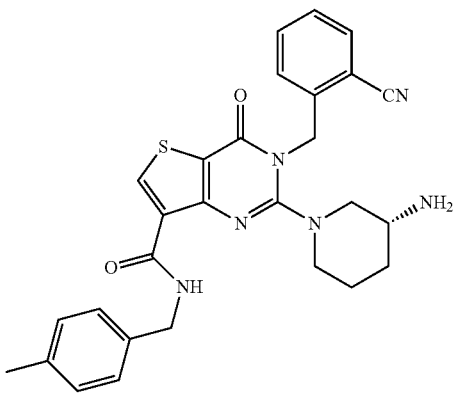<br>64 |
| (R)-2-(3-aminopiperidin-1-yl)-3-(2-cyanobenzyl)-N-cyclopropyl-4-oxo-3,4-dihydrothieno[3,2-d]pyrimidine-7-carboxamide | 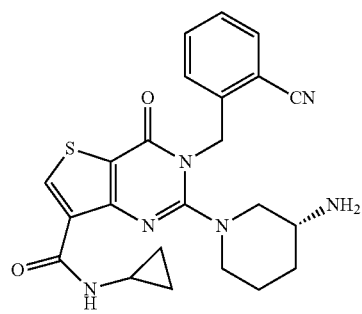<br>65 |
| (S)-methyl 2-(2-((R)-3-aminopiperidin-1-yl)-3-(2-cyanobenzyl)-4-oxo-3,4-dihydrothieno[3,2-d]pyrimidine-7-carboxamido)-2-phenylacetate | 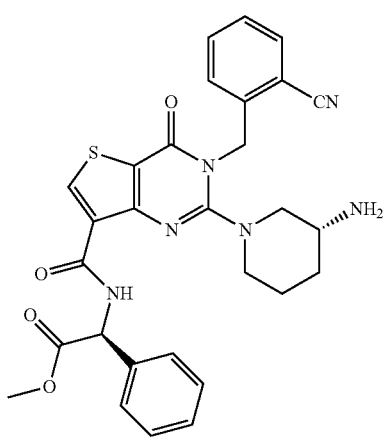<br>66 |

| Designation | Structure |
|---|---|
| (S)-methyl 2-(2-((R)-3-aminopiperidin-1-yl)-3-(2-cyanobenzyl)-4-oxo-3,4-dihydrothieno[3,2-d]pyrimidine-7-carboxamido)-3-phenylpropanoate | 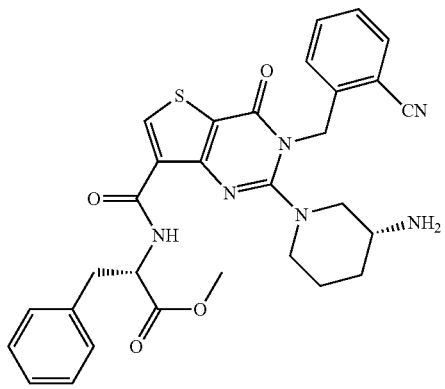<br>67 |
| (R)-2-(3-aminopiperidin-1-yl)-3-(2-cyanobenzyl)-4-oxo-N-(4-(trifluoromethyl)benzyl)-3,4-dihydrothieno[3,2-d]pyrimidine-7-carboxamide | 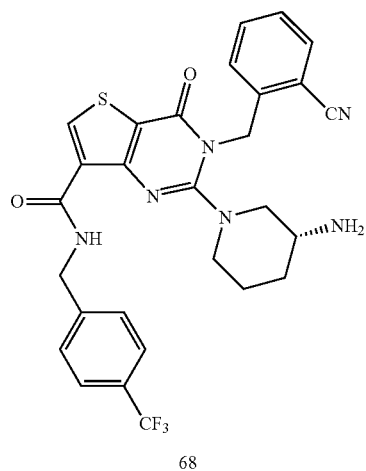<br>68 |
| (R)-2-((2-(3-aminopiperidin-1-yl)-7-(morpholine-4-carbonyl)-4-oxothieno[3,2-d]pyrimidin-3(4H)-yl)methyl)benzonitrile | 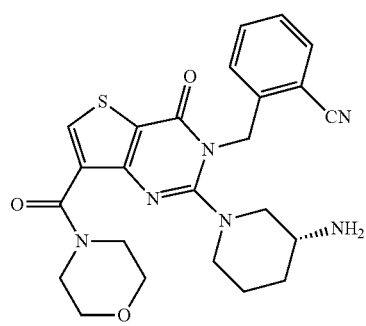<br>69 |

| Designation | Structure |
|---|---|
| (R)-2-((2-(3-aminopiperidin-1-yl)-7-(4-methylpiperazine-1-carbonyl)-4-oxothieno[3,2-d]pyrimidin-3(4H)-yl)methyl)benzonitrile | 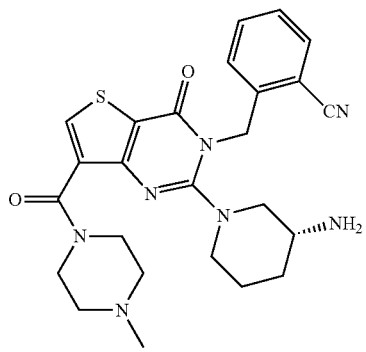 70 |
| (R)-2-(3-aminopiperidin-1-yl)-3-(2-cyanobenzyl)-N-ethyl-4-oxo-3,4-dihydrothieno[3,2-d]pyrimidine-7-carboxamide | 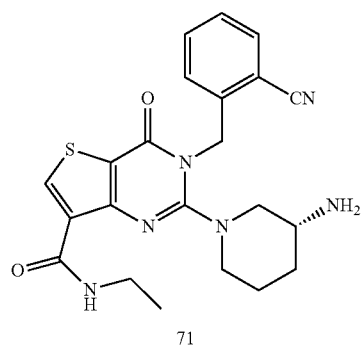 71 |
| (R)-2-(3-aminopiperidin-1-yl)-3-(2-cyanobenzyl)-N-isopropyl-4-oxo-3,4-dihydrothieno[3,2-d]pyrimidine-7-carboxamide | 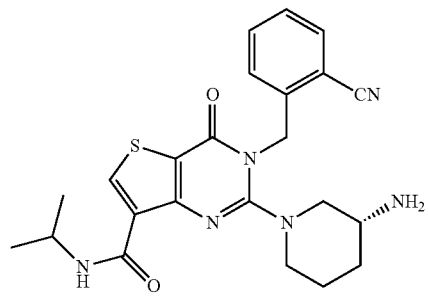 72 |
| (R)-2-(3-aminopiperidin-1-yl)-3-(2-cyanobenzyl)-N-(cyclopropylmethyl)-4-oxo-3,4-dihydrothieno[3,2-d]pyrimidine-7-carboxamide | 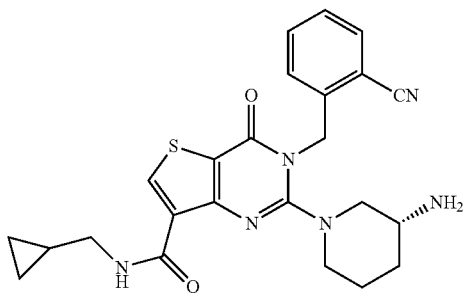 73 |

| Designation | Structure |
|---|---|
| (R)-2-(3-aminopiperidin-1-yl)-3-(2-cyanobenzyl)-N-(2-methoxyethyl)-4-oxo-3,4-dihydrothieno[3,2-d]pyrimidine-7-carboxamide | 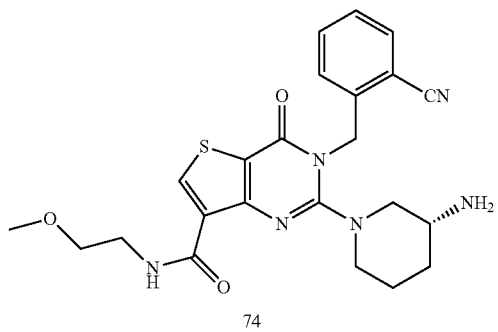<br>74 |
| (R)-2-(3-aminopiperidin-1-yl)-3-(2-cyanobenzyl)-N-(3-methoxypropyl)-4-oxo-3,4-dihydrothieno[3,2-d]pyrimidine-7-carboxamide | 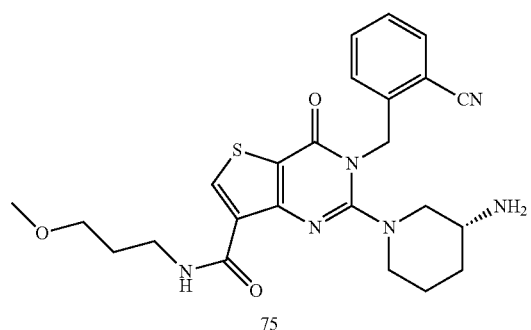<br>75 |
| (R)-2-((2-(3-aminopiperidin-1-yl)-4-oxo-7-(pyrrolidine-1-carbonyl)thieno[3,2-d]pyrimidin-3(4H)-yl)methyl)benzonitrile | 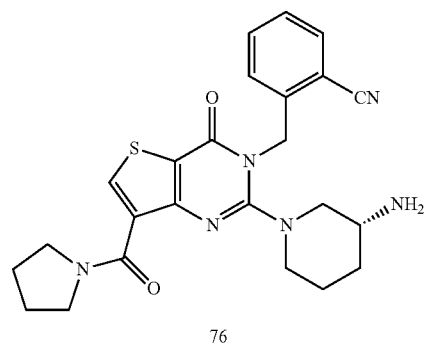<br>76 |
| (R)-2-(3-aminopiperidin-1-yl)-N-butyl-3-(2-cyanobenzyl)-4-oxo-3,4-dihydrothieno[3,2-d]pyrimidine-7-carboxamide | 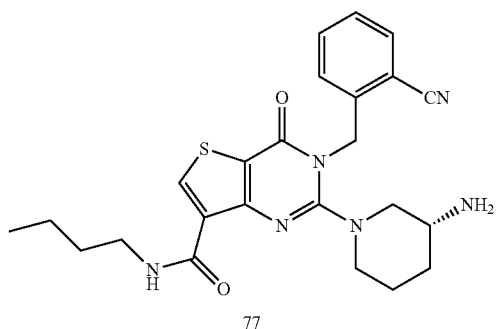<br>77 |

-continued

| Designation | Structure |
|---|---|
| (R)-2-(3-aminopiperidin-1-yl)-3-(2-cyanobenzyl)-N-isopentyl-4-oxo-3,4-dihydrothieno[3,2-d]pyrimidine-7-carboxamide | 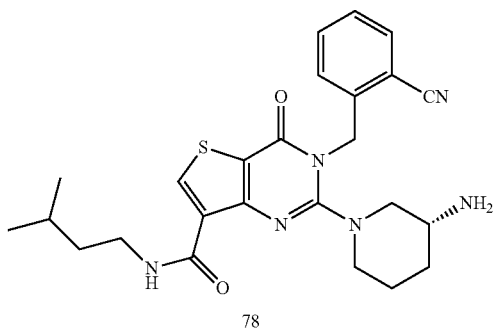<br>78 |
| (R)-2-(3-aminopiperidin-1-yl)-3-(2-cyanobenzyl)-N-isobutyl-4-oxo-3,4-dihydrothieno[3,2-d]pyrimidine-7-carboxamide | 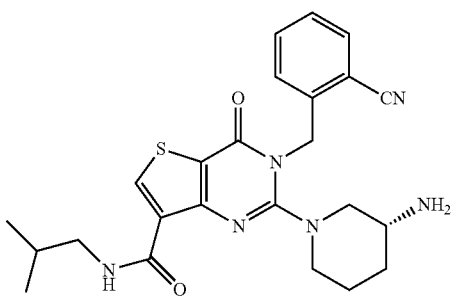 [SMILES: CC(C)CNC(=O)c1csc2c(=O)n(Cc3ccccc3C#N)c(N3CCC[C@@H](N)C3)nc12]<br>79 |
| (R)-2-(3-aminopiperidin-1-yl)-3-(2-cyanobenzyl)-N-cyclohexyl-4-oxo-3,4-dihydrothieno[3,2-d]pyrimidine-7-carboxamide | 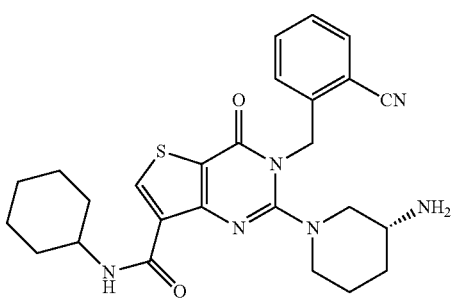 [SMILES: N#Cc1ccccc1Cn1c(N2CCC[C@@H](N)C2)nc2c(C(=O)NC3CCCCC3)csc2c1=O]<br>80 |
| (R)-2-(3-aminopiperidin-1-yl)-3-(2-cyanobenzyl)-4-oxo-N-(tetrahydro-2H-pyran-4-yl)-3,4-dihydrothieno[3,2-d]pyrimidine-7-carboxamide | 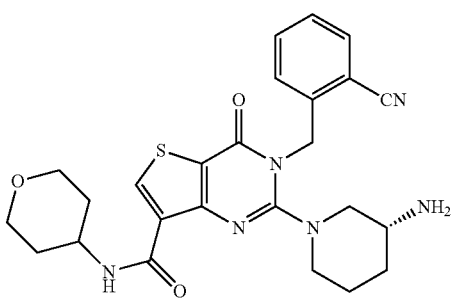 [SMILES: N#Cc1ccccc1Cn1c(N2CCC[C@@H](N)C2)nc2c(C(=O)NC3CCOCC3)csc2c1=O]<br>81 |

| Designation | Structure |
|---|---|
| (R)-2-(3-aminopiperidin-1-yl)-3-(2-cyanobenzyl)-N-(oxetan-3-ylmethyl)-4-oxo-3,4-dihydrothieno[3,2-d]pyrimidine-7-carboxamide | 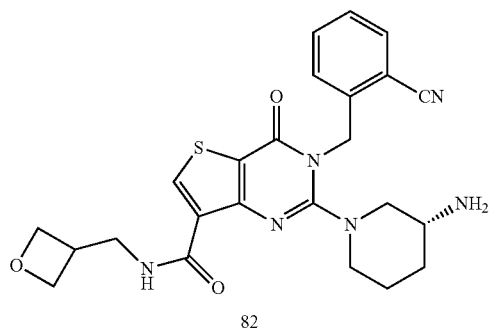<br>82 |
| (R)-2-(3-aminopiperidin-1-yl)-3-(2-cyanobenzyl)-4-oxo-3,4-dihydrothieno[3,2-d]pyrimidine-7-carbonitrile | 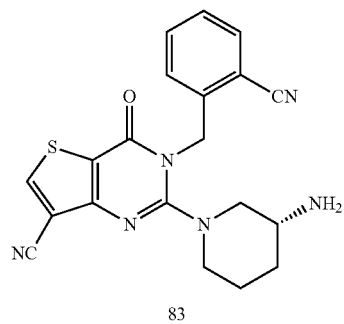<br>83 |
| (R)-2-((7-amino-2-(3-aminopiperidin-1-yl)-4-oxothieno[3,2-d]pyrimidin-3(4H)-yl)methyl)benzonitrile | 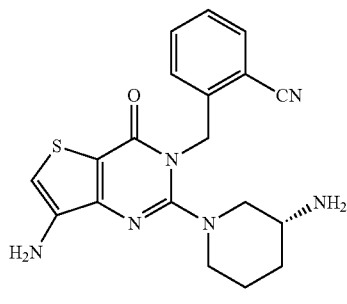<br>84 |
| (R)-N-(2-(3-aminopiperidin-1-yl)-3-(2-cyanobenzyl)-4-oxo-3,4-dihydrothieno[3,2-d]pyrimidin-7-yl)methanesulfonamide | 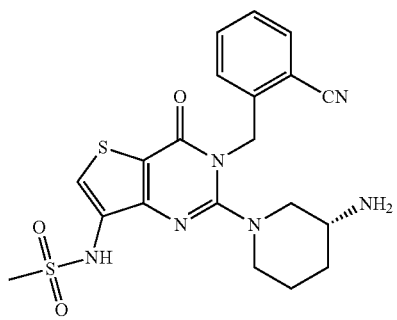 [SMILES: CS(=O)(=O)Nc1csc2c(=O)n(Cc3ccccc3C#N)c(N3CCC[C@@H](N)C3)nc12]<br>85 |

| Designation | Structure |
|---|---|
| (R)-N-(2-(3-aminopiperidin-1-yl)-3-(2-cyanobenzyl)-4-oxo-3,4-dihydrothieno[3,2-d]pyrimidin-7-yl)acetamide | 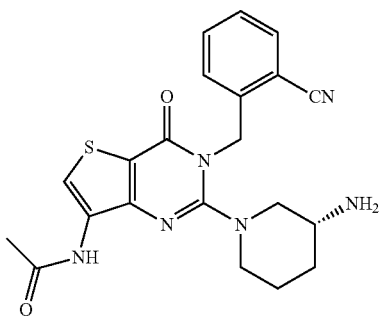 [SMILES: CC(=O)Nc1csc2c(=O)n(Cc3ccccc3C#N)c(N3CCC[C@@H](N)C3)nc12]<br>86 |
| 2-((2-((R)-3-aminopiperidin-1-yl)-4-oxo-7-((((S)-tetrahydrofuran-3-yl)oxy)methyl)thieno[3,2-d]pyrimidin-3(4H)-yl)methyl)benzonitrile | 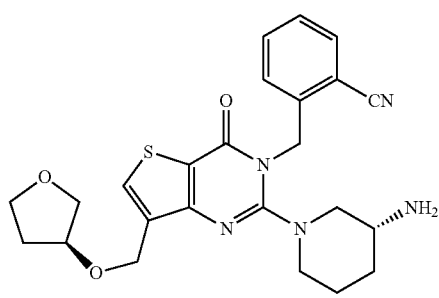 [SMILES: N#Cc1ccccc1Cn1c(N2CCC[C@@H](N)C2)nc2c(CO[C@H]3CCOC3)csc2c1=O]<br>87 |
| (R)-ethyl 3-(2-(3-aminopiperidin-1-yl)-3-(2-cyanobenzyl)-4-oxo-3,4-dihydrothieno[3,2-d]pyrimidine-7-carboxamido)propanoate | 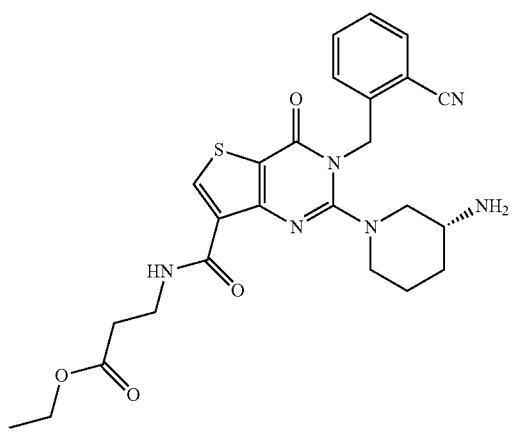 [SMILES: CCOC(=O)CCNC(=O)c1csc2c(=O)n(Cc3ccccc3C#N)c(N3CCC[C@@H](N)C3)nc12]<br>88 |

| Designation | Structure |
|---|---|
| (R)-ethyl 4-(2-(3-aminopiperidin-1-yl)-3-(2-cyanobenzyl)-4-oxo-3,4-dihydrothieno[3,2-d]pyrimidine-7-carboxamido)butanoate | 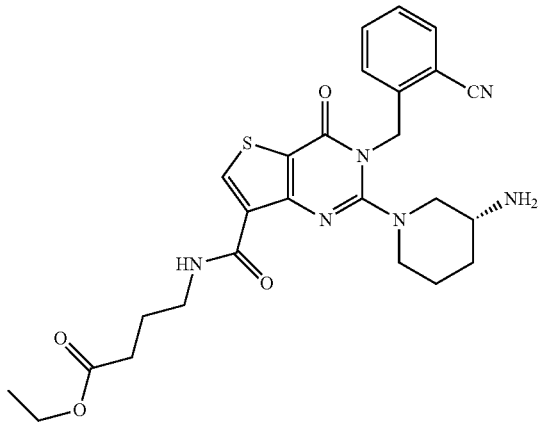 [SMILES: CCOC(=O)CCCNC(=O)c1csc2c(=O)n(Cc3ccccc3C#N)c(N3CCC[C@@H](N)C3)nc12]<br>89 |
| (R)-2-(3-aminopiperidin-1-yl)-3-(2-cyanobenzyl)-N-(2-(methylsulfonyl)ethyl)-4-oxo-3,4-dihydrothieno[3,2-d]pyrimidine-7-carboxamide | 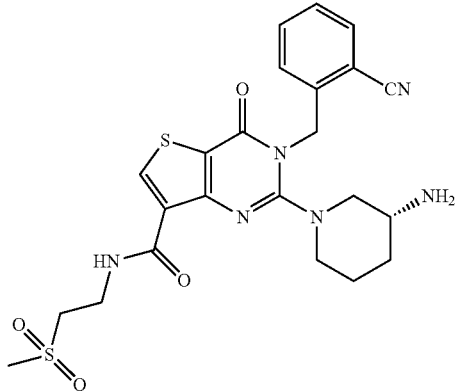 [SMILES: CS(=O)(=O)CCNC(=O)c1csc2c(=O)n(Cc3ccccc3C#N)c(N3CCC[C@@H](N)C3)nc12]<br>90 |
| (S)-methyl 1-(2-((R)-3-aminopiperidin-1-yl)-3-(2-cyanobenzyl)-4-oxo-3,4-dihydrothieno[3,2-d]pyrimidine-7-carbonyl)pyrrolidine-2-carboxylate | 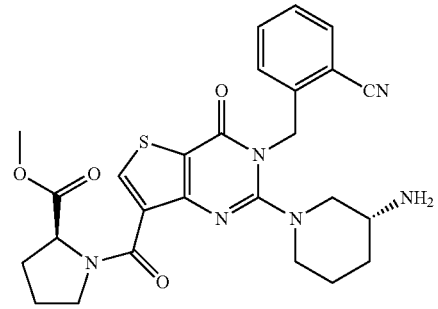<br>91 |
| 2-((R)-3-aminopiperidin-1-yl)-3-(2-cyanobenzyl)-4-oxo-N-((S)-2-oxotetrahydrofuran-3-yl)-3,4-dihydrothieno[3,2-d]pyrimidine-7-carboxamide | 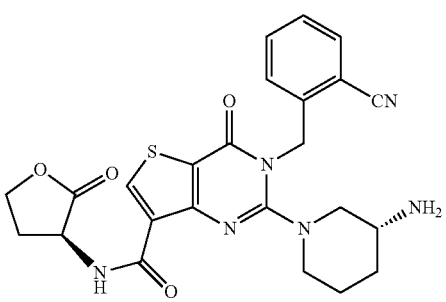<br>92 |

| Designation | Structure |
|---|---|
| (R)-2-(3-aminopiperidin-1-yl)-3-(2-cyanobenzyl)-N-(3-hydroxypropyl)-4-oxo-3,4-dihydrothieno[3,2-d]pyrimidine-7-carboxamide | 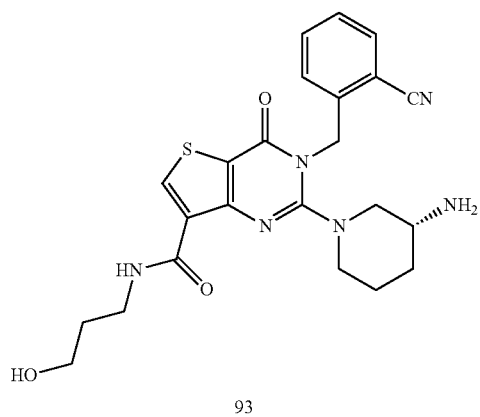<br>93 |
| (R)-2-((2-(3-aminopiperidin-1-yl)-6-((benzyloxy)methyl)-4-oxothieno[3,2-d]pyrimidin-3(4H)-yl)methyl)benzonitrile | 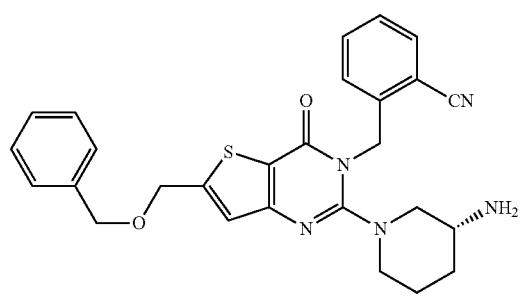 [SMILES: N#Cc1ccccc1Cn1c(N2CCC[C@@H](N)C2)nc2cc(COCc3ccccc3)sc2c1=O]<br>94 |
| (R)-2-((2-(3-aminopiperidin-1-yl)-6-(morpholinomethyl)-4-oxothieno[3,2-d]pyrimidin-3(4H)-yl)methyl)benzonitrile | 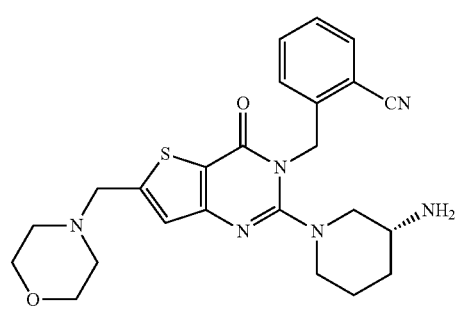 [SMILES: N#Cc1ccccc1Cn1c(N2CCC[C@@H](N)C2)nc2cc(CN3CCOCC3)sc2c1=O]<br>95 |
| (R)-(2-(3-aminopiperidin-1-yl)-3-(2-cyanobenzyl)-4-oxo-3,4-dihydrothieno[3,2-d]pyrimidin-6-yl)methyl acetate | 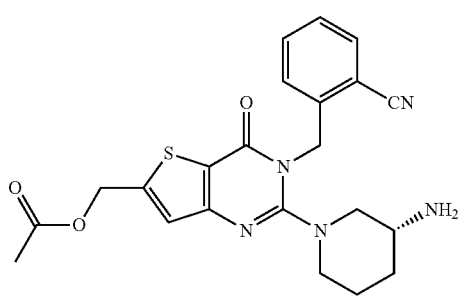 [SMILES: CC(=O)OCc1cc2nc(N3CCC[C@@H](N)C3)n(Cc3ccccc3C#N)c(=O)c2s1]<br>96 |

-continued

| Designation | Structure |
|---|---|
| (R)-2-((2-(3-aminopiperidin-1-yl)-6-(dibromomethyl)-4-oxothieno[3,2-d]pyrimidin-3(4H)-yl)methyl)benzonitrile | 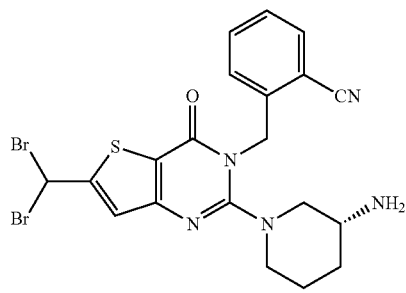 [SMILES: N#Cc1ccccc1Cn1c(N2CCC[C@@H](N)C2)nc2cc(C(Br)Br)sc2c1=O]<br>98 |
| (R)-methyl 2-(2-(3-aminopiperidin-1-yl)-3-(2-cyanobenzyl)-4-oxo-3,4-dihydrothieno[3,2-d]pyrimidine-6-carboxamido)acetate | 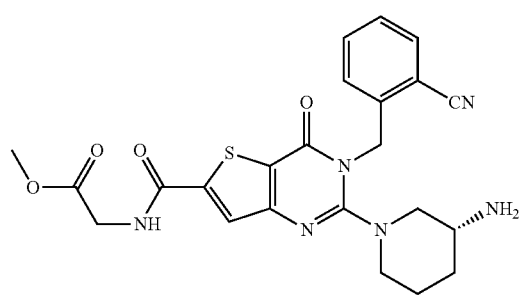 [SMILES: COC(=O)CNC(=O)c1cc2nc(N3CCC[C@@H](N)C3)n(Cc3ccccc3C#N)c(=O)c2s1]<br>99 |
| (S)-methyl 2-(2-((R)-3-aminopiperidin-1-yl)-3-(2-cyanobenzyl)-4-oxo-3,4-dihydrothieno[3,2-d]pyrimidine-6-carboxamido)-3-methylbutanoate | 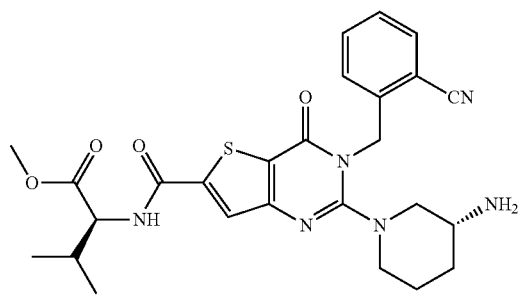 [SMILES: COC(=O)[C@@H](NC(=O)c1cc2nc(N3CCC[C@@H](N)C3)n(Cc3ccccc3C#N)c(=O)c2s1)C(C)C]<br>100 |
| (S)-methyl 2-(2-((R)-3-aminopiperidin-1-yl)-3-(2-cyanobenzyl)-4-oxo-3,4-dihydrothieno[3,2-d]pyrimidine-6-carboxamido)-3-(4-hydroxyphenyl)propanoate | 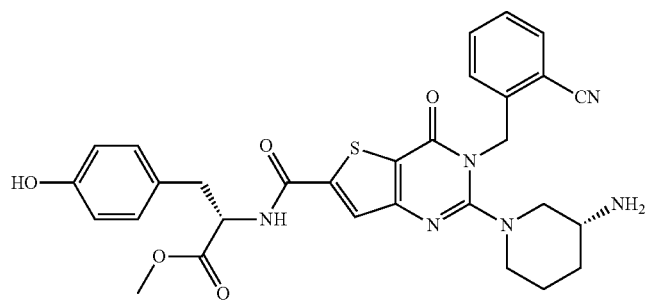 [SMILES: COC(=O)[C@H](Cc1ccc(O)cc1)NC(=O)c1cc2nc(N3CCC[C@@H](N)C3)n(Cc3ccccc3C#N)c(=O)c2s1]<br>101 |

| Designation | Structure |
|---|---|
| (S)-methyl 2-(2-((R)-3-aminopiperidin-1-yl)-3-(2-cyanobenzyl)-4-oxo-3,4-dihydrothieno[3,2-d]pyrimidine-6-carboxamido)-3-phenylpropanoate | 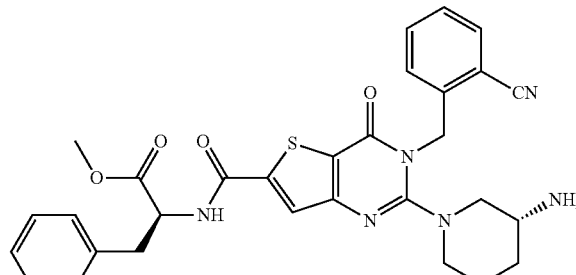<br>102 |
| (R)-2-(3-aminopiperidin-1-yl)-3-(2-cyanobenzyl)-4-oxo-N-(4-(trifluoromethyl)benzyl)-3,4-dihydrothieno[3,2-d]pyrimidine-6-carboxamide | 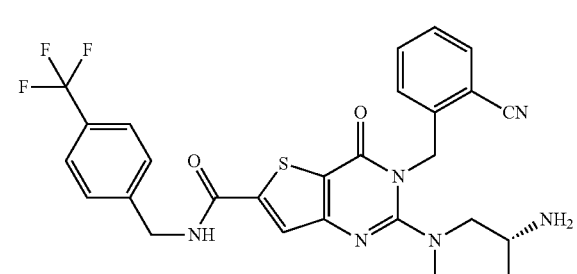<br>103 |
| (R)-2-(3-aminopiperidin-1-yl)-3-(2-cyanobenzyl)-N-methyl-4-oxo-3,4-dihydrothieno[3,2-d]pyrimidine-6-carboxamide | 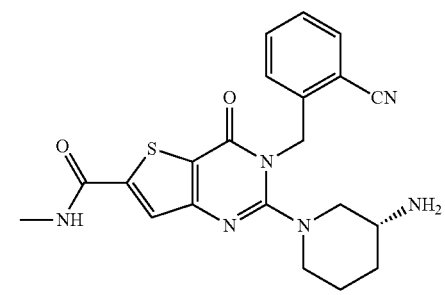 [SMILES: CNC(=O)c1cc2nc(N3CCC[C@@H](N)C3)n(Cc3ccccc3C#N)c(=O)c2s1]<br>104 |
| (R)-2-(3-aminopiperidin-1-yl)-3-(2-cyanobenzyl)-N,N-dimethyl-4-oxo-3,4-dihydrothieno[3,2-d]pyrimidine-6-carboxamide | 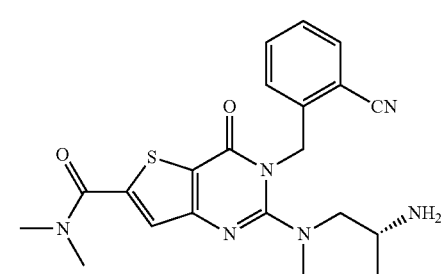<br>105 |

| Designation | Structure |
|---|---|
| (R)-2-(3-aminopiperidin-1-yl)-3-(2-cyanobenzyl)-N-(cyclopropylmethyl)-4-oxo-3,4-dihydrothieno[3,2-d]pyrimidine-6-carboxamide | 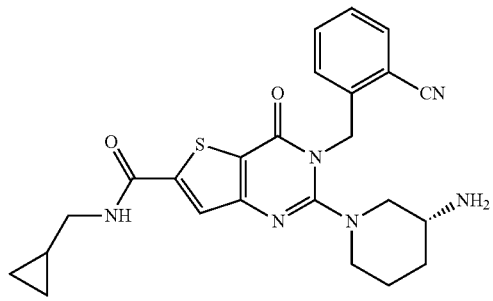 [SMILES: N#Cc1ccccc1Cn1c(N2CCC[C@@H](N)C2)nc2cc(C(=O)NCC3CC3)sc2c1=O]<br>106 |
| (R)-2-((2-(3-aminopiperidin-1-yl)-4-oxo-6-(pyrrolidine-1-carbonyl)thieno[3,2-d]pyrimidin-3(4H)-yl)methyl)benzonitrile | 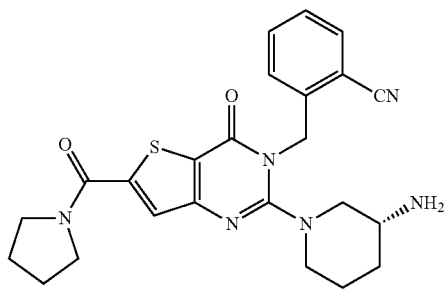 [SMILES: N#Cc1ccccc1Cn1c(N2CCC[C@@H](N)C2)nc2cc(C(=O)N3CCCC3)sc2c1=O]<br>107 |
| (R)-2-((2-(3-aminopiperidin-1-yl)-4-oxo-6-(piperidine-1-carbonyl)thieno[3,2-d]pyrimidin-3(4H)-yl)methyl)benzonitrile | 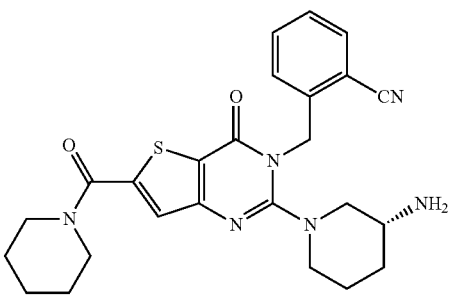 [SMILES: N#Cc1ccccc1Cn1c(N2CCC[C@@H](N)C2)nc2cc(C(=O)N3CCCCC3)sc2c1=O]<br>108 |
| (R)-2-(3-aminopiperidin-1-yl)-3-(2-cyanobenzyl)-N-(2-fluorobenzyl)-4-oxo-3,4-dihydrothieno[3,2-d]pyrimidine-6-carboxamide | 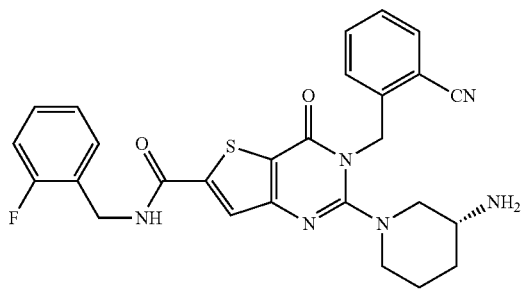 [SMILES: N#Cc1ccccc1Cn1c(N2CCC[C@@H](N)C2)nc2cc(C(=O)NCc3ccccc3F)sc2c1=O]<br>109 |

| Designation | Structure |
|---|---|
| (R)-2-(3-aminopiperidin-1-yl)-N-(2-chlorobenzyl)-3-(2-cyanobenzyl)-4-oxo-3,4-dihydrothieno[3,2-d]pyrimidine-6-carboxamide | 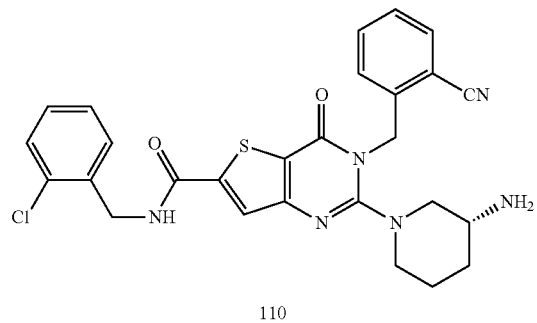<br>110 |
| (R)-2-(3-aminopiperidin-1-yl)-3-(2-cyanobenzyl)-N-(2-methoxyethyl)-4-oxo-3,4-dihydrothieno[3,2-d]pyrimidine-6-carboxamide | 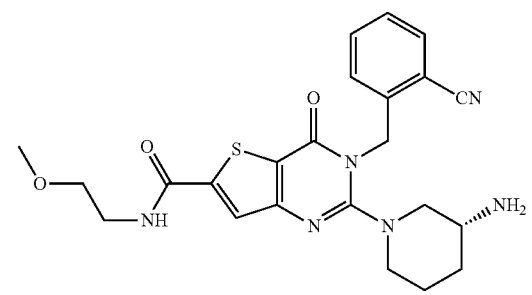 [SMILES: COCCNC(=O)c1cc2nc(N3CCC[C@@H](N)C3)n(Cc3ccccc3C#N)c(=O)c2s1]<br>111 |
| (R)-2-(3-aminopiperidin-1-yl)-3-(2-cyanobenzyl)-N-(3-methoxypropyl)-4-oxo-3,4-dihydrothieno[3,2-d]pyrimidine-6-carboxamide | 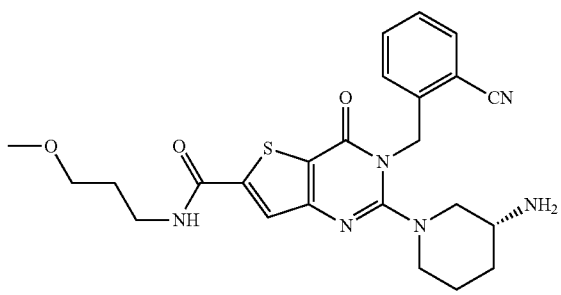 [SMILES: COCCCNC(=O)c1cc2nc(N3CCC[C@@H](N)C3)n(Cc3ccccc3C#N)c(=O)c2s1]<br>112 |
| (R)-2-(3-aminopiperidin-1-yl)-3-(2-cyanobenzyl)-N-ethyl-4-oxo-3,4-dihydrothieno[3,2-d]pyrimidine-6-carboxamide | 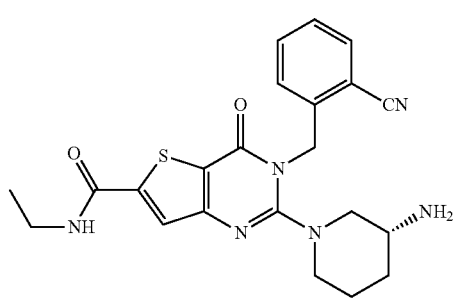 [SMILES: CCNC(=O)c1cc2nc(N3CCC[C@@H](N)C3)n(Cc3ccccc3C#N)c(=O)c2s1]<br>113 |

-continued

| Designation | Structure |
|---|---|
| (R)-2-((2-(3-aminopiperidin-1-yl)-6-(1,1-dioxidothiomorpholine-4-carbonyl)-4-oxothieno[3,2-d]pyrimidin-3(4H)-yl)methyl)benzonitrile | 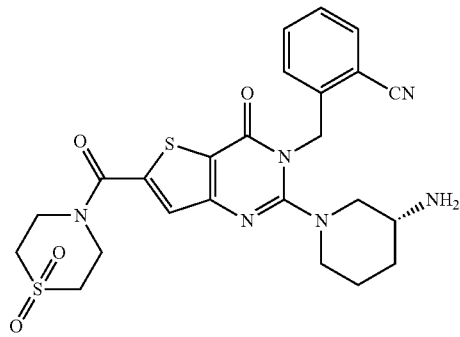 114 |
| (R)-2-(3-aminopiperidin-1-yl)-3-(2-cyanobenzyl)-N-isopropyl-4-oxo-3,4-dihydrothieno[3,2-d]pyrimidine-6-carboxamide | 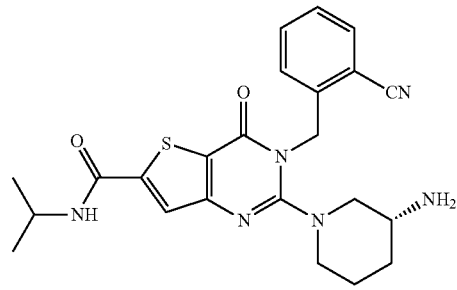 [SMILES: CC(C)NC(=O)c1cc2nc(N3CCC[C@@H](N)C3)n(Cc3ccccc3C#N)c(=O)c2s1] 115 |
| (R)-2-(3-aminopiperidin-1-yl)-3-(2-cyanobenzyl)-N-isobutyl-4-oxo-3,4-dihydrothieno[3,2-d]pyrimidine-6-carboxamide | 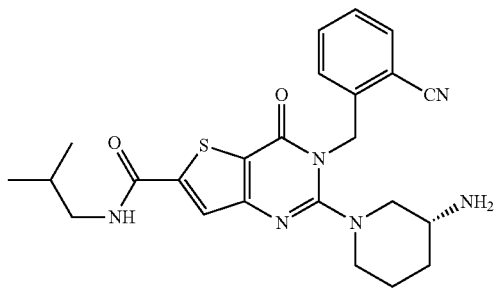 [SMILES: CC(C)CNC(=O)c1cc2nc(N3CCC[C@@H](N)C3)n(Cc3ccccc3C#N)c(=O)c2s1] 116 |
| (R)-2-(3-aminopiperidin-1-yl)-N-butyl-3-(2-cyanobenzyl)-4-oxo-3,4-dihydrothieno[3,2-d]pyrimidine-6-carboxamide | 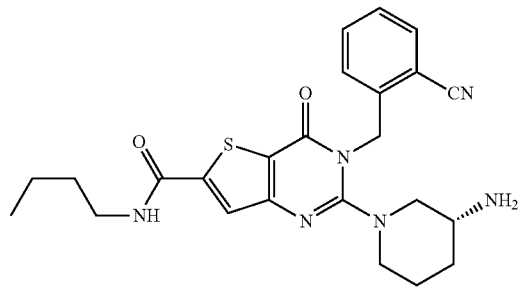 [SMILES: CCCCNC(=O)c1cc2nc(N3CCC[C@@H](N)C3)n(Cc3ccccc3C#N)c(=O)c2s1] 117 |

| Designation | Structure |
|---|---|
| (R)-2-((2-(3-aminopiperidin-1-yl)-6-(morpholine-4-carbonyl)-4-oxothieno[3,2-d]pyrimidin-3(4H)-yl)methyl)benzonitrile | 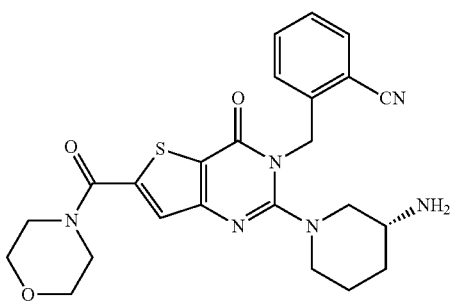 [SMILES: N#Cc1ccccc1Cn1c(N2CCC[C@@H](N)C2)nc2cc(C(=O)N3CCOCC3)sc2c1=O]⏎118 |
| (R)-2-(3-aminopiperidin-1-yl)-3-(2-cyanobenzyl)-N-cyclohexyl-4-oxo-3,4-dihydrothieno[3,2-d]pyrimidine-6-carboxamide | 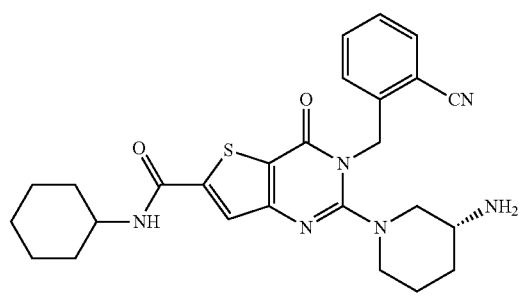 [SMILES: N#Cc1ccccc1Cn1c(N2CCC[C@@H](N)C2)nc2cc(C(=O)NC3CCCCC3)sc2c1=O]⏎119 |
| (R)-2-(3-aminopiperidin-1-yl)-3-(2-cyanobenzyl)-4-oxo-N-(3-(trifluoromethyl)benzyl)-3,4-dihydrothieno[3,2-d]pyrimidine-6-carboxamide | 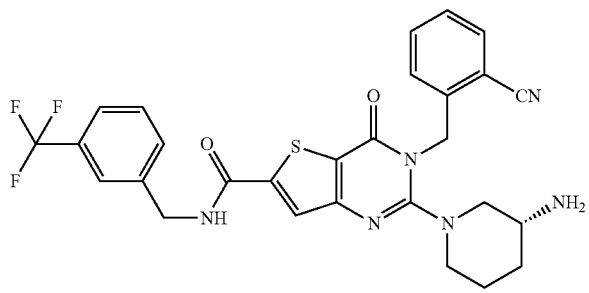 [SMILES: N#Cc1ccccc1Cn1c(N2CCC[C@@H](N)C2)nc2cc(C(=O)NCc3cccc(C(F)(F)F)c3)sc2c1=O]⏎120 |
| (R)-2-(3-aminopiperidin-1-yl)-3-(2-cyanobenzyl)-N-isopentyl-4-oxo-3,4-dihydrothieno[3,2-d]pyrimidine-6-carboxamide | 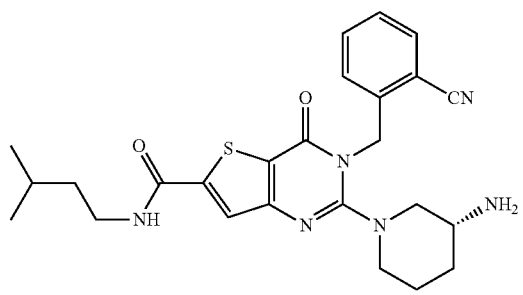 [SMILES: CC(C)CCNC(=O)c1cc2nc(N3CCC[C@@H](N)C3)n(Cc3ccccc3C#N)c(=O)c2s1]⏎121 |

| Designation | Structure |
|---|---|
| (R)-2-(3-aminopiperidin-1-yl)-3-(2-cyanobenzyl)-N-(4-methylbenzyl)-4-oxo-3,4-dihydrothieno[3,2-d]pyrimidine-6-carboxamide | 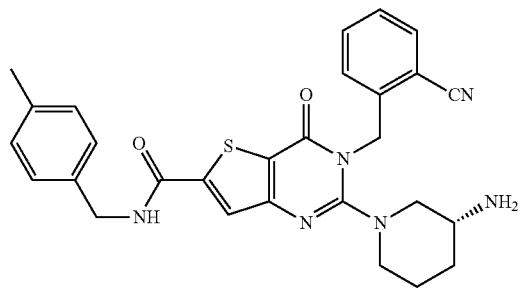 [SMILES: Cc1ccc(CNC(=O)c2cc3nc(N4CCC[C@@H](N)C4)n(Cc4ccccc4C#N)c(=O)c3s2)cc1]<br>122 |
| (R)-2-(3-aminopiperidin-1-yl)-3-(2-cyanobenzyl)-N-(2-hydroxyethyl)-4-oxo-3,4-dihydrothieno[3,2-d]pyrimidine-6-carboxamide | 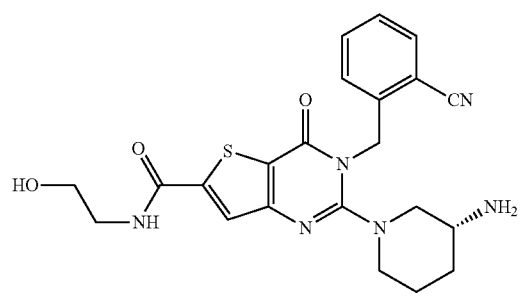 [SMILES: N#Cc1ccccc1Cn1c(N2CCC[C@@H](N)C2)nc2cc(C(=O)NCCO)sc2c1=O]<br>123 |
| (R)-2-((2-(3-aminopiperidin-1-yl)-6-(4-(hydroxymethyl)piperidine-1-carbonyl)-4-oxothieno[3,2-d]pyrimidin-3(4H)-yl)methyl)benzonitrile | 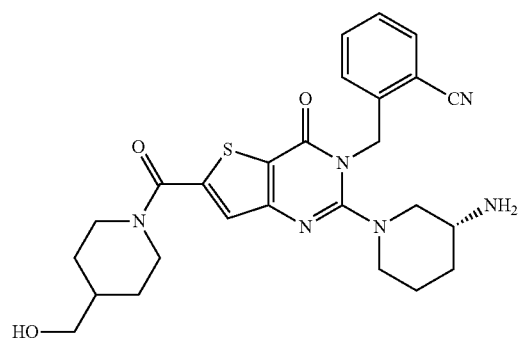 [SMILES: N#Cc1ccccc1Cn1c(N2CCC[C@@H](N)C2)nc2cc(C(=O)N3CCC(CO)CC3)sc2c1=O]<br>124 |
| (S)-methyl 1-(2-((R)-3-aminopiperidin-1-yl)-3-(2-cyanobenzyl)-4-oxo-3,4-dihydrothieno[3,2-d]pyrimidine-6-carbonyl)pyrrolidine-2-carboxylate | 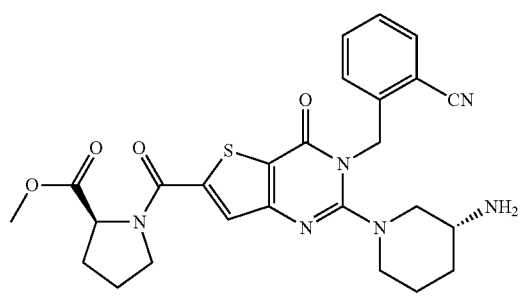 [SMILES: COC(=O)[C@@H]1CCCN1C(=O)c1cc2nc(N3CCC[C@@H](N)C3)n(Cc3ccccc3C#N)c(=O)c2s1]<br>125 |

-continued

| Designation | Structure |
|---|---|
| (R)-2-(3-aminopiperidin-1-yl)-3-(2-cyanobenzyl)-N-(2-(methylsulfonyl)ethyl)-4-oxo-3,4-dihydrothieno[3,2-d]pyrimidine-6-carboxamide | 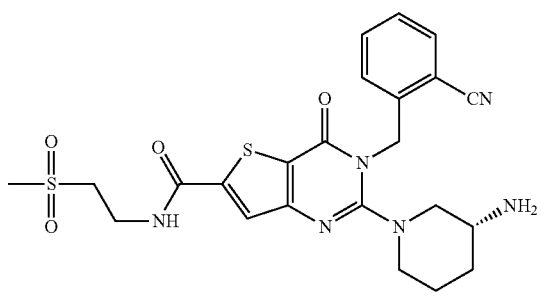 [SMILES: CS(=O)(=O)CCNC(=O)c1cc2nc(N3CCC[C@@H](N)C3)n(Cc3ccccc3C#N)c(=O)c2s1]<br>126 |
| 2-((R)-3-aminopiperidin-1-yl)-3-(2-cyanobenzyl)-4-oxo-N-((S)-2-oxotetrahydrofuran-3-yl)-3,4-dihydrothieno[3,2-d]pyrimidine-6-carboxamide | 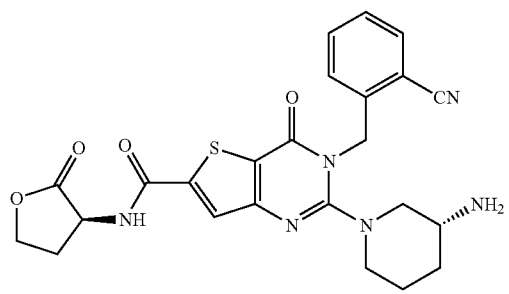 [SMILES: N#Cc1ccccc1Cn1c(N2CCC[C@@H](N)C2)nc2cc(C(=O)N[C@H]3CCOC3=O)sc2c1=O]<br>127 |
| 2-((2-((R)-3-aminopiperidin-1-yl)-6-((S)-2-(hydroxymethyl)pyrrolidine-1-carbonyl)-4-oxothieno[3,2-d]pyrimidin-3(4H)-yl)methyl)benzonitrile | 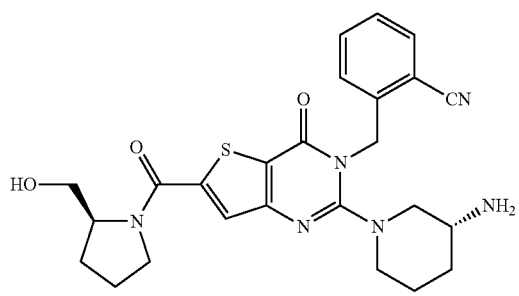 [SMILES: N#Cc1ccccc1Cn1c(N2CCC[C@@H](N)C2)nc2cc(C(=O)N3CCC[C@H]3CO)sc2c1=O]<br>128 |
| (R)-ethyl 1-(2-(3-aminopiperidin-1-yl)-3-(2-cyanobenzyl)-4-oxo-3,4-dihydrothieno[3,2-d]pyrimidine-6-carbonyl)piperidine-4-carboxylate | 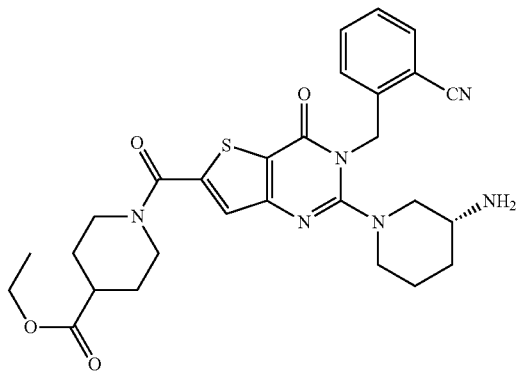 [SMILES: CCOC(=O)C1CCN(C(=O)c2cc3nc(N4CCC[C@@H](N)C4)n(Cc4ccccc4C#N)c(=O)c3s2)CC1]<br>129 |

| Designation | Structure |
|---|---|
| (R)-2-((2-(3-aminopiperidin-1-yl)-6-(((2-(methylsulfonyl)ethyl)amino)methyl)-4-oxothieno[3,2-d]pyrimidin-3(4H)-yl)methyl)benzonitrile | 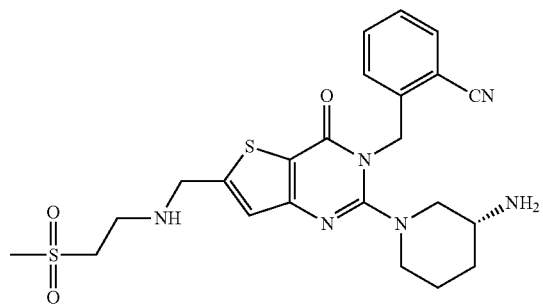 [SMILES: CS(=O)(=O)CCNCc1cc2nc(N3CCC[C@@H](N)C3)n(Cc3ccccc3C#N)c(=O)c2s1]<br>130 |
| (R)-2-((2-(3-aminopiperidin-1-yl)-6-((2-methoxyethoxy)methyl)-4-oxothieno[3,2-d]pyrimidin-3(4H)-yl)methyl)benzonitrile | 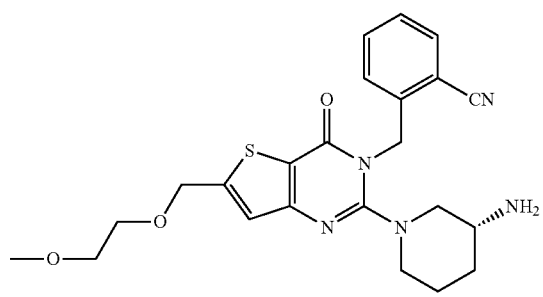 [SMILES: COCCOCc1cc2nc(N3CCC[C@@H](N)C3)n(Cc3ccccc3C#N)c(=O)c2s1]<br>131 |
| (R)-2-((2-(3-aminopiperidin-1-yl)-6-((cyclopropylamino)methyl)-4-oxothieno[3,2-d]pyrimidin-3(4H)-yl)methyl)benzonitrile | 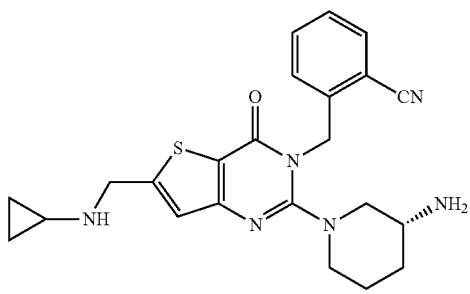 [SMILES: N#Cc1ccccc1Cn1c(N2CCC[C@@H](N)C2)nc2cc(CNC3CC3)sc2c1=O]<br>132 |
| (R)-N-(2-(3-aminopiperidin-1-yl)-3-(2-cyanobenzyl)-4-oxo-3,4-dihydrothieno[3,2-d]pyrimidin-7-yl)-4-methylbenzenesulfonamide | 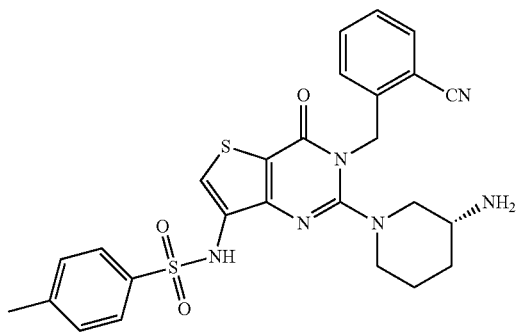 [SMILES: Cc1ccc(S(=O)(=O)Nc2csc3c(=O)n(Cc4ccccc4C#N)c(N4CCC[C@@H](N)C4)nc23)cc1]<br>133 |

| Designation | Structure |
|---|---|
| (R)-2-((2-(3-aminopiperidin-1-yl)-4-oxo-6-((2-oxo-2-phenylethyl)amino)thieno[3,2-d]pyrimidin-3(4H)-yl)methyl)benzonitrile | 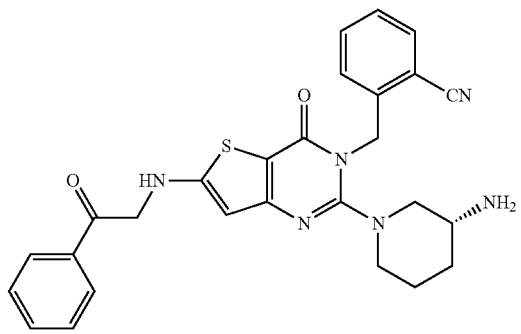 [SMILES: N#Cc1ccccc1Cn1c(N2CCC[C@@H](N)C2)nc2cc(NCC(=O)c3ccccc3)sc2c1=O]<br>134 |
| (R)-2-((2-(3-aminopiperidin-1-yl)-6-(difluoromethyl)-4-oxothieno[3,2-d]pyrimidin-3(4H)-yl)methyl)benzonitrile | 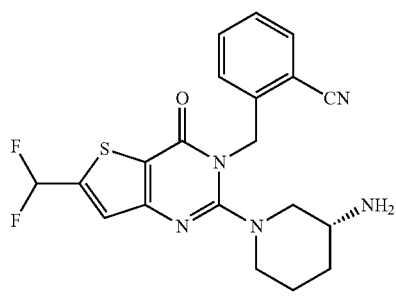 [SMILES: N#Cc1ccccc1Cn1c(N2CCC[C@@H](N)C2)nc2cc(C(F)F)sc2c1=O]<br>135 |
| (R)-2-((2-(3-aminopiperidin-1-yl)-7-(difluoromethyl)-4-oxothieno[3,2-d]pyrimidin-3(4H)-yl)methyl)benzonitrile | 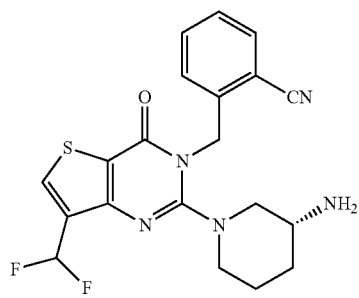 [SMILES: N#Cc1ccccc1Cn1c(N2CCC[C@@H](N)C2)nc2c(C(F)F)csc2c1=O]<br>136 |
| (R)-2-((2-(3-aminopiperidin-1-yl)-6-(3,3-difluoroazetidine-1-carbonyl)-4-oxothieno[3,2-d]pyrimidin-3(4H)-yl)methyl)benzonitrile | 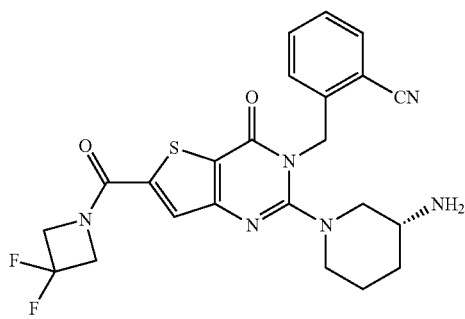 [SMILES: N#Cc1ccccc1Cn1c(N2CCC[C@@H](N)C2)nc2cc(C(=O)N3CC(F)(F)C3)sc2c1=O]<br>137 |

| Designation | Structure |
|---|---|
| (R)-2-((2-(3-aminopiperidin-1-yl)-6-(3,3-difluoropyrrolidine-1-carbonyl)-4-oxothieno[3,2-d]pyrimidin-3(4H)-yl)methyl)benzonitrile | 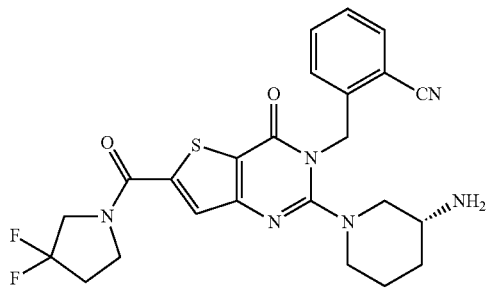 [SMILES: N#Cc1ccccc1Cn1c(N2CCC[C@@H](N)C2)nc2cc(C(=O)N3CCC(F)(F)C3)sc2c1=O]<br>138 |
| (R)-2-((2-(3-aminopiperidin-1-yl)-6-(4,4-difluoropiperidine-1-carbonyl)-4-oxothieno[3,2-d]pyrimidin-3(4H)-yl)methyl)benzonitrile | 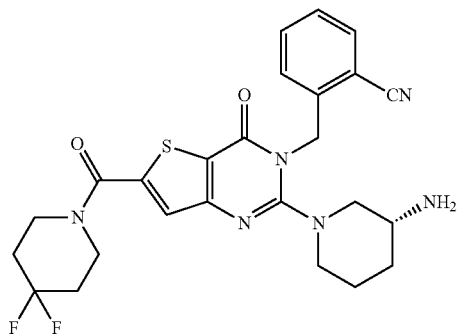<br>139 |
| (R)-2-((2-(3-amino-1-yl)-6-(3,3-difluoropiperidine-1-carbonyl)-4-oxothieno[3,2-d]pyrimidin-3(4H)-yl)methyl)benzonitrile | 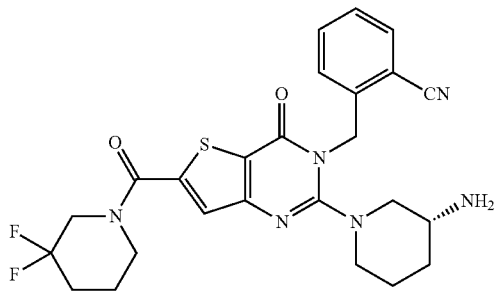 [SMILES: N#Cc1ccccc1Cn1c(N2CCC[C@@H](N)C2)nc2cc(C(=O)N3CCCC(F)(F)C3)sc2c1=O]<br>140 |
| (R)-2-((2-(3-aminopiperidin-1-yl)-6-(4-fluoropiperidine-1-carbonyl)-4-oxothieno[3,2-d]pyrimidin-3(4H)-yl)methyl)benzonitrile | 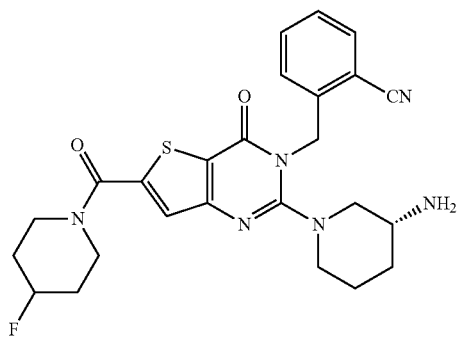 [SMILES: N#Cc1ccccc1Cn1c(N2CCC[C@@H](N)C2)nc2cc(C(=O)N3CCC(F)CC3)sc2c1=O]<br>141 |

| Designation | Structure |
|---|---|
| (R)-2-((2-(3-aminopiperidin-1-yl)-6-(3-fluoroazetidine-1-carbonyl)-4-oxothieno[3,2-d]pyrimidin-3(4H)-yl)methyl)benzonitrile | 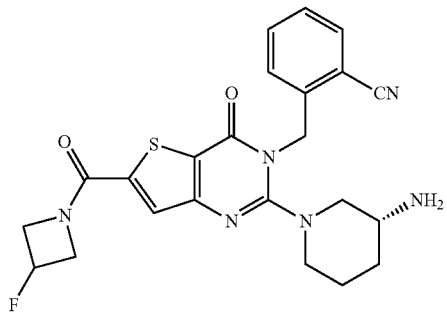 [SMILES: N#Cc1ccccc1Cn1c(N2CCC[C@@H](N)C2)nc2cc(C(=O)N3CC(F)C3)sc2c1=O]<br>142 |
| (R)-ethyl 3-(2-(3-aminopiperidin-1-yl)-3-(2-cyanobenzyl)-4-oxo-3,4-dihydrothieno[3,2-d]pyrimidine-6-carboxamido)propanoate | 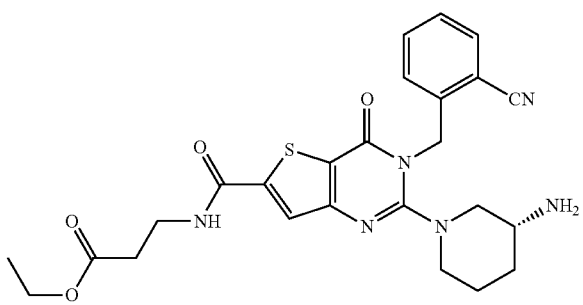 [SMILES: CCOC(=O)CCNC(=O)c1cc2nc(N3CCC[C@@H](N)C3)n(Cc3ccccc3C#N)c(=O)c2s1]<br>143 |
| (R)-ethyl 4-(2-(3-aminopiperidin-1-yl)-3-(2-cyanobenzyl)-4-oxo-3,4-dihydrothieno[3,2-d]pyrimidine-6-carboxamido)butanoate | 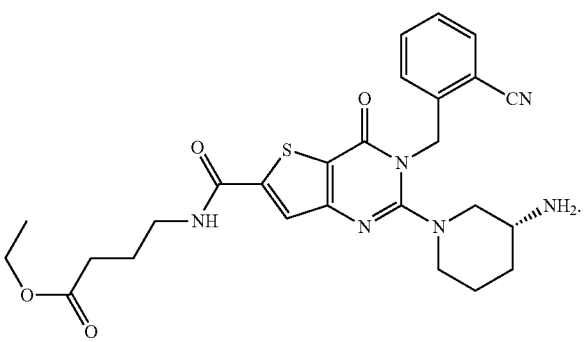 [SMILES: CCOC(=O)CCCNC(=O)c1cc2nc(N3CCC[C@@H](N)C3)n(Cc3ccccc3C#N)c(=O)c2s1]<br>144 |

11. A method for preparing a thieno[3,2-d]pyrimidin-4-one compound, an enantiomer, a diastereoisomer, a racemate and mixtures thereof, and a pharmaceutically acceptable salt thereof, wherein the preparation is completed by using 2,4-dimethoxythieno[3,2-d]pyrimidine, 7-bromo-2,4-dimethoxythieno[3,2-d]pyrimidine and 7-methyl-2,4-dimethoxythieno[3,2-d]pyrimidine as raw material, and performing substitution, chlorination, hydrolysis, benzyl substitution and amino substitution on 6-position and 7-position, and the method is carrid out through the following scheme:

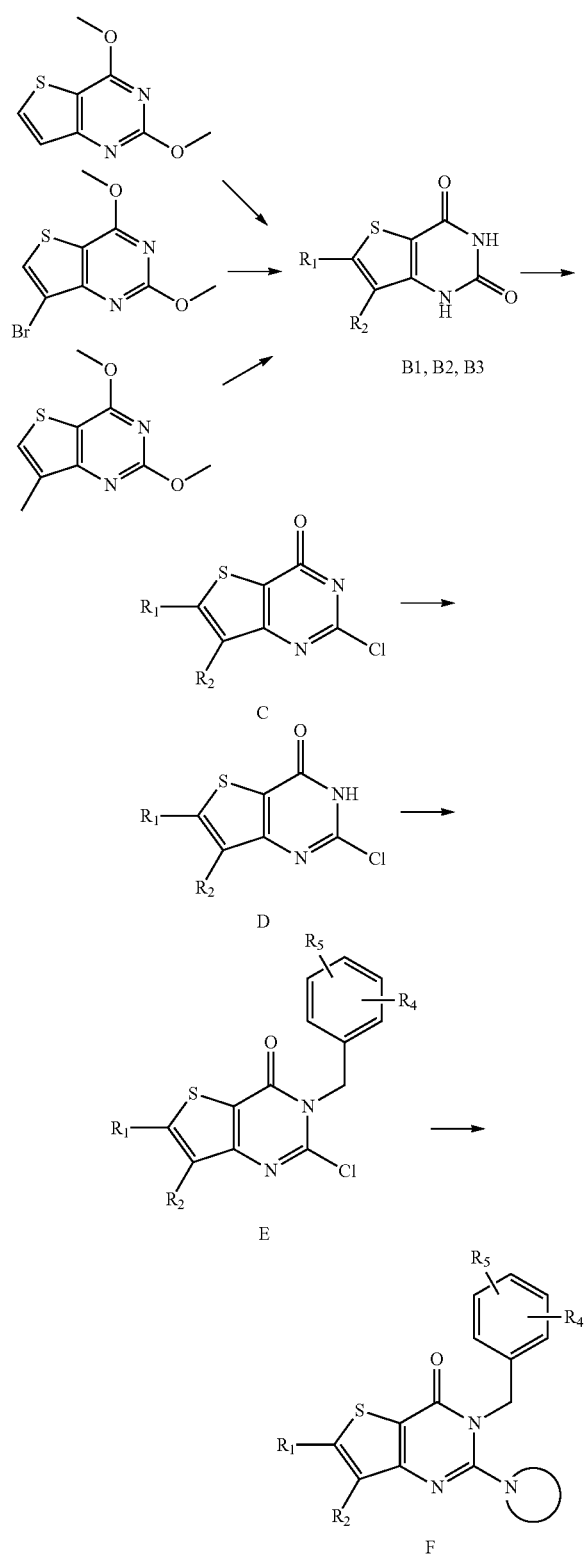

B1, B2, B3

C

D

E

F wherein, $R_1$, $R_2$, $R_4$, and $R_5$ are defined as claim 1;
1) synthesis of 6,7-substituted-thieno[3,2-d]pyrimidin-2,4-dione compound B1, B2 and B3:

2,4-dimethoxythieno[3,2-d]pyrimidine, 7-bromo-2,4-dimethoxythieno[3,2-d]pyrimidine or 7-methyl-2,4-dimethoxythieno[3,2-d]pyrimidine is dissolved in tetrahydrofuran, substituted tetrahydrofuran or diethyl ether and stirred for 15-30 minutes at −78° C., and then 1-3 equivalents of 2.5 M n-butyl lithium solution in n-hexane is added dropwise and stirred for another 1-2 hours at −78° C., and then a substituent reagent to be added is added dropwise; upon addition, the reaction mixture is stirred for another 15-30 minutes and then stirred for 1 hour at room temperature, after that the reaction solution is poured into saturated $NH_4Cl$ solution and extracted by organic solvent, and then 6,7-substituted-2,4-dimethoxythieno[3,2-d]pyrimidine compound A1, A2 or A3 is obtained by column chromatography;

6,7-substituted-2,4-dimethoxythieno[3,2-d]pyrimidine compound A1, A2 or A3 is dissolved in organic acid and 4 equivalents of iodide is added, after stirred for 1-5 hours at reflux, the reaction solution is poured into ice water and stirred for 30 minutes, a large amount of solids are precipitated, the solids were filtered by suction, washed with water and dried, thereby obtaining the product 6,7-substituted-thieno[3,2-d]pyrimidin-2,4-dione compound B1 or B2;

specific synthesis strategy is as follows:

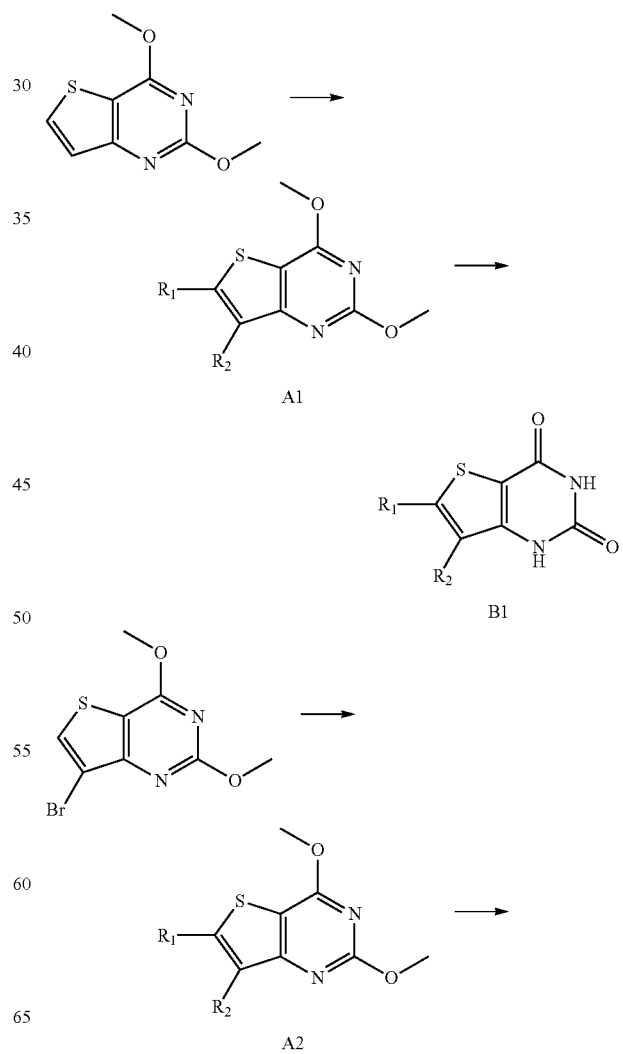

A1

B1

A2

-continued

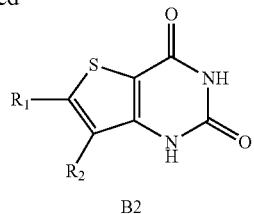

B2

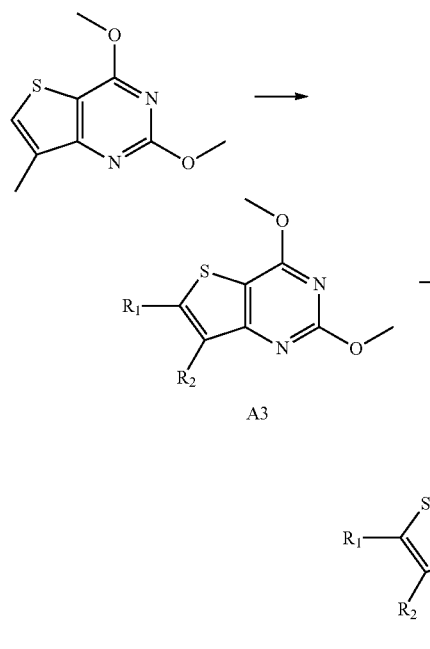

2) synthesis of 6,7-substituted-2,4-dichlorothieno[3,2-d]pyrimidine compound C:

6,7-substituted-thieno[3,2-d]pyrimidin-2,4-dione compound B1, B2 or B3 is dissolved in phosphorus oxychloride, after refluxed for 2-18 hours, the reaction solution is poured into ice water and stirred for 30 minutes, and then a large amount of solids are precipitated, the solids were filtered by suction, washed with water and dried, thereby obtaining the product 6,7-substituted-2,4-dichlorothieno[3,2-d]pyrimidine compound C;

synthesis strategy is as follows:

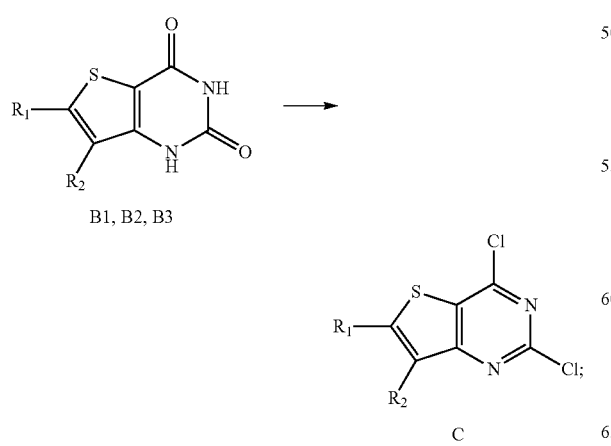

3) synthesis of 6,7-substituted-2-chlorothieno[3,2-d]pyrimidin-4-one compound D:

6,7-substituted-2,4-dichlorothieno[3,2-d]pyrimidine compound C is dissolved in organic solvent, an appropriate amount of aqueous alkali solution is added under nitrogen and stirred for 2-18 hours at room temperature, the organic solvent is evaporated from the reaction solution and an acid is added to adjust pH to neutral under stirring, and then a large amount of solids are precipitated, the solids were filtered by suction, washed with water and dried, thereby obtaining the product 6,7-substituted-2-chlorothieno[3,2-d]pyrimidin-4-one compound D;

specific synthesis strategy is as follows:

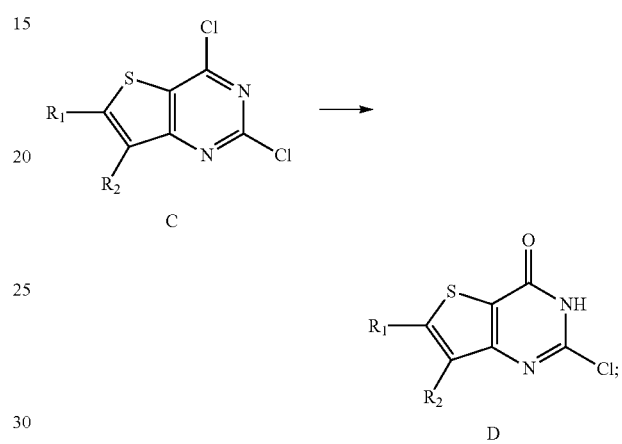

4) synthesis of 6,7-substituted-3-substitutedbenzyl-2-chlorothieno[3,2-d]pyrimidin-4-one compound E;

6,7-substituted-2-chlorothieno[3,2-d]pyrimidin-4-one compound D is dissolved in the mixture of glycol dimethyl ether and DMF, 60% of NaH is added at −10~5° C., then anhydrous lithium bromide is added and then substituted benzyl bromide or benzyl chloride is added and reacted for 4-18 hours at 40-100° C., after cooled, an appropriate amount of water is added, and a large amount of solids are precipitated, the solids were filtered by suction, washed with water and dried, thereby obtaining the product 6,7-substituted-3-substituted benzyl-2-chlorothieno[3,2-d]pyrimidin-4-one compound E;

specific synthesis strategy is as follows:

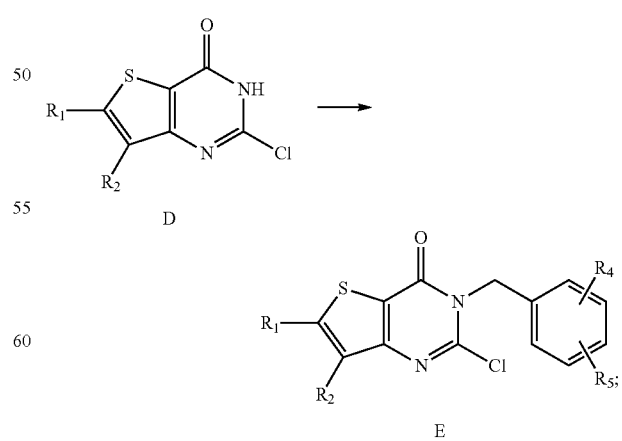

5) synthesis of 6,7-substituted-3-substituted benzyl-2-substituted aminothieno[3,2-d]pyrimidin-4-one compound F:

6,7-substituted-3-substituted benzyl-2-chlorothieno[3,2-d]pyrimidin-4-one compound E is dissolved in organic solvent and 1-4 equivalents of alkali is added, and then

is added and reacted for 1-16 hours at 60-130° C., the reaction solution is exacted, and 6,7-substituted-3-substituted benzyl-2-substituted aminothieno[3,2-d]pyrimidin-4-one compound F is obtained by column chromatography;
specific synthesis strategy is as follows:

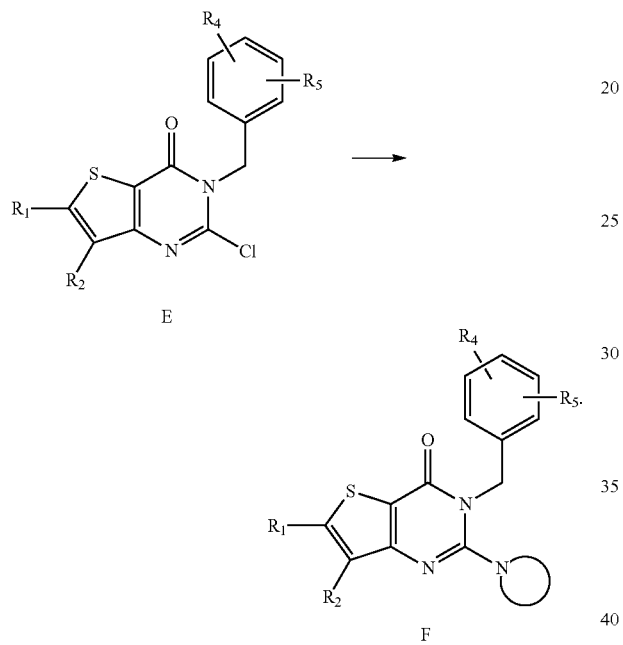

12. The method of claim 11, wherein said acid is organic acid or inorganic acid, said organic acid is acetic acid, trifluoroacetic acid, formic acid, and said inorganic acid is hydrochloric acid, sulfuric acid or phosphoric acid;
said base is organic base or inorganic base, said organic base is selected from sodium carbonate, potassium carbonate, cesium carbonate, sodium bicarbonate, potassium phosphate, potassium dihydrogen phosphate, sodium hydroxide, lithium hydroxide and potassium hydroxide, and said organic base is selected from triethylamine, pyridine, diazabicyclo and N,N-diisopropylethylamine;
said reagent added dropwise in step 1) is selected from an F reagent, an iodine reagent, a boric acid reagent and N,N-dimethylformamide, wherein, the F reagent is diethylaminosulphur trifluoride, the iodine reagent is iodine or N-iodosuccinimide; and the boric acid reagent is triethyl borate;
said organic solvent in step 3) and step 5) is selected from tetrahydrofuran, acetonitrile, acetone, 1,4-dioxane, alcohols, diethyl ether, N,N-dimethylformamide, glycol dimethyl ether, N,N-dimethylformamide and dimethyl sulfoxide.
13. A pharmaceutical composition comprising the therapeutically effective amount of one or more the thieno[3,2-d]pyrimidin-4-one compounds, enantiomers, diastereoisomers, racemates and mixtures thereof, or pharmaceutically acceptable salts thereof of claim 1 as effective ingredients, and further comprising pharmaceutically acceptable carriers.
14. The thieno[3,2-d]pyrimidin-4-one compound, an enantiomer, a diastereoisomer, a racemate and mixtures thereof, and a pharmaceutically acceptable salt thereof according to claim 1, wherein, in general formula I:
$R_1$ or $R_2$ is $(CH_2)_m OR_6$, $(CH_2)_m NR_6 R_7$,

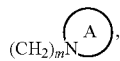

$(CH_2)_m COOR_8$, $CONR_9 R_{10}$, or

15. The thieno[3,2-d]pyrimidin-4-one compound, an enantiomer, a diastereoisomer, a racemate and mixtures thereof, and a pharmaceutically acceptable salt thereof according to claim 1, wherein, in general formula I:
$R_1$ is H, $CBr_2H$, $CCl_2H$, $CF_2H$, a cyano, $CF_3$, an aldehyde group,
$CH_2)_m OR_6$, $(CH_2)_m NR_6 R_7$,

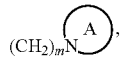

$(CH_2)_m COOR_8$, $CONR_9 R_{10}$, or

and $R_2$ is $(CH_2)_m OR_6$, $(CH_2)_m NR_6 R_7$,

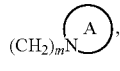

$(CH_2)_m COOR_8$, $CONR_9 R_{10}$,
r

16. The thieno[3,2-d]pyrimidin-4-one compound, an enantiomer, adiastereoisomer, a racemate and mixtures thereof, and a pharmaceutically acceptable salt thereof according to claim 1, wherein, in general formula I:

$R_2$ is H, a halogen, $CBr_2H$, $CCl_2H$, $CF_2H$, a cyano, $CF_3$, or an aldehyde group; and $R_1$ is $(CH_2)_mOR_6$, $(CH_2)_mNR_6R_7$,

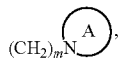

$(CH_2)_mCOOR_8$, $CONR_9R_{10}$, or

17. The thieno[3,2-d]pyrimidin-4-one compound of structural general formula I, an enantiomer, a diastereoisomer, a racemate and mixtures thereof, and a pharmaceutically acceptable salt thereof according to claim 1, wherein, the thieno[3,2-d]pyrimidin-4-one compound is one of the following compounds: compound 28, 38, 40, 43 45, 55-58, 60-61, 67, 70-75, 77, 79, 86, 88-90, 92-94, 96, 98, 104, 106, 108, 109, 111, 113, and 115-129.

18. A method for inhibiting DPPIV comprising the step of administrating thieno [3,2-d]pyrimidin-4-one compound, the enantiomer, the diastereoisomer, the racemate and mixtures thereof, and the pharmaceutically acceptable salt thereof of claim 1 to a subject in need thereof.

19. A method for treating type 2 diabetes comprising the step of administrating thieno [3,2-d]pyrimidin-4-one compound, the enantiomer, the diastereoisomer, the racemate and mixtures thereof, and the pharmaceutically acceptable salt thereof of claim 1 to a subject in need thereof.

* * * * *